(12) United States Patent
Marvin et al.

(10) Patent No.: US 10,060,920 B2
(45) Date of Patent: Aug. 28, 2018

(54) GENETICALLY ENCODED BIOSENSORS

(71) Applicants: Howard Hughes Medical Institute, Chevy Chase, MD (US); The Brigham & Women's Hospital, Inc., Boston, MA (US)

(72) Inventors: Jonathan S. Marvin, Arlington, VA (US); Loren Looger, Sterling, VA (US); Richard T. Lee, Weston, MA (US); Eric Schreiter, Ashburn, VA (US)

(73) Assignees: Howard Hughes Medical Institute, Chevy Chase, MD (US); The Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/904,574

(22) Filed: Feb. 26, 2018

(65) Prior Publication Data
US 2018/0209972 A1  Jul. 26, 2018

Related U.S. Application Data

(62) Division of application No. 15/664,326, filed on Jul. 31, 2017, now Pat. No. 9,939,437, which is a division of application No. 14/350,199, filed as application No. PCT/US2012/059219 on Aug. 8, 2012, now Pat. No. 9,719,992.

(60) Provisional application No. 61/544,867, filed on Oct. 7, 2011.

(51) Int. Cl.
| | |
|---|---|
| G01N 33/557 | (2006.01) |
| G01N 33/68 | (2006.01) |
| C07K 14/245 | (2006.01) |
| C07K 14/435 | (2006.01) |
| C07K 14/195 | (2006.01) |
| G01N 33/58 | (2006.01) |

(52) U.S. Cl.
CPC ......... *G01N 33/557* (2013.01); *C07K 14/195* (2013.01); *C07K 14/245* (2013.01); *C07K 14/43595* (2013.01); *G01N 33/582* (2013.01); *G01N 33/68* (2013.01); *G01N 33/6812* (2013.01); *C07K 2319/20* (2013.01); *C07K 2319/24* (2013.01); *C07K 2319/60* (2013.01); *G01N 2400/00* (2013.01); *G01N 2458/00* (2013.01)

(58) Field of Classification Search
None
See application file for complete search history.

(56) References Cited

U.S. PATENT DOCUMENTS

| | | | |
|---|---|---|---|
| 6,133,502 A | 10/2000 | Kasuga et al. | |
| 6,175,057 B1 | 1/2001 | Mucke et al. | |
| 6,180,849 B1 | 1/2001 | Streuli et al. | |
| 9,719,992 B2 | 8/2017 | Marvin et al. | |
| 2004/0118681 A1* | 6/2004 | Hellinga | C12Q 1/001 204/403.01 |

FOREIGN PATENT DOCUMENTS

| | | |
|---|---|---|
| WO | WO 2006/044612 | 4/2006 |
| WO | WO 2006/110728 | 10/2006 |

OTHER PUBLICATIONS

Tanaika et al., "Design Strategies of Fluorescent Biosensors Based on Biological Macromolecular Receptors", Sensors, 2010, vol. 10, pp. 1355-1376, doi:10.3390/s100201355.*
International Search Report and Written Opinion in International Application No. PCT/US2012/059219, dated Jun. 10, 2013, 18 pages.
International Preliminary Report on Patentability in International Application No. PCT/US2012/059219, dated Apr. 17, 2014, 11 pages.
Invitation to Pay Additional Fees in International Application No. PCT/US2012/059219, 2013.
Andrade and Wei et al., "Adsorption of complex proteins at interfaces," Pure and Appl. Chem., 1992, 64(11):1777-1781.
Baird et al.,"Circular permutation and receptor insertion within green fluorescent proteins," Proc. Natl. Acad. Sci., USA, 1999, 96:11241-11246.
Belousov et al., "Genetically encoded fluorescent indicator for intracellular hydrogen peroxide," Nat. Methods, 2006, 3:281-286.
Berg et al., "A genetically encoded fluorescent reporter of ATP:ADP ratio," Nat. Methods., 2009, 105:365-370.
Bloom et al., "Protein stability promotes evolvability," Proc. Natl. Acad. Sci., 2006, 103:5869-5874.
Bogner and Ludewig, "Visualization of arginine influx into plant cells using a specific FRET-sensor," J. Fluoresc., 2007, 17:350-360.
Brinster et al., "Expression of a microinjected immunoglobulin gene in the spleen of transgenic mice," Nature, 1983, 306:332-336.
Choi et al., "Evolutionary conservation in multiple faces of protein interaction," Proteins, 2009, 77(1):14-25.
Cubitt et al., "Understanding, improving and using green fluorescent proteins," Trends Biochem., 1995, 20:448-455.
Cuneo et al., "The crystal structure of a thermophilic glucose binding protein reveals adaptations that interconvert mono and di-saccharide binding sites," J. Mol. Biol., 2006, 362:259-270.
Deuschle et al., "Genetically encoded for metabolites," Cytometry, 2005, 64:3-9.
Deuschle et al., "Construction and optimization of a family of genetically encoded metabolite sensors by semirational protein engineering," Protein Sci, 2005, 14:2304-2314.
Dwyer and Hellinga, "Periplasmic binding proteins: a versatile superfamily for protein engineering," Curr. Opin. Struc. Biol., 2004, 14:495-504.
Evdokimov et al., "Structural basis for oligosaccharide recognition by Pyrococcus furiosus maltodextrin-binding protein," J. Mol. Biol., 2001, 305:891-904.

(Continued)

*Primary Examiner* — Suzanne Marie Noakes
(74) *Attorney, Agent, or Firm* — Fish & Richardson P.C.

(57) ABSTRACT

The present disclosure provides, inter alia, genetically encoded recombinant peptide biosensors comprising analyte-binding framework portions and signaling portions, wherein the signaling portions are present within the framework portions at sites or amino acid positions that undergo a conformational change upon interaction of the framework portion with an analyte.

29 Claims, 65 Drawing Sheets

Specification includes a Sequence Listing.

(56) References Cited

OTHER PUBLICATIONS

Fallon and Quiocho, "A closed compact structure of native Ca(2+)-calmodulin," Structure, 2003, 11:1303-1307.

Fan et al., "A periplasmic glutamate/aspartate binding protein from Shigella flexneri: Gene cloning, over-expression, purification and preliminary crystallographic studies of the recombinant protein," Protein Pept. Lett., 2006, 13:513-516.

Frommer et al., "Genetically encoded biosensors based on engineered fluorescent proteins," Chem. Soc. Rev., 2009, 38:2833-2841.

Gautam et al., "Exploration of fluorescent protein voltage probes based on circularly permuted fluorescent proteins," Frontiers in Neuroengineering, 2009, 2(14): 1-8.

Gong et al., "Extracting consistent knowledge from highly inconsistent cancer gene data sources," BMC: Bioinformatics, 2010, 11:76, 8 pages.

Gu et al., "A novel analytical method for in vivo phosphate tracking," FEBS Letters, 2006, 580:5885-5893.

Guntas and Mansell, "Directed evolution of protein switches and their application to the creation of ligand-binding proteins," Proc. Natl. Acad. Sci., 2005, 102:11224-11229.

Guntas and Ostermeier, "Creation of an allosteric enzyme by domain insertion," J. Mol. Biol., 2004, 336:263-273.

Guntas et al., "A molecular switch created by in vitro recombination of nonhomologous genes," Chem. Biol., 2004, 11:1483-1487.

Jaeger et al., "Improved predictions of secondary structures for RNA," Proc. Natl. Acad. Sci. USA, 1989, 86:7706-10.

Kim and Ostermeier, "Modulation of effector affinity by hinge region mutations also modulates switching activity in an engineered allosteric TEM1 beta-lactamase switch," Arch. Biochem. Biophys., 2006, 446:44-51.

Kuboniwa et al., "Solution structure of calcium-free calmodulin," Nat. Struc. Biol., 1996, 2:768-776.

Markwardt et al., "An improved cerulean fluorescent protein with enhanced brightness and reduced reversible photoswitching," PLoS One, 2011, 6(3) e17896, 11 pages.

Martineau et al., "Genetic approach to the role of tryptophan residues in the activities and fluorescence of a bacterial periplasmic maltose-binding protein," J. Mol. Biol., 1990, 214:337-352.

Marvin and Hellinga, "Manipulation of ligand binding affinity by exploitation of conformational coupling," Nat. Struc. Biol., 2001, 8:795-798.

Marvin, J.S. & Hellinga, H.W., Engineering Biosensors by Introducing Fluorescent Allosterc Signal Transducers: Construction of a Novel Glucose Sensor, J. Am. Chem. Soc. 1998, 120, 7-11.

Marvin et al., "The rational design of allosteric interactions in a monomeric protein and its applications to the construction of biosensors," Proc. Natl. Acad. Sci. USA, 1997, vol. 94, pp. 4366-4371.

Nakai et al., "A high signal-to-noise Ca(2+) probe composed of a single green fluorescent protein," Nat. Biotechnol., 2001, 19:137-141.

Nausch et al., "Differential patterning of cGMP in vascular smooth muscle cells revealed by single GFP-linked biosensors," Proc. Natl. Acad. Sci. USA., 2008, 105:365-370.

NCBI Reference Sequence: NP_290668.1, 2013, 2 pages.

Okumoto et al., "Detection of glutamate release from neurons by genetically encoded surface-displayed FRET nanosensors," Proc. Natl. Acad. Sci. USA., 2005, 102:8740-8745.

Okumoto, "Imaging approach for monitoring cellular metabolites and ions using genetically encoded biosensors," Curr. Opin. Biotechnol., 2010, 21:45-54.

Quiocho and Ledvina, "Atomic structure and specificity of bacterial periplasmic receptors for active transport and chemotaxis: variation of common themes," Mol. Microbiol., 1996, 20:17-25.

Quiocho et al., "Extensive features of tight oligosaccharide binding revealed in high-resolution structures of the maltodextrin transport/chemosensory receptor," Structure, 1997, 5:997-1015.

Shaner et al., "Advances in fluorescent protein technology," J. Cell. Sci., 2007, 120:4247-4260.

Sharff et al., "Crystallographic evidence of a large ligand-induced hinge-twist motion between the two domains of the maltodextrin binding protein involved in active transport and chemotaxis," Biochemistry, 1992, 31:10657-10663.

Tainaka et al., "Design Strategies of Fluorescent Biosensors Based on Biological Macromolecular Receptors," Sensors, 2010, 10(2): 1355-1376.

Tian et al., "Imaging neural activity in worms, flies and mice with improved GCaMP calcium indicators," Nat. Methods, 2009, 6:875-881.

Topell and Glockshuber, "Circular permutation of the green fluorescent protein," Methods in Molecular Biology, 2002, 183:31-48.

Zhang et al., "Creating new fluorescent probes for cell biology," Nat Rev Mol Cell Biol., 2002, 3:906-908.

\* cited by examiner

FIG. 8A pRSET Leader: MRGSHHHHHHGMASMTGGQQMGRDLYDDDDKDRWGSKIEEGKLVIWINGDKGYNGLAEVGKKFEKDTGIKVTVEHPDKLE MBP 1-175: EKFPQVAATGDGPDIIFWAHDRFGGYAQSGLLAEITPDKAFQDKLYPFTWDAVRYNGKLIAYPIAVEALSLIYNKDLLPN MBP 1-175: PPKTWEEIPALDKELKAKGKSALMFNLQEPYFTWPLIAADGGYAFKYENGGSHNVYITMADKQKNGIKANFKIRHNIEDGG cpGFP 147-238: VQLAYHYQQNTPIGDPVLLPDNHYLSTQSKLSKDPNEKRDHMVLLEFVTAAGITLGMDELYKGGTGGSMVSKGEELFTG cpGFP 1-146: VVPILVELDGDVNGHKFSVSGEGEGDATYGKLTLKFICTTGKLPVPWPTLVTTLTYGVQCFSRYPDHMKQHDFFKSAMPE cpGFP 1-146: GYIQERTIFFKDDGNYKTRAEVKFEGDTLVNRIELKGIDFKEDGNLGHKLEYNFNGGKYDIKDVGVDNAGAKAGLTFLV MBP 176-370: DLIKNKHMNADTDYSIAEAAFNKGETAMTINGPWAWSNIDTSKVNIGVTVLPTFKGQPSKPFVGVLSAGINAASPNKELA MBP 176-370: KEFLENYLLTDEGLEAVNKDKPLGAVALKSYEEELVKDPRIAATMENAQKGEIMPNIPQMSAFWYAVRTAVINAASGRQT

MBP 176-370: VDEDLIKDAQTRITKGSHHHHHHG.

FIG. 8B pRSET Leader
MRGSHHHHHHGMASMTGGQQMGRDLYDDDDKDRWGS

MBP 1-175
KIEEGKLVIWINGDKGYNGLAEVGKKFEKDTGIKVTVEHPDKLE

MBP 1-175
EKFPQVAATGDGPDIIFWAHDREGGYAQSGLLAEITPDKAFQDKLYPFTWDAVRYNGKLIAYPIAVEALSLIYNKDLLPN

MBP 1-175
PPKTWEEIPALDKELKAKGKSALMFNLQEPYFTWPLIAADGGYAFKYENHLSHNVYIMADKQRNGIKANFKIRHNIEDGG cpGFP 147-238
VQLAYHYQQNTPIGDGPVLLPDNHYLSTQSKLSKDPNEKRDHMVLLEFVTAAGITLGMDELYK

Linker  cpGFP 1-146
GGTGGSMVSKGEELFTG cpGFP 1-146
VVPILVELDGDVNGHKFSVSGEGEGDATYGKLTLKFICTTGKLPVPWPTLVTTLTYGVQCFSRYPDHMKQHDFFKSAMPE MBP 176-370
GYIQERTIFFKDDGNYKTRAEVKFEGDTLVNRIELKGIDFKEDGNILGHKLEYNFNGKYDIKDVGVDNAGAKAGLTFLV MBP 176-370
DLIKNHMNADTDYSIAEAAFNKGETAMTINGPWAWSNIDTSKVNYGVTVLPTFKGQPSKPFVGVLSAGINAASPNKELA MBP 176-370
KEFLENYLLTDEGLEAVNKDKPLGAVALKSYEEELVKDPRTAATMENAQGEIMPNIPQMSAFWYAVRTAVINAASGRQT

MBP 176-370
VDEDLKDAQTRITKGSHHHHHHG.

FIG. 9B

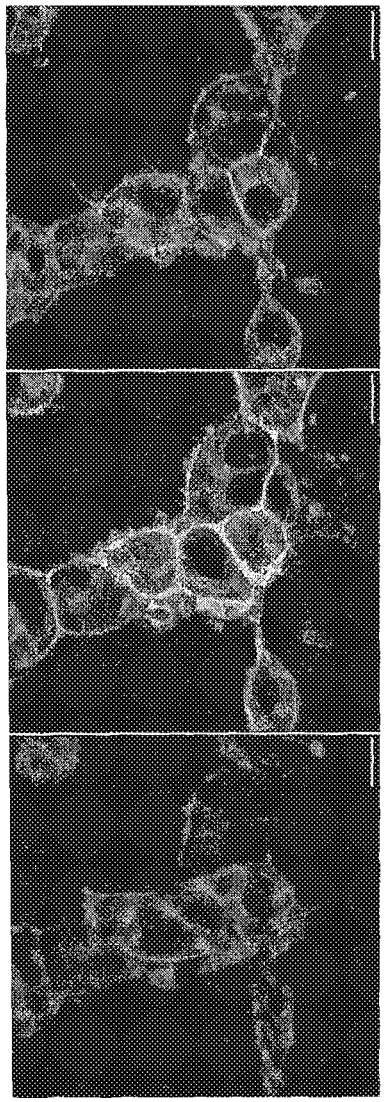

MRGSHHHHHHGMASMTGGQQMGRDLYDDDDKDRWGSKIEEGKVVIWHAMQPNELEVFQSLAEEYMALCPEVEIVFEQKPN

LEDALKAAIPTGQGPDLFIWAHDMIGKFAEAGLLEPIDEYVTEDLLNEFAPMAQDAMQYKGHYYALPFAAETVAIIYSKE

MVSEPPKTFDEMKAIMEKYYDPANEKYGIAWPINAYFISAIAQAFGGSHNVYIMADKQRNGIKANFKIRHNIEDGGVQLA

YHYQQNTPIGDGPVLLPDNHYLSTQSKLSKDPNEKRDHMVLLEFVTAAGITLGMDELYKGGTGGSMVSKGEELFTGVVPI

LVELDGDVNGHKFSVSGEGEGDATYGKLTLKFICTTGKLPVPWPTLVTTLTYGVQCFSRYPDHMKQHDFFKSAMPEGYIQ

ERTIFFKDDGNYKTRAEVKFEGDTLVNRIELKGIDFKEDGNILGHKLEYNFNFEYYFDDKTEQPGLDKPETIEGFKFEFT

EIWPYMAPTGDYNTQQSIFLEGRAPMMVNGPWSINDVKKAGINFGVVPLPPIIKDGKEYWPRPYGGVKLIYFAAGIKNKD

AAWKFAKWLTTSEESIKTLALELGYIPVLTKVLDDPEIKNDPVIYGFGQAVQHAYLMPKSPKMSAVWGGVDGAINELLQD

PQNADIEGILKKYQQEILNNMQGSHHHHHHG.

FIG. 24B

MRGSHHHHHHGMASMTGGQQMGRDLYDDDDKDRWGSKIEEGKVVIWHAMQPNELEVFQSLAEEYMALCPEVEIVFEQKPN

LEDALKAAIPTGQGPDLFIWAHDWIGKFAEAGLLEPIDEYVTEDLLNEFAPMAQDAMQYKGHYYALPFAAETVAIIYSKE

MVSEPPKTFDEMKAIMEKYYDPANEKYGIAWPINAYFISAIAQAFGGYYFDDKITEQPGLDKPETIEGFKFFTEIWPYMA

PTGDYNTQQSIFLEGRAPMMVNGPWSINDVKKAGINFGVPLPPIIKDGKEYWPRPYGGVKLIYFAAGIKNKDAAWKFAK

WLTTSEESIKTLALELGYIPVLTKVLDDPETSHNVYIMADKQKNGIKANFKIRHNIEDGGVLAYHYQQNTPIGDGPVLL

PDNHYLSTQSKLSKDPNEKRDHMVLLEFVTAAGITLGMDELYKGGTGGSMVSKGEELFTGVVPILVELDGDVNGHKFSVS

GEGEGDATYGKLTLKFICTTGKLPVPWPTLVTTLFYGVQCFSRYPDMKQHDFFKSAMPEGYIQERTIFFKDDGNYKTRA

EVKFEGDTLVNRIELKGIDFKEDGNILGHKLEYNFNKNDPVIYGFGQAVHQAYLMPKSPKMSAVWGGVDGAINELLQDPQ

NADIEGILKKYQQEILNNMQGS.

FIG. 25A pRSET Leader MRGSHHHHHHGMASMTGGQQMGRDLYDDDDKDRWGS

PfMBP 1-316 KIEEGKVVIWHAMQPNELEVFQSLAEEYMALCPEVEIVFEQKPN
LEDALKAAIPTGQGPDLFIWAHDWIGKFAEAGLLEPIDEYVTEDLLNEFAPMAQDAMQYKGHYYALPFAAETVAIIYSKE
MVSEPPKTFDEMKAIMEKYDPANEKYGIAWPINAYFISAIAQAFGYYFDDKTEQPGLDKPETIEGFKFFTEIWPYMA
PTGDYNTQQSIFLEGRAPMVNGPWSINDVKKAGINFGVVPLPPIIKDGKEYWPRPYGGVKLIYFAAGIKNKDAAWKFAK
WLTTSEESIKTLALELGYIPVLTKVLDDPEIPPSHNVYIMADKQNGIKANFIRHNIEDGGVQLAYHYQNTPIGDGPV cpGFP 147-238 SHNVYIMADKQNGIKANFKIRHNIEDGGVQLAYHYQNTPIGDGPV

Linker cpGFP 147-238 LLPDNHYLSTQSKLSKDPNEKRDHMVLLEFVTAAGITLGMDELYKGGTGGSMVSKGEELFTGVVPILVELDGDVNGHKFS cpGFP 1-146 VSGEGEGDATYGKLTLKFICTTGKLPVPWPTLVTTLTYGVQCFSRYPDHMKQHDFFKSAMPEGYIQERTIFFKDDGNYKT

PfMBP 317-380 RAEVKFEGDTLVNRIELKGIDFKEDGNILGHKLEYNFNKNDPVIYGFGQAVQHAYLMPKSPKMSAVWGGVDGAINEFLQD
PQNADIEGILKKYQQEILNNMQGS.

His6 tag: MHHHHHHGSEEQEKALNFGIISTESQQNLKPQWTPFLQDMEKKLGVKVNAFFAPDYAGIIQGMRFNKVDIAWYGNLSAME EcPhnD 1-90: AVDRANGQVFAQTVAADGSSHNVYIMADKQRNGIKANFKIRHNIEDGGVQLAYHYQQNTPIGDGPVLLPDNHYLSTQSKL cpGFP 147-238: SKDPNEKRDHMVLLEFVTAAGITLGMDELYKGGTGGSMVSKGEELFTGVVPILVELDGDVNGHKFSVSGEGEGDATYGKL Linker / cpGFP 1-146: TLKFICTTGKLPVPWPTLVTTLTYGVQCFSRYPDHMKQHDFFKSAMPEGYIQERTIFFKDGNYKTRAEVKFEGDTLVNR cpGFP 1-146: IELKGIDFKEDGNILGHKLEYNFNPGYWSVLIVNKDSPINNLNDLLAKRKDLFGNGDPNSTSGFLVPGYYVFAKNNISA EcPhnD 91-313: SDFKRTVNAGHETNALAVANKQVDVATNNTENLDKLKTSAPEKLKELKVIWKSPLIPGDPIVWRKNLSETTKDKIYDFFM EcPhnD 91-313: NYGKTPEEKAVIERLGMAPFRASSDLQVPIRQLALFKEMQSVKDNKGLNEQDKLAKTTAIQAQLDDLRLNNALSAMSS EcP_313: VSKAVQ.

567

```
                                          EcPhnD 1-90                                          80
His6-tag   MHHHHHHGSEEQEKALNFGIISTESQQNLKPQWTPFLQDMEKKLGVKVNAFFAPDYAGIIQGMRFNKVDIAWYGNLSAME
         O        N         O        O         O        N         O        O EcPhnD 1-90                             cpGFP 147-238                                 160
         AVDRANGQVFAQTVAADADNVYIMADKQRNGIKANFKIRHNIEDGGVQLAYHYQQNTPIGDGPVLLPDNHYLSTQSKLSK
         O        N         O        O         O        N         O        O cpGFP 147-238            Linker                cpGFP 1-146                   240
         SKDPNEKRDHMVLLEFVTAAGITLGMDELYKGGTGGSMVSKGEELFTGVVPILVELDGDVNGHKFSVSGEGEGDATYGKL
         O        N         O        O         O        N         O        O cpGFP 1-146                                           320
         TLKFICTTGKLPVPWPTLVTTLLTYGVQCFSRYPDHMKQHDFFKSAMPEGYIQERTIFFKDGNYKTRAEVKFEGDTLVNR
         O        N         O        O         O        N         O        O cpGFP 1-146                                EcPhnD 91-313                         400
         IELKGIDFKEDGNILGHKLEYNFNPGYWSVLIVNKDSPINNLNDLLAKRDLTFGNGDPNSTSGELVPGYYVFAKNNISA
         O        N         O        O         O        N         O        O EcPhnD 91-313                                        480
         GKTPEEKAVLERLGWAPFRASSDLQLVPIRQLALFKEMQSVKDNKGLNEQDKLAKTTAIQAQLDDLDRRNNARSAMSSVS
         O        N         O        O         O        N         O        O EcPhnD 91-313                                        560
         NYGKTPEEKAVLERLGWAPFRASSDLQLVPIRQLALFKEMQSVKDNKGLNEQDKLAKTTAIQAQLDDLDRINNALSAMSS
         O        N         O        O         O        N         O        O EcP 313                                                                               567
         VSKAVQ.
         O        N

Segments (top to bottom, with sequence):

pRSET Leader: MRGSHHHHHHGMASMTGGQQMGRDLYDDDDKDRWGSKLEIFSWWAGDEGPALEALIRLYKQKYPGVEVINATVTGGAGVN (80)

TtGBP 1-326: ARAVLKTRMLGGDPPPDTFQVHAGMELIGTWVANRMEDLSALFRQEGWLQAFPKGLIIDLISYKGGIWSVPVNIHRSNVMW (160)

TtGBP 1-326: YLPAKLKEMGVNPPRTWDEFLATCQTLKQGLEAPIALGENWTQHLMESVALAVLGPDDWNNLMNGKLKFTDPKAVRAW (240)

TtGBP 1-326: ARAVLKTRMLGGDPPDTFQVAAGMELIGTWVANRMEDSALFRQEGWLQAFPKGLIDLISYKGGIWSVPVNIHRSNVMW (160)

TtGBP 1-326 / cpGFP 147-238: AKNRQNAINWLRLVGSKEGQDTFNPLKGSIAARLDSDPSKYGGSHNVYIMADKQRNGIKANFKIRHNIEDGVQLAYHYQ (400)

cpGFP 147-238 / Linker / cpGFP 1-146: QNTPIGDGPVLLPDNHYLSTQSKLSKDPNEKRDHMVLLEFVTAAGITLGMDELYKGGTGGSMVSKGEELFTGVVPILVEL (480)

cpGFP 1-146: DGDVNGHKFSVSGEGEGDATYGKLTLKFICTTGKLPVPWPTLVTTLTYGVQCFSRYPDHMKQHDFFKSAMPEGYIQERTI (560)

cpGFP 1-146 / TtGBP 327-394: FFKDDGNYKTRAEVKFEGDTLVNRIELKGIDFKEDGNILGHKLEYNFNPNAYGQSAMRDWRSNRIVGSLVHGAVAPESF (640)

TtGBP 327-394: MSQFGTVMEIFLQTRNPQAAANAAQAIADQVGLGRLGQ. (679)

FIG. 37D pRSET Leader — MRGSHHHHHHGMASMTGGQQMGRDLYDDDDKDRWGS —

TtGBP 1-326:
- KLEIFSWWAGDEGPALEALIRLYQKYPGVEVINATVTGGAGVN (80)
- ARAVLKTRMLGGDPPDTFQVHAGMELIGTWVANRMEDLSALFRQEGWLQAFPKGLIDLISYKGGIWSVPVNIHRSNVMW (160)
- YLPAKLIKEWGVNPPRTWDEFLATCQTLKQGLEAPIALGENWTQQHLMESVALAVLGPDDWNNLWNGKLKFTDPKAVRAW (240)
- EVFGRVLDCANKDAAGLSWQQAVDRVVQGKAAFNVMGDWAAGYMTTLKLKPGTDFAWAPSPGTQGVFMMLSDSFGLPKG (320)
- AKNRQNAINWLRLVGSKEGQDTFNPLKGSIAARLDSDPSKY (326)

cpGFP 147-238 — YGGSHNVYIMADKQRNGIKANFKIRHNIEDGGVQLAYHYQ (400)

Linker — cpGFP 1-146:
- QNTPIGDGPVLLPDNHYLSTQSKLSKDPNEKRDHMVLLEFVTAAGITLGMDELYKGGTGGSMVSKGEELFTGVPILVEL (480)
- DGDVNGHKFSVSGEGEGDATYGKLTLKFICTTGKLPVPWPTLVTTLTYGVQCFSRYPDHMKQHDFFKSAMPEGYIQERTI (560)
- FFKDDGNYKTRAEVKFEGDTLVNRIELKGIDFKEDGNILGHKLEYNFNNPNAYGQSAMRDWRSNRIVGSLVAGAVAPESF (640)

TtGBP 327-394 — MSQFGTVMEIFLQTRNPQAAANAAQAIADQVGLGRLGQ. (679)

MKIKTGARIL ALSALTTMMF SASALAKIEE GKLVIWINGD KGYNGLAEVG
KKFEKDTGIK VTVEHPDKLE EKFPQVAATG DGPDIIFWAH DRFGGYAQSG
LLAEITPDKA FQDKLYPFTW DAVRYNGKLI AYPIAVEALS LIYNKDLLPN
PPKTWEEIPA LDKELKAKGK SALMFNLQEP YFTWPLIAAD GGYAFKYENG
KYDIKDVGVD NAGAKAGLTF LVDLIKNKHM NADTDYSIAE AAFNKGETAM
TINGPWAWSN IDTSKVNYGV TVLPTFKGQP SKPFVGVLSA GINAASPNKE
LAKEFLENYL LTDEGLEAVN KDKPLGAVAL KSYEEELAKD PRIAATMENA
QKGEIMPNIP QMSAFWYAVR TAVINAASGR QTVDEALKDA QTRITK

FIG. 41

MRRATYAFAL LAILVLGVVA SGCIGGGTTT
PTQTSPATQP TTTQTPTQTE TQAVEGGSGK
VVIWHAMQPN ELEVFQSLAE EYMALCPEVE
IVFEQKPNLE DALKAAIPTG QGPDLFIWAH
DWIGKFAEAG LLEPIDEYVT EDLLNEFAPM
AQDAMQYKGH YYALPFAAET VAIIYNKEMV
SEPPKTFDEM KAIMEKYYDP ANEKYGIAWP
INAYFISAIA QAFGGYYFDD KTEQPGLDKP
ETIEGFKFFF TEIWPYMAPT GDYNTQQSIF
LEGRAPMMVN GPWSINDVKK AGINFGVVPL
PPIIKDGKEY WPRPYGGVKL IYFAAGIKNK
DAAWKFAKWL TTSEESIKTL ALELGYIPVL
TKVLDDPEIK NDPVIYGFGQ AVQHAYLMPK
SPKMSAVWGG VDGAINEILQ DPQNADIEGI
LKKYQQEILN NMQG

FIG. 42

MNAKIIASLA FTSMFSLSTL LNPAYAEEQE
KALNFGIIST ESQQNLKPQW TPFLQDMEKK
LGVKVNAFFA PDYAGIIQGMI RFNKVDIAWY
GNLSAMEAVD RANGQVFAQT VAADGSPGYW
SVLIVNKDSP INNLNDLLAK RKDLTFGNGD
PNSTSGFLVP GYYVFAKNNI SASDFKRTVN
AGHETNALAV ANKQVDVATN NTENLDKLKT
SAPEKLKELK VIWKSPLIPG DPIVWRKNLS
ETTKDKIYDF FMINYGKTPEE KAVLERLGWA
PFRASSDLQL VPIRQLALFK EMQSVKDNKG
LN

MQLRKPATAI LALALSAGLA QADDAAPAAG
STLDKIAKNG VIVVGHRESS VPFSYYDNQQ
KVVGYSQDYS NAIVEAVKKK LNKPDLQVKL
IPITSQNRIP LLQNGTFDFE CGSTTNNVER
QKQAAFSDTI FVVGTRLLTK KGGDIKDFAN
LKDKAVVVTS GTTSEVLLNK LNEEQKMNMR
IISAKDHGDS FRTLESGRAV AFMMDDALLA
GERAKAKKPD NWEIVGKPQS QEAYGCMLRK
DDPQFKKLMD DTIAQVQTSG EAEKWFDKWF
KNPIPPKNLN MNFELSDEMK ALFKEPNDKA LN

FIG. 44

MRKWLLAIGM VLGLSALAQG GKLEIFSWWA
GDEGPALEAL IRLYKQKYPG VEVINATVTG
GAGVNARAVL KTRMLGGDPP DTFQVHAGME
LIGTWVVANR MEDLSALFRQ EGWLQAFPKG
LIDLISYKGG IWSVPVNIHR SNVMWYLPAK
LKEWGVNPPR TWDEFLATCQ TLKQKGLEAP
LALGENWTQQ HLWESVALAV LGPDDWNNLW
NGKLKFTDPK AVRAWEVFGR VLDCANKDAA
GLSWQQAVDR VVQGKAAFNV MGDWAAGYMT
TTLKLKPGTD FAWAPSPGTQ GVFMMLSDSF
GLPKGAKNRQ NAINWLRLVG SKEGQDTFNP
LKGSIAARLD SDPSKYNAYG QSAMRDWRSN
RIVGSLVHGA VAPESFMSQF GTVMEIFLQT
RNPQAAANAA QAIADQVGLG RLGQ

FIG. 45

MIRTLSLKFM LAGAVCMATL TAGSAFAAEP
ESCGTVRFSD VGWTDITATT ATATTILEAL
GYETDVKVLS VPVTYTSLKN KDIDVFLGNW
MPTMEADIAP YREDKSVETV RENLAGAKYT
LATNAKGAEL GIKDFKDIAA HKDELDGKIY
GIEPGNDGNR LIIDMVEKGT FDLKGFEVVE
SSEQGMLAQV ARAEKSGDPI VFLGWEPHPM
NANFKLTYLS GGDDVFGPNY GGATVHTNVR
AGYTTECPNV GKLLQNLSFS LQMENEIMGK
ILNDGEDPEK AAAAWLKDNP QSIEPWLSGV
ATKDGGDGLA AVKAALGL

FIG. 46

MGGGRSTETS SSSGGDGGAT KKKVVVGTDA
AFAPFEYMQK GKIVGFDVDL LDAVMKAAGL
DYELKNIGWD PLFASLQSKE VDMGISGITI
TDERKQSYDF SDPYFEATQV ILVKQGSPVK
NALDLKGKTI GVQNATTGQE AAEKLFGKGP
HIKKFETTVV AIMELLNGGV DAVITDNAVA
NEYVKNNPNK KLQVIEDPKN FASEYYGMIF
PKNSELKAKV DEALKNVINS GKYTEIYKKW
FGKEPKLDRL

FIG. 47

MKKSLLSAVA LTAMVAFGGS AWADVVIAVG
APLTGPNAAF GAQIQKGAEQ AAKDINAAGG
INGEQIKIVL GDDVSDPKQG ISVANKFVAD
GVKFVVGHFN SGVSIPASEV YAENGILEIT
PAATNPVFTE RGLWNTFRTC GRDDQQGGIA
GKYLADHFKD AKVAIIHDKT PYGQGLADET
KKAANAAGVT EVMYEGVNVG DKDFSALISK
MKEAGVSIIY WGGLHTEAGL IIRQAADQGL
KAKLVSGDGI VSNELASIAG DAVEGTLNTF
GPDPTLRPEN KELVEKFKAA GFNPEAYTLY
SYAAMQAIAG AAKAAGSVEP EKVAEALKKG
SFPTALGEIS FDEKGDPKLP GYVMYEWKKG
PDGKFTYIQQ

FIG. 48

MNIKGKALLA GCIALAFSNM ALAEDIKVAV
VGAMSGPVAQ YGDQEFTGAE QAVADINAKG
GIKGNKLQIV KYDDACDPKQ AVAVANKVVN
DGIKYVIGHL CSSSTQPASD IYEDEGILMI
TPAATAPELT ARGYQLIIRT TGLDSDQGPT
AAKYILEKVK PQRIAIVHDK QQYGEGLARA
VQDGLKKGNA NVVFFDGITA GEKDFSTLVA
RLKKEN

FIG. 50

| Segment | Sequence | End |
|---|---|---|
| pRSET Leader | MRGSHHHHHHGMASMTGGQQMGRDLYDDDDKDRWGS | |
| TtGBP 1-326 | KLEIFSWWAGDEGPALEALIRLYQKYPGVEVINATVTGGAGVN | 80 |
| TtGBP 1-326 | ARAVLKTRMLGGDPPDTFQVAAGMELIGTWVVANRMEDLSALFRQEGWLQAFPKGLIDLISYKGGIWSVPVNIHRSNVMW | 160 |
| TtGBP 1-326 | YLPAKLKEWGVNPPRTWDEFLATCQTLKQKGLEAPLALGENWTQQHLWESVALAVIGPDDWNNLWNGKLKFTDPKAVRAW | 240 |
| TtGBP 1-326 | EVFGRVLDCANKDAAGLSWQQAVDRVVQGKAAFNVMGDWAAGYMTTLKLKPGTDFAWAPSPGTQGVFMVSDSFGLPKG | 320 |
| TtGBP 1-326 / cpGFP 147-238 | AKNRQNAINMLRLVGSKEGQDTFNPLKGSTAARLDSDPSKYPASHNVYIMADKQRNGIKANFKIRHNIEDGGVQLAYHYQ | 400 |
| cpGFP 147-238 / Linker / cpGFP 1-146 | QNTPIGDPVLLPDNHYLSTQSKLSKDPNEKRDHMVLLEFVTAAGITLGMDELYKGGTGGSMVSKGEELFTGVVPILVEL | 480 |
| cpGFP 1-146 | DGDVNGHKFSVSGEGEGDATYGKLTLKFICTTGKLPVPWPTLVTTLTYGVQCFSRYPDHMKQHDFFKSAMPEGYIQERTI | 560 |
| cpGFP 1-146 / TtGBP 327-394 | FFKDDGNYKTRAEVKFEGDTLVNRIELKGIDFKEDGNILGHKLEYNFNNPNAYGQSAMRDWRSNRIVGSLVAGAVAPESF | 640 |
| TtGBP 327-394 | MSQFGTVMEIFLQTRNPQAANAAQAIADQVGLGRLGQ. | 679 |

Structure I

Wherein:

" [F] " is a framework portion;

" [S] " is a first signaling portion;

"———" is an optional linker;

GENETICALLY ENCODED BIOSENSORS

CROSS REFERENCE TO RELATED APPLICATIONS

This application is a divisional of U.S. application Ser. No. 15/664,326 filed Jul. 31, 2017, which is a divisional of U.S. application Ser. No. 14/350,199, filed Nov. 18, 2014, which is a 35 U.S.C. § 371 of International Application No. PCT/US2012/059219, filed Oct. 8, 2012, which claims priority to U.S. Application No. 61/544,867 filed Oct. 7, 2011.

TECHNICAL FIELD

This disclosure relates to genetically encoded biosensors and methods for the design, production, and use of such biosensors.

BACKGROUND

Protein-based sensors that transduce microscopic binding events into macroscopically observable signals are available to allow real-time visualization of a variety of biological events and/or molecules (Frommer et al., Chem. Soc. Rev., 38:2833-2841, 2009). Such sensors can be targeted and/or expressed in living cells, tissues, and organisms, and permit imaging with minimally invasive techniques (Okumoto, Curr. Opin. Biotechnol., 21:45-54, 2010). Application of these sensors is limited by the narrow range of analytes that can be detected and/or by their inability to distinguish signal over noise.

SUMMARY

The present disclosure provides genetically encoded recombinant peptides containing an analyte-binding framework portion linked (e.g., operably linked) to a signaling portion, wherein the signaling portion is allosterically regulated by the framework portion upon interaction of the framework portion with an analyte (e.g., a defined, selected, and/or specific analyte). These constructs can be used as biosensors, e.g., to transduce microscopic binding events into macroscopically observable signals.

The present disclosure provides, in part, recombinant peptides for use as biosensors (e.g., recombinant peptide biosensors) that include (e.g., comprise, consist essentially of, or consist of), e.g., include at least, an analyte-binding framework portion and a signaling portion. As described in further detail herein, such signaling portions are present within the framework portion at a site or amino acid position that undergoes a conformational change (e.g., a conformational change sufficient to alter a physical and/or functional characteristic of the signaling portion, e.g., a substantial conformational change) upon interaction of the framework portion with a defined, specific, or selected analyte (e.g. such as an analyte to which the framework portion or a region thereof, and/or the biosensor, specifically binds). For example, in some instances, the signaling portion is allosterically regulated by the framework portion such that signaling from the signaling portion is altered (e.g. wherein a first level of signaling is altered or changed to a second level of signaling that can be distinguished using routine methods of detection from the first) upon interaction of the framework portion with the analyte. In some instances, signaling by the signaling portion can detectably increase or decrease upon interaction of the framework portion with the analyte. In some instances, signaling by the signaling portion upon interaction of the biosensor with a defined, specific, or selected analyte (e.g. such as an analyte to which the framework portion or a region thereof, and/or the biosensor, specifically binds) can be proportional or can correlate with to the level of interaction between the framework portion and the analyte such that the level of interaction can be determined from the signaling or alteration thereof.

In some instances, framework portions of the biosensors disclosed herein have a first structure in the absence of an analyte and a second structure that is detectably distinct from the first structure in the presence of the analyte. In some instances, the conformational change between the first structure and the second structure allosterically regulates the signaling portion.

In some instances, framework portions of the biosensors disclosed herein can be, or can include (e.g., comprise, consist essentially of, or consist of), periplasmic binding proteins (PBP) or variants of a PBP. In some instances, exemplary PBPs or variants thereof can include, but are not limited to, peptides with at least 90% identity to a peptide selected from the group consisting of SEQ ID NO:105, SEQ ID NO: 106, SEQ ID NO:107, SEQ ID NO:108, SEQ ID NO:109, SEQ ID NO: 110, SEQ ID NO:111, SEQ ID NO:113, and SEQ ID NO:114. In some instances, exemplary PBPs or variants thereof can include, but are not limited to, peptides with at least 95% identity to a peptide selected from the group consisting of SEQ ID NO:105, SEQ ID NO: 106, SEQ ID NO:107, SEQ ID NO:108, SEQ ID NO:109, SEQ ID NO: 110, SEQ ID NO:111, SEQ ID NO:113, and SEQ ID NO:114. In some instances, exemplary PBPs or variants thereof can include, but are not limited to, peptides selected from the group consisting of SEQ ID NO:105, SEQ ID NO: 106, SEQ ID NO:107, SEQ ID NO:108, SEQ ID NO:109, SEQ ID NO: 110, SEQ ID NO:111, SEQ ID NO:113, and SEQ ID NO:114. In some instances, exemplary PBPs or variants thereof can include, but are not limited to, peptides selected from the group consisting of SEQ ID NO:105, SEQ ID NO: 106, SEQ ID NO:107, SEQ ID NO:108, SEQ ID NO:109, SEQ ID NO: 110, SEQ ID NO:111, SEQ ID NO:113, and SEQ ID NO:114 comprising 10 or fewer conservative amino acid substitutions. PBPs or variants thereof disclosed herein can be truncated.

In some instances, signaling portions of the biosensors disclosed herein can be or can include (e.g., comprise, consist essentially of, or consist of) one or more (e.g., one, two three, four, five, and less than ten) circularly permuted fluorescent proteins (cpFPs). Such cpFPs can be include but are not limited to, for example, green fluorescent proteins, yellow fluorescent proteins, red fluorescent proteins, and/or blue fluorescent proteins.

In some instances, biosensors disclosed herein, e.g., analyte-binding framework portions of biosensors disclosed herein, can bind (e.g., bind specifically) to glucose. Such sensors can be referred to as glucose binding biosensors or glucose biosensors.

In some instances, biosensors disclosed herein, e.g., analyte-binding framework portions of biosensors disclosed herein, can bind (e.g., bind specifically) to maltose. Such sensors can be referred to as maltose binding biosensors or maltose biosensors.

In some instances, biosensors disclosed herein, e.g., analyte-binding framework portions of biosensors disclosed herein, can bind (e.g., bind specifically) to phosphonate. Such sensors can be referred to as phosphonate binding biosensors or phosphonate biosensors.

In some instances, biosensors disclosed herein, e.g., analyte-binding framework portions of biosensors disclosed herein, can bind (e.g., bind specifically) to glutamate. Such sensors can be referred to as glutamate binding biosensors or glutamte biosensors.

In some instances, biosensors disclosed herein can include (e.g., comprise, consist essentially of, or consist of): an amino acid sequence with at least 90% identity to a recombinant peptide biosensor selected from the group consisting of SEQ ID NO: 1, 2, 3, 4, 5, 6, 7, 8, 50, 51, 52, and 53, wherein the recombinant peptide biosensor binds specifically to maltose; a recombinant peptide biosensor selected from the group consisting of SEQ ID NO: 1, 2, 3, 4, 5, 6, 7, 8, 50, 51, 52, and 53 comprising 10 or fewer conservative amino acid substitutions, wherein the recombinant peptide biosensor binds specifically to maltose; and/or a recombinant peptide biosensor selected from the group consisting of SEQ ID NO: 1, 2, 3, 4, 5, 6, 7, 8, 50, 51, 52, and 53.

In some instances, biosensors disclosed herein can include (e.g., comprise, consist essentially of, or consist of): an amino acid sequence with at least 90% identity to a recombinant peptide biosensor selected from the group consisting of SEQ ID NO: 62 and 63, wherein the recombinant peptide biosensor binds specifically to glutamate; a recombinant peptide biosensor selected from the group consisting of SEQ ID NO: 62 and 63 comprising 10 or fewer conservative amino acid substitutions, wherein the recombinant peptide biosensor binds specifically to glutamate; and/or a recombinant peptide biosensor selected from the group consisting of SEQ ID NO: 62 and 63.

In some instances, biosensors disclosed herein can include (e.g., comprise, consist essentially of, or consist of): an amino acid sequence with at least 90% identity to a recombinant peptide biosensor selected from the group consisting of SEQ ID NO: 77 and 78, wherein the recombinant peptide biosensor binds specifically to phosphonate; a recombinant peptide biosensor selected from the group consisting of SEQ ID NO: 77 and 78 comprising 10 or fewer conservative amino acid substitutions, wherein the recombinant peptide biosensor binds specifically to phosphonate; and/or a recombinant peptide biosensor selected from the group consisting of SEQ ID NO: 77 and 78.

In some instances, biosensors disclosed herein can include (e.g., comprise, consist essentially of, or consist of): an amino acid sequence with at least 90% identity to a recombinant peptide biosensor selected from the group consisting of SEQ ID NO: 91, 92, 93 and 94, wherein the recombinant peptide biosensor binds specifically to glucose; a recombinant peptide biosensor selected from the group consisting of SEQ ID NO: 91, 92, 93 and 94 comprising 10 or fewer conservative amino acid substitutions, wherein the recombinant peptide biosensor binds specifically to glucose; and/or a recombinant peptide biosensor selected from the group consisting of SEQ ID NO: 91, 92, 93 and 94.

In some instances, biosensors disclosed herein can include (e.g., comprise, consist essentially of, or consist of): SEQ ID NO:91; SEQ ID NO:92; SEQ ID NO:93; SEQ ID NO:95.

In some instances, any recombinant biosensor disclosed herein can be isolated and/or purified. The terms "isolated" or "purified," when applied to a biosensor disclosed herein includes nucleic acid proteins and peptides that are substantially free or free of other cellular material or culture medium when produced by recombinant techniques, or substantially free or free of precursors or other chemicals when chemically synthesized.

The disclosure also provides, in part, nucleic acids (e.g., isolated and/or purified nucleic acids) encoding any one or more of the recombinant peptide biosensors disclosed herein. For example, nucleic acids can encode: an amino acid sequence with at least 90% identity to a recombinant peptide biosensor selected from the group consisting of SEQ ID NO: 1, 2, 3, 4, 5, 6, 7, 8, 50, 51, 52, and 53, wherein the recombinant peptide biosensor binds specifically to maltose; a recombinant peptide biosensor selected from the group consisting of SEQ ID NO: 1, 2, 3, 4, 5, 6, 7, 8, 50, 51, 52, and 53 comprising 10 or fewer conservative amino acid substitutions, wherein the recombinant peptide biosensor binds specifically to maltose; a recombinant peptide biosensor selected from the group consisting of SEQ ID NO: 1, 2, 3, 4, 5, 6, 7, 8, 50, 51, 52, and 53; an amino acid sequence with at least 90% identity to a recombinant peptide biosensor selected from the group consisting of SEQ ID NO: 62 and 63, wherein the recombinant peptide biosensor binds specifically to glutamate; a recombinant peptide biosensor selected from the group consisting of SEQ ID NO: 62 and 63 comprising 10 or fewer conservative amino acid substitutions, wherein the recombinant peptide biosensor binds specifically to glutamate; a recombinant peptide biosensor selected from the group consisting of SEQ ID NO: 62 and 63; an amino acid sequence with at least 90% identity to a recombinant peptide biosensor selected from the group consisting of SEQ ID NO: 77 and 78, wherein the recombinant peptide biosensor binds specifically to phosphonate; a recombinant peptide biosensor selected from the group consisting of SEQ ID NO: 77 and 78 comprising 10 or fewer conservative amino acid substitutions, wherein the recombinant peptide biosensor binds specifically to phosphonate; a recombinant peptide biosensor selected from the group consisting of SEQ ID NO: 77 and 78; an amino acid sequence with at least 90% identity to a recombinant peptide biosensor selected from the group consisting of SEQ ID NO: 91, 92, 93 and 94, wherein the recombinant peptide biosensor binds specifically to glucose; a recombinant peptide biosensor selected from the group consisting of SEQ ID NO: 91, 92, 93 and 94 comprising 10 or fewer conservative amino acid substitutions, wherein the recombinant peptide biosensor binds specifically to glucose; a recombinant peptide biosensor selected from the group consisting of SEQ ID NO: 91, 92, 93 and 94; and/or SEQ ID NO:91; SEQ ID NO:92; SEQ ID NO:93; SEQ ID NO:95.

In some instances, the disclosure includes vectors containing one or a plurality of the nucleic acids disclosed herein and cells containing such vectors. In some instances, the disclosure provides cells containing one or a plurality of nucleic acids disclosed herein.

In some instances, the disclosure includes kits related to the biosensors and nucleic acids disclosed herein Such kits can include or contain, for example, a biosensor, a nucleic acid encoding a biosensor, vectors, and/or cells, provided herein.

In some instances, the disclosure provides methods related to the biosensors and nucleic acids disclosed herein. Such methods can include methods of making, using, and/or selling the biosensors and nucleic acids disclosed herein. For example, methods can include methods for producing genetically encoded recombinant peptide biosensors. In such instances, methods can include, for example, selecting a framework portion that binds specifically to a target analyte and that undergoes a conformational change upon interacting binding to the target analyte, identifying a site or amino acid position within the selected framework portion where or around which the conformational change occurs, and inserting a signaling portion into the site or amino acid position. In some instances, framework portions include periplasmic binding proteins (PBPs) disclosed herein. Exemplary PBPs include PBPs that bind (e.g., bind specifically) to glucose.

In some instances, the present disclosure includes methods for detecting glucose, e.g., in a sample containing a level of glucose. Such methods can include, detecting a level of fluorescence emitted by a recombinant peptide biosensor, the peptide biosensor having an amino acid sequence selected from the group consisting of SEQ ID NO: 91, 92, 93 and 94, and correlating the level of fluorescence with the presence of glucose. In some instances, recombinant peptide biosensors used in the methods herein are expressed from nucleic acids. In some instances, methods include contacting the recombinant peptide biosensor with a test sample (e.g., a sample comprising glucose). In some instances, methods can include the level of fluorescence emitted by a biosensor (e.g., a biosensor bound to glucose) with a concentration glucose in the sample. Such correlation can include, for example, comparing the level of fluorescence with a level of fluorescence emitted by the recombinant peptide biosensor in the presence of a sample comprising a known concentration or range of concentrations of glucose. In some instance, the level of fluorescence emitted by the recombinant peptide biosensor in the presence (e.g., bound or bound specifically to) of a sample comprising a known concentration or range of concentrations of glucose is stored on an electronic database.

One of skill will appreciate that such methods can be adapted for any defined, specific, or selected analyte. For example, in some instances, the disclosure provides methods for detecting a defined, selected, or specific analyte. These methods can include detecting a level of fluorescence emitted by a recombinant peptide biosensor expressed from a nucleic acid and correlating the level of fluorescence with the presence the defined, selected, or specific analyte. In some instances, methods include contacting the recombinant peptide biosensor with a sample comprising the analyte. In some instances, methods include correlating the level of fluorescence with a concentration of the analyte. In some instances, methods include comparing the level of fluorescence with a level of fluorescence emitted by the recombinant peptide biosensor in the presence of a sample comprising a known concentration or range of concentrations of the analyte, wherein the level of fluorescence emitted by the recombinant peptide biosensor in the presence of a sample comprising a known concentration or range of concentrations of the analyte is stored on an electronic database.

In some instances, the present disclosure provides methods for detecting a defined, selected, or specific analyte, the method comprising detecting a level of fluorescence emitted by a recombinant peptide biosensor of any one of claims 1-36; and correlating the level of fluorescence with the presence of a defined, selected, or specific analyte. In some instances, recombinant peptide biosensors can be expressed from a nucleic acid. In some instances, methods can include contacting the recombinant peptide biosensor with a sample comprising the analyte. In some instances, methods can include correlating the level of fluorescence with a concentration of the analyte and, optionally, comparing the level of fluorescence with a level of fluorescence emitted by the recombinant peptide biosensor in the presence of a sample comprising a known concentration or range of concentrations of the analyte. In some instances, the level of fluorescence emitted by the recombinant peptide biosensor in the presence of a sample comprising a known concentration or range of concentrations of the analyte is stored on an electronic database.

Methods herein can be performed in vitro.

In some instances, the present disclosure provides compositions containing any one or a plurality of the peptide biosensors and/or nucleic acids disclosed herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 8A|Amino acid sequence of MBP-175-cpGFP (SEQ ID NO:4).

FIG. 8B|Amino acid sequence of MBP-175-cpGFP.L1-HL (SEQ ID NO:5).

FIG. 9B|Amino acid sequence of MBP-311-cpGFP.L2-NP (SEQ ID NO:7).

FIGS. 20A-20C|Images showing EcMBP-cpGFP.PPYF.T203V expressing HEK cells. Images of individual HEK293 cells expressing membrane displayed PPYF.T203V in the absence of maltose (a), in the presence of 1 mM maltose (b), and after washout with maltose-free buffer (c). Scale bars are 10 μm.

FIG. 24B|Amino acid sequence of PfMBP171cpGFP.L2-FE (SEQ ID NO:51)

FIG. 25A|Amino acid sequence of PfMBP316-cpGFP (SEQ ID NO:52)

FIG. 25B|Amino acid sequence of PfMBP316-cpGFP.L1-NP (SEQ ID NO:53)

FIG. 34A|Amino acid sequence of EcPhnD90-cpGFP (SEQ ID NO:77).

FIG. 34B|Amino acid sequence of EcPhnD90-cpGFP.L1AD+L297R+L301R (SEQ ID NO: 78).

FIG. 37A|Amino acid sequence of TtGBP326-cpGFP (SEQ ID NO:91).

FIG. 37C|Amino acid sequence of TtGBP326.H66A (SEQ ID NO:93).

FIG. 37D|Amino acid sequence of TtGBP326.H348A (SEQ ID NO:94).

FIG. 41|Amino acid sequence of Escherichia coli maltodextrin-binding protein (EcMBP) (SEQ ID NO: 105).

FIG. 42|Amino acid sequence of Pyrococcus furiosus maltose-binding protein (PfMBP) (SEQ ID NO: 106).

FIG. 43|Amino acid sequence of E. coli glutamate-binding protein (EcYbeJ) (SEQ ID NO:107).

FIG. 44|Amino acid sequence of E. coli phosphonate-binding protein (EcPhnD) (SEQ ID NO:108).

FIG. 45|Amino acid sequence of Thermus thermophilus glucose-binding protein (TtGBP) (SEQ ID NO:109).

FIG. 46|Amino acid sequence of UniProt accession number Q92N37 (SEQ ID NO: 110).

FIG. 47|Amino acid sequence of UniProt accession number D0VWX8 (SEQ ID NO:111).

FIG. 48|Amino acid sequence of UniProt accession number Q7CX36 (SEQ ID NO:112).

FIG. 49|Amino acid sequence of UniProt accession number P0AD96 (SEQ ID NO:113).

FIG. 50|Amino acid sequence of TtGBP326.L1PA.L2NP.H66A.H348A.L276V (SEQ ID NO:114).

DETAILED DESCRIPTION

The present disclosure is based, at least in part, on the discovery of structures and methods related to and useful for genetically encoded biosensors. Specifically, the disclosure provides genetically encoded recombinant or chimeric peptides for use as biosensors and methods for the design, production, and use of such biosensors. As described below, these sensors can be employed (e.g., expressed) in biological systems to detect and/or monitor a wide range of target analytes (e.g., a defined, selected, and/or specific analytes) due, in part, to the signal change generated by the sensors upon binding to their respective analyte(s), which signal change allows bound and unbound sensors to be distinguished.

While the disclosure encompasses generic biosensors and methods related thereto, examples of particular binding sensors, including biosensors for detecting maltose, sucrose, maltotriose, glutamate, phosphonate, and glucose are also disclosed.

Compositions

Provided herein are genetically encoded biosensors, i.e., nucleic acids encoding peptides, and/or the encoded peptides (e.g., isolated peptides), for use as biosensors. Biosensors herein include genetically encoded recombinant peptides containing an analyte-binding framework portion linked (e.g., operably linked) to at least one independent signaling portion, wherein the independent signaling portion is allosterically modulated or regulated by the framework portion upon interaction of the framework portion with an analyte (e.g., a defined, selected, and/or specific analyte), such that signaling from the signaling portions is altered upon interaction of the framework portion with the analyte.

Figure 53:
FIG. 53|A schematic of Structure I as described herein.

In some instances, an independent signaling portion is present at a site within the framework portion that undergoes a conformational change upon interaction of the framework portion with an analyte such that the conformational change allosterically modulates or regulates signaling by the signaling portion. For example, biosensors herein can include structure I (FIG. 53).

As described herein, he signaling portion is present at a site within the framework portion that undergoes a conformational change upon interaction of the framework portion with an analyte.

In some instances, signaling by the signaling portion is detectably altered upon interaction (e.g., binding) of the framework portion with an analyte. For example, signaling by the signaling portion can detectably increase or detectably decrease upon interaction (e.g., binding) of the framework portion with an analyte. In some cases, biosensors have a signal change upon binding (e.g., specific binding) to their respective analyte of at least about, for example, ±0.5, and/or an increase or decrease in signal of at least about, for example, 10%, 20%, 30%, 40%, 50%, 60%, 70%, 80%, 90%, 100%, 250%, 500%, 750%, 1000%, or more than 1000%, e.g., relative to unbound biosensor. In some increases, the level of signal change is linked to background signal. Values represented here can be converted and/or expressed into any conventional units using ordinary skill. For example, units can be expressed as 'signal change' (as used above), $\Delta F/F$ and/or as signal-to-noise ratio (e.g., $\Delta F/F$ multiplied by the square root of the number of photons collected). In some instances, signaling by a biosensor can be intensity based.

In some instances, biosensors herein are distinguishable from Förster resonance energy transfer, also known as fluorescence resonance energy transfer (FRET)-based sensors, which require donor and acceptor chromophores, e.g., that function in concert, in that they include independently functioning or detectable signaling portions. For example, in some instances, signaling by a first signaling portion of a biosensor herein is independent of signaling by a second signaling portion within the same or a distinct biosensor. As noted above, signaling portions are allosterically regulated by the framework portion to which they are linked upon interaction of the framework portion with an analyte (e.g., a defined, selected, and/or specific analyte).

Framework Portions

Framework portions include genetically encoded macromolecules (e.g., proteins or peptides) that undergo conformational alteration (e.g., a structural change) upon interaction (e.g., binding) with, or to, an analyte (e.g., an analyte-binding dependent conformational alteration). For example, genetically encoded framework portions can have a first structure in the absence of an analyte (e.g., in an unbound or open state) and a second structure, that is detectably distinct (e.g., differences in structures before and after a conformational change can be observed using methods known in the art) from the first structure, in the presence of an analyte (e.g., in a bound or closed state), e.g., under physiologic conditions. In some instances, the conformational change that occurs upon interaction with an analyte (e.g., an analyte-binding dependent conformational alteration) is detectably distinct (e.g., can be observed using methods known in the art) from a conformational change that may occur for the same protein or peptide under other physiological conditions (e.g., a change in conformation induced by altered temperature, pH, voltage, ion concentration, phosphorylation).

Methods for identifying proteins or peptides that exhibit suitable conformational characteristics and/or for observing differences in structure between structures or before and after a conformational change are known in the art and/or are described herein. Such methods can include, for example, one or more of structural analysis, crystallography, NMR, EPR using Spin label techniques, Circular Dichroism (CD), Hydrogen Exchange surface Plasmon resonance, calorimetry, and/or FRET.

In some instances, framework portions can have a first structure in the absence of an analyte (e.g., in an unbound or open state) and a second structure, that is detectably distinct (e.g., can be observed using methods known in the art) from the first structure, in the presence of an analyte (e.g., in a bound or closed state), e.g., under physiologic conditions, wherein the structural change between the open and closed state can allosterically modulate an independent signaling portion recombinantly (e.g., artificially introduced) present within the framework portion (see, e.g., Structure I in FIG. 53).

Framework portions can also interact (e.g., bind) with at least one analyte (e.g., at least one defined, specific, and/or selected analyte). In some instances, a framework portion can interact specifically with one analyte (e.g., at least one defined, specific, and/or selected analyte). In such cases, affinity of binding between the framework binding peptide and the analyte can be high or can be controlled (e.g., with millimolar, micromolar, nanomolar, or picomolar affinity). Alternatively, the single framework binding protein can bind two or more analytes (e.g., two or more defined, specific, and/or selected analytes). In such cases, affinity of binding to the two or more analytes can be the same or distinct. For example, the affinity of binding can be greater for one analyte than it is for a second or third, etc., analyte. In some instances, binding between a framework portion and an analyte (e.g., at least one defined, specific, and/or selected analyte) have an affinity of for example, 10 mM to 1 pM.

As used herein, the term "analyte" can include naturally occurring and/or synthetic sugars, amino acids, proteins (e.g., proteins, peptides, and/or antibodies), hormones, ligands, chemicals (e.g., small molecules), pharmaceuticals, nucleic acids, cells, tissues, and combinations thereof.

In some instances, biosensors can include one, two, or more framework binding portions that bind (e.g., binds specifically) a single analyte (e.g., a single defined, specific, and/or selected analyte) or distinct analytes (e.g., two or more distinct defined, specific and/or selected analytes). Alternatively or in addition, the framework portion can be chimeric. In such cases, a first part of the framework portion can be a first peptide or can be derived from a first peptide, and a second part of the framework portion can be a second peptide or can be derived from a second peptide, wherein the first a second peptides are combined to result in a single peptide.

Accordingly, framework portions can include macromolecules that undergo a conformational change upon interaction with an analyte. One non-limiting example of a suitable macromolecule is Calmodulin (CaM). CaM is in an extended shape in the absence of $Ca^{2+}$ and in a condensed conformation in the presence of $Ca^{2+}$ (Kuboniwa et al., Nat. Struc. Biol., 2:768-776, 1996 and Fallon and Quiocho, Structure, 11:1303-1307, 2003).

In some instances, a framework binding portion can be a bacterial protein or can be derived from a bacterial protein. Suitable bacterial proteins can include, but are not limited to, for example, periplasmic binding proteins (PBPs).

PBPs from bacteria are generally useful in the biosensors herein at least because they undergo dramatic conformational changes upon ligand binding (Ouiocho et al. Mol. Microbiol., 20:17-225, 1996). X-ray crystal structures of the apo (open) and bound (closed) forms of various PBPs reveal that these proteins have two (typically, although some have more) domains that undergo a large hinge-twist movement relative to each other in a Venus flytrap manner (Dwyer and Hellinga, Curr. Opin. Struc. Biol., 14:495-504, 2004). This conformational change has been exploited to create a number of FRET-based genetically encoded sensors (see, e.g., Deuschle et al., Pro. Sci, 14:2304-2314, 2005; Deuschle et al., Cytometry, 64:3-9, 2005; Okumoto et al., Proc. Natl. Acad. Sci. USA., 102:8740-8745, 2005; Bogner and Ludewig, J. Fluoresc., 17:350-360, 2007; and Gu et al., FEBS Letters, 580:5885-5893, 2006). In addition, the ligand-binding diversity of the PBP superfamily is large (Dwyer and Hellinga, Curr. Opin. Struc. Biol., 14:495-504, 2004).

In some instances, framework portions can include, for example, one or more of: arabinose-binding protein(s), glucose/galactose-binding protein(s), histidine-binding protein(s), maltose-binding protein(s), glutamine-binding protein(s), maltotriose-binding protein(s), RBP, ribose-binding protein(s), acetylcholine binding protein(s), choline binding protein(s), lysine binding protein(s), arginine binding protein(s), gamma aminobutyric acid (GABA) binding protein(s), ion-binding protein(s), peptide-binding protein(s), lactate-binding protein(s), histamine-binding protein(s), and/or Leucine/Isoleucine/Valine binding protein(s), including full length proteins, fragments, and/or variants thereof.

In some instances, exemplary framework portions can include: SEQ ID NO:105, which is *Escherichia coli* maltodextrin-binding protein (EcMBP) (UniProt accession number P0AEX9); SEQ ID NO: 106, which is *Pyrococcus Furiosus* maltotriose-binding protein (PfMBP) (UniProt accession number P58300); SEQ ID NO:107, which is *E. coli* glutamate-binding protein (EcYbeJ) (UniProt accession number Q1R3F7); SEQ ID NO:108, which is *E. coli* phosphonate-binding protein (EcPhnD) (UniProt accession number P37902); and/or SEQ ID NO:109, which is *Thermus thermophilus* glucose-binding protein (TtGBP) (UniProt accession number Q72KX2, including full length proteins, fragments, and/or variants thereof.

In some instances, exemplary framework portions can include SEQ ID NO: 110 (UniProt accession number Q92N37); SEQ ID NO:111 (UniProt accession number D0VWx8, SEQ ID NO:112 (UniProt accession number Q7CX36), and/or SEQ ID NO:113 (UniProt accession number P0AD96, including full length proteins, fragments, and/or variants thereof.

In some instances, framework portions, or biosensors, do not include signal peptides, or portions of signal peptides, that would otherwise be present in the peptide from which the framework portion is derived.

Signaling Portions

Biosensors herein include one or more genetically encoded signaling portions (e.g., independent signaling portions) within the amino acid sequence of a framework portion at a site(s) within the framework portion that undergo(es) a conformational change upon interaction of the framework portion with an analyte (e.g., a defined, specific, and/or selected analyte).

Signaling portions (e.g., independent signaling portions) include genetically encoded molecules (e.g., peptides or proteins) that can be allosterically induced to emit a detectable signal (e.g., an analyte-binding dependent signal).

In some instances, the detectable signal is detectably distinct (e.g., can be distinguished using methods known in the art and/or disclosed herein) from a signal emitted by the molecule prior to allosteric inducement (e.g., signaling portions can emit a detectable signal in two detectably distinct states. For example, first signal can be emitted in unbound state and a second signal can be emitted in bound state). As noted above, in some instances, the detectable signal is proportional to the degree of allosteric inducement. In some instances, if two or more signaling portions are present in a biosensor, then two or more detectably distinct signals can be emitted by the biosensor.

In some instances, a genetically encoded independent signaling portion is a genetically encoded fluorescent protein (FP), e.g., a macromolecule containing a functional group (e.g., a fluorophore) that absorbs energy of a specific wavelength and re-emits energy at a different (but equally specific) wavelength, including, for example, circularly permuted FP (cpFP).

As used herein, the term "fluorophore" relates to a functional group in a molecule which will absorb energy of a specific wavelength and re-emit energy at a different (but equally specific) wavelength. In some instances, fluorophore containing molecules include fluorescent proteins. The fluorophore in green fluorescent protein (GFP) includes Ser-Tyr-Gly sequence (i.e., Ser65-dehydroTyr66-Gly67), which is post-translationally modified to a 4-(p-hydroxybenzylidene)-imidazolidin-5. Exemplary genetically encoded fluorescent proteins include, but are not limited to, fluorescent proteins from coelenterate marine organisms, e.g., *Aequorea victoria, Trachyphyllia geoffroyi,* coral of the *Discosoma* genus, *Rennilla mulleri, Anemonia sulcata, Heteractis crispa, Entacmaea quadricolor,* and/or GFP (including the variants S65T and EGFP, *Rennilla mulleri* GFP), cyan fluorescent protein (CFP), including Cerulean, and mCerulean3 (described by Markwardt et al., PLoS ONE, 6(3) e17896.doi:10.1371/journal.pone.0017896), CGFP (CFP with Thr203Tyr: Has an excitation and emission wavelength that is intermediate between CFP and EGFP), yellow fluorescent protein (YFP, e.g., GFP-Ser65Gly/Ser72Ala/Thr203Tyr; YFP (e.g., GFP-Ser65Gly/Ser72Ala/Thr203Tyr) with Val68Leu/Gln69Lys); Citrine (i.e., YFP-Val68Leu/Gln69Met), Venus (i.e., YFP-Phe46Leu/Phe64Leu/Met153Thr/Val163Ala/Ser175Gly), PA-GFP (i.e., GFP-Val/163Ala/Thr203His), Kaede), red fluorescent protein (RFP, e.g., long wavelength fluorescent protein, e.g., DsRed (DsRed1, DsRed2, DsRed-Express, mRFP1, drFP583, dsFP593, asFP595), eqFP611, and/or other fluorescent proteins known in the art (see, e.g., Zhang et al., Nature Reviews, Molecular and Cellular Biology, 3:906-908, 2002).

As set forth above, in some instances, fluorophore containing molecules include fluorescent proteins that can be or that are circularly permutated. Circular permutation methods are known in the art (see, e.g., Baird et al., Proc. Natl. Acad. Sci., 96:11241-11246, 1999; Topell and Glockshuber, Methods in Molecular Biology, 183:31-48, 2002).

In some instances, single-FP sensors have a number of advantages: they preserve spectral bandwidth for multi-analyte imaging; their saturated states may be nearly as bright as the parental FP, and their ligand-free states may be arbitrarily dim, providing large theoretical fluorescence increases. This allows for much greater changes in fluorescence and thus increased signal-to-noise ratios and greater resistance to photobleaching artifacts (Tian et al., Nat. Methods, 6:875-881, 2009).

In some instances, issues arising from long-term effects such as gene regulation and protein expression and degradation can be identified by simply fusing the intensity-based sensor to a another fluorescent protein of different color, to serve as a reference channel.

In some instances, biosensors can include circularly permuted YFP (cpYFP) as a cpFP. cpYFP has been used as a reporter element in the creation of sensors for H2O2 (HyPer) (Belousov et al., Nat. Methods, 3:281-286, 2006), cGMP (FlincG) (Nausch et al., Proc. Natl. Acad. Sci. USA., 105: 365-370, 2008), ATP:ADP ratio (Perceval) (Berg et al., Nat. Methods., 105:365-370, 2008), and calcium ions (Nakai et al., Nat. Biotechno., 19:137-141, 2001), including full length, fragments, and/or variants thereof.

Linker Portions

As shown in Structure I (FIG. 53), biosensors herein can optionally include one or more genetically encoded linkers positioned between or operably linking the framework portion and the signaling portion. Linker portions can include at least one naturally occurring or synthetic amino acid (discussed below) as exemplified by SEQ ID NOs: 9-49, 54-61, 64-76, 79-90, 95-104. In some instances, linker can include one or more of SEQ ID NOs: 9-49, 54-61, 64-76, 79-90, 95-104, and/or portions of SEQ ID NOs: 9-49, 54-61, 64-76, 79-90, 95-104. For example, linkers can include, but are not limited to, one or more of: PxSHNVY (SEQ ID NO:114), xPSHNVY (SEQ ID NO:115), xxSHNVY (SEQ ID NO:116), xxSHNVF (SEQ ID NO:117), PxSHNVF (SEQ ID NO:118), PxSYNVF (SEQ ID NO:119), xxSYNVF (SEQ ID NO:120), PxSYNVF (SEQ ID NO:121), xxSYNVF (SEQ ID NO:122), PxSxNVY (SEQ ID NO:123), PxSHxVY (SEQ ID NO:124), PxSHNxY (SEQ ID NO:125), PxSHNVx (SEQ ID NO:126), FNxxY (SEQ ID NO:127), FNxY (SEQ ID NO:128), FNY (SEQ ID NO:129), FxY (SEQ ID NO:130), xxY (SEQ ID NO:131), WxY (SEQ ID NO:132), xKY, (SEQ ID NO:133), FNPxY (SEQ ID NO:134), FNxPY (SEQ ID NO:135), HNS (SEQ ID NO:136), GGS (SEQ ID NO:137), xxS (SEQ ID NO:138), xxK (SEQ ID NO:139), GGK (SEQ ID NO:140), PXS (SEQ ID NO:141), xPS (SEQ ID NO:142), Px (SEQ ID NO:143), xP (SEQ ID NO:144), IxxS (SEQ ID NO:145), NxPK (SEQ ID NO:146), NPcK (SEQ ID NO:147), PPxSH (SEQ ID NO:148), PPxxSH (SEQ ID NO:149), PPPxSH (SEQ ID NO:150), PPxPSH (SEQ ID NO:151), xxSH (SEQ ID NO:152), PPxx (SEQ ID NO:153), FNxKN (SEQ ID NO:154), FNxxKN (SEQ ID NO:155), FNxPKN (SEQ ID NO:156), FNPxKN (SEQ ID NO:157), FNxx (SEQ ID NO:158), N, ADGSSH (SEQ ID NO:159), ADxxSH (SEQ ID NO:160), ADxPSH (SEQ ID NO:161), ADPxSH (SEQ ID NO:162), ADxx (SEQ ID NO:163), ADxxSH (SEQ ID NO:164), FNPG (SEQ ID NO:165), FNxxPG (SEQ ID NO:166), xxPG (SEQ ID NO:167), FNxx (SEQ ID NO:168), FNPx (SEQ ID NO:169), KYxxSH (SEQ ID NO:170), KYPxSH (SEQ ID NO:171), KYxPSH (SEQ ID NO:172), FxxP (SEQ ID NO:173), FNxP (SEQ ID NO:174), and/or FNPx (SEQ ID NO:175), where "x" indicates any amino acid.

Exemplary Biosensor Constructs

As noted above, biosensors herein include genetically encoded biosensors, i.e., nucleic acids encoding biosensors, and/or the encoded biosensors (e.g., isolated biosensors), for use as biosensors. In some instances, nucleic acids encoding biosensors include isolated nucleic acids. In some instances, the portion of a nucleic acid encoding a biosensor can include a single reading frame encoding the biosensor. For example, a biosensor can be encoded by a portion of a nucleic acid that falls within a start codon and a stop codon.

In some instances, biosensors are isolated (e.g., biosensors are substantially free of contaminating and/or non-biosensor components).

In some instances, biosensors can include, for example, one or more framework portions selected from the group consisting of: arabinose-binding protein(s), glucose/galactose-binding protein(s), histidine-binding protein(s), maltose-binding protein(s), maltotriose-binding protein(s), glutamine-binding protein(s), RBP, ribose-binding protein(s), acetylcholine binding protein(s), choline binding protein(s), lysine binding protein(s), arginine binding protein(s), gamma aminobutyric acid (GABA) binding protein(s), ion-binding protein(s), peptide-binding protein(s), lactate-binding protein(s), histamine-binding protein(s), and/or Leucine/Isoleucine/Valine binding protein(s), including full length proteins, fragments, and/or variants thereof, including full length proteins, fragments and/or variants thereof, and at least one independent signaling portion present at a site within the framework portion that undergoes a conformational change upon interaction of the framework portion with an analyte.

In some instances, biosensors can include, for example, one or more framework portions selected from the group consisting of: SEQ ID NO:105, which is *Escherichia coli* maltodextrin-binding protein (EcMBP) (UniProt accession number P0AEX9); SEQ ID NO: 106, which is *Pyrococcus Furiosus* maltose-binding protein (PfMBP) (UniProt accession number P58300); SEQ ID NO:107, which is *E. coli* glutamate-binding protein (EcYbeJ) (UniProt accession number Q1R3F7); SEQ ID NO:108, which is *E. coli* phosphonate-binding protein (EcPhnD) (UniProt accession number P37902); and/or SEQ ID NO:109, which is *Thermus thermophilus* glucose-binding protein (TtGBP) (UniProt accession number Q72KX2), including full length proteins, fragments and/or variants thereof, and at least one independent signaling portion present at a site within the framework portion that undergoes a conformational change upon interaction of the framework portion with an analyte.

In some instances, biosensors can include, for example, one or more framework portions selected from the group consisting of: SEQ ID NO: 110 (UniProt accession number Q92N37); SEQ ID NO:111 (UniProt accession number D0VWx8, SEQ ID NO:112 (UniProt accession number Q7CX36), and/or SEQ ID NO:113 (UniProt accession number P0AD96), including full length proteins, fragments and/or variants thereof, and at least one independent signaling portion present at a site within the framework portion that undergoes a conformational change upon interaction of the framework portion with an analyte.

In some instances, biosensors include any one or more:

Maltose biosensors SEQ ID NOs: 1-8 (i.e., *Escherichia coli* maltodextrin-binding protein (EcMBP)) or SEQ ID NOs: 50-53 (*Pyrococcus Furiosus* maltose-binding protein (PfMBP)), including full length proteins, fragments and/or variants thereof;

Glutamate biosensors SEQ ID NOs: 62-63 (*E. coli* glutamate-binding protein (EcYbeJ)), including full length proteins, fragments and/or variants thereof;

Phosphonate biosensors SEQ ID NOs: 77-78 (*E. coli* phosphonate-binding protein (EcPhnD)), including full length proteins, fragments and/or variants thereof; and/or Glucose biosensors SEQ ID NOs: 91-94 (*Thermus thermophilus* glucose-binding protein (TtGBP)), including full length proteins, fragments and/or variants thereof.

In some instances, nucleic acids encoding and/or amino acid sequences of any of the framework portions, signaling portions, linker portions, or biosensors (e.g., SEQ ID NOs:

1, 2, 3, 4, 5, 6, 7, 8, 50, 51, 52, 53, 62, 63, 77, 78, 91, 92, 93, and/or 94) (e.g., any amino acid sequence) disclosed herein can be modified to generate fragments (e.g., truncated peptides) and/or variants (e.g., peptides with a defined sequence homology to the peptides disclosed herein). Variants can include framework portions, signaling portions, linker portions, or biosensors with amino acid sequences with homology to the framework portions, signaling portions, linker portions, or biosensors disclosed herein and/or truncated forms of the framework portions, signaling portions, linker portions, or biosensors herein. In some instances, truncated forms of the framework portions, signaling portions, linker portions, or biosensors herein can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 37, 38, 39, 40, 41, 42, 43, 44, 45, 46, 47, 48, 49, 50, 50-100, 101-150, fewer amino acids than the framework portions, signaling portions, linker portions, and/or biosensors herein, e.g., wherein the truncated biosensor variants retain at least at portion of the binding and/or signaling properties of same biosensor without truncation (e.g., at least 50%, 60%, 70%, 80%, 90%, or 100% of the binding and/or signaling properties of the same biosensor without truncation). In addition, truncations can be made at the amino-terminus, the carboxy-terminus, and/or within the body of the framework portions, signaling portions, linker portions, and/or biosensors herein.

While variants are generally observed and discussed at the amino acid level, the actual modifications are typically introduced or performed at the nucleic acid level. For example, variants with 95%, 96%, 97%, 98, or 99% sequence identity to SEQ ID NOs:91, 92, 93, and/or 94 can be generated by modifying the nucleic acids encoding SEQ ID NOs: 91, 92, 93, and/or 94 using techniques (e.g., cloning techniques) known in the art and/or that are disclosed herein.

As with all peptides, polypeptides, and proteins, including fragments thereof, it is understood that modifications to the amino acid sequence can occur that do not alter the nature or function of the peptides, polypeptides, or proteins. Such modifications include conservative amino acids substitutions and are discussed in greater detail below.

The peptides, polypeptides, and proteins, including fragments thereof, provided herein are biosensors whose activity can be tested or verified, for example, using the in vitro and/or in vivo assays described herein.

In some instances, any of the framework portions, signaling portions, or biosensors (e.g., SEQ ID NOs: 1, 2, 3, 4, 5, 6, 7, 8, 50, 51, 52, 53, 62, 63, 77, 78, 91, 92, 93, and/or 94) (e.g., any amino acid sequence) described herein can be modified and varied so long as their desired function is maintained. For example, the polypeptides can be modified as long as the resulting variant polypeptides have the same or better characteristics as the polypeptide from which they derived. For example, the variants can have the same or better affinity for their respective analyte.

In some instances, the interacting face of a modified peptide can be the same (e.g., substantially the same) as an unmodified peptide (methods for identifying the interacting face of a peptide are known in the art (Gong et al., BMC: Bioinformatics, 6:1471-2105 (2007); Andrade and Wei et al., Pure and Appl. Chem., 64(11):1777-1781 (1992); Choi et al., Proteins: Structure, Function, and Bioinformatics, 77(1):14-25 (2009); Park et al., BMC: and Bioinformatics, 10:1471-2105 (2009)), e.g., to maintain binding to an analyte. Alternatively, amino acids within the interacting face can be modified, e.g., to decrease binding to an analyte and/or to change analyte specificity.

The interacting face of a peptide is the region of the peptide that interacts or associates with other molecules (e.g., other proteins). Generally, amino acids within the interacting face are naturally more highly conserved than those amino acids located outside the interacting face or interface regions of a protein. In some instances, an amino acid within the interacting face region of any of the framework portions or biosensors (e.g, SEQ ID NOs: 1, 2, 3, 4, 5, 6, 7, 8, 50, 51, 52, 53, 62, 63, 77, 78, 91, 92, 93, and/or 94) (e.g., any amino acid sequence) disclosed herein can be the same as the amino acid shown in any of the framework portions or biosensors (e.g, SEQ ID NOs: 1, 2, 3, 4, 5, 6, 7, 8, 50, 51, 52, 53, 62, 63, 77, 78, 91, 92, 93, and/or 94) (e.g., any amino acid sequence) disclosed herein or can be include conservative amino acid substitutions. In some instances, an amino acid within the interacting face region any of the framework portions or biosensors (e.g, SEQ ID NOs: 1, 2, 3, 4, 5, 6, 7, 8, 50, 51, 52, 53, 62, 63, 77, 78, 91, 92, 93, and/or 94) (e.g., any amino acid sequence) disclosed herein can be substituted with an amino acid that increases the interaction between the framework portion or biosensors (e.g, SEQ ID NOs: 1, 2, 3, 4, 5, 6, 7, 8, 50, 51, 52, 53, 62, 63, 77, 78, 91, 92, 93, and/or 94) (e.g., any amino acid sequence) and an analyte.

In some instances, genetically encoded biosensors can include peptides that have at least 80, 85, 90, 95, 96, 97, 98, 99 percent identity to the framework portions, signaling portions, or biosensors (e.g., SEQ ID NOs: 1, 2, 3, 4, 5, 6, 7, 8, 50, 51, 52, 53, 62, 63, 77, 78, 91, 92, 93, and/or 94) (e.g., any amino acid sequence) described herein. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman, Adv. Appl. Math, 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-10 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

Amino acid sequence modifications typically fall into one or more of three classes: substitutional, insertional, or deletional modifications. Insertions include amino and/or terminal fusions as well as intra-sequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions can be made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. In some instances, substitutions can be conservative amino acid substitutions. In some instances, variants herein can include one or more conservative amino acid substitutions. For example, variants can include 1, 2, 3, 4, 5, 6, 7, 8, 9, 10, 11, 12, 13, 14, 15, 16, 17, 18, 19, 20, 20-30, 30-40, or 40-50 conservative amino acid substitutions. Alternatively, variants can include 50 or fewer, 40 or fewer, 30 or fewer, 20 or fewer, 10 or fewer, 9 or fewer, 8 or fewer, 7 or fewer, 6 or fewer, 5 or fewer, 4 or fewer, 3 or fewer, or 2 or fewer conservative amino acid substitutions. Such substitutions generally are made in accordance with the following Table 1 and are referred to as conservative substitutions. Methods for predicting tolerance to protein modification are known in the art (see, e.g., Guo et al., Proc. Natl. Acad. Sci., USA, 101(25):9205-9210 (2004)).

TABLE 1

Conservative Amino Acid Substitutions

| Amino Acid | Substitutions (others are known in the art) |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

In some instances, substitutions are not conservative. For example, an amino acid can be replaced with an amino acid that can alter some property or aspect of the peptide. In some instances, non-conservative amino acid substitutions can be made, e.g., to change the structure of a peptide, to change the binding properties of a peptide (e.g., to increase or decrease the affinity of binding of the peptide to an analyte and/or to alter increase or decrease the binding specificity of the peptide).

Modifications, including the specific amino acid substitutions, are made by known methods. By way of example, modifications are made by site-specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Nucleic Acids

The disclosure also features nucleic acids encoding the biosensors (e.g., SEQ ID NOs: 1, 2, 3, 4, 5, 6, 7, 8, 50, 51, 52, 53, 62, 63, 77, 78, 91, 92, 93, and/or 94) described herein, including variants and/or fragments of the biosensors (e.g., variants and/or fragments of SEQ ID NOs: 1, 2, 3, 4, 5, 6, 7, 8, 50, 51, 52, 53, 62, 63, 77, 78, 91, 92, 93, and/or 94). These sequences include all degenerate sequences related to the specific polypeptide sequence, i.e., all nucleic acids having a sequence that encodes one particular polypeptide sequence as well as all nucleic acids, including degenerate nucleic acids, encoding the disclosed variants and derivatives of the polypeptide sequences. Thus, while each particular nucleic acid sequence may not be written out herein, it is understood that each and every sequence is in fact disclosed and described herein through the disclosed polypeptide sequences.

In some instances, nucleic acids can encode biosensors with 95, 96, 97, 98, or 99 identity to SEQ ID NOs: 1, 2, 3, 4, 5, 6, 7, 8, 50, 51, 52, 53, 62, 63, 77, 78, 91, 92, 93, and/or 94.

In some instances, nucleic acids can encode SEQ ID NOs: 1, 2, 3, 4, 5, 6, 7, 8, 50, 51, 52, 53, 62, 63, 77, 78, 91, 92, 93, and/or 94 containing 1, 2, 3, 4, 5, 6, 7, 8, 9, 10, 11, 12, 13, 14, 15, 16, 17, 18, 19, 20, 20-30, 30-40, or 40-50 conservative amino acid substitutions.

In some instances, nucleic acids can encode SEQ ID NOs: 1, 2, 3, 4, 5, 6, 7, 8, 50, 51, 52, 53, 62, 63, 77, 78, 91, 92, 93, and/or 94 containing 50 or fewer, 40 or fewer, 30 or fewer, 20 or fewer, 10 or fewer, 9 or fewer, 8 or fewer, 7 or fewer, 6 or fewer, 5 or fewer, 4 or fewer, 3 or fewer, or 2 or fewer conservative amino acid substitutions Also provided herein are vectors comprising the biosensors (e.g, SEQ ID NOs: 1, 2, 3, 4, 5, 6, 7, 8, 50, 51, 52, 53, 62, 63, 77, 78, 91, 92, 93, and/or 94) described herein, including variants and/or fragments of the biosensors (e.g, SEQ ID NOs: 1, 2, 3, 4, 5, 6, 7, 8, 50, 51, 52, 53, 62, 63, 77, 78, 91, 92, 93, and/or 94). For example:

Vectors can include nucleic acids that encode biosensors with 95, 96, 97, 98, or 99 identity to SEQ ID NOs: 1, 2, 3, 4, 5, 6, 7, 8, 50, 51, 52, 53, 62, 63, 77, 78, 91, 92, 93, and/or 94.

Vectors can include nucleic acids that encode SEQ ID NOs: 1, 2, 3, 4, 5, 6, 7, 8, 50, 51, 52, 53, 62, 63, 77, 78, 91, 92, 93, and/or 94 containing 1, 2, 3, 4, 5, 6, 7, 8, 9, 10, 11, 12, 13, 14, 15, 16, 17, 18, 19, 20, 20-30, 30-40, or 40-50 conservative amino acid substitutions.

Vectors can include nucleic acids that encode SEQ ID NOs: 1, 2, 3, 4, 5, 6, 7, 8, 50, 51, 52, 53, 62, 63, 77, 78, 91, 92, 93, and/or 94 containing 50 or fewer, 40 or fewer, 30 or fewer, 20 or fewer, 10 or fewer, 9 or fewer, 8 or fewer, 7 or fewer, 6 or fewer, 5 or fewer, 4 or fewer, 3 or fewer, or 2 or fewer conservative amino acid substitutions Examples of suitable vectors include, but are not limited to, plasmids, artificial chromosomes, such as BACs, YACs, or PACs, and viral vectors. As used herein, vectors are agents that transport the disclosed nucleic acids into a cell without degradation and, optionally, include a promoter yielding expression of the nucleic acid molecule in the cells into which it is delivered.

Viral vectors can include, for example, Adenovirus, Adeno-associated virus, herpes virus, Vaccinia virus, Polio virus, Sindbis, and other RNA viruses, including these viruses with the HIV backbone. Any viral families which share the properties of these viruses which make them suitable for use as vectors are suitable. Retroviral vectors, in general are described by Coffin et al., Retroviruses, Cold Spring Harbor Laboratory Press (1997), which is incorporated by reference herein for the vectors and methods of making them. The construction of replication-defective adenoviruses has been described (Berkner et al., J. Virology 61:1213-20 (1987); Massie et al., Mol. Cell. Biol. 6:2872-83 (1986); Haj-Ahmad et al., J. Virology 57:267-74 (1986); Davidson et al., J. Virology 61:1226-39 (1987); Zhang et al., BioTechniques 15:868-72 (1993)). Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating Vaccinia virus vectors.

Non-viral based vectors can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clontech (Pal Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

Promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. β-actin promoter or EF1α promoter, or from hybrid or chimeric promoters (e.g., CMV promoter fused to the β-actin promoter). Of course, promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), enhancers derived from a eukaryotic cell viruses can be used. Examples of such can include the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Promoters of this type can include the CMV promoter, the SV40 promoter, the β-actin promoter, the EF1α promoter, and the retroviral long terminal repeat (LTR).

The provided vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the E. coli lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

The disclosure further provides cells comprising the biosensors (e.g, SEQ ID NOs: 1, 2, 3, 4, 5, 6, 7, 8, 50, 51, 52, 53, 62, 63, 77, 78, 91, 92, 93, and/or 94) described herein, including variants and/or fragments of the biosensors (e.g, SEQ ID NOs: 1, 2, 3, 4, 5, 6, 7, 8, 50, 51, 52, 53, 62, 63, 77, 78, 91, 92, 93, and/or 94). Cells can include, for example, eukaryotic and/or prokaryotic cells. For example, cells can include, but are not limited to cells of E. coli, Pseudomonas, Bacillus, Streptomyces; fungi cells such as yeasts (Saccharomyces, and methylotrophic yeast such as Pichia, Candida, Hansenula, and Torulopsis); and animal cells, such as CHO, R1.1, B-W and LM cells, African Green Monkey kidney cells (for example, COS 1, COS 7, BSC1, BSC40, and BMT10), insect cells (for example, Sf9), human cells and plant cells. Suitable human cells can include, for example, HeLa cells or human embryonic kidney (HEK) cells. In general, cells that can be used herein are commercially available from, for example, the American Type Culture Collection (ATCC), P.O. Box 1549, Manassas, Va. 20108. See also F. Ausubel et al., Current Protocols in Molecular Biology, John Wiley & Sons, New York, N.Y., (1998).

Optionally, the biosensors (e.g., SEQ ID NOs: 1, 2, 3, 4, 5, 6, 7, 8, 50, 51, 52, 53, 62, 63, 77, 78, 91, 92, 93, and/or 94) described herein, including variants and/or fragments of the biosensors (e.g., SEQ ID NOs: 1, 2, 3, 4, 5, 6, 7, 8, 50, 51, 52, 53, 62, 63, 77, 78, 91, 92, 93, and/or 94) can be located in the genome of the cell (e.g., can be stably expressed in the cell) or can be transiently expressed in the cell.

Methods of making the provided cells are known and the method of transformation and choice of expression vector will depend on the host system selected. Transformation and transfection methods are described, e.g., in F. Ausubel et al., Current Protocols in Molecular Biology, John Wiley & Sons, New York, N.Y., (1998), and, as described above, expression vectors may be chosen from examples known in the art.

There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based deliver systems. Such methods are well known in the art and readily adaptable for use with the compositions and methods described herein.

By way of example, the provided polypeptides and/or nucleic acid molecules can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004). The provided polypeptides can be delivered by subviral dense bodies (DBs). DBs transport proteins into target cells by membrane fusion. Methods for making and using DBs are described in, for example, Pepperl-Klindworth et al., Gene Therapy 10:278-84 (2003). The provided polypeptides can be delivered by tegument aggregates. Methods for making and using tegument aggregates are described in International Publication No. WO 2006/110728.

Also provided are transgenic animals comprising one or more cells the biosensors (e.g, SEQ ID NOs: 1, 2, 3, 4, 5, 6, 7, 8, 50, 51, 52, 53, 62, 63, 77, 78, 91, 92, 93, and/or 94) described herein, including variants and/or fragments of the biosensors (e.g, SEQ ID NOs: 1, 2, 3, 4, 5, 6, 7, 8, 50, 51, 52, 53, 62, 63, 77, 78, 91, 92, 93, and/or 94). As used herein, the term animal refers to non-human animals, including, mammals, amphibians and birds. Specifically, examples include sheep, feline, bovines, ovines, pigs, horses, rabbits, guinea pigs, mice, hamsters, rats, non-human primates, and the like. As used herein, transgenic animal refers to any animal, in which one or more of the cells of the animal contain a heterologous nucleic acid. The heterologous nucleic acid can be introduced using known transgenic techniques. The nucleic acid is introduced into the cell, directly or indirectly. For example, the nucleic acid can be introduced into a precursor of the cell or by way of deliberate genetic manipulation, such as by microinjection or by infection with a recombinant virus. The nucleic acid may be integrated within a chromosome, or it may be an extrachromosomally replicating DNA.

Methods for making transgenic animals using a variety of transgenes have been described in Wagner et al. (1981) Proc. Nat. Acad. Sci. USA, 78:5016-5020; Stewart et al. (1982) Science, 217:1046-1048; Constantini et al. (1981) Nature, 294:92-94; Lacy et al. (1983) Cell, 34:343-358; McKnight et al. (1983) Cell, 34:335-341; Brinstar et al. (1983) Nature, 306:332-336; Palmiter et al. (1982) Nature, 300:611-615; Palmiter et al. (1982) Cell, 29:701-710; and Palmiter et al. (1983) Science, 222:809-814. Such methods are also described in U.S. Pat. Nos. 6,175,057; 6,180,849; and 6,133,502.

By way of example, the transgenic animal can be created by introducing a nucleic acid into, for example, an embryonic stem cell, an unfertilized egg, a fertilized egg, a spermatozoon or a germinal cell containing a primordial germinal cell thereof, preferably in the embryogenic stage in the development of a non-human mammal (more preferably in the single-cell or fertilized cell stage and generally before the 8-cell phase). The nucleic acid can be introduced by known means, including, for example, the calcium phosphate method, the electric pulse method, the lipofection method, the agglutination method, the microinjection method, the particle gun method, the DEAE-dextran method and other such method. Optionally, the nucleic acid is introduced into a somatic cell, a living organ, a tissue cell or other cell by gene transformation methods. Cells including the nucleic acid may be fused with the above-described germinal cell by a commonly known cell fusion method to create a transgenic animal.

For embryonic stem (ES) cells, an ES cell line may be employed, or embryonic cells may be obtained freshly from a host, e.g., mouse, rat, guinea pig, and the like. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the nucleic acid. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the nucleic acid, and males and females having the modification are mated to produce homozygous progeny transgenic animals.

Kits comprising one or more containers and the nucleic acid sequences, polypeptides, vectors, cells, provided herein, or combinations thereof, are also provided. For example, provided is a kit comprising (i) a nucleic acid sequence encoding a biosensor described herein (e.g., one or more of SEQ ID NOs: 1, 2, 3, 4, 5, 6, 7, 8, 50, 51, 52, 53, 62, 63, 77, 78, 91, 92, 93, and/or 94), including variants and/or fragments of the biosensor (e.g, variants or fragments of one or more of SEQ ID NOs: 1, 2, 3, 4, 5, 6, 7, 8, 50, 51, 52, 53, 62, 63, 77, 78, 91, 92, 93, and/or 94), (ii) a polypeptide comprising a biosensor described herein (e.g, one or more of SEQ ID NOs: 1, 2, 3, 4, 5, 6, 7, 8, 50, 51, 52, 53, 62, 63, 77, 78, 91, 92, 93, and/or 94), including variants and/or fragments of the biosensor (e.g., variants or fragments of one or more of SEQ ID NOs: 1, 2, 3, 4, 5, 6, 7, 8, 50, 51, 52, 53, 62, 63, 77, 78, 91, 92, 93, and/or 94), (iii) a vector comprising the nucleic acid of (i), (iv) a cell comprising the nucleic acid or (i) and/or the polypeptide of (ii), (v) a cell comprising the vector of (iii). The kit can comprise any combination of (i)-(v). Optionally, the kit further comprises reagents for using the nucleic acid or peptide biosensors, vectors, and/or cells. For example, if the kit comprises cells, the kit may also comprise cell culture medium. Optionally, the kit further comprises instructions for use. Optionally, the kit further comprises a GPCR, a GPCR-encoding nucleic acid sequence.

Design and Production/Manufacture Methods

Using the methods described herein, it is possible to design, produce, and/or adapt genetically encoded biosensors to assays for a variety of classes of analytes. The provided materials and methods facilitate the discovery of new compounds targeting a wide array of protein targets, including but not limited to: endogenous targets responsible for disease state progression, targets on pathogens for treating infectious diseases, and endogenous targets to be avoided (thus screening early for potential drug side effects and toxicity).

Methods herein provide systematic and generic approaches for the design and production of genetically encoded recombinant peptides containing an analyte-binding framework portion linked (e.g., operably linked) to a signaling portion, wherein the signaling portion is allosterically modulated or regulated by the framework portion upon interaction of the framework portion with an analyte. Generally, methods include: (i) selecting one or more target analytes; (ii) selecting a framework portion (e.g., a PBP) that interacts with (e.g., interacts specifically with) or binds to (e.g., binds specifically to) the target analyte and that undergoes a conformational change upon interacting with or binding to the analyte; (iii) identifying sites or amino acid positions within the framework portion (e.g., the PBP) where the conformational change occurs; and (iv) inserting or cloning a signaling portion into the site or amino acid position identified in (iii). Methods can, optionally, further include: (v) modifying or optimizing linker sequences between the framework portion and the signaling portion, for example, by genetic manipulation (e.g., by point mutation); (vi) modifying or optimizing analyte binding; (vii) modifying the signal generated by the biosensor; and/or (viii) cloning the biosensor into a suitable vector.

In some instances: (iii) includes identification of insertion sites by analysis of the structure (e.g., crystal structure) of the selected framework portion (e.g., the selected PBP) in one or both of its open and closed states to determine amino acid positions at which analyte-binding dependent structural changes occur. In instances where structures for both open and closed states are not available, analysis can be conducted by analogy to a structurally similar framework portion (e.g., PBP); (iv) includes cloning a signaling portion (e.g., a cpFP) at the site identified in (iii) such that the analyte-binding dependent structural change observed in (iii) will result in a conformational change in the signaling portion (e.g., the cpFP) and allosteric modulation of the signaling portion; (v) includes generating a library of mutants of biosensors with distinct linker sequences (e.g., by point mutation), screening the library of mutants to identify mutants with enhanced properties (e.g., improved signal-to-noise ratio), and selecting mutants with enhanced properties (e.g., improved signal-to-noise ratio); (vi) includes increasing or decreasing binding or affinity of the framework portion to the analyte, e.g., by modifying amino acids in the interacting face of the framework portion or regions within the framework portion that are critical for analyte binding; (vii) includes increasing or decreasing signal emission by the signaling portion and/or changing the color of the signal where the signaling portion is a FP (e.g., a cpFP). Methods including (i)-(viii) are exemplified in the Examples section herein.

Methods of Use

The disclosure further provides methods for using the biosensors disclosed herein (e.g., one or more of SEQ ID NOs: 1, 2, 3, 4, 5, 6, 7, 8, 50, 51, 52, 53, 62, 63, 77, 78, 91, 92, 93, and/or 94), including variants and/or fragments of the biosensor (e.g., variants or fragments of one or more of SEQ ID NOs: 1, 2, 3, 4, 5, 6, 7, 8, 50, 51, 52, 53, 62, 63, 77, 78, 91, 92, 93, and/or 94)) to detect analytes, e.g., in biological systems. Such methods can include, for example:

Use of a maltose biosensor disclosed herein (e.g., one or more of SEQ ID NOs: 1, 2, 3, 4, 5, 6, 7, 8, 50, 51, 52, and/or 53 including variants and/or fragments of SEQ ID NOs: 1, 2, 3, 4, 5, 6, 7, 8, 50, 51, 52, and/or 53) to detect maltose, e.g., in a biological system;

Use of a glutamate biosensor disclosed herein (e.g., one or more of SEQ ID NOs: 62 and/or 63 including variants and/or fragments of SEQ ID NOs: 62 and/or 63) to detect glutamate, e.g., in a biological system;

Use of a phosphonate biosensor disclosed herein (e.g., one or more of SEQ ID NOs: 77 and/or 78 including variants and/or fragments of SEQ ID NOs: 77 and/or 78) to detect phosphonate, e.g., in a biological system; and/or Use of a glucose biosensor disclosed herein (e.g., one or more of SEQ ID NOs: 91, 92, 93 and/or 94 including variants and/or fragments of SEQ ID NOs: 91, 92, 93 and/or 94) to detect glucose, e.g., in a biological system.

Techniques for performing such methods are known in the art and/or are exemplified herein. For example, methods can include introducing one or more biosensors into a biological system (e.g., a cell); expressing the one or more biosensors in the biological system (e.g., the cell); monitoring the signal emitted by the expressed biosensor in the biological system; and correlating the signal emitted by the expressed biosensor in the biological system with a level of the analyte in the biological system.

EXAMPLES

The invention is further described in the following examples, which do not limit the scope of the invention described in the claims.

Example 1: Maltose Indicators

Genetically encoded maltose indicators were generated using *Escherichia coli* maltodextrin-binding protein (EcMBP) as a framework and either circularly permuted β-lactamase (cpBla) or circularly permuted fluorescent protein (cpFP) as a signal. Data describe below suggest that cpBla and cpFP are not interchangeable.

Allosteric coupling of ligand binding to fluorescence was hypothesized to require:

i) that the site in into which cpGFP is inserted have the capacity to transduce the global conformational change the scaffold protein (EcMBP in this example) to the local environment of the chromophore in cpGFP; and ii) that the local environment of the chromophore (e.g., linkers) be optimized to maximize the difference in emission between unbound (apo) and the bound (in this example maltose-bound) states.

Example 1A: Identification of cpGFP Insertion Sites in EcMBP

Figure 1:
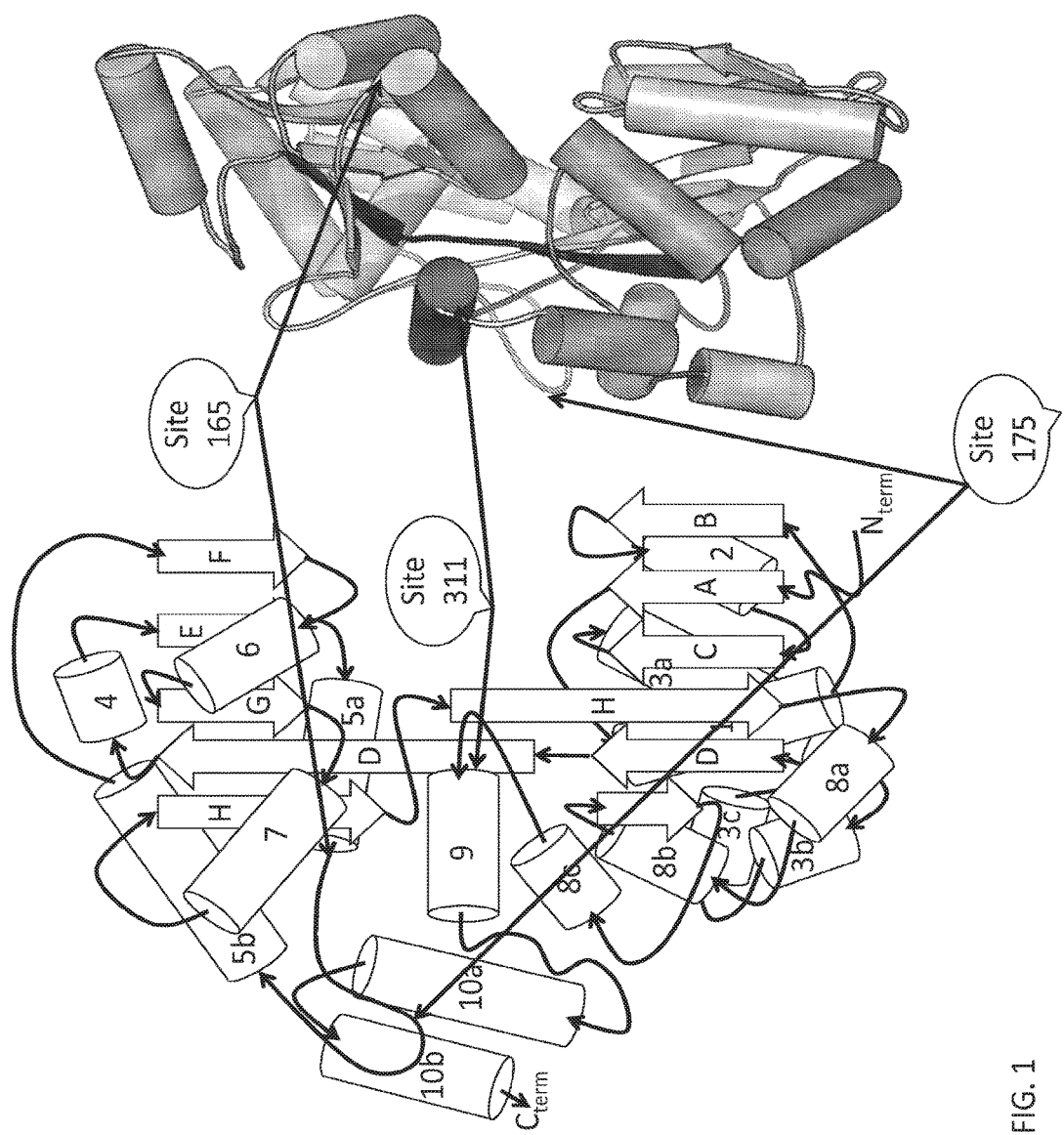
FIG. 1|Cartoon representation showing ligand bound *Escherichia Coli* malto-dextrin-binding protein (EcMBP) and potential circularly-permuted fluorescent protein (cpFP) insertion sites.

Potential insertion sites were identified using the crystal structures of the maltose-bound, closed form of EcMBP (Ouiocho et al., Structure, 5:997-1015, 1997) and the ligand-free, open form of EcMBP shown in FIG. 1 (Sharff et al., Biochemistry, 31:10657-10663, 1992) to guide rational design of EcMBP-cpGFP fusions that would result in maltose-dependent GFP fluorescence.

Figures 6A, 6B:
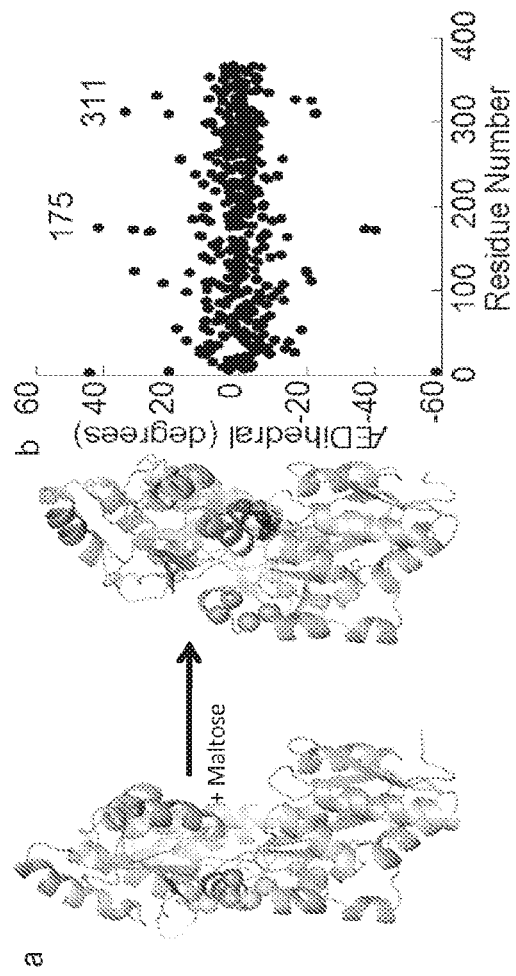
FIG. 6A-B|Changes in EcMBP upon maltose binding and locations at which circularly-permuted fluorescent protein (cpFP) was inserted are shown as colored spheres at the Cα positions. Yellow: 165-166, Green: 175-176, Cyan: 311-312, Violet: 317-318(A). (B) shows backbone structural changes. The Cα dihedral is calculated from the four atoms: Cαi+2, Cαi+1, Cαi, Cαi-1. ΔDihedral is calculated as the difference in dihedrals between the closed (1ANF) and open (1OMP) states of MBP, and corrected to fall within a range of -180° to 180°. The regions near residues 175 and 311 are labeled. There is a crystallographic artifact at the N-terminus resulting in the appearance of significant structural changes.
Figure 7A:
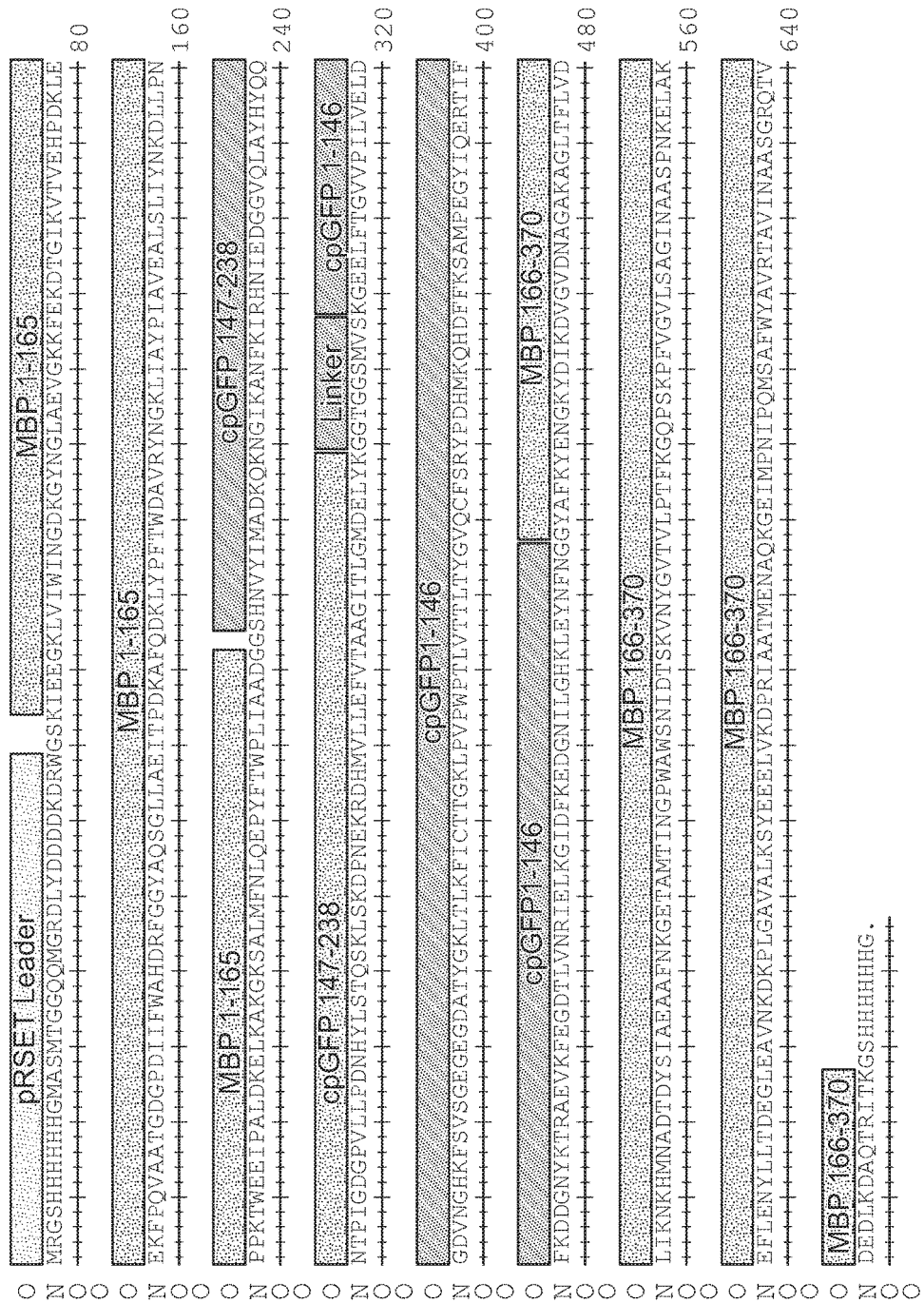
FIG. 7A|Amino acid sequence of MBP-165-cpGFP (SEQ ID NO:1).
Figure 7B:
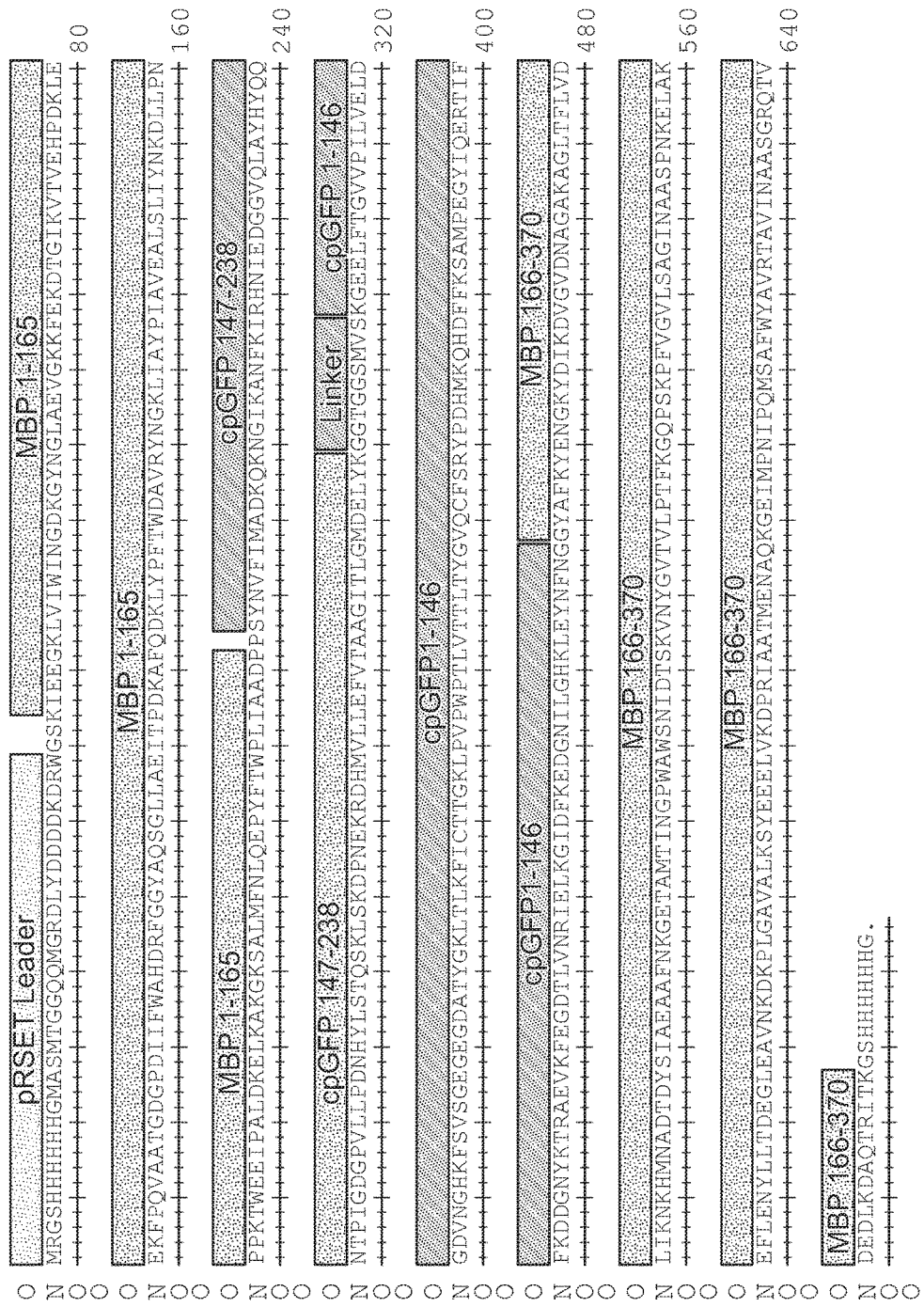
FIG. 7B|Amino acid sequence of MBP-165-cpGFP.PPYF (SEQ ID NO:2).
Figure 7C:
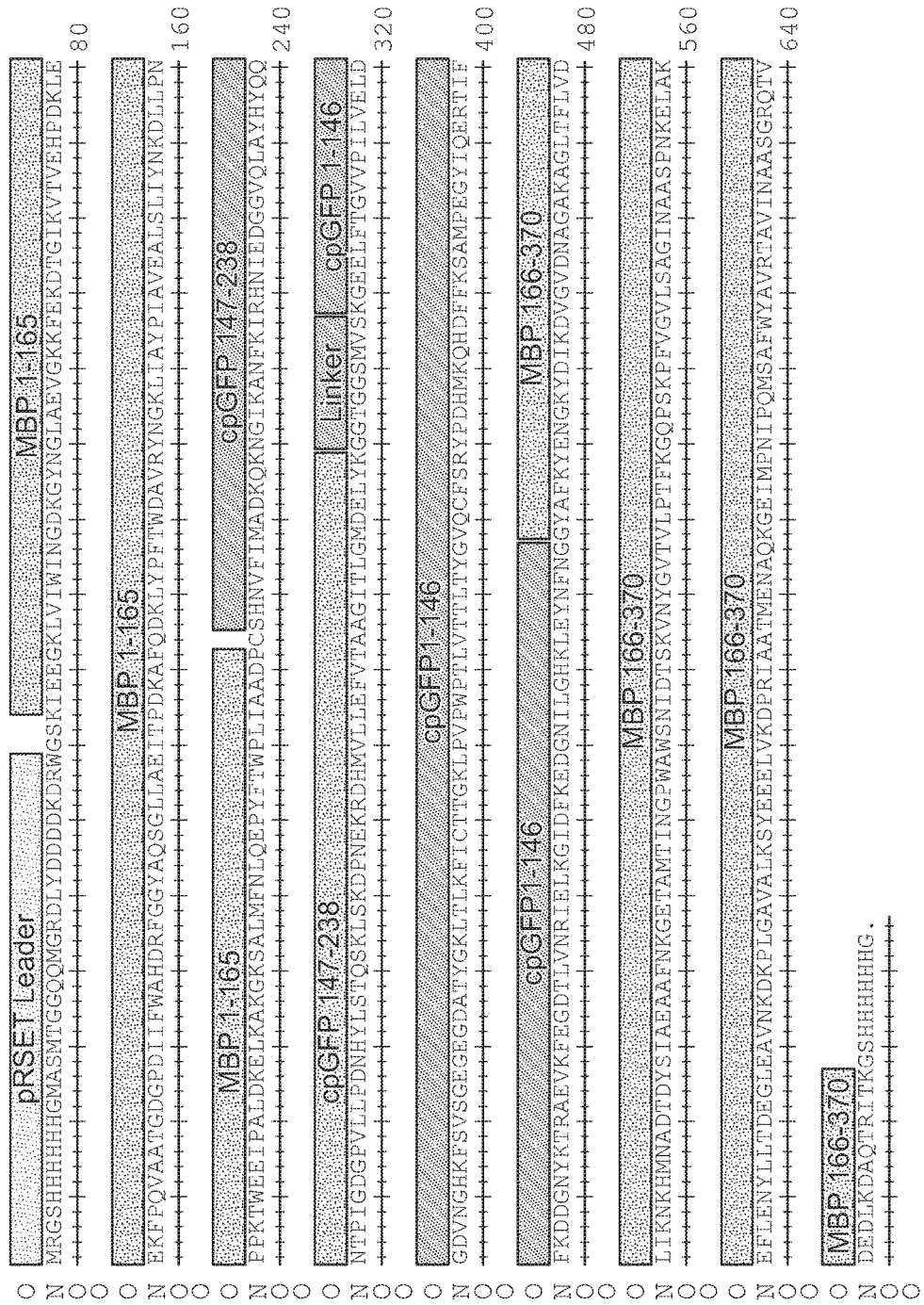
FIG. 7C|Amino acid sequence of MBP-165-cpGFP.PCF (SEQ ID NO:3).
Figure 9A:
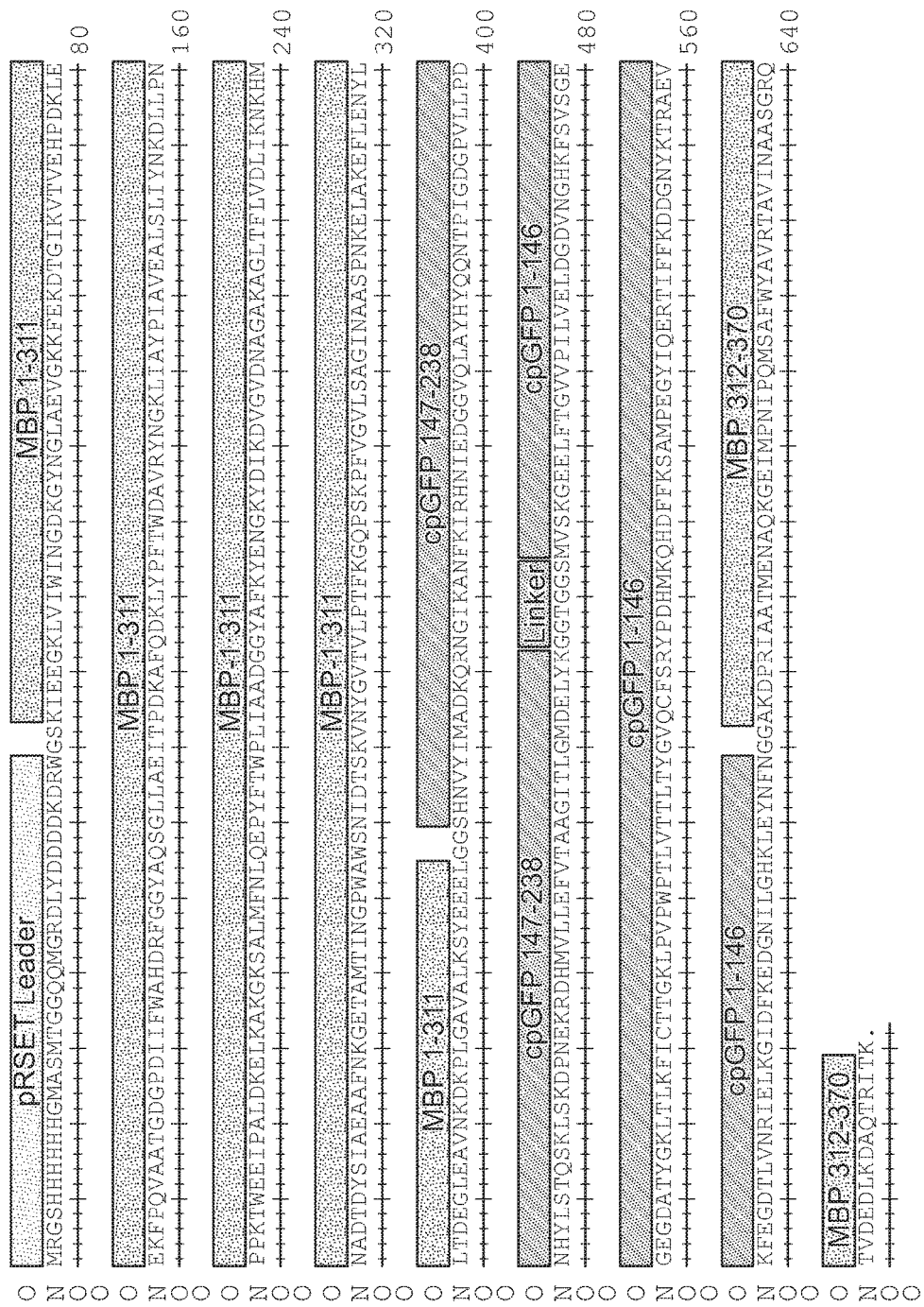
FIG. 9A|Amino acid sequence of MBP-311-cpGFP (SEQ ID NO:6).
Figure 10:
FIG. 10|Amino acid sequence of MBP-317-cpGFP (SEQ ID NO:8).

For (i), the change in dihedral angle (defined by the Cα atoms spanning four residues) was analyzed to identify maltose-dependent structural changes in sequentially adjacent residues (FIG. 6); this analysis showed that the Cα chain is "torqued" around residues 175 (ΔDihedral=+41°) and 311 (ΔDihedral=−22°) upon ligand binding. This sequential conformational change was predicted to be coupled to structural changes of an inserted cpGFP, resulting in maltose-dependent fluorescence for the fusion protein.

Previous studies using randomly digested and reassembled circularly permuted β-lactamase (cpBla) and EcMBP showed maltose-dependent β-lactamase activity in proteins with insertions of cpBla at EcMBP residues 165 and 317 (Guntas et al., Chem. Biol., 11:1483-1487, 2004; Guntas and Ostermeier, J. Mol. Biol., 336:263-273, 2004).

Since the ΔDihedral of EcMBP165 is +11° (moderate change) and EcMBP317 is +2° (no real change), four EcMBP-cpGFP templates were constructed by inserting cpGFP into EcMBP at sites 165, 175 (identified herein), 311 (identified herein), and 317 to test our predictive method and the interchangeability of cpBla and cpGFP at sites identified from the EcMBP-cpBla screen. These constructs were named MBP165-cpGFP, MBP175-cpGFP, MBP311-cpGFP, and MBP317-cpGFP (names were modified to encompass variants (e.g., with modified linker sequences). The cpGFP used is cpGFP146 described in Baird et al. (Proc. Natl. Acad. Sci., USA, 96:11241-11246, 1999). PCR assembly was used to construct fusion proteins with GlyGly-linkers between EcMBP and each terminus of cpGFP. The amino acid sequence of each construct is shown in FIGS. 6-9. The sequences of SEQ ID NOs:1-3 shown in FIGS. 7A-7C (i.e., MBP165-cpGFP) differ in the linker sequence between MBP 1-165 and cpGFP 147-238 (linker 1: see the line ending in amino acid 240)). The sequences of SEQ ID NOs: 4-5 shown in FIGS. 8A-8B (i.e., MBP175-cpGFP) differ in the sequence between MBP 1-175 and cpGFP 147-238 (linker 1: see the line ending in amino acid 240)). The sequences of SEQ ID NOs: 6-7 shown in FIGS. 9A-9B (i.e., MBP311-cpGFP) differ in the sequence between cpGFP 1-146 and MBP 312-370 (linker 2: see the line ending in amino acid 640)). Each construct includes 3 linkers: A linker between the C-terminus of the C-terminal portion of MBP and the N-terminus of cpGFP (i.e., linker 2), a linker between the N-terminus of cpGFP and C-terminus of the N-terminal portion of MBP, and a linker in cpGFP (i.e., linker 3).

Example 1B: Linker Optimization

Libraries of variants of SEQ ID NOs: 1-8 were generated with randomized linkers by single-stranded uracil template mutagenesis (see Kunkel et al., Methods Enzymol., 204: 125-139, 1991) using the primers listed below:

```
165 Linker 1 Primers:
PLIAADGxxNVYIM            (SEQ ID NO: 9)

PLIAADxxNVYIM             (SEQ ID NO: 10)

PLIAADGGxxNVYIM           (SEQ ID NO 11)

PLIAADGxPNVYIMG           (SEQ ID NO: 12)

PLIAADGIxNVYIMG           (SEQ ID NO: 13)

PLIAADPxSHNVYIM           (SEQ ID NO: 14)

PLIAADxPSHNVYIM           (SEQ ID NO: 15)

PLIAADxxSHNVYIM           (SEQ ID NO: 16)

PLIAADxxSHNVFIM           (SEQ ID NO: 17)

PLIAADPxSHNVFIM           (SEQ ID NO: 18)

PLIAADPxSYNVFIM           (SEQ ID NO: 19)

PLIAADxxSYNVFIM           (SEQ ID NO: 20)

PLIAADPxSYNVFIM           (SEQ ID NO: 21)

PLIAADxxSYNVFIM           (SEQ ID NO: 22)

PLIAADPxSxNVYIM           (SEQ ID NO: 23)

PLIAADPxSHxVYIM           (SEQ ID NO: 24)

PLIAADPxSHNxYIM           (SEQ ID NO: 25)

PLIAADPxSHNVxIM           (SEQ ID NO: 26)

165 Linker 2 Primers:
KLEYNFNxxYAFKYEN          (SEQ ID NO: 27)

KLEYNFNxYAFKYEN           (SEQ ID NO: 28)

KLEYNFNYAFKYEN            (SEQ ID NO: 29)

KLEYNFxYAFKYEN            (SEQ ID NO: 30)

KLEYNxxYAFKYEN            (SEQ ID NO: 31)

KLEYNWxYAFKYEN            (SEQ ID NO: 32)

KLEYNxKYAFKYEN            (SEQ ID NO: 33)

KLEYNFNPxYAFKYEN          (SEQ ID NO: 34)

KLEYNFNxPYAFKYEN          (SEQ ID NO: 35)

175 Linker 1 Primers:
AFKYENxxSHNVYIM           (SEQ ID NO: 36)

175 Linker 2 Primers:
KLEYNFNxxKYDIKDV          (SEQ ID NO: 37)

311 Linker 1 Primers:
KSYEELxxSHNVYIM           (SEQ ID NO: 38)

KSYEELPxSHNVYIM           (SEQ ID NO: 39)

KSYEELxPSHNVYIM           (SEQ ID NO: 40)

311 Linker 2 Primers:
KLEYNFNxxAKDPRIA          (SEQ ID NO: 41)

KLEYNFNPxAKDPRIA          (SEQ ID NO: 42)

KLEYNFNxPAKDPRIA          (SEQ ID NO: 43)

317 Linker 1 Primers:
ELAKDPRxSHNVYIM           (SEQ ID NO: 44)

ELAKDPRxxSHNVYIM          (SEQ ID NO: 45)

ELAKDPRxxxSHNVYIM         (SEQ ID NO: 46)

317 Linker 2 Primers:
KLEYNFNxAATMENA           (SEQ ID NO: 47)

KLEYNFNxxAATMENA          (SEQ ID NO: 48)

KLEYNFNxxxAATMENA         (SEQ ID NO: 49)
```

Where "x" indicates that a degenerate primer (with DNA sequence "NNS") was used to encode all 20 possible amino acids.

About 400 variants were screened in semi-high-throughput fashion, measuring fluorescence intensity of clarified cell lysate in the absence and presence of 10 mM maltose.

Figures 11A, 11B, 11C, 11D:
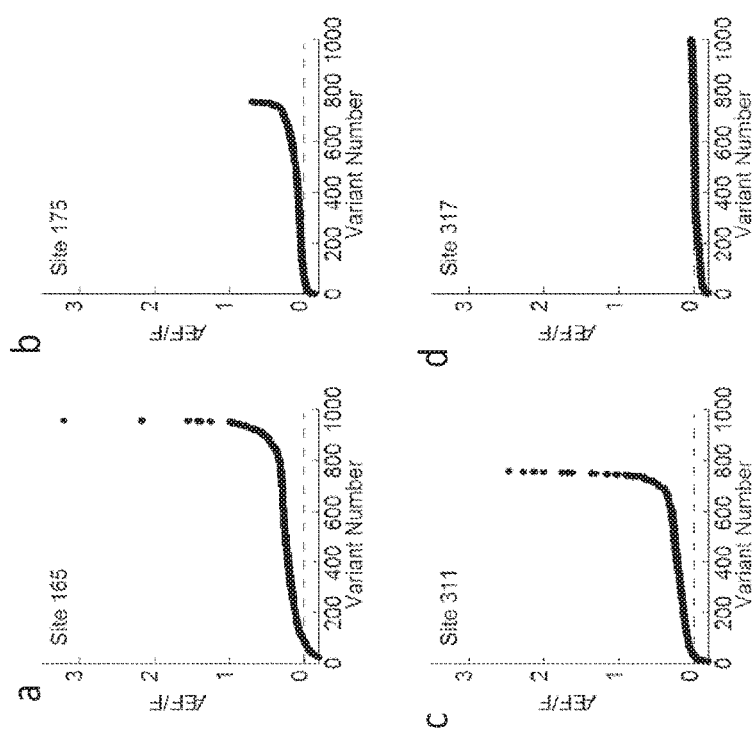
FIGS. 11A-11D|Line charts showing EcMBP plot of ΔF/F for clarified lysate screen of cpGFP linker-screens at insertion points 165, 175, 311, and 317. The horizontal dashed line at zero indicates no fluorescence change. Standard deviations in ΔF/F are less than 10% of an average ΔF (repetitions for MBP165-cpGFP.PPYF yields ΔF/F values of 2.51, 2.63, and 2.54).
Figure 12:
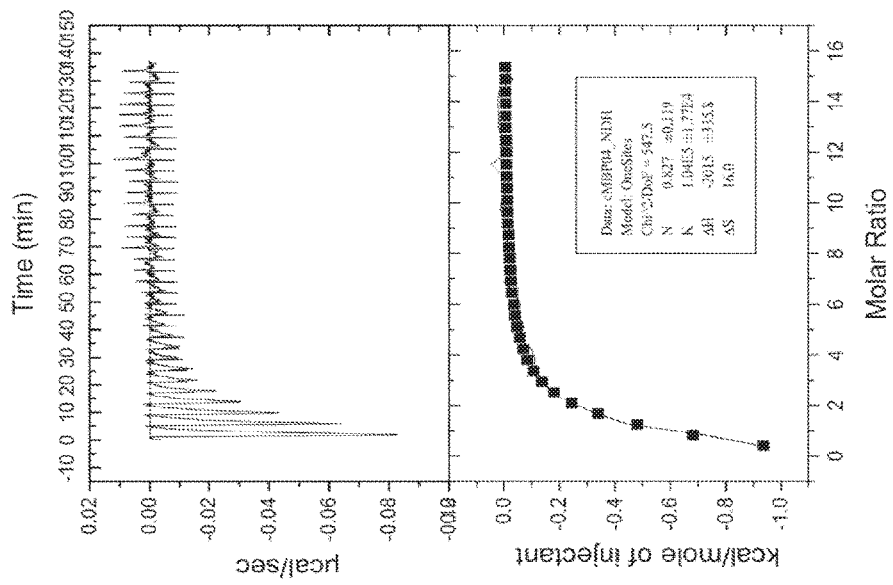
FIG. 12|Isothermal titration calorimetry (ITC) of MBP317-cpGFP with maltose.

Insertion of cpGFP as MBP317, a site previously reported for cpBla, did not show maltose-dependent fluorescence (FIG. 11) even though the framework protein still bound maltose, as determined by isothermal titration calorimetry (FIG. 12). These data demonstrate that identification of insertion sites by a method other than insertion of cpGFP (such as insertion of cpBla) is not sufficient to identify sites that transduce ligand binding to changes in fluorescence intensity Insertion of cpGFP at residue 165 of EcMBP (EcMBP165-cpGFP), another position reported in cpBla studies (Guntas and Ostermeier, supra) with -GlyGly-linkers flanking the cpGFP resulted in a protein in which fluorescence increased 20% ($\Delta F/F=0.2$) upon addition of saturating maltose.

Screening a fully-degenerate, length-two library ("XX") at either the EcMBP-cpGFP linker (linker 1) or the cpGFP-EcMBP linker (linker 2) yielded proteins with maltose-dependent fluorescent increases >300% or decreases >50% (FIG. 11). Many of the variants with increased $\Delta F/F$ values had linkers containing proline(s). Subsequent libraries constructed from oligonucleotides encoding XP or PX and randomization of the residues in GFP from residue 146 to 150 were screened, yielding a final variant with: a two-proline EcMBP-cpGFP linker, a two-glycine cpGFP-EcMBP linker, GFP-H148Y, and GFP-Y151F. This variant, called "EcMBP165-cpGFP.PPYF" (abbreviated PPYF (SEQ ID NO:2)) has a $\Delta F/F=2.5$, a Kd for maltose of 3 µM. Screens also identified variant EcMBP311-cpGFP.L2-NP (-AsnPro- at linker 2 (SEQ ID NO:7)), which has a $\Delta F/F$ of 1.0 and a Kd for maltose of 2 µM. This variant has an inferior maltose-dependent fluorescence increase than PPYF, but demonstrates generality of the cpFP insertion method.

EcMBP175-cpGFP was also screened with XX linkers, and a few variants with $\Delta F/F \approx 1$ were identified (FIG. 11). One mutant, with the first linker encoding HL (EcMBP175-cpGFP.L1-HL (SEQ ID NO:5)), has a $\Delta F/F=0.5$ and a Kd for maltose of 1.3 µM.

These data support that choice of insertion site by structural analysis is preferable to random insertion.

Example 1C: Modifying Ligand Binding and/or Fluorescent Properties of Sensors

One objective in the development of generic biosensors is for the framework to permit independent optimization of binding and signaling properties. Analysis of whether biosensors herein permit such optimization was tested using the high-SNR sensor PPYF, by: (i) rationally altering maltose-binding affinity; (ii) changing the ligand-binding specificity from maltose to sucrose, and (iii) creating a family of sensors in multiple colors.

Figure 13:
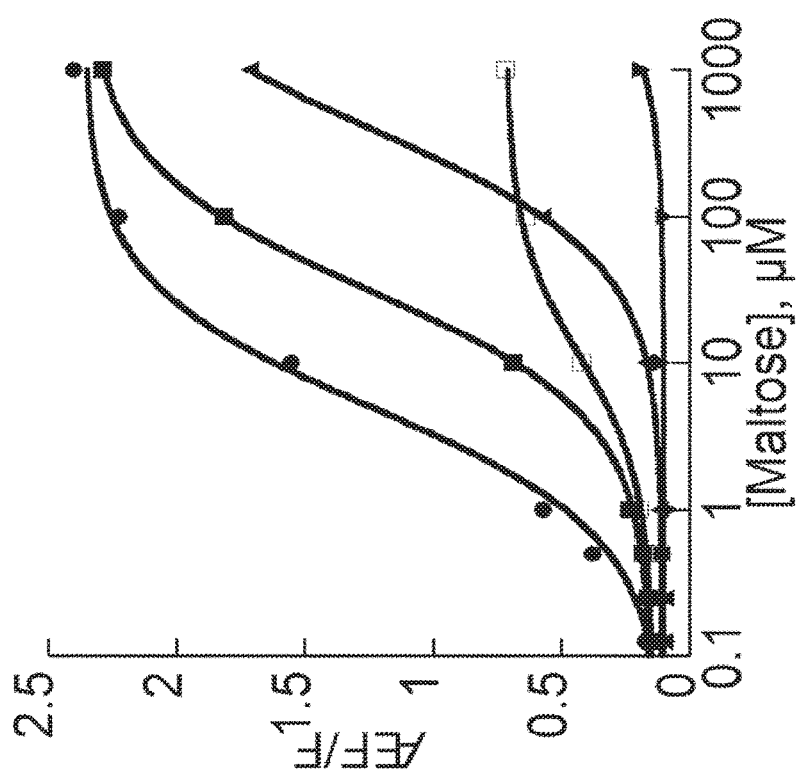
FIG. 13|Graph showing EcMBP165-cpGFP.PPYF affinity variant binding maltose-binding curves. Binding curves for affinity variants of MBP165-cpGFP.PPYF. Data is fit to a single-binding site isotherm. Curve-fit affinities are: WT binding pocket, 5 μM (●); W230A, 32 μM (■); W62A, 375 μM (▲); W340A, >1 mM (▼); I329W, 11 μM (□).

As a first step, the impacts of mutations of three tryptophan side-chains in the maltose-binding pocket (W230, W62, and W340) were tested. These sites have previously been shown to lower the affinity of EcMBP for maltose by one, two, or three orders of magnitude, respectively, when mutated to alanine (Martineau et al., J. Mol. Biol., 214:337-352, 1990). A mutation to the hinge region, I329W, was also made to PPYF, as this has been shown to increase maltose affinity by about 2-fold in both wild-type EcMBP (Marvin and Hellinga, Nat. Struc. Biol., 8:795-798, 2001) and in the EcMBP-cpBla switches (Guntas et al., Chem. Biol., 11:1483-1487, 2004; Kim and Ostermeier, Arch. Biochem. Biophys., 446:44-51, 2006). As shown in FIG. 13, for the PPYF sensor, the three tryptophan-to-alanine binding-pocket mutations behaved as expected, lowering affinity by between one and three orders of magnitude. In contrast, the I329W mutation did not increase affinity as expected, but rather decreased it. $\Delta F/F$ also decreased. This data suggests that the mechanism of fluorescence change in this sensor is dependent on subtle interactions between EcMBP and cpGFP that are linked to the I329W mutation.

Figures 14A, 14B, 14C, 14D:
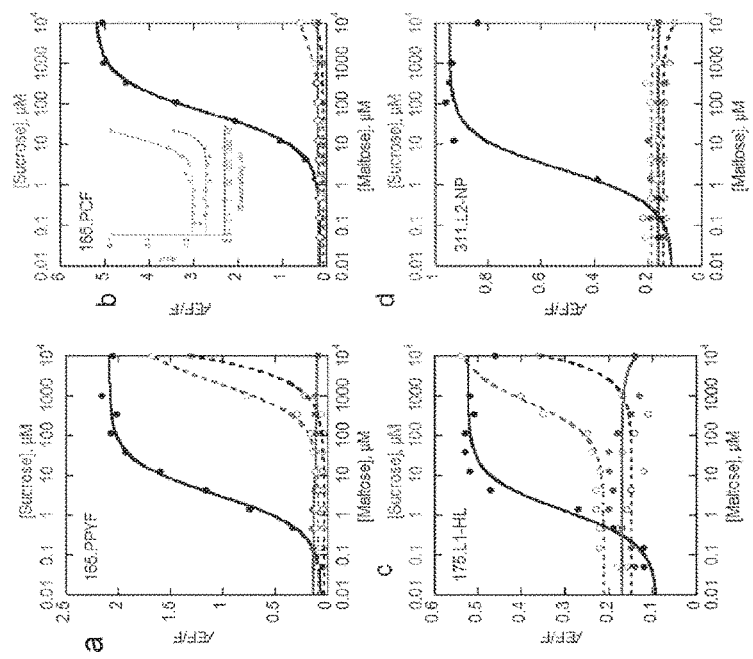
FIGS. 14A-14D|Line graphs showing maltose and sucrose binding curves for wild-type and 5-7 variants of the EcMBP-cpGFP sensors. Maltose (black) and sucrose (red) binding curves for wild-type (filled, solid lines) and 5-7 variants (open, dashed lines) of the MBP-cpGFP sensors. MBP165-cpGFP.PPYF (a); MBP165-cpGFP.PCF (b); MBP175-cpGFP.L1-HL (c); MBP311-cpGFP.L2-NP (d).

As an alternative test for changing the ligand-binding specificity of the sensor while preserving fluorescence signaling, "5-7" mutations (D14L, K15F, W62Y, E111Y), previously shown to confer EcMBP with an affinity for sucrose (Guntas and Mansell, Proc. Natl. Acad. Sci., 102:11224-11229, 2005), were made to PPYF. As shown in FIG. 14A, the mutations conferred to the sensor about 2 mM affinity for sucrose and ~3 mM affinity for maltose. To address a discrepancy between expected (micromolar) and observed (millimolar) affinity for disaccharides, the 5-7 mutations were made to sensors with cpGFP inserted at different positions in EcMBP, and with different linker compositions. In the context of EcMBP165-cpGFP.PCF, the 5-7 mutations conferred very low (but observable) binding preference for sucrose over maltose (FIG. 14B). The trend of higher (but still weak) affinity for sucrose (~0.6 mM) over maltose (~6 mM) continued when the 5-7 mutations are made in the context of EcMBP175-cpGFP.L1-HL (FIG. 14C). In the context of EcMBP311-cpGFP.L2-NP, the 5-7 mutations appeared to eliminate all binding (FIG. 14D). The preference for sucrose over maltose of the 5-7 variants of the sensors is consistent with the binding properties of the 5-7 variants of EcMBP alone and EcMBP-cpBla (Guntas and Mansell, Proc. Natl. Acad. Sci., 102:11224-11229, 2005). The lower affinity for both ligands of the 5-7 variants of the sensors may be the consequence of the inserted cpGFP shifting the open and closed equilibrium.

These data suggest that ligand binding and fluorescent properties of biosensors can be independently modified.

Example 1D: Modifying Sensor Color

The color of GFP can be altered by changing the amino acids that either comprise or interact with the chromophore (see Shaner et al., J. Cell. Sci. 120:4247-4260, 2007, for a review).

Using PPYF as a template, mutations Y66W (to yield a cyan variant, "cpCFP"), L64F+T65G+V68L+T203Y (yellow, "cpYFP"), and Y66H (blue, "cpBFP") mutations were made (see Cubitt et al., Trends Biochem., 20:448-455, 1995, for exemplary methods). As shown in FIG. 15, the variants exhibit fluorescence emission spectra consistent with their respective intended designs.

Figures 15A, 15B, 15C, 15D:
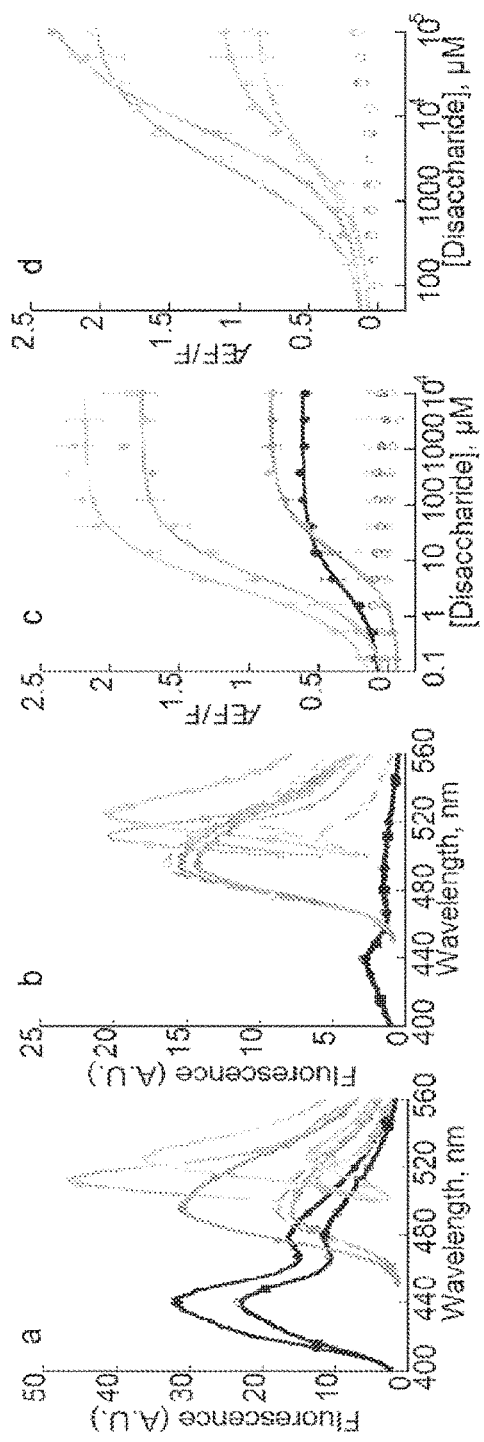
FIGS. 15A-15D|Line graphs showing emission spectra for colored variants of EcMBP sensors. Fluorescence emission spectra of the MBP165-Blue, Cyan, Green, and Yellow wild-type sensors (a) and the 5-7 variants (b) in the absence of ligand (dashed lines, open circles), with 10 mM maltose (solid lines, filled circles), or 10 mM sucrose (solid lines, filed squares). Sensors were excited at 383, 433, 485, and 485 nm, respectively. Titration of maltose and sucrose in the Blue, Cyan, Green, and Yellow MBP165 wild-type sensors (c) and for the 5-7 variants (d). Filled circles are titration of maltose, open circles are titration of sucrose. For the wild-type sensors, Kds for maltose binding are: Blue 3.3 μM, Cyan 13 μM, Green 4.5 μM, Yellow 3.3 μM. No sucrose binding is observed. For the 5-7 variants, Kd of Green is 2.4 mM (sucrose) and 7.1 mM (maltose). Kd of Yellow is 2.5 mM (sucrose) and 4.5 mM (maltose).

The $\Delta F/F$ of the color variants in response to maltose is different (in each case inferior) from the $\Delta F/F$ of 2.5 observed in PPYF-green. The EcMBP165-cpYFP.PPYF sensor, which has the same covalent chromophore structure as PPYF, has the greatest $\Delta F/F$ of the three spectral variants (FIG. 15A). EcMBP165-cpCFP.PPYF has a lower $\Delta F/F$ than the green and yellow variants, but by incorporating previously identified mutations, (L1-PC+GFP-Y151F; the resulting protein is called EcMBP165.cpCFP.PCF), a variant with $\Delta F/F=0.8$ was obtained (FIG. 15A).

Figure 16:
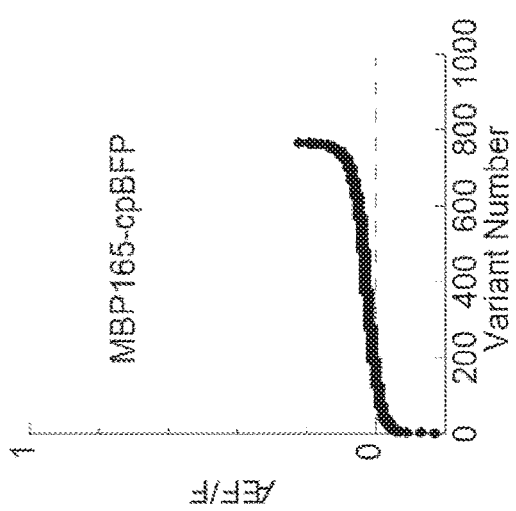
FIG. 16|Plot of ΔF/F for clarified lysate screen of MBP165-cpBFP linker-screen. The horizontal dashed line at zero indicates no fluorescence change.

The EcMBP165-cpBFP.PPYF variant, while dimly fluorescent, is not a sensor, and a screen of 800 linker variants failed to produce any variant with $\Delta F/F>0.2$ (FIG. 16). Since EcMBP165-cpBFP.PPYF was very dim, Azurite mutations T65S+V150I+V224R were included to increase brightness and stability, and make EcMBP165-cpAzurite a good template for linker screening. Using oligonucleotides encoding XX amino acid linkers, a variant was obtained, EcMBP165-cpAzurite.L2-FE, that had $\Delta F/F=0.8$ (FIG. 15).

Example 1E: Modifying Sensor Color and Ligand Specificity/Affinity

The four sucrose-binding "5-7" mutations described above that conferred weak sucrose affinity in the green sensor (EcMBP165-cpGFP.PPYF) were converted to blue, cyan, and yellow maltose sensors (EcMBP165-cpAzurite.L2-FE, EcMBP165-cpCFP.PCF, and EcMBP165-cpYFP.PPYF). The green and yellow sensors showed increased fluorescence upon addition of 10 mM sucrose, but the cyan and blue proteins did not (FIG. 15A). Like the green variant, the yellow variant had no detectable sucrose affinity with the wild type binding pocket (FIG. 15C) and millimolar affinity for both sugars, with preference for sucrose over maltose (FIG. 15D).

Figures 17A, 17B:
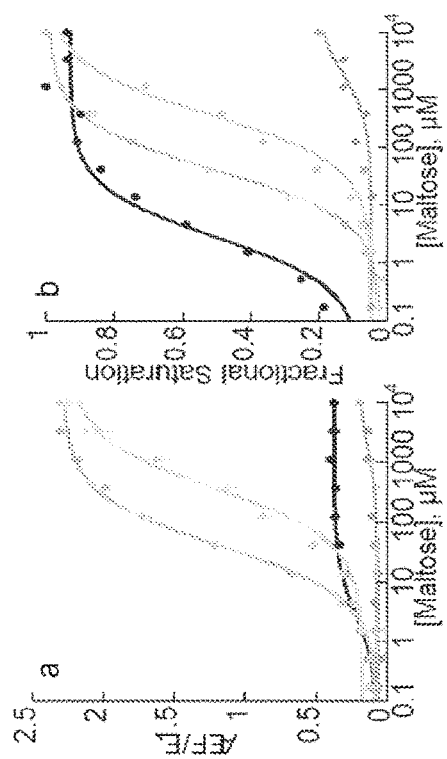
FIGS. 17A-17B|Line graphs showing maltose binding. Blue (wt binding pocket) has an affinity of 2.7 μM. Green (W230A) has an affinity of 40 μM. Yellow (W62A) has an affinity of 350 μM. Cyan (W340A) has an affinity of approximately 1.7 mM. Data is plotted at ΔF/F (a) or normalized to Fractional Saturation (b).

As seen in FIG. 17, as maltose concentration increased, the blue sensor increased in fluorescence first (Kd~2.7 then the green (Kd~40 then the yellow (Kd~350 and at high maltose concentrations, the cyan variant began to increase its fluorescence (Kd~1.7 mM).

Example 1F: Imaging Bacteria

The ultimate value of genetically encoded fluorescent sensors is in their utility for observing analyte flux in living cells and organisms. In a simple proof-of-principle experiment, *Escherichia coli* expressing PPYF or PPYF.T203V (see "Second-generation maltose sensors" below) were imaged in the green fluorescence channel in the absence of maltose, and then re-imaged after addition of saturating maltose to the media.

Figures 18A, 18B, 18C:
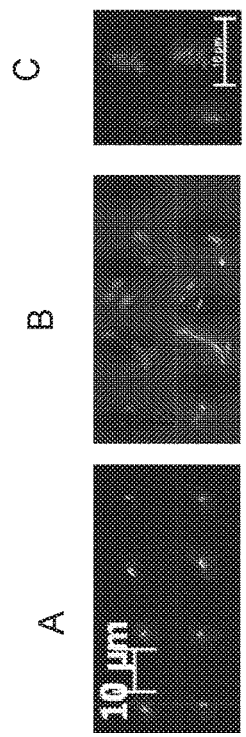
FIGS. 18A-18C|Images bacterial cells expressing (a) EGFP, (b) PPYF, or (c) PPYF.T203V in the absence (top) and presence (bottom) of maltose.

As shown in FIG. 18, bacteria expressing the sensors clearly became brighter, while control bacteria expressing EGFP appeared unchanged. Increased fluorescence was quantified by measuring the peak (gray-value) pixel intensity of each bacterium. Those expressing PPYF undergo an approximate doubling of fluorescence (bacterium-averaged $\Delta F/F=1.1\pm0.4$), those expressing PPYF.T203V have slightly increased $\Delta F/F$ ($\Delta F/F=1.29\pm0.2$), while those expressing EGFP have no change in fluorescence ($\Delta F/F=-0.01\pm0.05$).

Example 1F: 2-Photon Imaging of Mammalian Cells

Multi-photon microscopy opened new frontiers for in vivo fluorescence imaging, in particular for neuronal activity visualization through the use of genetically encoded calcium indicators (Tian et al., Nat. Methods, 3:281-286, 2009; Denk et al., Science, 248:73-76, 1990; Denk and Svoboda, Neuron, 18:351-357, 1997).

Figures 19A, 19B:
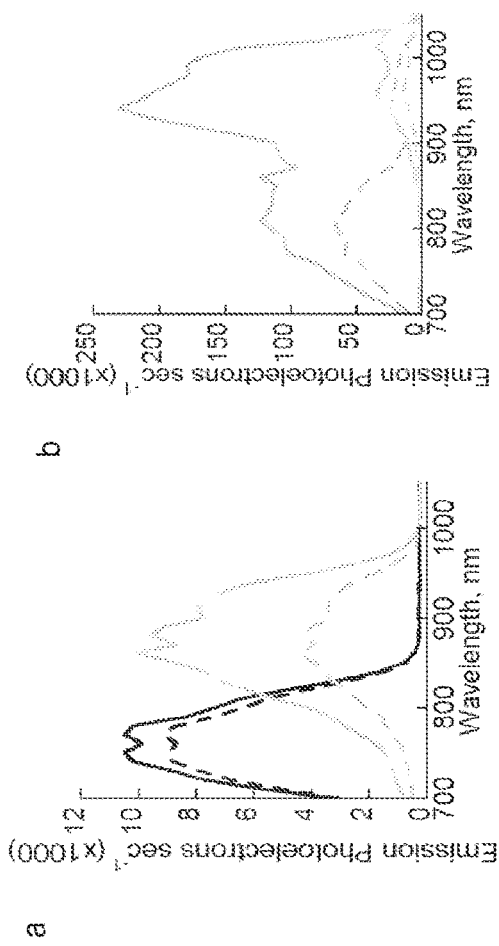
FIGS. 19A-19B|Line graphs showing EcMBP-cpGFP.PPYF.T203V 2-photon excitation spectra. MBP165-cpAzurite.L2-FE (a), -cpCFP.PCF (a), -cpGFP.PPYF (b), and -cpYFP.PPYF (b) were excited at the wavelengths indicated and emission measured through appropriate wavelength filters. Two graphs are shown to present different y-axis scales. Optimal ΔF/F values for 2-photon excitation of the spectral variants of MBP165 are: -cpAzurite, 1.1 (ex 760 nm); -cpCFP, 2.3 (ex 830-960 nm); -cpGFP, 10.0 (ex 940 nm); -cpYFP, 2.6 (ex 940 nm).

To demonstrate that the maltose sensors described herein have the potential to be used for 2-photon imaging, fluorescence excitation spectra were collected. As shown in FIG. 19, with a 535 nm bandpass emission filter (50 nm bp), EcMBP165-cpGFP.PPYF showed a 10-fold maltose-dependent increase in fluorescence when excited at 940 nm. All four spectral variants showed a significant maltose-dependent increase in 2-photon fluorescence.

Example 1G: Sub-Cloning Maltose Sensors

EcMBP165-cpGFP.PPYF.T203V (see "Second-generation maltose sensors" below) were cloned into a modified version of the pDisplay vector (Invitrogen) for extracellular display on the surface of transiently transfected human embryonic kidney (HEK293) cells.

Figures 21A, 21B:
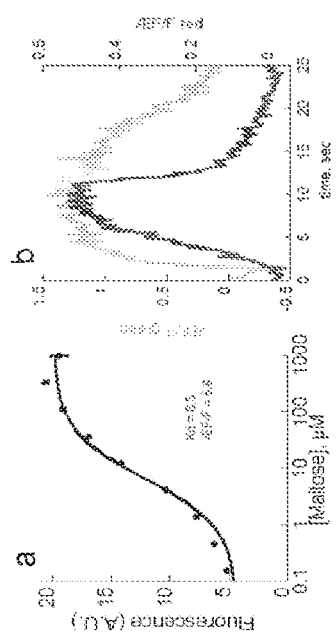
FIGS. 21A-21B|Graphs showing quantification of fluorescence of EcMBP-cpGFP.PPYF.T203V when displayed on the surface of HEK cells. (a) Concentration dependence. (b) Observed fluorescence after a "puff" of HBSS solution containing 1 mM maltose and 2.5 nM Alexa Fluor® 568 (Invitrogen, Carlsbad, Calif.).

As shown in FIG. 20, the sensor localized to the plasma membrane and increased in brightness in a concentration-dependent manner when perfused with buffers of varying maltose concentration. The $\Delta F/F$ is 5.8-fold, very close to that of the soluble protein produced in *E. coli*, with the mid-point of the maltose-dependent fluorescence increase being 6.5 µM (FIG. 21A), very similar to the affinity determined on purified protein (5 µM). Furthermore, the surface displayed sensor responded rapidly to a pulse of 1 mM maltose (FIG. 21A), indicating that the time course for its action is useful for transient events.

Example 1H: Crystal Structure Analysis of Maltose Sensors

Figures 22A, 22B, 22C, 22D:
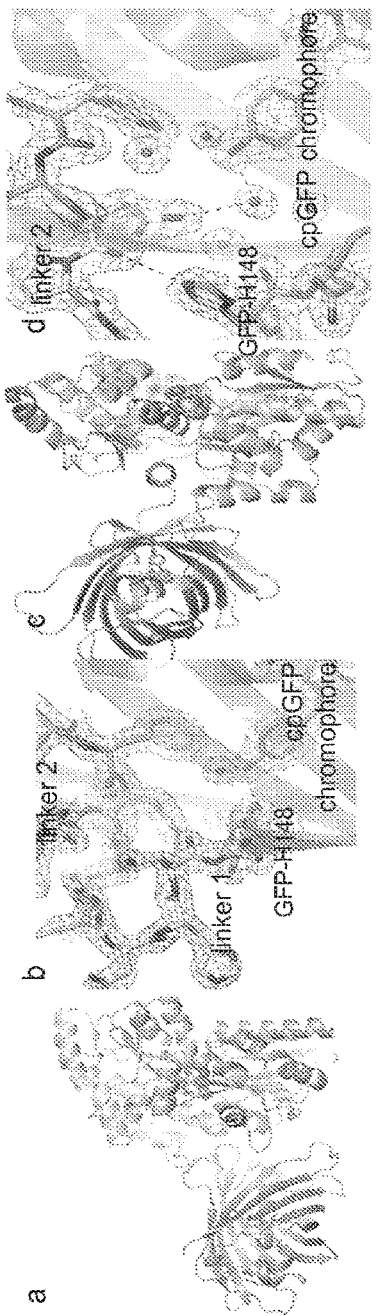
FIGS. 22A-22D|Cartoon representations and close-up views of inter-domain linkers and selected amino acids of the cpGFP chromophore environment of the structure of MBP175-cpGFP.L1-HL (A and B) and MBP311-cpGFP.L2-NP (C and D) bound to maltose. The MBP domain is colored as in FIG. 1. The cpGFP domain is green and the inter-domain linkers are colored white. The cpGFP chromophore is displayed as sticks and the bound maltose as red and white spheres. Ordered water molecules are represented as red spheres. Selected hydrogen bonds are displayed as dashed black lines. β-strands 10 and 11 of cpGFP are displayed as semi-transparent for clarity. The 2Fo-Fc electron density map calculated with the displayed residues omitted from the model is shown as blue mesh.

High-resolution structures of several of the maltose sensors described above were generated. Crystallization trials were performed with EcMBP165-cpGFP.PPYF, EcMBP175-cpGFP.L1-HL, and EcMBP311-cpGFP.L2-NP in the presence and absence of excess maltose, from which both EcMBP175-cpGFP.L1-HL and EcMBP311-cpGFP.L2-NP crystallized in the presence of maltose. X-ray structures were solved to 1.9 and 2.0 Å resolution, respectively, by molecular replacement (FIGS. 22A-22C).

The structures of the cpGFP and EcMBP domains of the sensors are superimposable with published crystal structures of cpGFP (from GCaMP2; RMSD=0.36 and 0.38 Å, respectively, for comparing 221 common Cα atoms) and EcMBP-maltose (RMSD=0.43 and 0.37 Å, 370 Cα). The structure of EcMBP is largely unperturbed by insertion of the cpGFP domain; only residues around the 175 and 311 insertion sites showed any significant displacement.

GFP-H148, which H-bonds the GFP chromophore in the structure of native GFP, also directly H-bonded to the chromophore in the EcMBP175-cpGFP.L1-HL-maltose structure (FIG. 22B), although a different rotamer was observed. In the EcMBP311-cpGFP.L2-NP-maltose structure, GFP-H148 is pulled away from the chromophore and is largely replaced by the Asn from linker 2, which makes H-bond interactions to both strand 8 of the GFP barrel and the chromophore phenolate oxygen (through a water molecule, FIG. 22D). GFP-H148, meanwhile, seemed to stabilize the conformation of linker 2 of EcMBP311-cpGFP.L2-NP by H-bonding the backbone carbonyl of the linker 2 Asn. There is some solvent access to the cpGFP chromophore through the hole in the GFP barrel created by circular permutation, although the inter-domain linkers block much of the opening in both structures. Relatively few contacts are made between the cpGFP and EcMBP domains.

Figure 5:
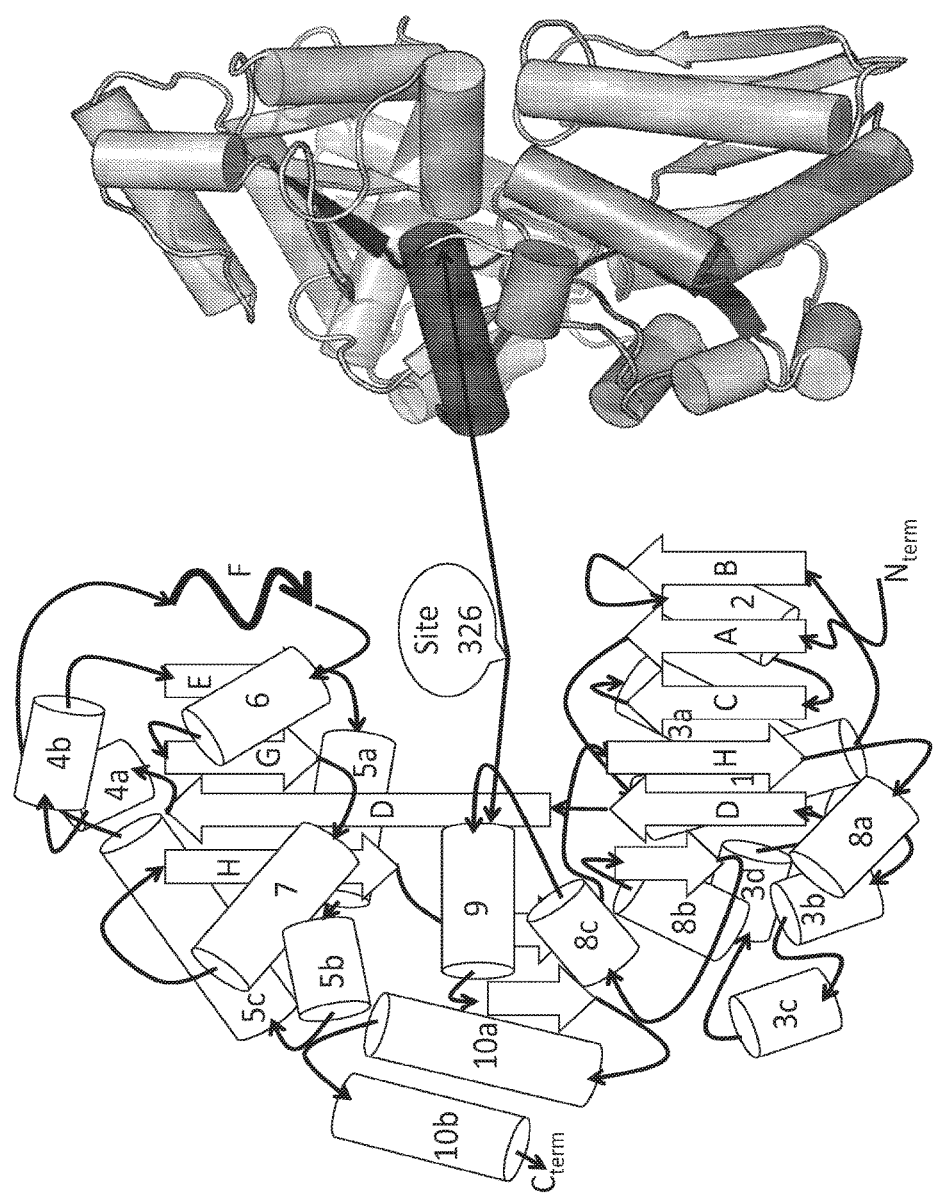
FIG. 5|Cartoon representation showing ligand bound *Thermus thermophilus* glucose binding protein (TtGBP) and potential cpFP insertion sites.

Based on the structures of two maltose-bound sensors, the sensing mechanism likely involves a shift in the relative position of linker 1 and linker 2 induced by the conformational change in the EcMBP domain associated with maltose binding (FIG. 5). The register shift of interactions between the two linkers could alter the proximity of linker 2 and nearby side-chains to the cpGFP chromophore and change the water structure in the cpGFP opening, leading to a shift in the chromophore protonation equilibrium. This might explain why rigid proline is preferred in either linker, since conformational changes upon ligand binding might be better propagated through the rigid linkers to the cpGFP chromophore environment.

Example 1I: Generation of Second-Generation Maltose Sensors

In an attempt to increase brightness and $\Delta F/F$ of GCaMP, the local environment of the chromophore was altered by randomizing residues within cpGFP, and screening for improved variants (Tian et al., nat. Methods, 6:875-881, 2009).

Figures 23A, 23B, 23C, 23D:
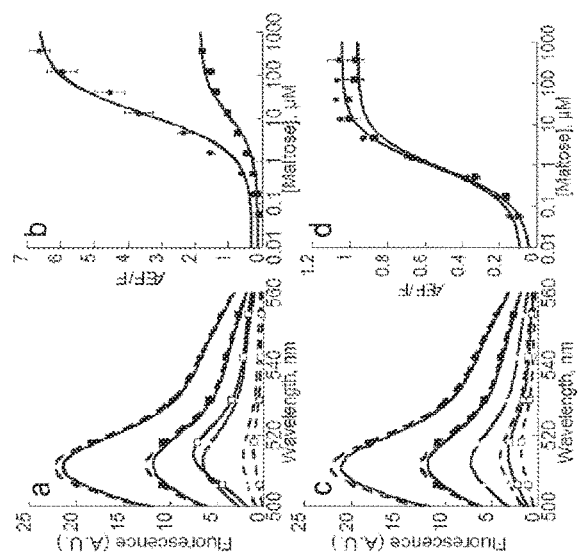
FIGS. 23A-23D|EcMBP-cpGFP: effect of T203V mutation on fluorescence. (a) Emission spectra of 1 μM purified eGFP (filled circles), cpGFP (filled squares), MBP165-cpGFP.PPYF (open circles), and MBP165-cpGFP.PPYF+T203V (open squares) in the absence (dashed lines) or presence (solid lines) of 1 mM maltose. cpGFP is half as bright as eGFP, and the saturated MBP165-cpGFP.PPYF variants are about half as bright as cpGFP. (b) Titration of maltose for MBP165-cpGFP.PPYF (filled squares), and MBP165-cpGFP.PPYF+T203V (filled circles). Affinities for each protein are the same, but with different ΔF/F. (c) Emission spectra of 1 μM purified eGFP (filled circles), cpGFP (filled squares), MBP311-cpGFP.L2-NP (open circles), and MBP311-cpGFP.L2-NP+T203V (open squares) in the absence (dashed lines) or presence (solid lines) of 1 mM maltose. Note that mutation T203V decreases the fluorescence of both the apo-state and the saturated state of MBP311-cpGFP.L2-NP. (d) Titration of maltose for MBP311-cpGFP.L2-NP (filled squares), and MBP311-cpGFP.L2-NP+T203V (filled circles). Affinities for each protein are the same, but with ΔF/F slightly increased for the T203V variant.

As shown in FIG. 23, in the context of EcMBP165-cpGFP.PPYF, the T203V mutation decreases the fluorescence emission of the apo-state by half (FIG. 23A), while saturated fluorescence and affinity are unchanged (FIG. 23B), increasing ΔF/F to 6.5. In the maltose-saturated state, PPYF itself has about a quarter the brightness of EGFP, and half the brightness of cpGFP.

In the context of EcMBP311-cpGFP.L2-NP, the T203V mutation decreases the brightness of both the apo-state and the saturated-state equally, resulting in no significant change in ΔF/F (FIGS. 23C and D).

These results indicate that the benefits of the T203V mutation are not universally transferable, and that cpGFP-based fluorescent sensors need to be optimized individually.

Example 2: Maltotriose Indicators

Figure 2:
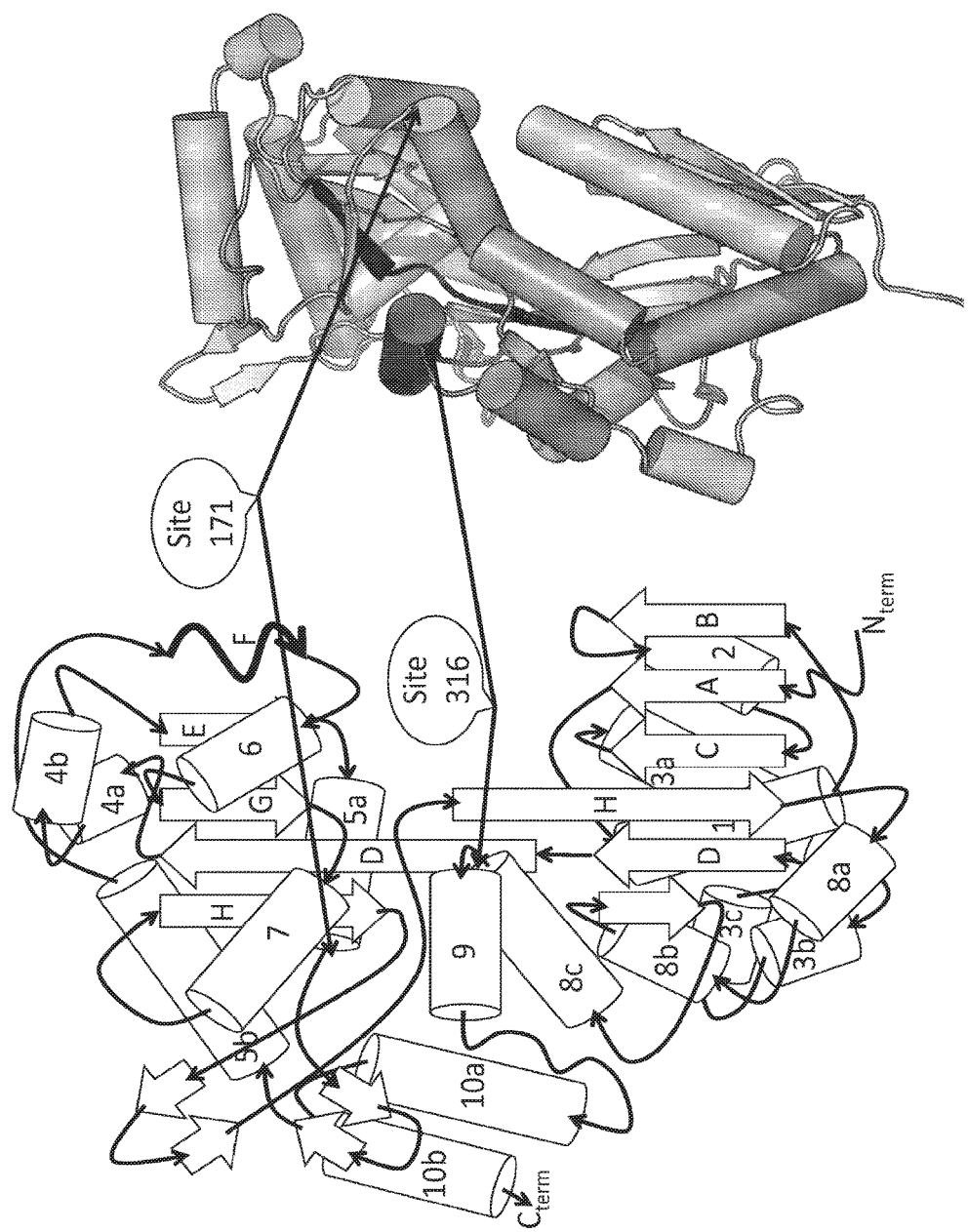
FIG. 2|Cartoon representation showing ligand bound *Pyrococcus furiosus* maltotriose binding protein (PfMBP) and potential cpFP insertion sites.

Genetically encoded maltotriose indicators were created using *Pyrococcus furiosus* maltotriose binding protein. As described below, only the structure of the ligand-bound state *P. furiosus* maltotriose binding protein (PfMBP) is available. As shown in FIGS. 1 and 2, PfMBP is homologous to EcMBP (compare FIGS. 1 and 2). Two sensors were made, PfMBP171 and PfMBP316, the insertion points for which were selected based on homology to EcMBP165 and EcMBP311, respectively. Linkers were optimized. PfMBP sensors have a ΔF/F of ~1.2.

*Pyrococcus furiosus* is a thermophilic organism. Proteins from thermophiles have been shown to be more amenable to mutation than those from mesophiles (Bloom et al., Proc. Natl. Acad. Sci., 103:5869-5874, 2006). As an alternative to developing new sensors by inserting cpGFP into PBPs, it should also be possible to generate new sensors by changing the ligand-binding specificity of an existing PBP-based sensor.

It has previously been shown that the binding sites of PBPs can be reengineered to accommodate novel ligands (Looger et al., Nature, 423:185-190, 2003). However, those re-design efforts used framework proteins from mesophiles and suffered from poor stability. We hypothesized that PfMBP, which is intrinsically more stable than EcMBP, is more tolerant of mutations. To test this hypothesis, we characterized and compared the stability of PfMBP to EcMBP, PfMBP-cpGFP sensors to EcMBP-cpGFP sensors, PfMBP binding site mutants to EcMBP binding site mutants, and PfMBP-cpGFP sensor binding site mutants to EcMBP-cpGFP sensor binding site mutants. Conclusively, the PfMBP variants were more stable than the EcMBP variants. Finally, we demonstrate that the increased thermo-stability of the PfMBP-cpGFP sensors is useful for the measurement of maltotriose at temperatures as high at 60° C., whereas the EcMBP-cpGFP sensors are only useful for the measurement of maltose at temperatures as high as 40° C.

Example 2A: Identification of cpGFP Insertion Sites in PfMBP

The ligand-bound (closed) structure of PfMBP is available (Evdokimov et al., J. Mol. Biol., 305:891-904, 2001), but the unbound structure is not. Accordingly, insertion sites for the PfMBP-cpGFP sensors were identified by homology to EcMBP.

Figure 24A:
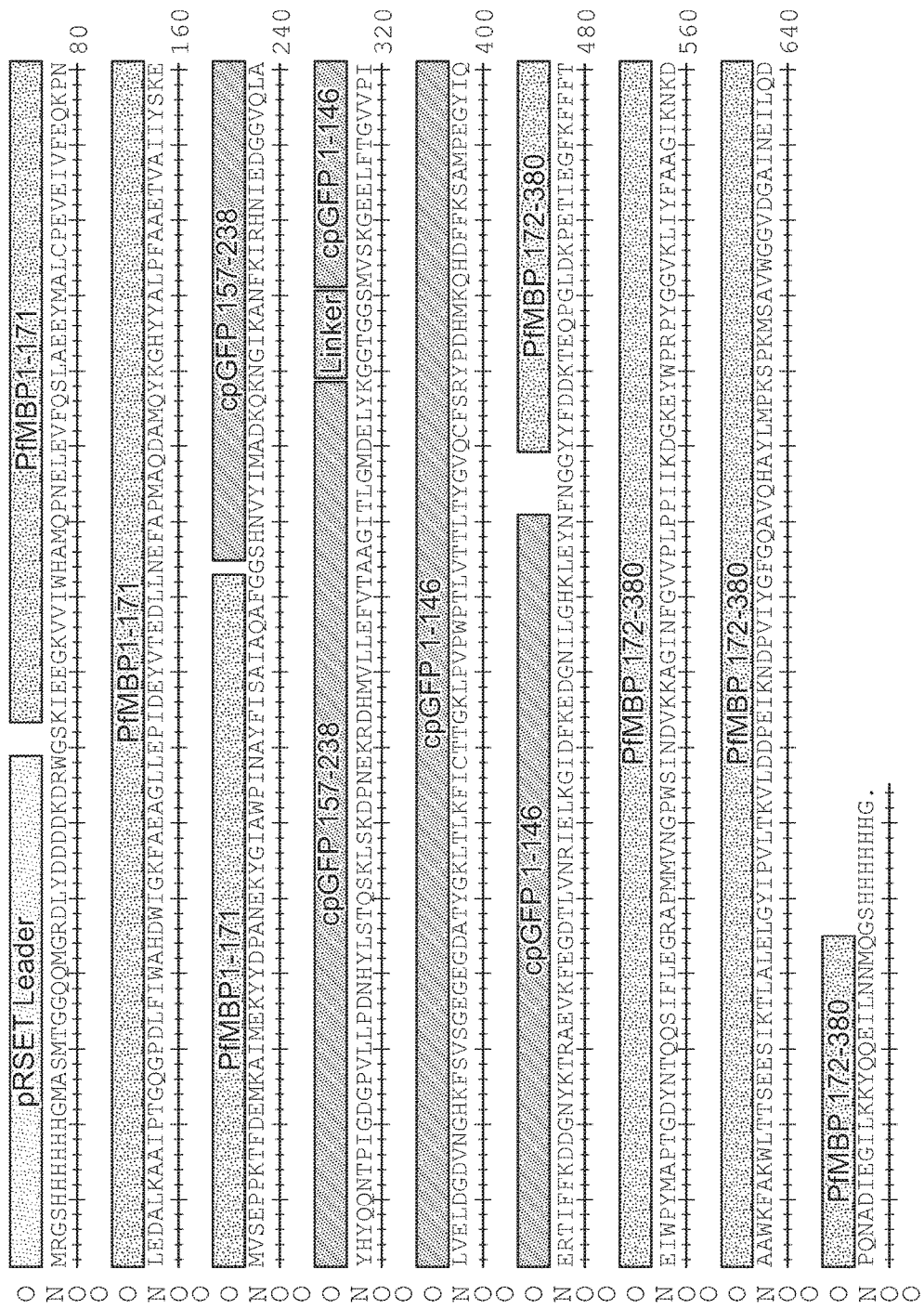
FIG. 24A|Amino acid sequence of PfMBP171-cpGFP (SEQ ID NO:50)

Sites were selected based on the structural similarities between PfMBP and EcMBP. Two sites were selected. One of these sites is EcMBP311, which is homologous to PfMBP316. This site is at juncture between the end of the cluster of helices (Helices 8a, 8b, 8c) and the start of the "equatorial" spanning helix (Helix 9). Another site that was made into a sensor in EcMBP was EcMBP165, which is homologous to PfMBP171. cpGFP was inserted into PfMBP at each of these sites. The sequences of the resulting constructs, PfMBP171-cpGFP and PfMBP316-cpGFP, are shown in FIGS. 24 and 25, respectively.

Example 2B: Linker Optimization

Libraries of variants of SEQ ID NOs: 50-53 were generated with randomized linkers by single-stranded uracil template mutagenesis using the primers listed below:

```
175 Linker 1 Primers:
AIAQAFxxSHNVYIMA            (SEQ ID NO: 54)

AIAQAFPxSHNVYIMA            (SEQ ID NO: 55)

171 Linker 2 Primers:
KLEYNFNxxYYFDDKTE           (SEQ ID NO: 56)

316 Linker 1 Primers
VLDDPExxHNVYIM              (SEQ ID NO: 57)

VLDDPEIxxSHNVYIM            (SEQ ID NO: 58)

316 Linker 2 Primers
KLEYNFxxNDPVIY              (SEQ ID NO: 59)

KLEYNFNxPKNDPVIY            (SEQ ID NO: 60)

KLEYNFNPxKNDPVIY            (SEQ ID NO: 61)
```

Where "x" indicates that a degenerate primer (with DNA sequence "NNS") was used to encode all 20 possible amino acids.

Several thousand variants were screened in semi-high-throughput fashion, measuring fluorescence intensity of clarified cell lysate in the absence and presence of 1 mM maltotriose.

Figures 26A, 26B:
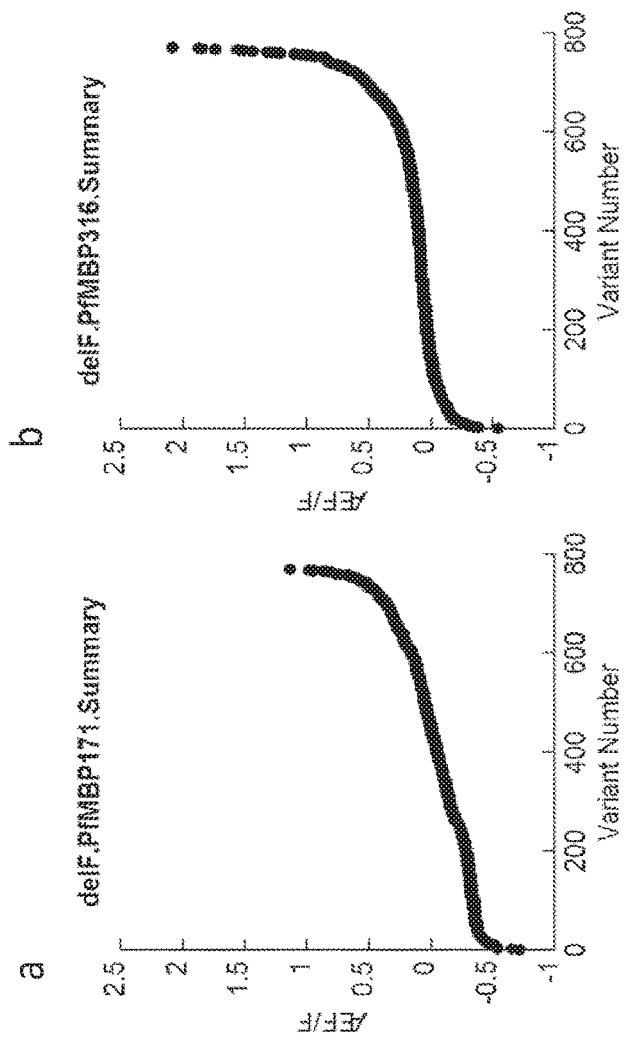
FIG. 26A-26B|Plot of ΔF/F for clarified lysate screen of cpGFP linker-screens at insertion points 171 (A) and 316 (B).

Screening a fully-degenerate, length-two library ("XX") at either the PfMBP171-cpGFP linker (linker 1) or the cpGFP-PfMBP linker (linker 2) yielded proteins with maltotriose-dependent fluorescent increases >100% or decreases >20% (FIG. 26A). A variant from this group with a GlyGly PfMBP-cpGFP linker and a PheGlu cpGFP-PfMBP linker was selected for further characterization. This variant, called "PfMBP171-cpGFP.L2FE" has a ΔF/F=1.2, a Kd for maltotriose of <1 μM.

Screening a fully-degenerate, length-two library ("XX") at either the PfMBP316-cpGFP linker (linker 1) or the cpGFP-PfMBP linker (linker 2) also yielded proteins with maltotriose-dependent fluorescent increases >100% or decreases >20% (FIG. 26B). A variant from this group with a GlyGly PfMBP-cpGFP linker and a PheGlu cpGFP-PfMBP linker was selected for further characterization. This variant, called "PfMBP316-cpGFP.L1-NP" has a ΔF/F=1.2, a Kd for maltotriose of 40 μM.

These data support that structurally homologous frameworks can be compared to identify insertion sites for cpGFP.

Example 2C: Characterization of the Thermostability of the PfMBP and PfMBP-cpGFP Compared to EcMBP and EcMBP-cpGFP Thermal stability of PfMBP171-cpGFP.L2FE was measured using circular-dichroism (CD) and compared to the original EcMBP and PfMBP binding proteins, along with cpGFP. Following the changes by means of CD allowed determination of whether different transitions happened in alpha, beta, or both kinds of structures.

Figures 27A, 27B, 27C, 27D:
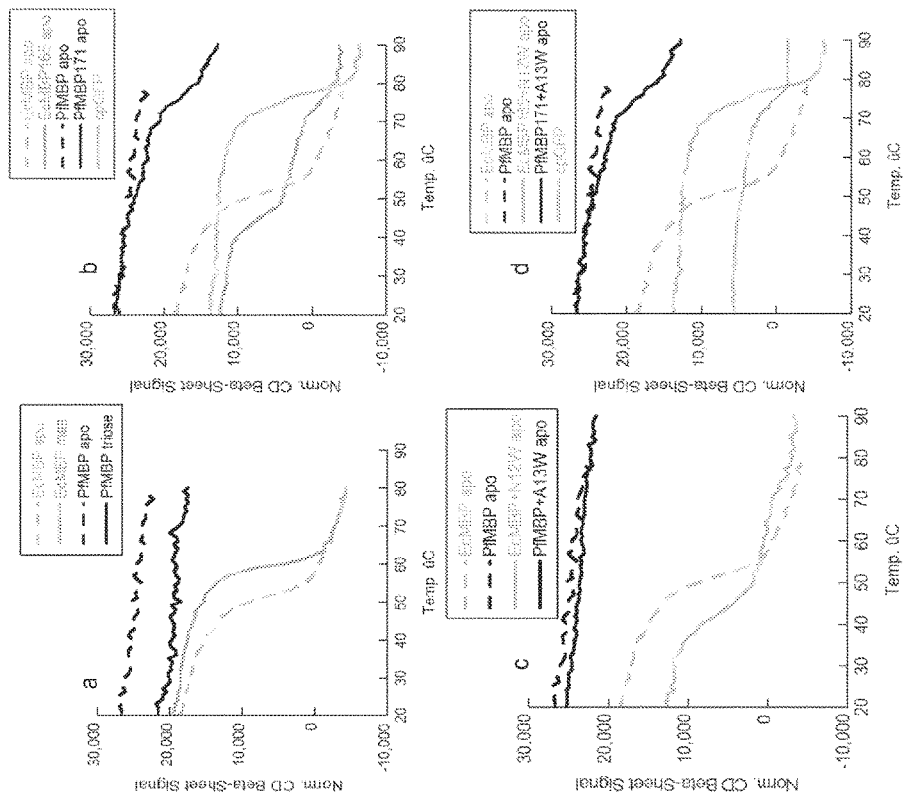
FIGS. 27A-27D|Plot of Beta-sheet circular dichroism (CD) signal as a function of temperature.

Given that cpGFP is a beta barrel, strong transitions in the beta signal alone were associated with changes in this kind of structure. In the same way, transitions in both kinds of signals were associated with the binding protein structure. As shown in FIG. 27A, PfMBP is significantly more thermostable than EcMBP. In fact, while EcMBP denatured at about 50° C., PfMBP did not denature at temperatures less than 80° C. Also, the addition of maltose to EcMBP stabilized the protein by about 10° C.

As shown in FIG. 27B, the stability of the EcMBP component of the EcMBP165-cpGFP.PPYF sensor decreased from 50° C. to 45° C. with insertion of cpGFP, while the intrinsic stability of cpGFP in the sensor remained unchanged. There was little change in the stability of the PfMBP component of the PfMBP171-cpGFP.L2FE sensor with insertion of cpGFP (FIG. 27B). Moreover, PfMBP seemed to exert a small stabilizing effect over the inserted cpGFP, as shown by the change in the steepness and melting point of the curve of the soluble form and the PfMBP171-cpGFP.L2FE sensor. All the associations made between transitions and domain unfolding were supported by CD spectra taken at the beginning and the end of each temperature ramp.

Analysis of whether the PfMBP scaffold was more tolerant of mutation than the EcMBP scaffold was also performed. Proof-of-principle mutations were made to the ligand-binding sites of EcMBP and PfMBP, and their respective sensors. In EcMBP, Asn12 was mutated to Trp to result in steric clashes with the surrounding residues, and backbone, of the binding pocket. The homologous mutation in PfMBP is Ala13Trp, which would be expected to have the same effect.

As shown in FIG. 27C, N12W decreased the Tm of EcMBP from 50° C. to 40° C., while the corresponding mutation in PfMBP, A13W, had no noticeable effect. This data confirms that the thermo-philic protein is more tolerant of mutations to the binding site. Furthermore, in the context of the sensors, the N12W mutation to EcMBP165-cpGFP-.PPYF completely destabilized the binding protein component of the sensor (FIG. 27D), while the A13W mutation in PfMBP171-cpGFP.L2FE had no effect on stability (FIG. 27D).

Example 2D: Tolerance of PfMBP Sensor to Increased Temperature

Fluorescence of the protein in the apo and ligand-bound states at was measured at different temperatures.

Figures 28A, 28B:
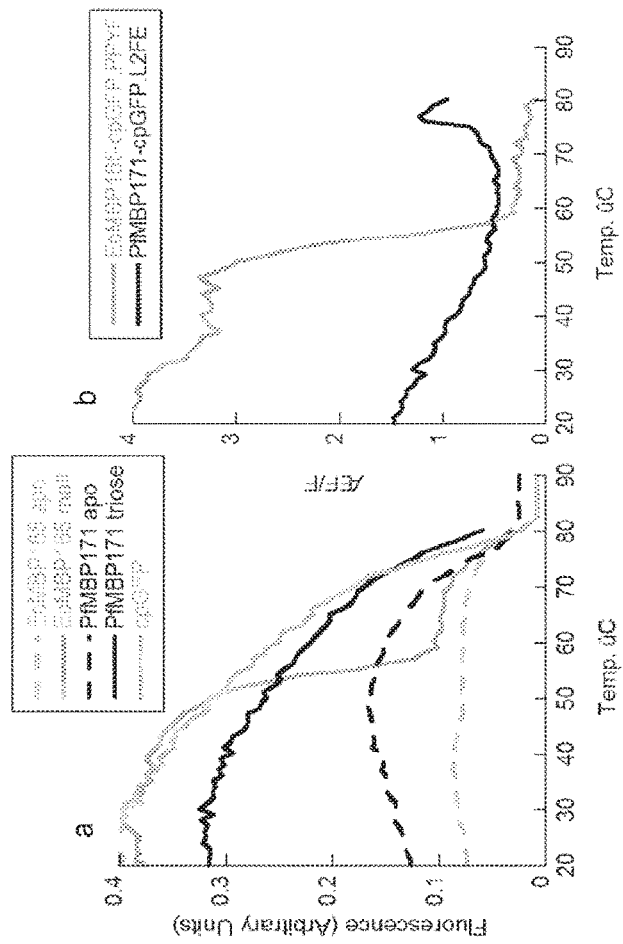
FIGS. 28A-28B|PfMBP Fluorescence vs. temperature. (A) Plot of fluorescence as a function of temperature in the presence (solid) or absence (dashed) of ligand. (B) Plot of ΔF/F as a function of temperature. Using the data from panel (a), ΔF/F for each protein (Fbound-Fapo/Fapo) was calculated for each temperature.

As shown in FIG. 28A, fluorescence of the EcMBP165-cpGFP.PPYF sensor in the bound state was higher than it is in the apo-state at lower temperatures, by about 4-fold. However, at around 55° C. (the unfolding transition of the EcMBP component) the fluorescence of the EcMBP165-cpGFP.PPYF sensor dropped precipitously. As a result, EcMBP165-cpGFP.PPYF is unsuitable for detection of maltose at temperatures greater than 50° C. (FIG. 28B). In contrast, PfMBP171-cpGFP.L2FE retained its maltotriose binding capabilities at high temperatures (FIGS. 28A and 28B), and is limited only by the intrinsic fluorescence of the cpGFP component, which decays at about 80° C. (FIG. 28A).

Example 2E: Measurement of Maltodextrins in Hot Liquids

Figures 28C, 28D, 28E:
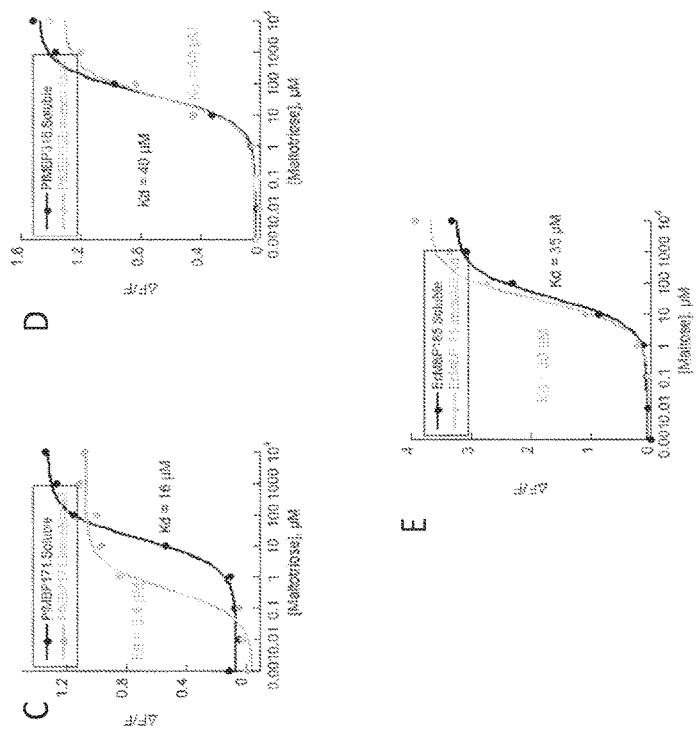
FIGS. 28C-28E|Line graphs showing the function of immobilized and soluble proteins.

To demonstrate that the soluble and immobilized sensors function similarly, PfMBP171-cpGFP.L2FE, PfMBP316-cpGFPL1XXX, and EcMBP165-cpGFP.PPYF.T203V were immobilized via their N-terminal poly-histidine tags on to the surface of Ni-NTA coated glass. In a fluorescence plate reader, the immobilized proteins performed similarly to their soluble counterparts (see FIGS. 28C, 28D, and 28F).

Next, a prototype device was constructed, with a light guide providing the excitation light and returning the fluorescent emitted light back to the photodetector, the biosensor protein immobilized to Ni-NTA coated coverslips, and the coverslip attached to the end of the light guide. The "wand" of the detector was dipped into different compositions of solutions, each with varying concentrations of maltose or maltotriose. Experiments were performed at different temperatures. PfMBP-cpGFP sensor performed better at higher temperatures (as high as 60° C.) than the EcMBP-cpGFP sensor.

Example 3: Glutamate Indicators

Figure 3:
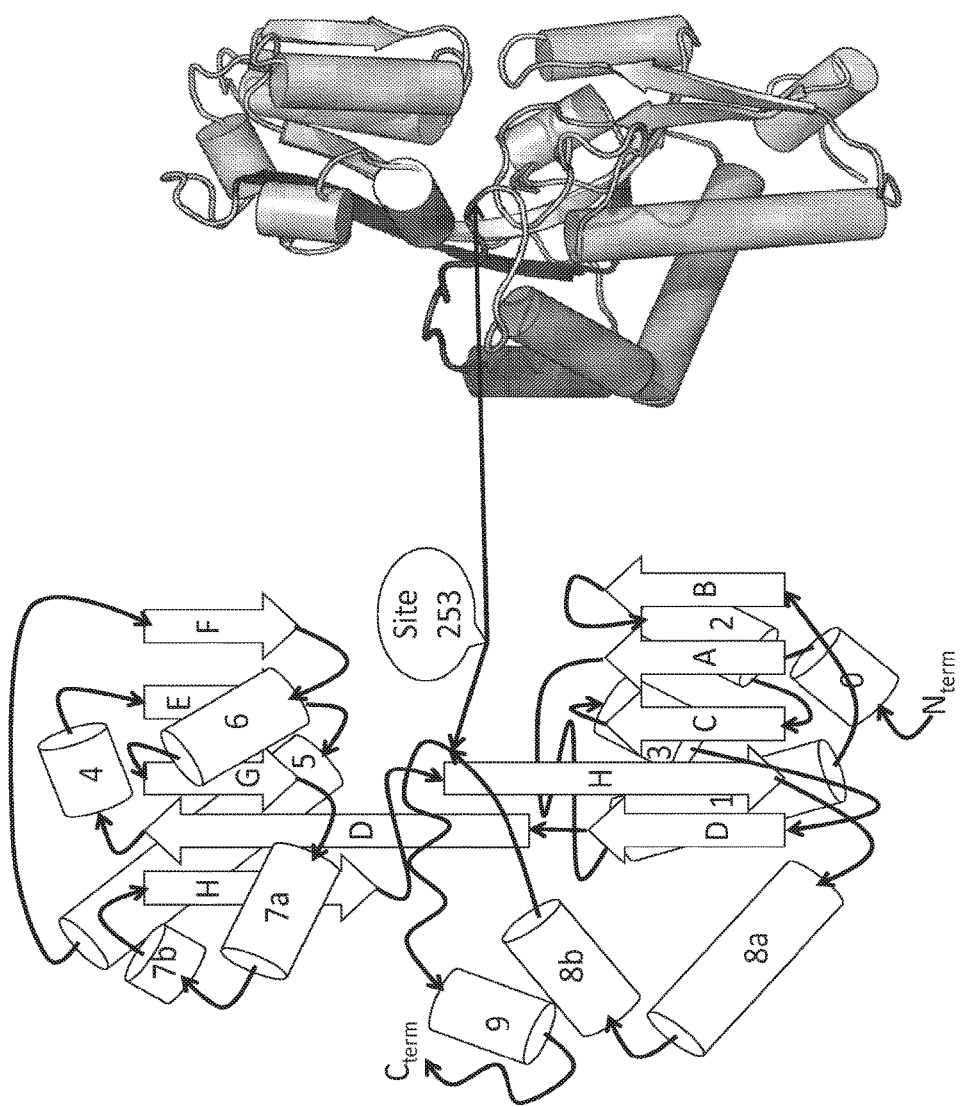
FIG. 3|Cartoon representation showing ligand bound *E. coli* glutamate-binding protein (EcYbeJ) and potential cpFP insertion sites.

Glutamate indicators were created from *Escherichia coli* glutamate-binding protein (EcYbeJ). As with PfMBP in Example 2, only the structure of the ligand-bound EcYbeJ is available. EcYbeJ is homologous to EcMBP, but to a lesser degree. The best homology match between a site in EcYbeJ and a site in a binding protein for which an intensity-based sensor has already been created is EcYbeJ253 and EcMBP311 (described herein). As shown in FIG. 3, both sites are at the junction of "Rising Helix 8" and the "Equatorial Helix/Coil." The amino acid composition of the cpGFP and EcYbeJ junction was made the same as that of the EcMBP311-cpGFP sensor (Linker 2=NP). The amino acid composition of the EcYbeJ junction and cpGFP was optimized to LV (Linker 1=LV). The variant has a ΔF/F of 5.

Example 3A: Identification of cpGFP Insertion Sites

The ligand-bound (closed) structure of *Shigella flexneri* glutamate binding protein is available (Fan et al., Protein Pept. Lett., 13:513-516, 2006). This protein has only 4 amino acid mutations relative to EcYbeJ, and is thus an appropriate model.

Insertion sites for the EcYbeJ-cpGFP sensors were identified by homology to EcMBP. Based on the topology map (FIG. 3), position 311 in EcMBP was identified as an acceptable insertion site for EcYbeJ. EcMBP311 is equivalent to EcYbeJ253. EcYbeJ253 is at juncture between the end of the cluster of helices (Helices 8a, 8b, 8c) and the start of the "equatorial" spanning helix (Helix 9). In YbeJ, the structure that is homologous to the equatorial helix is the equatorial coil (depicted in red, to match the red coloring of Helix 9).

Figure 29A:
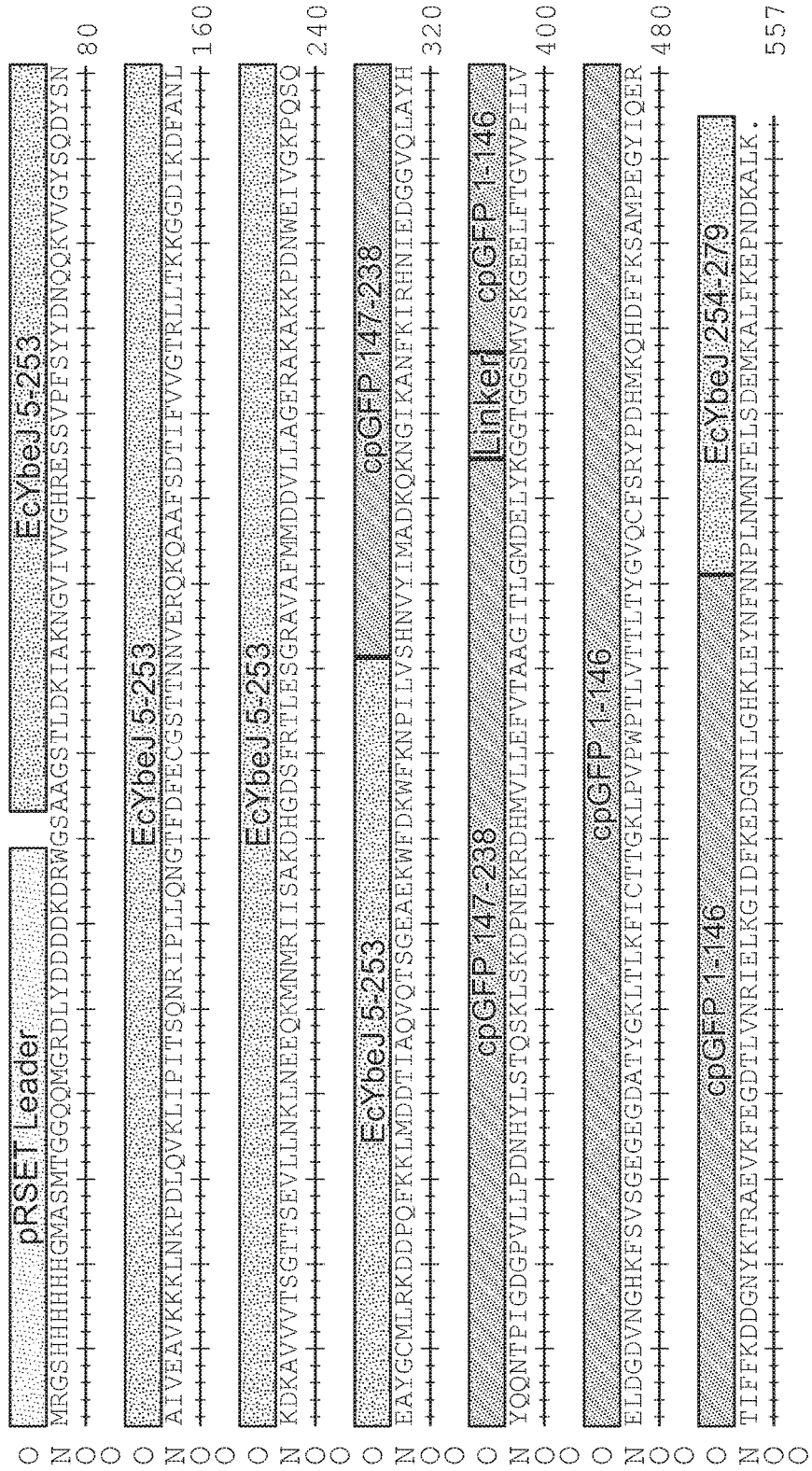
FIG. 29A|Amino acid sequence of EcYbeJ253-cpGFP (SEQ ID NO:62).
Figure 29B:
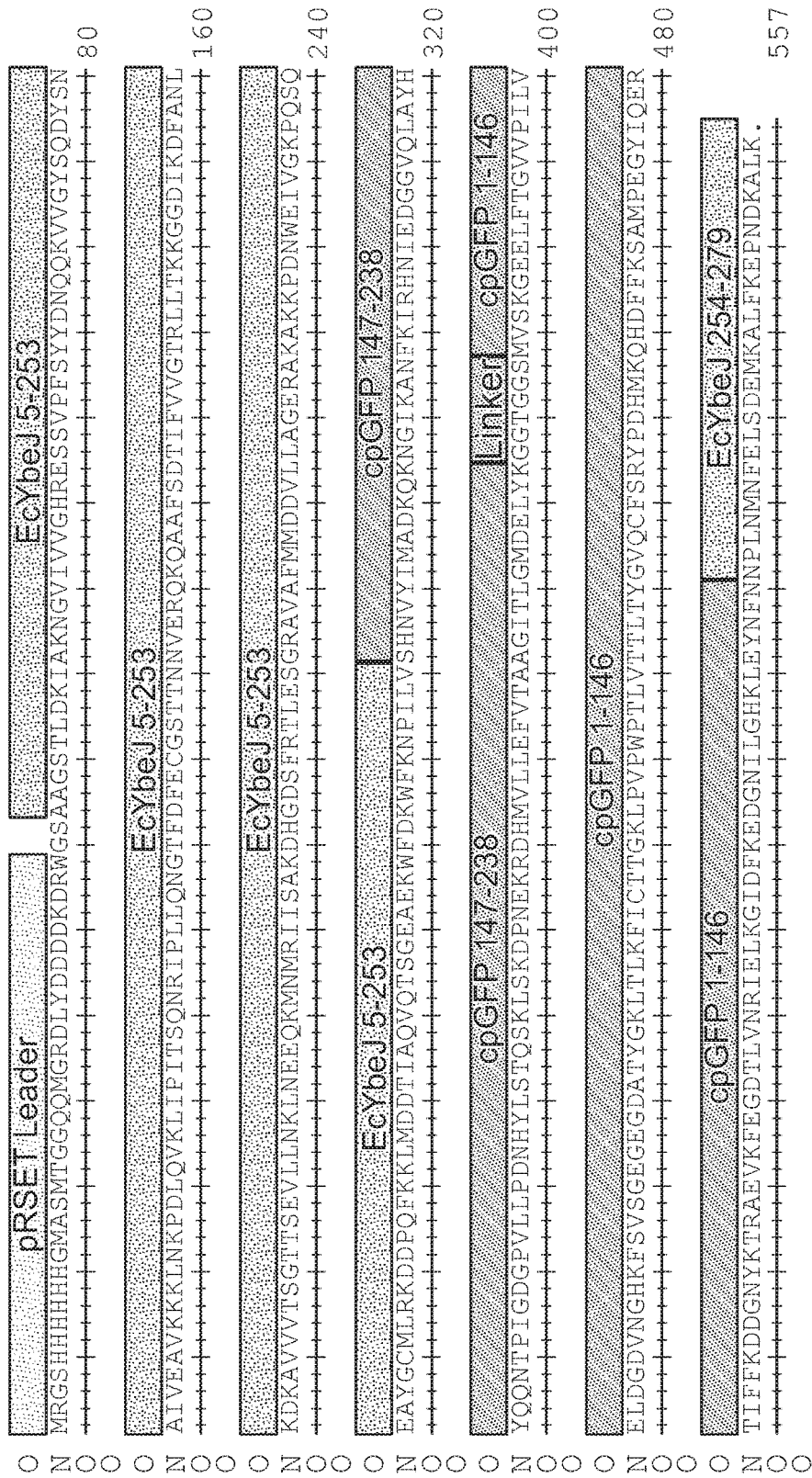
FIG. 29B|Amino acid sequence of EcYbeJ253-cpGFP.L1LVL2NP (SEQ ID NO:63).

Intrinsic affinity of wild-type YbeJ for glutamate (~1 µM) was too high to permit high-throughput screening of linker libraries. Endogenous glutamate (from the growth media) saturates the sensor, making measurement of the unbound state technically challenging. A mutation to YbeJ (A184V), in the "hinge" of the protein were made. Mutation of this residue to Trp or Arg have previously been shown to decrease affinity in FRET-based sensors (see Okumoto et al., Proc. Natl. Acad. Sci., 102:8740-8745, 2005). EcYbeJ253 (A184V)-cpGFP has an affinity for glutamate of about 100 µM. All references to EcYbeJ253-cpGFP, unless otherwise noted, refer to the A184V variant. The sequences of the EcYbeJ constructs are shown in FIG. 29.

Example 3B: Linker Optimization

Libraries of variants of SEQ ID NOs: 62-63 were generated with randomized linkers by single-stranded uracil template mutagenesis using the primers listed below:

```
253 Linker 1 Primers:
FKNPIPPxSHNVYIMA            (SEQ ID NO: 64)

FKNPIPPxxSHNVYIMA           (SEQ ID NO: 65)

FKNPIPPPxSHNVYIMA           (SEQ ID NO: 66)

FKNPIPPxPSHNVYIMA           (SEQ ID NO: 67)

KWFKNPIxxSHNVYIMA           (SEQ ID NO: 68)

FKNPIPPxxNVYIMAD            (SEQ ID NO: 69)

KWFKNPIxxNVYIMAD            (SEQ ID NO: 70)

253 Linker 2 Primers:
KLEYNFNxKNLNMNF             (SEQ ID NO: 71)

KLEYNFNxxKNLNMNF            (SEQ ID NO: 72)

KLEYNFNxPKNLNMNF            (SEQ ID NO: 73)

KLEYNFNPxKNLNMNF            (SEQ ID NO: 74)

GHKLEYNxxLNMNF              (SEQ ID NO: 75)

KLEYNFNxxLNMNF              (SEQ ID NO: 76)
```

Where "x" indicates that a degenerate primer (with DNA sequence "NNS") was used to encode all 20 possible amino acids.

Several thousand variants were screened in semi-high-throughput fashion, measuring fluorescence intensity of clarified cell lysate in the absence and presence of 10 mM glutamate.

Figure 30:
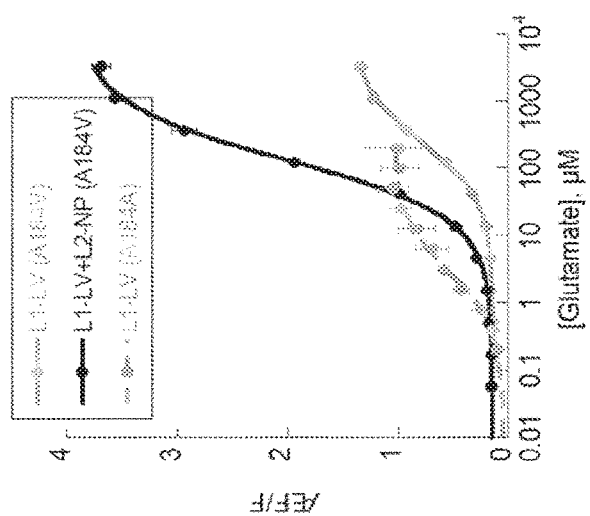
FIG. 30|EcYbeJ binding curves. Plot of ΔF/F as a function of [Glutamate], µM. The first generation sensor, EcYbeJ253.L1-LV (with the A184V) mutation (grey, solid) has an affinity for glutamate of about 100 µM and a ΔF/F of 1.2. The reversion of that affinity mutation, V184A, in the L1-LV background increases affinity to 1 (grey dashed). The second generation sensor, with the L2-NP linker optimization and the A184V mutation, has a ΔF/F of at least 4 and an affinity for glutamate of about 100 µM (black solid).

Screening a fully-degenerate, length-two library ("XX") at the EcYbeJ253-cpGFP linker (linker 1) identified a sensor with glutamate-dependent fluorescent increases of ~100%. This variant has a LeuVal EcYbeJ-cpGFP linker (L1-LV) and was used as the framework for optimization of the cpGFP-EcYbeJ253 linker (linker 2). The results of that screen yielded a protein with glutamate-dependent fluorescent increase of ~500% and a linker 2 composition of AsnPro. As shown in FIG. 30, this variant, called "EcYbeJ253-cpGFP.L1LVL2NP" has a ΔF/F=5, a Kd for glutamate of 100 μM. Interestingly, the composition of the second linker, AsnPro, is the same as the linker composition of EcMBP311-cpGFP.L2NP.

Example 3C: Detection of Extracellular Glutamate

EcYbeJ253-cpGFP.L1LVL2NP was cloned into the pDisplay™ vector to allow targeting and anchoring of the sensor to the plasma membrane. The resulting construct was transfected into cultured mammalian cells (HEK293) to visualize the addition of glutamate to extracellular media. Constructs were also generated in a bacterial expression vector with the epitope tags individually and in combination.

Figure 31:
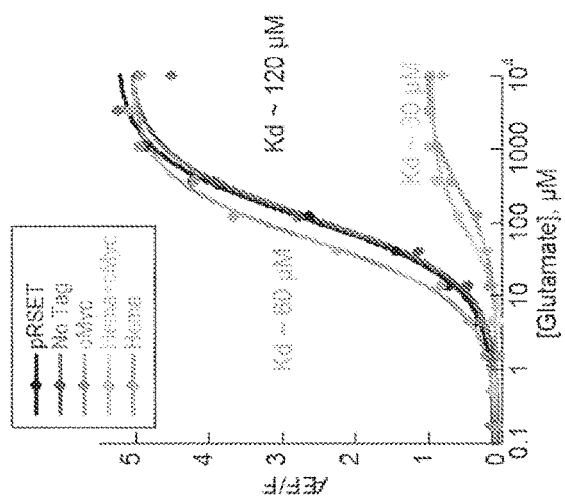
FIG. 31|EcYbeJ Hema/cMyc analysis. The effect of N- and C-terminal tags on ΔF/F and glutamate affinity were determined by expressing variously tagged versions of the EcYbeJ253.L1LVL2NP protein in bacteria. The presence of the pRSET leader sequence (black) has no effect on ΔF/F (~5) or affinity (~120 when compared to the version without a tag (grey). The addition of the cMyc tag to the C-terminus retains ΔF/F and increases affinity slightly, to 60 µM. The addition of the N-terminal hemagglutinin tag, with (green) or without (orange) the cMyc tag, decreases ΔF/F substantially.
Figures 32A, 32B:
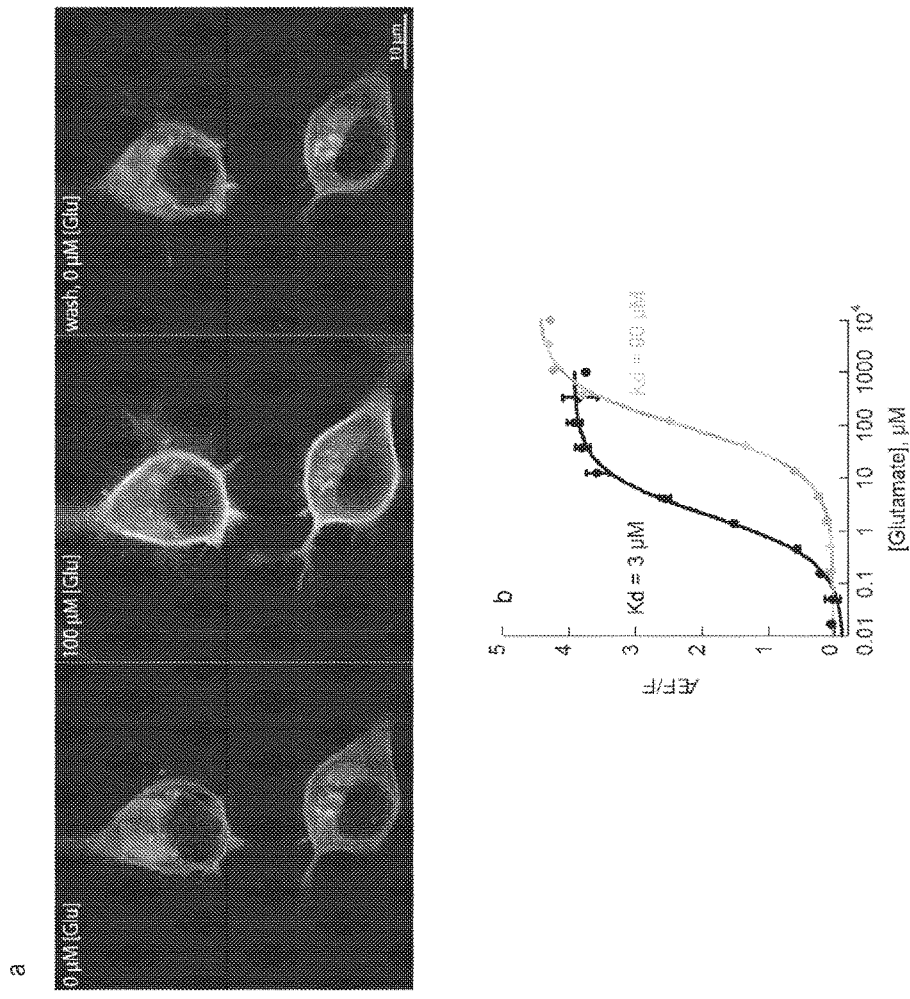
FIGS. 32A-32B|EcYbeJ253-cpGFP.L1LVL2NP.pMinDis expressed in HEK293 cells. (A) Images of the sensor expressing HEK cells in the absence of glutamate (left), with 100 µM glutamate (center), and re-imaged after wash-out of glutamate with buffer (right). (B) By measuring the equilibrium ΔF/F with different concentrations of glutamate in the buffer, an in situ binding affinity (black) can be obtained. The surface displayed sensor has a higher affinity (3 µM) for glutamate than the soluble sensor (grey), which is about 90 µM.

As shown in FIG. 31, the hemagglutinin tag interferes with the fluorescence change. EcYbeJ253-cpGFP.L1LVL2NP was re-cloned into a derivative of the pDisplay™ vector, lacking the hemagglutinin tag, called pMinDis (for Minimal Display). This new construct, when expressed in HEK293 cells, shows a change in fluorescence intensity under 2-photon excitation that is approximately the same as the soluble protein (see FIG. 32) with higher affinity, of about 1 (see FIG. 32).

Figure 33:
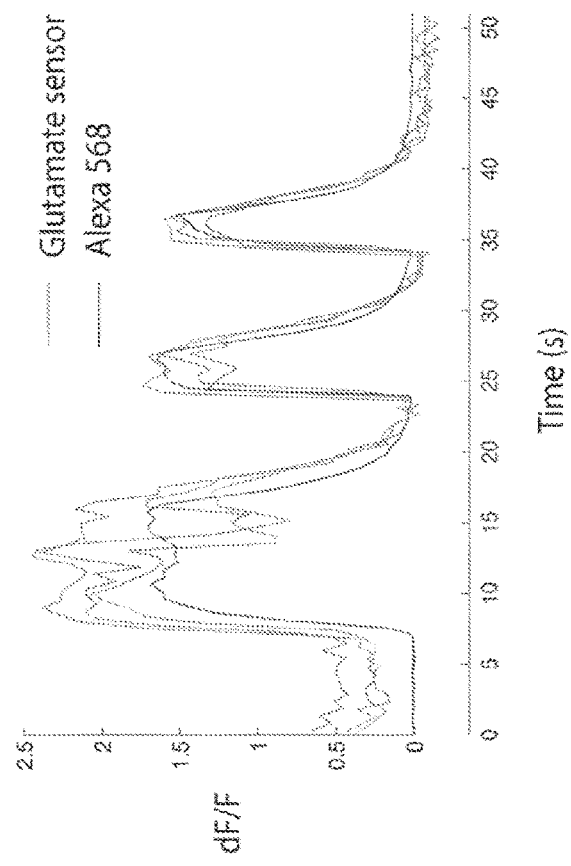
FIG. 33|EcYbeJ253-cpGFP.L1LVL2NP.pMinDis expressed in neuronal culture, and responds rapidly to added glutamate (green). Red shows signal of 2.5 nM Alexa Fluor® 568 (Invitrogen, Carlsbad, Calif.), also in pipette.

To demonstrate that the sensor is functional in neurons, and not just cultured HEK cells, the gene from EcYbeJ253-cpGFP.L1LVL2NP was cloned into an adeno-associated virus vector (AAV) under control of the synapsin promoter. Virus particles were generated and used to infect cultured primary hippocampus neurons from rats 7 days after culturing. 14 days after culturing (and 7 days after infection), the infected neurons were imaged under 2-photon microscopy (FIG. 33).

Example 4: Phosphonate Indicators

Figure 4:
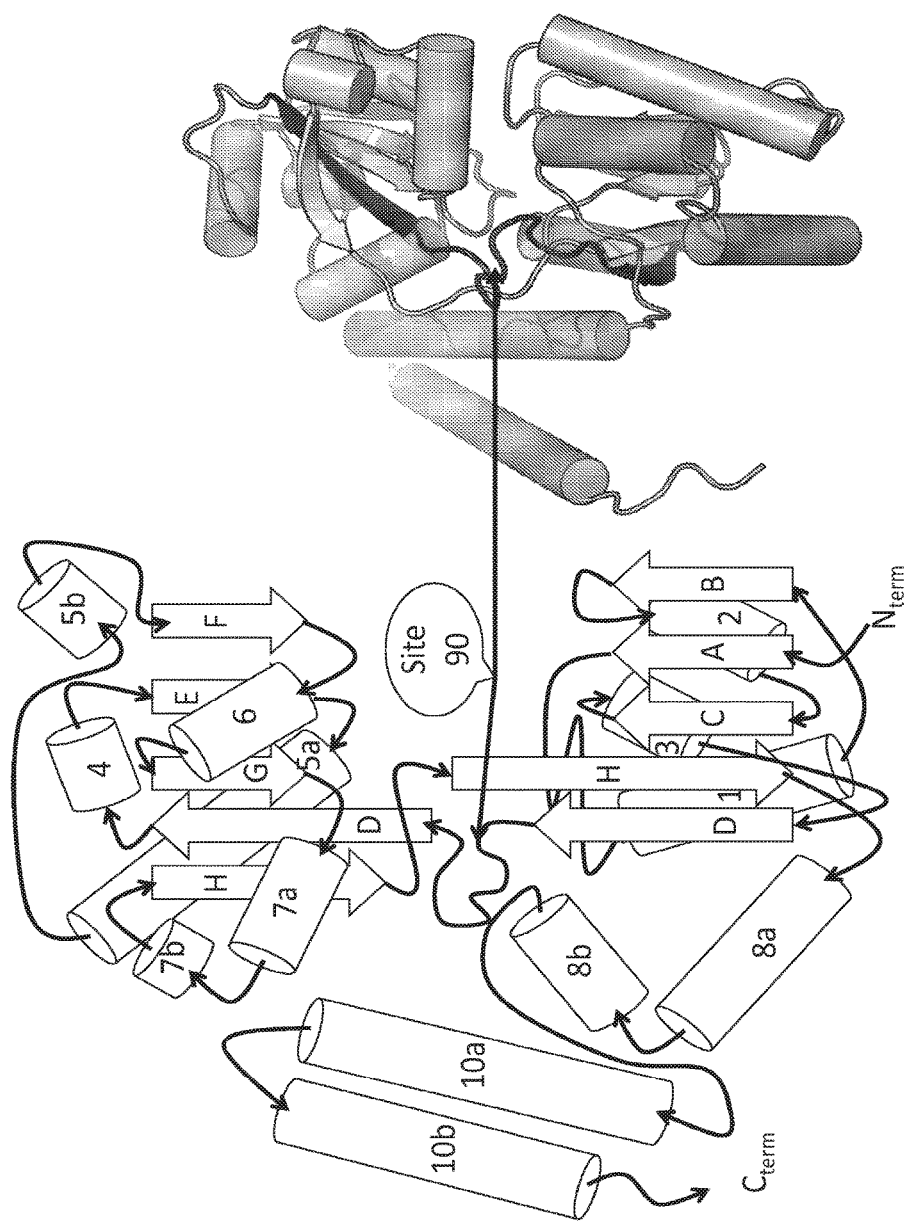
FIG. 4|Cartoon representation showing ligand bound *E. coli* phosphonate-binding protein (EcPhnD) and potential cpFP insertion sites.

An indicator for phosphonate compounds was created from *Escherichia coli* phosphonate-binding protein (EcPhnD). In this instance, only the structure of the ligand-bound state was available at the time the sensor was conceived. EcPhnD is homologous to EcMBP to a lesser degree and to EcYbeJ to a greater degree. The best homology match between a site in EcPhnD and a site in a binding protein for which an intensity-based sensor has already been created is EcPhnD90 and EcYbeJ253. There is no "Rising Helix 8" in EcPhnD, but there is an "Equatorial Helix/Coil" (FIG. 4). cpGFP was inserted at the Equatorial Helix/Coil and linkers were optimized to yield a sensor with ΔF/F of 1.2. EcPhnD is a dimmer, so, a pair of mutations (L297R+L301R) were made to convert it to a monomer. The monomer variant has a ΔF/F of 1.6.

Example 4A: Identification of cpGFP Insertion Sites in EcPhnD

Insertion sites for the EcPhnD-cpGFP sensors were identified using the ligand-bound (closed) structure of EcPhnD by homology to EcMBP. Based on the topology map (FIG. 4), position 311 in EcMBP was identified as an acceptable insertion site in EcPhnD. EcMBP311 corresponds to EcPhnD90. This site is at the point where the rising strand (Strand D) of EcPhnD has a small bend in it that runs equatorial to the rest of the sheets in the protein. Even though it is topologically different from the "equatorial" spanning helix (Helix 9) of EcMBP its equatorial alignment is similar, and with just the closed structure at the time, in an environment that was expected to undergo significant dihedral change upon binding ligand. Sequences of EcPhnD constructs are shown in FIG. 34.

Example 4B: Linker Optimization

Libraries of variants of SEQ ID NOs: 77-78 were generated with randomized linkers by single-stranded uracil template mutagenesis using the primers listed below:

```
90 Linker 1 Primers:
QTVAADGSSHNVYIMA            (SEQ ID NO: 79)

QTVAADxxSHNVYIMA            (SEQ ID NO: 80)

QTVAADxPSHNVYIMA            (SEQ ID NO: 81)

QTVAADPxSHNVYIMA            (SEQ ID NO: 82)

QTVAADxxNVYIMA              (SEQ ID NO: 83)

QTVAADxxSHNVYIMA            (SEQ ID NO: 84)
```

-continued

| VFQTVAxxSHNVYIMA | (SEQ ID NO: 85) |

```
90 Linker 2 Primers:
```
| HKLEYNFNPGYWSVLI | (SEQ ID NO: 86) |
| HKLEYNFNxxPGYWSVLI | (SEQ ID NO: 87) |
| HKLEYNxxPGYWSVLI | (SEQ ID NO: 88) |
| HKLEYNFNxxYWSVLI | (SEQ ID NO: 89) |
| HKLEYNFNPxYWSVLI | (SEQ ID NO: 90) |

Where "x" indicates that a degenerate primer (with DNA sequence "NNS") was used to encode all 20 possible amino acids.

Several thousand variants were screened in semi-high-throughput fashion, measuring fluorescence intensity of clarified cell lysate in the absence and presence of 100 uM 2AEP.

Screening a number of fully-degenerate, libraries at the EcPhnD90-cpGFP linker (linker 1) yielded a protein with 2AEP-dependent fluorescent increases of >100%. This variant has a AlaAsp EcPhnD-cpGFP linker (L1-AD) and a ΔF/F of 1.2. The variant came from a linker that also deleted two residues, effectively making the insertion point of cpGFP occur after residue D88, and then skipping to residue P91 at the cpGFP-EcPhnD linker.

Figures 35A, 35B, 35C:
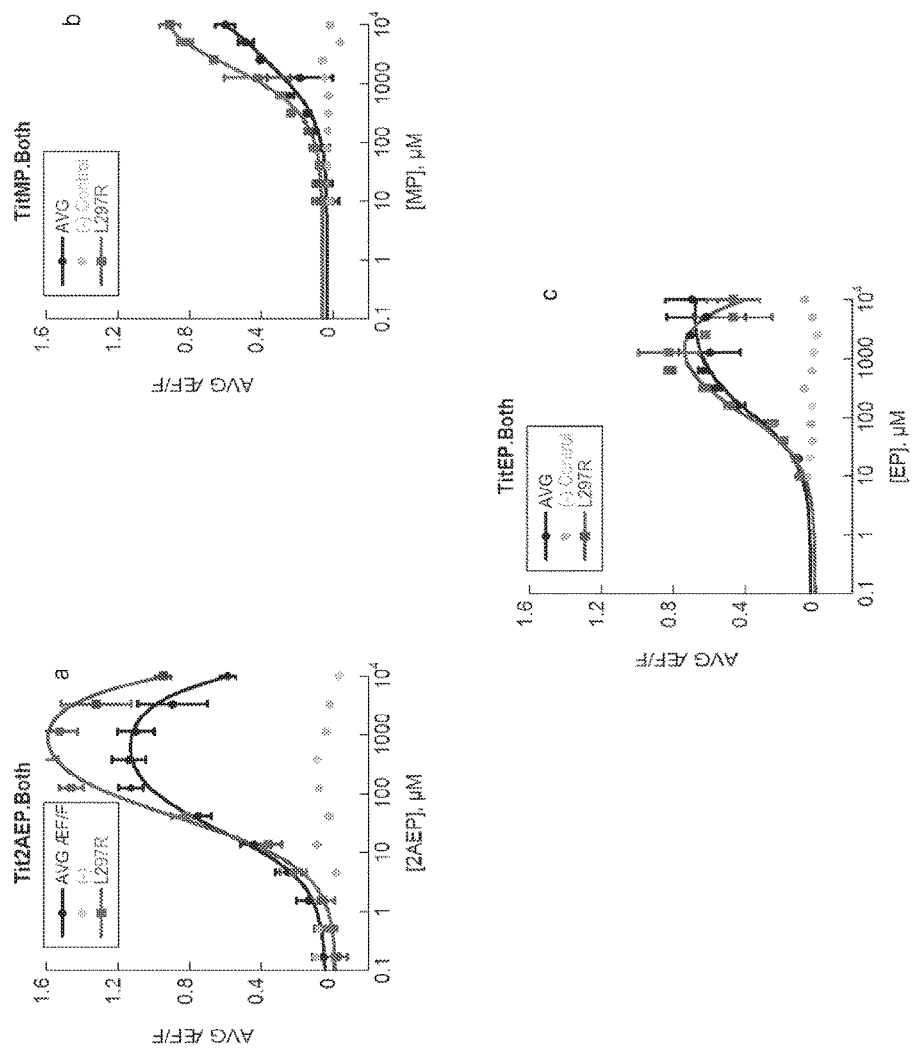
FIGS. 35A-35C|EcPhnD90-cpGFP Binding Curves. For both the L1AD and the L1AD+L297R+L301R variants, binding was determined for (A) 2-aminoethylphosphonate (2AEP), (B) methylphosphonate (MP), and (C) ethylphosphonate (EP).

It was observed from the crystal structure that EcPhnD forms a dimer. To disrupt the dimer inter-face and potentially simplify the observable binding behavior of the EcPhnD protein, two mutations, L297R and L301R, were introduced into the dimerization helices. These mutations were expected, by charge repulsion, to disrupt the dimer interface. As shown in FIG. 35, incorporation of L279R and L301R mutations into EcPhnD90-cpGFP.L1AD caused ΔF/F to increases to 1.6 in response to 2AEP.

Figures 36A, 36B, 36C:
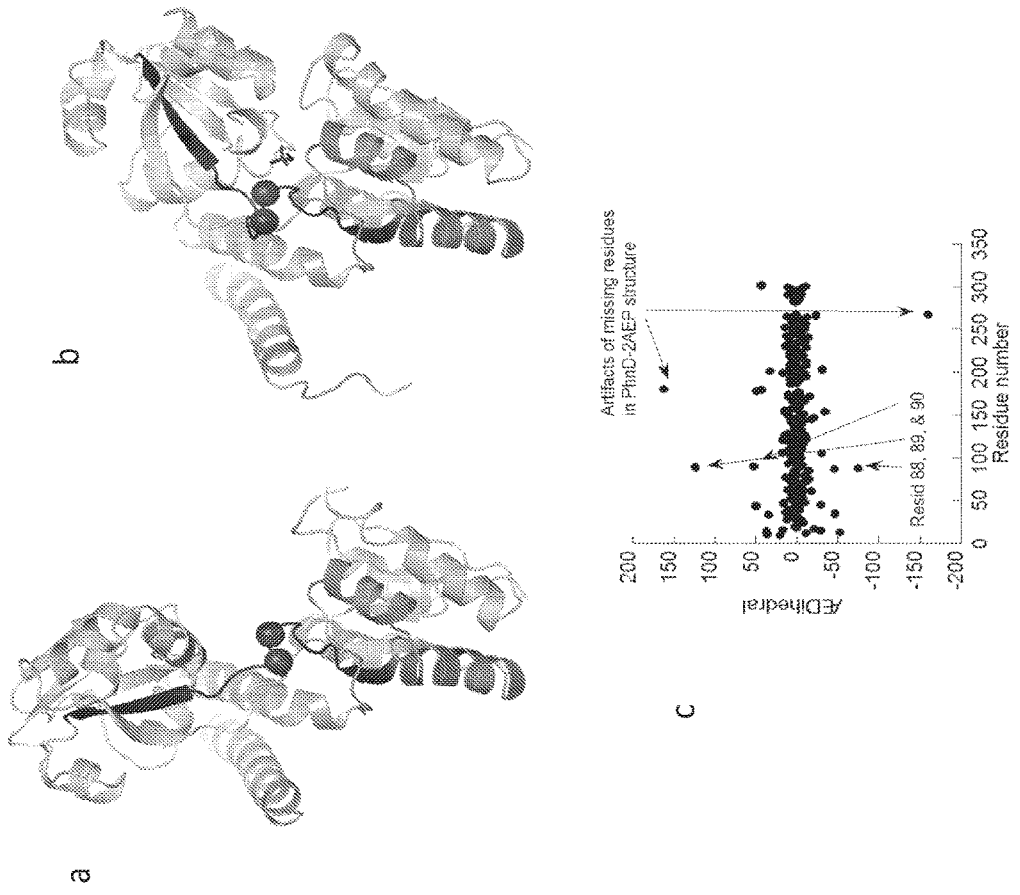
FIGS. 36A-36C|The crystal structures of the ligand-free (A), open state (with H157A mutation to the binding pocket) and the ligand-bound (B), closed state of EcPhnD clearly shows a large conformational change. Residues in between which cpGFP is inserted in EcPhnD90-cpGFP are marked by red spheres, in the equatorial strand (red). (C) Analysis of the change in Cα dihedral (ΔDihedral) clearly shows that residues for which there is the greatest ΔDihedral upon going from the open to the closed state are residues 88 (ΔDihedral=–75°), 89 (ΔDihedral=123°), and 90 (ΔDihedral=52°).

Further attempts to crystallize the open, ligand-unbound form of the protein were successful after making a mutation to the binding site, H157A, that substantially decreased affinity for phosphonate compounds. This mutant was crystallized in the absence of ligand, and the open state of the protein solved. The ΔDihedral analysis (FIG. 36) showed that the region of greatest dihedral change was the group of residues from 88-90, just one amino acid away from the site chosen by homology to the equatorial helix.

These data further indicate that ΔDihedral metric is sufficient for identifying sites in PBPs into which cpGFP can be inserted and result in intensity-based fluorescent sensors.

Example 5: Glucose Indicators

Glucose indicators were created from *Thermus thermophilus* glucose binding protein (TtGBP). In this instance, only the structure of the ligand-bound state is available. TtGBP is very homologous to EcMBP and PfMBP (compare FIG. 5 with FIGS. 1 and 2). The insertion point (TtGBP326) was chosen by homology to EcMBP311 and PfMBP316. The amino acid composition of the cpGFP and TtGBP junction was made the same as that of the EcMBP311-cpGFP and EcYbeJ253 sensors (Linker 2=NP). Linker 1 was optimized (Linker 1=PA) and the TtGBP326 sensor have a ΔF/F of ~2.5. To improve its utility for the measuring glucose concentrations in human blood, the affinity was weakened from its native ~1 μM to 1.5 mM by mutation of two residues in the binding pocket (H66A+H348A).

Example 5A: Identification of cpGFP Insertion Sites in TtGBP

Figure 37B:
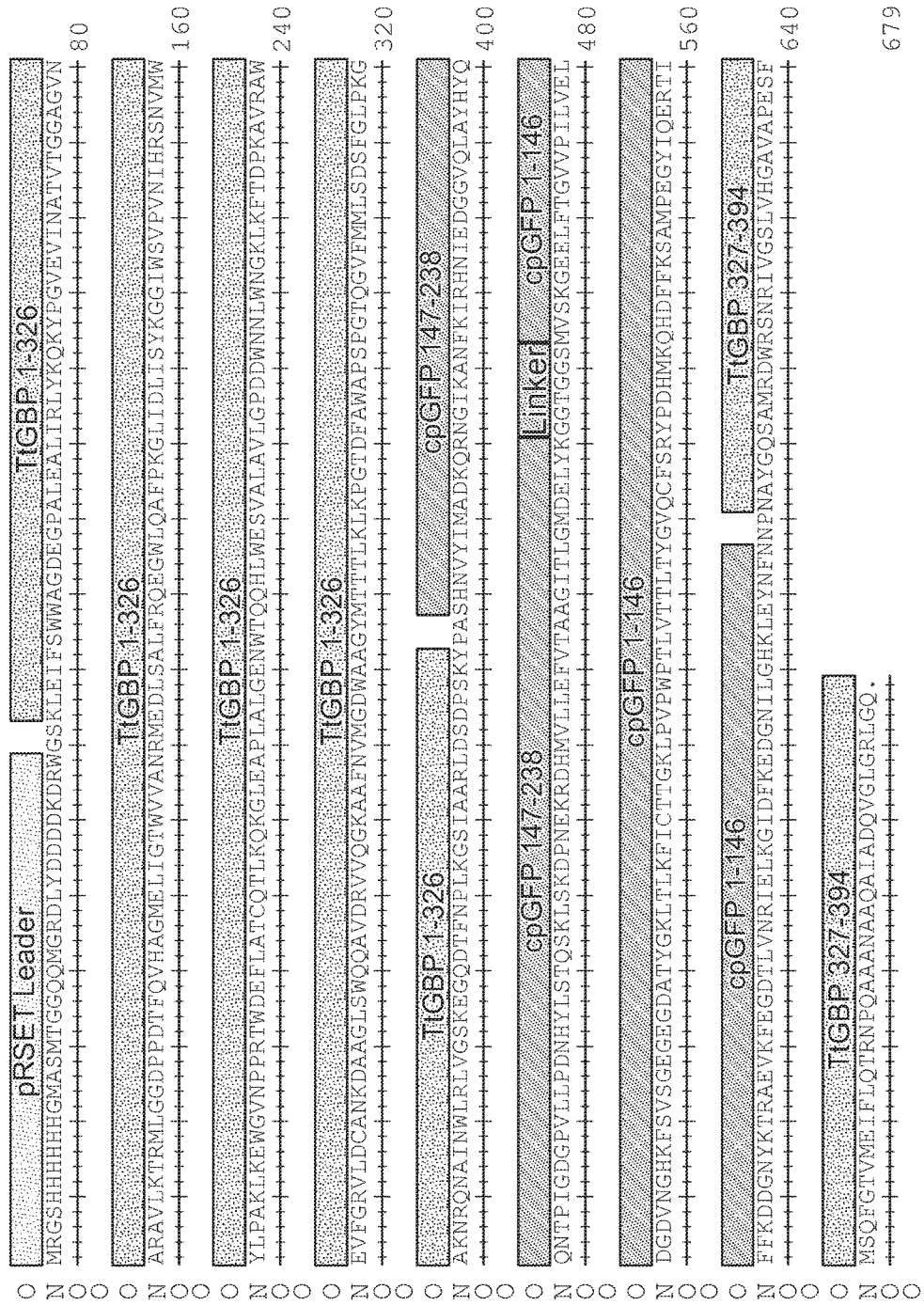
FIG. 37B|Amino acid sequence of TtGBP326.L1-PA (SEQ ID NO:92).

The ligand-bound (closed) structure of TtGBP is available (Cuneo et al., J. Mol. Biol., 362:259-270, 2006). Accordingly, insertion sites for the TtGBP-cpGFP sensors were identified by homology to EcMBP and PfMBP. Based on the topology map (FIG. 5), it is apparent that TtGBP, PfMBP, and EcMBP are structurally similar in the closed, ligand-bound state. Positions in EcMBP determined by the dihedral analysis (see above) were predicted to be acceptable insertion sites in TtGBP. EcMBP311 is homologous to TtGBP326. This site is at juncture between the end of the cluster of helices (Helices 8a, 8b, 8c) and the start of the "equatorial" spanning helix (Helix 9). The amino acid sequence of the TtGBP construct is shown in FIG. 37.

Example 5B: Linker Optimization

Libraries of variants of SEQ ID NO:91 were generated with randomized linkers by single-stranded uracil template mutagenesis using the primers listed below:

```
326 Linker 1 Primers:
```
| DSDPSKYxxSHNVYIM | (SEQ ID NO: 95) |
| DSDPSKYPxSHNVYIM | (SEQ ID NO: 96) |
| DSDPSKYxPSHNVYIM | (SEQ ID NO: 97) |
| RLDSDPSxxSHNVYIM | (SEQ ID NO: 98) |
| DSDPSKYxxNVYIM | (SEQ ID NO: 99) |

```
326 Linker 2 Primers:
```
| KLEYNFNxxNAYGQSA | (SEQ ID NO: 100) |
| KLEYNFxxPNAYGQSA | (SEQ ID NO: 101) |
| GHKLEYNxxNAYGQSA | (SEQ ID NO: 102) |
| KLEYNFNxPNAYGQSA | (SEQ ID NO: 103) |
| KLEYNFNPxNAYGQSA | (SEQ ID NO: 104) |

Where "x" indicates that a degenerate primer (with DNA sequence "NNS") was used to encode all 20 possible amino acids.

Several hundred variants were screen in semi-high-throughput fashion, measuring fluorescence intensity of clarified cell lysate in the absence and presence of 10 mM glucose.

Figure 38:
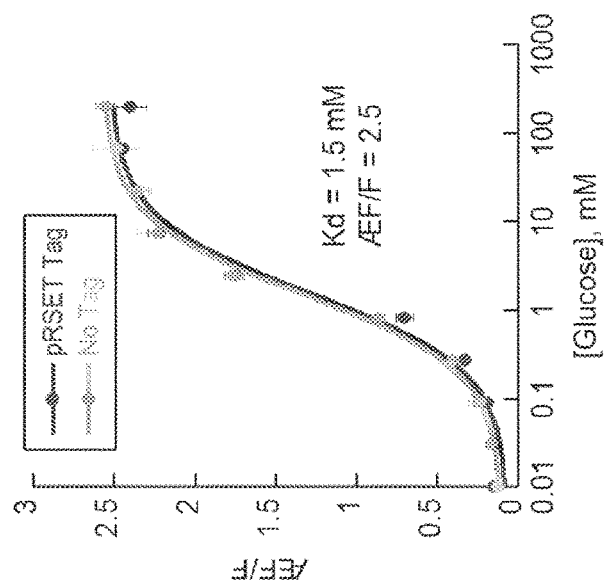
FIG. 38|TtGBP326-cpGFP Binding Curves. Plot of ΔF/F as a function of [Glucose], mM.

Linker 1 was optimized (Linker 1=PA) and the TtGBP326-cpGFP.L1PAL2NP sensor has a ΔF/F of ~2.5 (see FIG. 38). Additionally, the TtGBP sensor was tested with and without the N-terminal pRSET tag and no difference was observed. Specifically, both sensors exhibited an affinity for glucose of about 1.5 mM and a ΔF/F of 2.5.

Data showing that it was possible to construct a glucose sensor by replacing the EcMBP or PfMBP with TtGBP, retaining the composition of linker 2, and optimizing the composition of linker 1, indicates that the methods for generating sensors disclosed herein can be used to generate sensors using any suitable framework.

Example 5C: Detecting Changes in Glucose Concentration In Vivo

The TtGBP326-cpGFP.L1PAL2NP sensor was cloned into a variant of the pDisplay™ vector lacking the N-terminal secretion sequence, the N-terminal hemagglutinin tag, the C-terminal cMyc tag, and the C-terminal PDGFR membrane anchoring domain.

Figure 39:
FIG. 39|An image showing TtGBP326-cpGFP expressed as a transgenic reporter of intracellular glucose in cultured human cells.

The TtGBP sensor was cloned into a mammalian expression vector (based on the pDisplay™ vector described in Example 3 above) with the secretion, epitope, and transmembrane anchoring peptides removed, thus resulting in cytosolic expression of the TtGBP326-cpGFP.L1PAL2NP+H66A+H348A sensor. The construct was transfected into HEK293 cells. As shown in FIG. 39, the TtGBP sensor was expressed in the cytosol.

Figures 40A, 40B:
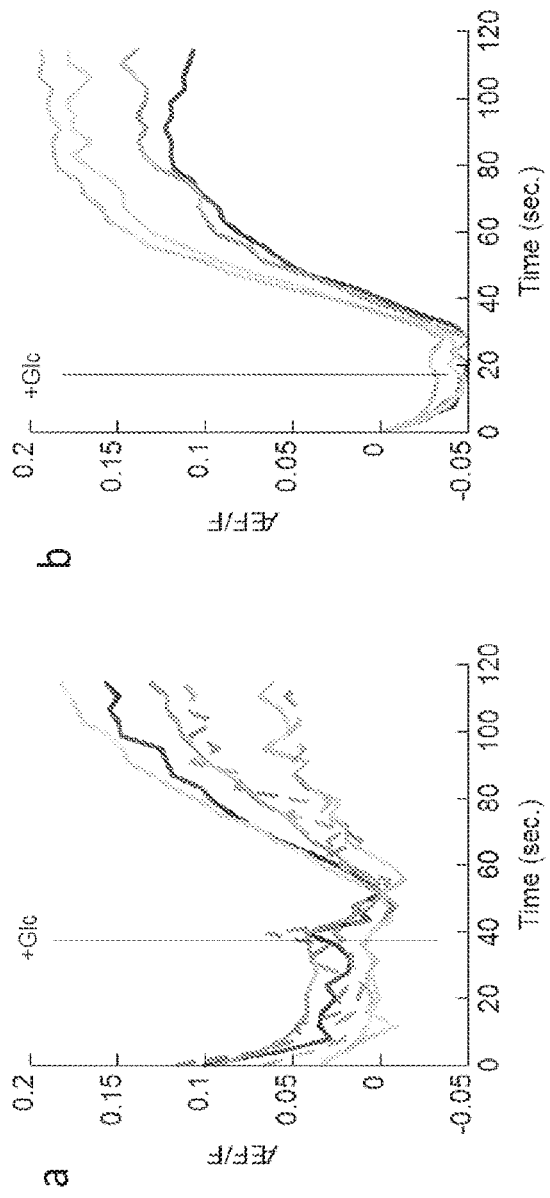
FIGS. 40A-40B|Are line graphs showing that the addition of extracellular glucose increases TtGBP326-cpGFP fluorescence in human cells.

As shown in FIG. 40, addition of 10 mM glucose to the media increases fluorescence.

Figure 51:
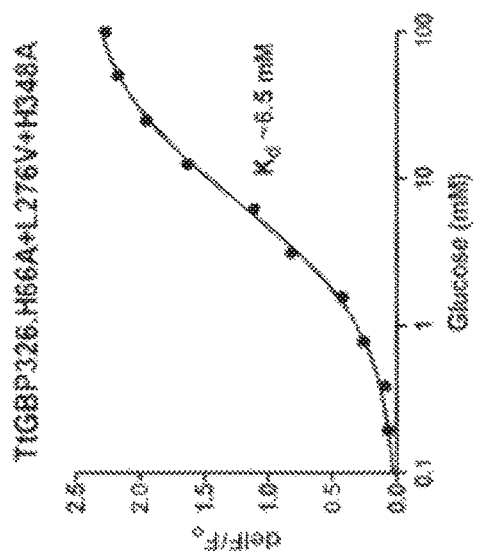
FIG. 51|A line graph showing binding of TtGBP326.L1PA.L2NP.H66A.H348A.L276V to glucose.

The TtGBP326-cpGFP.L1PAL2NP+H66A+H348A sensor was further modified by L276V mutation to produce TtGBP326.L1PA.L2NP.H66A.H348A.L276V (see FIG. 50). As shown in FIG. 51, this construct has an affinity for glucose of 6.5 mM.

Figure 52:
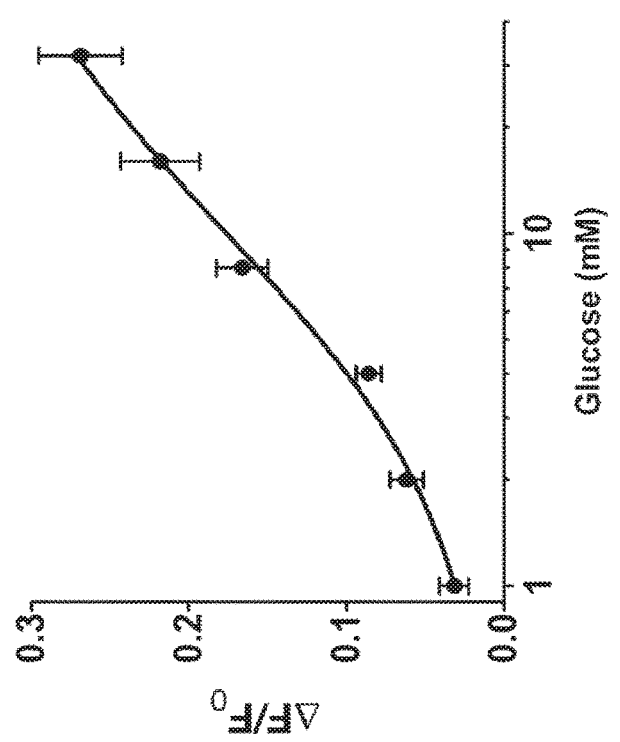
FIG. 52|A line graph showing fluorescence increase upon addition of glucose to HEK293 cells expressing TtGBP326.LIPA.L2NP.H66A.H348A.L276V on their extracellular surface.

Additionally, the TtGBP326.L1P1.L2NP.G66A.H348A.L276V was cloned into the pMinDis derivative of the pDisplay vector and expressed on the extracellular surface of HEK293 cells. After exchanging the HEK293 cell media for PBS, addition of glucose to the PBS led to an increase in fluorescence (see FIG. 52).

These data indicate, in part, that the pRSET tag is not essential to the function of the sensor and that the TtGBP326-cpGFP.L1PAL2NP sensor is capable of detecting changes in the concentration of glucose inside or on the external surface of human cells.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
<160> NUMBER OF SEQ ID NOS: 176

<210> SEQ ID NO 1
<211> LENGTH: 662
<212> TYPE: PRT
<213> ORGANISM: Artificial Sequence
<220> FEATURE:
<223> OTHER INFORMATION: recombinant peptide biosensor

<400> SEQUENCE: 1
```

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Ile Glu Glu Gly Lys Leu Val Ile Trp Ile Asn
        35                  40                  45

Gly Asp Lys Gly Tyr Asn Gly Leu Ala Glu Val Gly Lys Lys Phe Glu
    50                  55                  60

Lys Asp Thr Gly Ile Lys Val Thr Val Glu His Pro Asp Lys Leu Glu
65                  70                  75                  80

Glu Lys Phe Pro Gln Val Ala Ala Thr Gly Asp Gly Pro Asp Ile Ile
                85                  90                  95

Phe Trp Ala His Asp Arg Phe Gly Gly Tyr Ala Gln Ser Gly Leu Leu
            100                 105                 110

Ala Glu Ile Thr Pro Asp Lys Ala Phe Gln Asp Lys Leu Tyr Pro Phe
        115                 120                 125

Thr Trp Asp Ala Val Arg Tyr Asn Gly Lys Leu Ile Ala Tyr Pro Ile
    130                 135                 140

Ala Val Glu Ala Leu Ser Leu Ile Tyr Asn Lys Asp Leu Leu Pro Asn
145                 150                 155                 160

Pro Pro Lys Thr Trp Glu Glu Ile Pro Ala Leu Asp Lys Glu Leu Lys
                165                 170                 175

Ala Lys Gly Lys Ser Ala Leu Met Phe Asn Leu Gln Glu Pro Tyr Phe
            180                 185                 190

Thr Trp Pro Leu Ile Ala Ala Asp Gly Gly Ser His Asn Val Tyr Ile
        195                 200                 205

Met Ala Asp Lys Gln Lys Asn Gly Ile Lys Ala Asn Phe Lys Ile Arg
    210                 215                 220

-continued

His Asn Ile Glu Asp Gly Gly Val Gln Leu Ala Tyr His Tyr Gln Gln
225                 230                 235                 240

Asn Thr Pro Ile Gly Asp Gly Pro Val Leu Leu Pro Asp Asn His Tyr
            245                 250                 255

Leu Ser Thr Gln Ser Lys Leu Ser Lys Asp Pro Asn Glu Lys Arg Asp
        260                 265                 270

His Met Val Leu Leu Glu Phe Val Thr Ala Ala Gly Ile Thr Leu Gly
    275                 280                 285

Met Asp Glu Leu Tyr Lys Gly Gly Thr Gly Gly Ser Met Val Ser Lys
290                 295                 300

Gly Glu Glu Leu Phe Thr Gly Val Val Pro Ile Leu Val Glu Leu Asp
305                 310                 315                 320

Gly Asp Val Asn Gly His Lys Phe Ser Val Ser Gly Glu Gly Glu Gly
                325                 330                 335

Asp Ala Thr Tyr Gly Lys Leu Thr Leu Lys Phe Ile Cys Thr Thr Gly
            340                 345                 350

Lys Leu Pro Val Pro Trp Pro Thr Leu Val Thr Thr Leu Thr Tyr Gly
        355                 360                 365

Val Gln Cys Phe Ser Arg Tyr Pro Asp His Met Lys Gln His Asp Phe
370                 375                 380

Phe Lys Ser Ala Met Pro Glu Gly Tyr Ile Gln Glu Arg Thr Ile Phe
385                 390                 395                 400

Phe Lys Asp Asp Gly Asn Tyr Lys Thr Arg Ala Glu Val Lys Phe Glu
                405                 410                 415

Gly Asp Thr Leu Val Asn Arg Ile Glu Leu Lys Gly Ile Asp Phe Lys
            420                 425                 430

Glu Asp Gly Asn Ile Leu Gly His Lys Leu Glu Tyr Asn Phe Asn Gly
        435                 440                 445

Gly Tyr Ala Phe Lys Tyr Glu Asn Gly Lys Tyr Asp Ile Lys Asp Val
    450                 455                 460

Gly Val Asp Asn Ala Gly Ala Lys Ala Gly Leu Thr Phe Leu Val Asp
465                 470                 475                 480

Leu Ile Lys Asn Lys His Met Asn Ala Asp Thr Asp Tyr Ser Ile Ala
                485                 490                 495

Glu Ala Ala Phe Asn Lys Gly Glu Thr Ala Met Thr Ile Asn Gly Pro
            500                 505                 510

Trp Ala Trp Ser Asn Ile Asp Thr Ser Lys Val Asn Tyr Gly Val Thr
        515                 520                 525

Val Leu Pro Thr Phe Lys Gly Gln Pro Ser Lys Pro Phe Val Gly Val
    530                 535                 540

Leu Ser Ala Gly Ile Asn Ala Ala Ser Pro Asn Lys Glu Leu Ala Lys
545                 550                 555                 560

Glu Phe Leu Glu Asn Tyr Leu Leu Thr Asp Glu Gly Leu Glu Ala Val
                565                 570                 575

Asn Lys Asp Lys Pro Leu Gly Ala Val Ala Leu Lys Ser Tyr Glu Glu
            580                 585                 590

Glu Leu Val Lys Asp Pro Arg Ile Ala Ala Thr Met Glu Asn Ala Gln
        595                 600                 605

Lys Gly Glu Ile Met Pro Asn Ile Pro Gln Met Ser Ala Phe Trp Tyr
    610                 615                 620

Ala Val Arg Thr Ala Val Ile Asn Ala Ala Ser Gly Arg Gln Thr Val
625                 630                 635                 640

```
Asp Glu Asp Leu Lys Asp Ala Gln Thr Arg Ile Thr Lys Gly Ser His
            645                 650                 655

His His His His His Gly
            660
```

<210> SEQ ID NO 2
<211> LENGTH: 662
<212> TYPE: PRT
<213> ORGANISM: Artificial Sequence
<220> FEATURE:
<223> OTHER INFORMATION: recombinant peptide biosensor

<400> SEQUENCE: 2

```
Met Arg Gly Ser His His His His His Gly Met Ala Ser Met Thr
 1               5                  10                  15

Gly Gly Gln Gln Met Gly Arg Asp Leu Tyr Asp Asp Asp Lys Asp
                20                  25                  30

Arg Trp Gly Ser Lys Ile Glu Glu Gly Lys Leu Val Ile Trp Ile Asn
            35                  40                  45

Gly Asp Lys Gly Tyr Asn Gly Leu Ala Glu Val Gly Lys Lys Phe Glu
 50                  55                  60

Lys Asp Thr Gly Ile Lys Val Thr Val Glu His Pro Asp Lys Leu Glu
 65                  70                  75                  80

Glu Lys Phe Pro Gln Val Ala Ala Thr Gly Asp Gly Pro Asp Ile Ile
                85                  90                  95

Phe Trp Ala His Asp Arg Phe Gly Gly Tyr Ala Gln Ser Gly Leu Leu
            100                 105                 110

Ala Glu Ile Thr Pro Asp Lys Ala Phe Gln Asp Lys Leu Tyr Pro Phe
            115                 120                 125

Thr Trp Asp Ala Val Arg Tyr Asn Gly Lys Leu Ile Ala Tyr Pro Ile
        130                 135                 140

Ala Val Glu Ala Leu Ser Leu Ile Tyr Asn Lys Asp Leu Leu Pro Asn
145                 150                 155                 160

Pro Pro Lys Thr Trp Glu Glu Ile Pro Ala Leu Asp Lys Glu Leu Lys
                165                 170                 175

Ala Lys Gly Lys Ser Ala Leu Met Phe Asn Leu Gln Glu Pro Tyr Phe
            180                 185                 190

Thr Trp Pro Leu Ile Ala Ala Asp Pro Pro Ser Tyr Asn Val Phe Ile
        195                 200                 205

Met Ala Asp Lys Gln Lys Asn Gly Ile Lys Ala Asn Phe Lys Ile Arg
210                 215                 220

His Asn Ile Glu Asp Gly Gly Val Gln Leu Ala Tyr His Tyr Gln Gln
225                 230                 235                 240

Asn Thr Pro Ile Gly Asp Gly Pro Val Leu Leu Pro Asp Asn His Tyr
                245                 250                 255

Leu Ser Thr Gln Ser Lys Leu Ser Lys Asp Pro Asn Glu Lys Arg Asp
            260                 265                 270

His Met Val Leu Leu Glu Phe Val Thr Ala Ala Gly Ile Thr Leu Gly
        275                 280                 285

Met Asp Glu Leu Tyr Lys Gly Gly Thr Gly Gly Ser Met Val Ser Lys
290                 295                 300

Gly Glu Glu Leu Phe Thr Gly Val Val Pro Ile Leu Val Glu Leu Asp
305                 310                 315                 320

Gly Asp Val Asn Gly His Lys Phe Ser Val Ser Gly Glu Gly Glu Gly
                325                 330                 335
```

```
Asp Ala Thr Tyr Gly Lys Leu Thr Leu Lys Phe Ile Cys Thr Thr Gly
            340                 345                 350
Lys Leu Pro Val Pro Trp Pro Thr Leu Val Thr Thr Leu Thr Tyr Gly
        355                 360                 365
Val Gln Cys Phe Ser Arg Tyr Pro Asp His Met Lys Gln His Asp Phe
    370                 375                 380
Phe Lys Ser Ala Met Pro Glu Gly Tyr Ile Gln Glu Arg Thr Ile Phe
385                 390                 395                 400
Phe Lys Asp Asp Gly Asn Tyr Lys Thr Arg Ala Glu Val Lys Phe Glu
                405                 410                 415
Gly Asp Thr Leu Val Asn Arg Ile Glu Leu Lys Gly Ile Asp Phe Lys
            420                 425                 430
Glu Asp Gly Asn Ile Leu Gly His Lys Leu Glu Tyr Asn Phe Asn Gly
        435                 440                 445
Gly Tyr Ala Phe Lys Tyr Glu Asn Gly Lys Tyr Asp Ile Lys Asp Val
    450                 455                 460
Gly Val Asp Asn Ala Gly Ala Lys Ala Gly Leu Thr Phe Leu Val Asp
465                 470                 475                 480
Leu Ile Lys Asn Lys His Met Asn Ala Asp Thr Asp Tyr Ser Ile Ala
                485                 490                 495
Glu Ala Ala Phe Asn Lys Gly Glu Thr Ala Met Thr Ile Asn Gly Pro
            500                 505                 510
Trp Ala Trp Ser Asn Ile Asp Thr Ser Lys Val Asn Tyr Gly Val Thr
        515                 520                 525
Val Leu Pro Thr Phe Lys Gly Gln Pro Ser Lys Pro Phe Val Gly Val
    530                 535                 540
Leu Ser Ala Gly Ile Asn Ala Ala Ser Pro Asn Lys Glu Leu Ala Lys
545                 550                 555                 560
Glu Phe Leu Glu Asn Tyr Leu Leu Thr Asp Glu Gly Leu Glu Ala Val
                565                 570                 575
Asn Lys Asp Lys Pro Leu Gly Ala Val Ala Leu Lys Ser Tyr Glu Glu
            580                 585                 590
Glu Leu Val Lys Asp Pro Arg Ile Ala Ala Thr Met Glu Asn Ala Gln
        595                 600                 605
Lys Gly Glu Ile Met Pro Asn Ile Pro Gln Met Ser Ala Phe Trp Tyr
    610                 615                 620
Ala Val Arg Thr Ala Val Ile Asn Ala Ala Ser Gly Arg Gln Thr Val
625                 630                 635                 640
Asp Glu Asp Leu Lys Asp Ala Gln Thr Arg Ile Thr Lys Gly Ser His
                645                 650                 655
His His His His Gly
            660

<210> SEQ ID NO 3
<211> LENGTH: 659
<212> TYPE: PRT
<213> ORGANISM: Artificial Sequence
<220> FEATURE:
<223> OTHER INFORMATION: recombinant peptide biosensor

<400> SEQUENCE: 3

Met Arg Gly Ser His His His His His His Gly Met Ala Ser Met Thr
 1               5                  10                  15
Gly Gly Gln Gln Met Gly Arg Asp Leu Tyr Asp Asp Asp Lys Asp
            20                  25                  30
```

-continued

```
Arg Trp Gly Ser Lys Ile Glu Glu Gly Lys Leu Val Ile Trp Ile Asn
         35                  40                  45
Gly Asp Lys Gly Tyr Asn Gly Leu Ala Glu Val Gly Lys Lys Phe Glu
 50                  55                  60
Lys Asp Thr Gly Ile Lys Val Thr Val Glu His Pro Asp Lys Leu Glu
 65                  70                  75                  80
Glu Lys Phe Pro Gln Val Ala Ala Thr Gly Asp Gly Pro Asp Ile Ile
                 85                  90                  95
Phe Trp Ala His Asp Arg Phe Gly Gly Tyr Ala Gln Ser Gly Leu Leu
                100                 105                 110
Ala Glu Ile Thr Pro Asp Lys Ala Phe Gln Asp Lys Leu Tyr Pro Phe
            115                 120                 125
Thr Trp Asp Ala Val Arg Tyr Asn Gly Lys Leu Ile Ala Tyr Pro Ile
130                 135                 140
Ala Val Glu Ala Leu Ser Leu Ile Tyr Asn Lys Asp Leu Leu Pro Asn
145                 150                 155                 160
Pro Pro Lys Thr Trp Glu Glu Ile Pro Ala Leu Asp Lys Glu Leu Lys
                165                 170                 175
Ala Lys Gly Lys Ser Ala Leu Met Phe Asn Leu Gln Glu Pro Tyr Phe
            180                 185                 190
Thr Trp Pro Leu Ile Ala Ala Asp Pro Cys Ser His Asn Val Phe Ile
        195                 200                 205
Met Ala Asp Lys Gln Lys Asn Gly Ile Lys Ala Asn Phe Lys Ile Arg
    210                 215                 220
His Asn Ile Glu Asp Gly Gly Val Gln Leu Ala Tyr His Tyr Gln Gln
225                 230                 235                 240
Asn Thr Pro Ile Gly Asp Gly Pro Val Leu Leu Pro Asp Asn His Tyr
                245                 250                 255
Leu Ser Thr Gln Ser Lys Leu Ser Lys Asp Pro Asn Glu Lys Arg Asp
            260                 265                 270
His Met Val Leu Leu Glu Phe Val Thr Ala Ala Gly Ile Thr Leu Gly
        275                 280                 285
Met Asp Glu Leu Tyr Lys Gly Gly Ser Met Val Ser Lys Gly Glu Glu
    290                 295                 300
Leu Phe Thr Gly Val Val Pro Ile Leu Val Glu Leu Asp Gly Asp Val
305                 310                 315                 320
Asn Gly His Lys Phe Ser Val Ser Gly Glu Gly Glu Gly Asp Ala Thr
                325                 330                 335
Tyr Gly Lys Leu Thr Leu Lys Phe Ile Cys Thr Thr Gly Lys Leu Pro
            340                 345                 350
Val Pro Trp Pro Thr Leu Val Thr Thr Leu Thr Tyr Gly Val Gln Cys
        355                 360                 365
Phe Ser Arg Tyr Pro Asp His Met Lys Gln His Asp Phe Phe Lys Ser
    370                 375                 380
Ala Met Pro Glu Gly Tyr Ile Gln Glu Arg Thr Ile Phe Phe Lys Asp
385                 390                 395                 400
Asp Gly Asn Tyr Lys Thr Arg Ala Glu Val Lys Phe Glu Gly Asp Thr
                405                 410                 415
Leu Val Asn Arg Ile Glu Leu Lys Gly Ile Asp Phe Lys Glu Asp Gly
            420                 425                 430
Asn Ile Leu Gly His Lys Leu Glu Tyr Asn Phe Asn Gly Gly Tyr Ala
        435                 440                 445
Phe Lys Tyr Glu Asn Gly Lys Tyr Asp Ile Lys Asp Val Gly Val Asp
```

```
                    450                 455                 460
Asn Ala Gly Ala Lys Ala Gly Leu Thr Phe Leu Val Asp Leu Ile Lys
465                 470                 475                 480

Asn Lys His Met Asn Ala Asp Thr Asp Tyr Ser Ile Ala Glu Ala Ala
                485                 490                 495

Phe Asn Lys Gly Glu Thr Ala Met Thr Ile Asn Gly Pro Trp Ala Trp
            500                 505                 510

Ser Asn Ile Asp Thr Ser Lys Val Asn Tyr Gly Val Thr Val Leu Pro
            515                 520                 525

Thr Phe Lys Gly Gln Pro Ser Lys Pro Phe Val Gly Val Leu Ser Ala
        530                 535                 540

Gly Ile Asn Ala Ala Ser Pro Asn Lys Glu Leu Ala Lys Glu Phe Leu
545                 550                 555                 560

Glu Asn Tyr Leu Leu Thr Asp Glu Gly Leu Glu Ala Val Asn Lys Asp
                565                 570                 575

Lys Pro Leu Gly Ala Val Ala Leu Lys Ser Tyr Glu Glu Glu Leu Val
            580                 585                 590

Asp Lys Pro Arg Ile Ala Ala Thr Met Glu Asn Ala Gln Lys Gly Glu
        595                 600                 605

Ile Met Pro Asn Ile Pro Gln Met Ser Ala Phe Trp Tyr Ala Val Arg
610                 615                 620

Thr Ala Val Ile Asn Ala Ala Ser Gly Arg Gln Thr Val Asp Glu Asp
625                 630                 635                 640

Leu Lys Asp Ala Gln Thr Arg Ile Thr Lys Gly Ser His His His His
                645                 650                 655

His His Gly

<210> SEQ ID NO 4
<211> LENGTH: 661
<212> TYPE: PRT
<213> ORGANISM: Artificial Sequence
<220> FEATURE:
<223> OTHER INFORMATION: recombinant peptide biosensor

<400> SEQUENCE: 4

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Arg Trp Gly Ser Lys Ile Glu Glu Gly Lys Leu Val Ile Trp Ile Asn
            35                  40                  45

Gly Asp Lys Gly Tyr Asn Gly Leu Ala Glu Val Gly Lys Lys Phe Glu
50                  55                  60

Lys Asp Thr Gly Ile Lys Val Thr Val Glu His Pro Asp Lys Leu Glu
65                  70                  75                  80

Glu Lys Phe Pro Gln Val Ala Ala Thr Gly Asp Gly Pro Asp Ile Ile
                85                  90                  95

Phe Trp Ala His Asp Arg Phe Gly Gly Tyr Ala Gln Ser Gly Leu Leu
            100                 105                 110

Ala Glu Ile Thr Pro Asp Lys Ala Phe Gln Asp Lys Leu Tyr Pro Phe
        115                 120                 125

Thr Trp Asp Ala Val Arg Tyr Asn Gly Lys Leu Ile Ala Tyr Pro Ile
    130                 135                 140

Ala Val Glu Ala Leu Ser Leu Ile Tyr Asn Lys Asp Leu Leu Pro Asn
145                 150                 155                 160
```

```
Pro Pro Lys Thr Trp Glu Glu Ile Pro Ala Leu Asp Lys Glu Leu Lys
            165                 170                 175

Ala Lys Gly Lys Ser Ala Leu Met Phe Asn Leu Gln Glu Pro Tyr Phe
            180                 185                 190

Thr Trp Pro Leu Ile Ala Ala Asp Gly Gly Tyr Ala Phe Lys Tyr Glu
            195                 200                 205

Asn Gly Gly Ser His Asn Val Tyr Ile Met Ala Asp Lys Gln Lys Asn
            210                 215                 220

Gly Ile Lys Ala Asn Phe Lys Ile Arg His Asn Ile Glu Asp Gly Gly
225                 230                 235                 240

Val Gln Leu Ala Tyr His Tyr Gln Gln Asn Thr Pro Ile Gly Asp Gly
            245                 250                 255

Pro Val Leu Leu Pro Asp Asn His Tyr Leu Ser Thr Gln Ser Lys Leu
            260                 265                 270

Ser Lys Asp Pro Asn Glu Lys Arg Asp His Met Val Leu Leu Glu Phe
            275                 280                 285

Val Thr Ala Ala Gly Ile Thr Leu Gly Met Asp Glu Leu Tyr Lys Gly
            290                 295                 300

Gly Thr Gly Gly Ser Met Val Ser Lys Gly Glu Glu Leu Phe Thr Gly
305                 310                 315                 320

Val Val Pro Ile Leu Val Glu Leu Asp Gly Asp Val Asn Gly His Lys
            325                 330                 335

Phe Ser Val Ser Gly Glu Gly Glu Gly Asp Ala Thr Tyr Gly Lys Leu
            340                 345                 350

Thr Leu Lys Phe Ile Cys Thr Thr Gly Lys Leu Pro Val Pro Trp Pro
            355                 360                 365

Thr Leu Val Thr Thr Leu Thr Tyr Gly Val Gln Cys Phe Ser Arg Tyr
            370                 375                 380

Pro Asp His Met Lys Gln His Asp Phe Phe Lys Ser Ala Met Pro Glu
385                 390                 395                 400

Gly Tyr Ile Gln Glu Arg Thr Ile Phe Phe Lys Asp Asp Gly Asn Tyr
            405                 410                 415

Lys Thr Arg Ala Glu Val Lys Phe Glu Gly Asp Thr Leu Val Asn Arg
            420                 425                 430

Ile Glu Leu Lys Gly Ile Asp Phe Lys Glu Asp Gly Asn Ile Leu Gly
            435                 440                 445

His Lys Leu Glu Tyr Asn Phe Asn Gly Gly Lys Tyr Asp Ile Lys Asp
450                 455                 460

Val Gly Asp Asn Ala Gly Ala Lys Ala Gly Leu Thr Phe Leu Val Asp
465                 470                 475                 480

Leu Ile Lys Asn Lys His Met Asn Ala Asp Thr Asp Tyr Ser Ile Ala
            485                 490                 495

Glu Ala Ala Phe Asn Lys Gly Glu Thr Ala Met Thr Ile Asn Gly Pro
            500                 505                 510

Trp Ala Trp Ser Asn Ile Asp Thr Ser Lys Val Asn Tyr Gly Val Thr
            515                 520                 525

Val Leu Pro Thr Phe Lys Gly Gln Pro Ser Lys Pro Phe Val Gly Val
            530                 535                 540

Leu Ser Ala Gly Ile Asn Ala Ala Ser Pro Asn Lys Glu Leu Ala Lys
545                 550                 555                 560

Glu Phe Leu Glu Asn Tyr Leu Leu Thr Asp Glu Gly Leu Glu Ala Val
            565                 570                 575
```

```
Asn Lys Asp Lys Pro Leu Gly Ala Val Ala Leu Lys Ser Tyr Glu Glu
            580                 585                 590

Glu Leu Val Asp Lys Pro Arg Ile Ala Ala Thr Met Glu Asn Ala Gln
        595                 600                 605

Lys Gly Glu Ile Met Pro Asn Ile Pro Gln Met Ser Ala Phe Trp Tyr
    610                 615                 620

Ala Val Arg Thr Ala Val Ile Asn Ala Ala Ser Gly Gln Thr Val Asp
625                 630                 635                 640

Glu Asp Leu Lys Asp Ala Gln Thr Arg Ile Thr Lys Gly Ser His His
                645                 650                 655

His His His His Gly
            660

<210> SEQ ID NO 5
<211> LENGTH: 663
<212> TYPE: PRT
<213> ORGANISM: Artificial Sequence
<220> FEATURE:
<223> OTHER INFORMATION: recombinant peptide biosensor

<400> SEQUENCE: 5

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Arg Trp Gly Ser Lys Ile Glu Glu Gly Lys Leu Val Ile Trp Ile Asn
        35                  40                  45

Gly Asp Lys Gly Tyr Asn Gly Leu Ala Glu Val Gly Lys Lys Phe Glu
    50                  55                  60

Lys Asp Thr Gly Ile Lys Val Thr Val Glu His Pro Asp Lys Leu Glu
65                  70                  75                  80

Glu Lys Phe Pro Gln Val Ala Ala Thr Gly Asp Gly Pro Asp Ile Ile
                85                  90                  95

Phe Trp Ala His Asp Arg Phe Gly Gly Tyr Ala Gln Ser Gly Leu Leu
            100                 105                 110

Ala Glu Ile Thr Pro Asp Lys Ala Phe Gln Asp Lys Leu Tyr Pro Phe
        115                 120                 125

Thr Trp Asp Ala Val Arg Tyr Asn Gly Lys Leu Ile Ala Tyr Pro Ile
    130                 135                 140

Ala Val Glu Ala Leu Ser Leu Ile Tyr Asn Lys Asp Leu Leu Pro Asn
145                 150                 155                 160

Pro Pro Lys Thr Trp Glu Glu Ile Pro Ala Leu Asp Lys Glu Leu Lys
                165                 170                 175

Ala Lys Gly Lys Ser Ala Leu Met Phe Asn Leu Gln Glu Pro Tyr Phe
            180                 185                 190

Thr Trp Pro Leu Ile Ala Ala Asp Gly Gly Tyr Ala Phe Lys Tyr Glu
        195                 200                 205

Asn His Leu Ser His Asn Val Tyr Ile Met Ala Asp Lys Gln Lys Asn
    210                 215                 220

Gly Ile Lys Ala Asn Phe Lys Ile Arg His Asn Ile Glu Asp Gly Gly
225                 230                 235                 240

Val Gln Leu Ala Tyr His Tyr Gln Gln Asn Thr Pro Ile Gly Asp Gly
                245                 250                 255

Pro Val Leu Leu Pro Asp Asn His Tyr Leu Ser Thr Gln Ser Lys Leu
            260                 265                 270
```

```
Ser Lys Asp Pro Asn Glu Lys Arg Asp His Met Val Leu Glu Phe
            275                 280                 285

Val Thr Ala Ala Gly Ile Thr Leu Gly Met Asp Glu Leu Tyr Lys Gly
290                 295                 300

Gly Thr Gly Gly Ser Met Val Ser Lys Gly Glu Glu Leu Phe Thr Gly
305                 310                 315                 320

Val Val Pro Ile Leu Val Glu Leu Asp Gly Asp Val Asn Gly His Lys
                325                 330                 335

Phe Ser Val Ser Gly Glu Gly Glu Gly Asp Ala Thr Tyr Gly Lys Leu
            340                 345                 350

Thr Leu Lys Phe Ile Cys Thr Thr Gly Lys Leu Pro Val Pro Trp Pro
            355                 360                 365

Thr Leu Val Thr Thr Leu Thr Tyr Gly Val Gln Cys Phe Ser Arg Tyr
370                 375                 380

Pro Asp His Met Lys Gln His Asp Phe Phe Lys Ser Ala Met Pro Glu
385                 390                 395                 400

Gly Tyr Ile Gln Glu Arg Thr Ile Phe Phe Lys Asp Asp Gly Asn Tyr
                405                 410                 415

Lys Thr Arg Ala Glu Val Lys Phe Glu Gly Asp Thr Leu Val Asn Arg
            420                 425                 430

Ile Glu Leu Lys Gly Ile Asp Phe Lys Glu Asp Gly Asn Ile Leu Gly
            435                 440                 445

His Lys Leu Glu Tyr Asn Phe Asn Gly Gly Lys Tyr Asp Ile Lys Asp
            450                 455                 460

Val Gly Val Asp Asn Ala Gly Ala Lys Ala Gly Leu Thr Phe Leu Val
465                 470                 475                 480

Asp Leu Ile Lys Asn Lys His Met Asn Ala Asp Thr Asp Tyr Ser Ile
                485                 490                 495

Ala Glu Ala Ala Phe Asn Lys Gly Glu Thr Ala Met Thr Ile Asn Gly
            500                 505                 510

Pro Trp Ala Trp Ser Asn Ile Asp Thr Ser Lys Val Asn Tyr Gly Val
            515                 520                 525

Thr Val Leu Pro Thr Phe Lys Gly Gln Pro Ser Lys Pro Phe Val Gly
530                 535                 540

Val Leu Ser Ala Gly Ile Asn Ala Ala Ser Pro Asn Lys Glu Leu Ala
545                 550                 555                 560

Lys Glu Phe Leu Glu Asn Tyr Leu Leu Thr Asp Glu Gly Leu Glu Ala
                565                 570                 575

Val Asn Lys Asp Lys Pro Leu Gly Ala Val Ala Leu Lys Ser Tyr Glu
            580                 585                 590

Glu Glu Leu Val Lys Asp Pro Arg Ile Ala Ala Thr Met Glu Asn Ala
            595                 600                 605

Gln Lys Gly Glu Ile Met Pro Asn Ile Pro Gln Met Ser Ala Phe Trp
610                 615                 620

Tyr Ala Val Arg Thr Ala Val Ile Asn Ala Ala Ser Gly Arg Gln Thr
625                 630                 635                 640

Val Asp Glu Asp Leu Lys Asp Ala Gln Thr Arg Ile Thr Lys Gly Ser
                645                 650                 655

His His His His His Gly
            660

<210> SEQ ID NO 6
<211> LENGTH: 655
<212> TYPE: PRT
```

<213> ORGANISM: Artificial Sequence
<220> FEATURE:
<223> OTHER INFORMATION: recombinant peptide biosensor

<400> SEQUENCE: 6

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Ile Glu Gly Lys Leu Val Ile Trp Ile Asn
        35                  40                  45

Gly Asp Lys Gly Tyr Asn Gly Leu Ala Glu Val Gly Lys Lys Phe Glu
    50                  55                  60

Lys Asp Thr Gly Ile Lys Val Thr Val Glu His Pro Asp Lys Leu Glu
65                  70                  75                  80

Glu Lys Phe Pro Gln Val Ala Ala Thr Gly Asp Gly Pro Asp Ile Ile
                85                  90                  95

Phe Trp Ala His Asp Arg Phe Gly Gly Tyr Ala Gln Ser Gly Leu Leu
            100                 105                 110

Ala Glu Ile Thr Pro Asp Lys Ala Phe Gln Asp Lys Leu Tyr Pro Phe
        115                 120                 125

Thr Trp Asp Ala Val Arg Tyr Asn Gly Lys Leu Ile Ala Tyr Pro Ile
130                 135                 140

Ala Val Glu Ala Leu Ser Leu Ile Tyr Asn Lys Asp Leu Leu Pro Asn
145                 150                 155                 160

Pro Pro Lys Thr Trp Glu Glu Ile Pro Ala Leu Asp Lys Glu Leu Lys
                165                 170                 175

Ala Lys Gly Lys Ser Ala Leu Met Phe Asn Leu Gln Glu Pro Tyr Phe
            180                 185                 190

Thr Trp Pro Leu Ile Ala Ala Asp Gly Gly Tyr Ala Phe Lys Tyr Glu
        195                 200                 205

Asn Gly Lys Tyr Asp Ile Lys Asp Val Gly Val Asp Asn Ala Gly Ala
    210                 215                 220

Lys Ala Gly Leu Thr Phe Leu Val Asp Leu Ile Lys Asn Lys His Met
225                 230                 235                 240

Asn Ala Asp Thr Asp Tyr Ser Ile Ala Glu Ala Ala Phe Asn Lys Gly
                245                 250                 255

Glu Thr Ala Met Thr Ile Asn Gly Pro Trp Ala Trp Ser Asn Ile Asp
            260                 265                 270

Thr Ser Lys Val Asn Tyr Gly Val Thr Val Leu Pro Thr Phe Lys Gly
        275                 280                 285

Gln Pro Ser Lys Pro Phe Val Gly Val Leu Ser Ala Gly Ile Asn Ala
    290                 295                 300

Ala Ser Pro Asn Lys Glu Leu Ala Lys Glu Phe Leu Glu Asn Tyr Leu
305                 310                 315                 320

Leu Thr Asp Glu Gly Leu Glu Ala Val Asn Lys Asp Lys Pro Leu Gly
                325                 330                 335

Ala Val Ala Leu Lys Ser Tyr Glu Glu Glu Leu Gly Gly Ser His Asn
            340                 345                 350

Val Tyr Ile Met Ala Asp Lys Gln Arg Asn Gly Ile Lys Ala Asn Phe
        355                 360                 365

Lys Ile Arg His Asn Ile Glu Asp Gly Gly Val Gln Leu Ala Tyr His
    370                 375                 380

Tyr Gln Gln Asn Thr Pro Ile Gly Asp Gly Pro Val Leu Leu Pro Asp

```
                385                 390                 395                 400
Asn His Tyr Leu Ser Thr Gln Ser Lys Leu Ser Lys Asp Pro Asn Glu
                405                 410                 415

Lys Arg Asp His Met Val Leu Leu Glu Phe Val Thr Ala Ala Gly Ile
                420                 425                 430

Thr Leu Gly Met Asp Glu Leu Tyr Lys Gly Gly Thr Gly Gly Ser Met
                435                 440                 445

Val Ser Lys Gly Glu Glu Leu Phe Thr Gly Val Val Pro Ile Leu Val
                450                 455                 460

Glu Leu Asp Gly Asp Val Asn Gly His Lys Phe Ser Val Ser Gly Glu
465                 470                 475                 480

Gly Glu Gly Asp Ala Thr Tyr Gly Lys Leu Thr Leu Lys Phe Ile Cys
                485                 490                 495

Thr Thr Gly Lys Leu Pro Val Pro Trp Pro Thr Leu Val Thr Thr Leu
                500                 505                 510

Thr Tyr Gly Val Gln Cys Phe Ser Arg Tyr Pro Asp His Met Lys Gln
                515                 520                 525

His Asp Phe Phe Lys Ser Ala Met Pro Glu Gly Tyr Ile Gln Glu Arg
                530                 535                 540

Thr Ile Phe Phe Lys Asp Asp Gly Asn Tyr Lys Thr Arg Ala Glu Val
545                 550                 555                 560

Lys Phe Glu Gly Asp Thr Leu Val Asn Arg Ile Glu Leu Lys Gly Ile
                565                 570                 575

Asp Phe Lys Glu Asp Gly Asn Ile Leu Gly His Lys Leu Glu Tyr Asn
                580                 585                 590

Phe Asn Gly Gly Ala Lys Asp Pro Arg Ile Ala Ala Thr Met Glu Asn
                595                 600                 605

Ala Gln Lys Gly Glu Ile Met Pro Asn Ile Pro Gln Met Ser Ala Phe
                610                 615                 620

Trp Tyr Ala Val Arg Thr Ala Val Ile Asn Ala Ala Ser Gly Arg Gln
625                 630                 635                 640

Thr Val Asp Glu Asp Leu Lys Asp Ala Gln Thr Arg Ile Thr Lys
                645                 650                 655

<210> SEQ ID NO 7
<211> LENGTH: 655
<212> TYPE: PRT
<213> ORGANISM: Artificial Sequence
<220> FEATURE:
<223> OTHER INFORMATION: recombinant peptide biosensor

<400> SEQUENCE: 7

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Arg Trp Gly Ser Lys Ile Glu Glu Gly Lys Leu Val Ile Trp Ile Asn
                35                  40                  45

Gly Asp Lys Gly Tyr Asn Gly Leu Ala Glu Val Gly Lys Lys Phe Glu
                50                  55                  60

Lys Asp Thr Gly Ile Lys Val Thr Val Glu His Pro Asp Lys Leu Glu
65                  70                  75                  80

Glu Lys Phe Pro Gln Val Ala Ala Thr Gly Asp Gly Pro Asp Ile Ile
                85                  90                  95

Phe Trp Ala His Asp Arg Phe Gly Gly Tyr Ala Gln Ser Gly Leu Leu
```

```
                100             105             110
Ala Glu Ile Thr Pro Asp Lys Ala Phe Gln Asp Lys Leu Tyr Pro Phe
            115             120             125

Thr Trp Asp Ala Val Arg Tyr Asn Gly Lys Leu Ile Ala Tyr Pro Ile
130             135             140

Ala Val Glu Ala Leu Ser Leu Ile Tyr Asn Lys Asp Leu Leu Pro Asn
145             150             155             160

Pro Pro Lys Thr Trp Glu Ile Pro Ala Leu Asp Lys Glu Leu Lys
                165             170             175

Ala Lys Gly Lys Ser Ala Leu Met Phe Asn Leu Gln Glu Pro Tyr Phe
            180             185             190

Thr Trp Pro Leu Ile Ala Ala Asp Gly Gly Tyr Ala Phe Lys Tyr Glu
            195             200             205

Asn Gly Lys Tyr Asp Ile Lys Asp Val Gly Val Asp Asn Ala Gly Ala
            210             215             220

Lys Ala Gly Leu Thr Phe Leu Val Asp Leu Ile Lys Asn Lys His Met
225             230             235             240

Asn Ala Asp Thr Asp Tyr Ser Ile Ala Glu Ala Ala Phe Asn Lys Gly
                245             250             255

Glu Thr Ala Met Thr Ile Asn Gly Pro Trp Ala Trp Ser Asn Ile Asp
            260             265             270

Thr Ser Lys Val Asn Tyr Gly Val Thr Val Leu Pro Thr Phe Lys Gly
            275             280             285

Gln Pro Ser Lys Pro Phe Val Gly Val Leu Ser Ala Gly Ile Asn Ala
            290             295             300

Ala Ser Pro Asn Lys Glu Leu Ala Lys Glu Phe Leu Glu Asn Tyr Leu
305             310             315             320

Leu Thr Asp Glu Gly Leu Glu Ala Val Asn Lys Asp Lys Pro Leu Gly
                325             330             335

Ala Val Ala Leu Lys Ser Tyr Glu Glu Glu Leu Gly Gly Ser His Asn
            340             345             350

Val Tyr Ile Met Ala Asp Lys Gln Arg Asn Gly Ile Lys Ala Asn Phe
            355             360             365

Lys Ile Arg His Asn Ile Glu Asp Gly Gly Val Gln Leu Ala Tyr His
370             375             380

Tyr Gln Gln Asn Thr Pro Ile Gly Asp Gly Pro Val Leu Leu Pro Asp
385             390             395             400

Asn His Tyr Leu Ser Thr Gln Ser Lys Leu Ser Lys Asp Pro Asn Glu
                405             410             415

Lys Arg Asp His Met Val Leu Leu Glu Phe Val Thr Ala Ala Gly Ile
            420             425             430

Thr Leu Gly Met Asp Glu Leu Tyr Lys Gly Gly Thr Gly Gly Ser Met
            435             440             445

Val Ser Lys Gly Glu Glu Leu Phe Thr Gly Val Val Pro Ile Leu Val
            450             455             460

Glu Leu Asp Gly Asp Val Asn Gly His Lys Phe Ser Val Ser Gly Glu
465             470             475             480

Gly Glu Gly Asp Ala Thr Tyr Gly Lys Leu Thr Leu Lys Phe Ile Cys
                485             490             495

Thr Thr Gly Lys Leu Pro Val Pro Trp Pro Thr Leu Val Thr Thr Leu
            500             505             510

Thr Tyr Gly Val Gln Cys Phe Ser Arg Tyr Pro Asp His Met Lys Gln
            515             520             525
```

```
His Asp Phe Phe Lys Ser Ala Met Pro Glu Gly Tyr Ile Gln Glu Arg
            530                 535                 540

Thr Ile Phe Phe Lys Asp Asp Gly Asn Tyr Lys Thr Arg Ala Glu Val
545                 550                 555                 560

Lys Phe Glu Gly Asp Thr Leu Val Asn Arg Ile Glu Leu Lys Gly Ile
                565                 570                 575

Asp Phe Lys Glu Asp Gly Asn Ile Leu Gly His Lys Leu Glu Tyr Asn
            580                 585                 590

Phe Asn Asn Pro Ala Lys Asp Pro Arg Ile Ala Ala Thr Met Glu Asn
        595                 600                 605

Ala Gln Lys Gly Glu Ile Met Pro Asn Ile Pro Gln Met Ser Ala Phe
    610                 615                 620

Trp Tyr Ala Val Arg Thr Ala Val Ile Asn Ala Ala Ser Gly Arg Gln
625                 630                 635                 640

Thr Val Asp Glu Asp Leu Lys Asp Ala Gln Thr Arg Ile Thr Lys
                645                 650                 655

<210> SEQ ID NO 8
<211> LENGTH: 659
<212> TYPE: PRT
<213> ORGANISM: Artificial Sequence
<220> FEATURE:
<223> OTHER INFORMATION: recombinant peptide biosensor

<400> SEQUENCE: 8

Met Arg Gly Ser His His His His His His Gly Met Ala Ser Met Thr
  1               5                  10                  15

Gly Gly Gln Gln Met Gly Arg Asp Leu Tyr Asp Asp Asp Lys Asp
                20                  25                  30

Arg Trp Gly Ser Lys Ile Glu Gly Lys Leu Val Ile Trp Ile Asn
            35                  40                  45

Gly Asp Lys Gly Tyr Asn Gly Leu Ala Glu Val Gly Lys Lys Phe Glu
        50                  55                  60

Lys Asp Thr Gly Ile Lys Val Thr Val Glu His Pro Asp Lys Leu Glu
65                  70                  75                  80

Glu Lys Phe Pro Gln Val Ala Ala Thr Gly Asp Gly Pro Asp Ile Ile
                85                  90                  95

Phe Trp Ala His Asp Arg Phe Gly Gly Tyr Ala Gln Ser Gly Leu Leu
            100                 105                 110

Ala Glu Ile Thr Pro Asp Lys Ala Phe Gln Asp Lys Leu Tyr Pro Phe
        115                 120                 125

Thr Trp Asp Ala Val Arg Tyr Asn Gly Lys Leu Ile Ala Tyr Pro Ile
    130                 135                 140

Ala Val Glu Ala Leu Ser Leu Ile Tyr Asn Lys Asp Leu Leu Pro Asn
145                 150                 155                 160

Pro Pro Lys Thr Trp Glu Glu Ile Pro Ala Leu Asp Lys Glu Leu Lys
                165                 170                 175

Ala Lys Gly Lys Ser Ala Leu Met Phe Asn Leu Gln Glu Pro Tyr Phe
            180                 185                 190

Thr Trp Pro Leu Ile Ala Ala Asp Gly Gly Tyr Ala Phe Lys Tyr Glu
        195                 200                 205

Asn Gly Lys Tyr Asp Ile Lys Asp Val Gly Val Asp Asn Ala Gly Ala
    210                 215                 220

Lys Ala Gly Leu Thr Phe Leu Val Asp Leu Ile Lys Asn Lys His Met
225                 230                 235                 240
```

```
Asn Ala Asp Thr Asp Tyr Ser Ile Ala Glu Ala Ala Phe Asn Lys Gly
            245                 250                 255

Glu Thr Ala Met Thr Ile Asn Gly Pro Trp Ala Trp Ser Asn Ile Asp
            260                 265                 270

Thr Ser Lys Val Asn Tyr Gly Val Thr Val Leu Pro Thr Phe Lys Gly
            275                 280                 285

Gln Pro Ser Lys Pro Phe Val Gly Val Leu Ser Ala Gly Ile Asn Ala
            290                 295                 300

Ala Ser Pro Asn Lys Glu Leu Ala Lys Glu Phe Leu Glu Asn Tyr Leu
305                 310                 315                 320

Leu Thr Asp Glu Gly Leu Glu Ala Val Asn Lys Asp Lys Pro Leu Gly
            325                 330                 335

Ala Val Ala Leu Lys Ser Tyr Glu Glu Glu Leu Val Lys Asp Pro Arg
            340                 345                 350

Ser His Asn Val Tyr Ile Met Ala Asp Lys Gln Lys Asn Gly Ile Lys
            355                 360                 365

Ala Asn Phe Lys Ile Arg His Asn Ile Glu Asp Gly Gly Val Gln Leu
            370                 375                 380

Ala Tyr His Tyr Gln Gln Asn Thr Pro Ile Gly Asp Gly Pro Val Leu
385                 390                 395                 400

Leu Pro Asp Asn His Tyr Leu Ser Thr Gln Ser Lys Leu Ser Lys Asp
            405                 410                 415

Pro Asn Glu Lys Arg Asp His Met Val Leu Leu Glu Phe Val Thr Ala
            420                 425                 430

Ala Gly Ile Thr Leu Gly Met Asp Glu Leu Tyr Lys Gly Gly Thr Gly
            435                 440                 445

Gly Ser Met Val Ser Lys Gly Glu Glu Leu Phe Thr Gly Val Val Pro
            450                 455                 460

Ile Leu Val Glu Leu Asp Gly Asp Val Asn Gly His Lys Phe Ser Val
465                 470                 475                 480

Ser Gly Glu Gly Glu Gly Asp Ala Thr Tyr Gly Lys Leu Thr Leu Lys
            485                 490                 495

Phe Ile Cys Thr Thr Gly Lys Leu Pro Val Pro Trp Pro Thr Leu Val
            500                 505                 510

Thr Thr Leu Thr Tyr Gly Val Gln Cys Phe Ser Arg Tyr Pro Asp His
            515                 520                 525

Met Lys Gln His Asp Phe Phe Lys Ser Ala Met Pro Glu Gly Tyr Ile
            530                 535                 540

Gln Glu Arg Thr Ile Phe Phe Lys Asp Asp Gly Asn Tyr Lys Thr Arg
545                 550                 555                 560

Ala Glu Val Lys Phe Glu Gly Asp Thr Leu Val Asn Arg Ile Glu Leu
            565                 570                 575

Lys Gly Ile Asp Phe Lys Glu Asp Gly Asn Ile Leu Gly His Lys Leu
            580                 585                 590

Glu Tyr Asn Phe Asn Ala Ala Thr Met Glu Asn Ala Gln Lys Gly Glu
            595                 600                 605

Ile Met Pro Asn Ile Pro Gln Met Ser Ala Phe Trp Tyr Ala Val Arg
            610                 615                 620

Thr Ala Val Ile Asn Ala Ala Ser Gly Arg Gln Thr Val Asp Glu Asp
625                 630                 635                 640

Leu Lys Asp Ala Gln Thr Arg Ile Thr Lys Gly Ser His His His His
            645                 650                 655
```

His His Gly

```
<210> SEQ ID NO 9
<211> LENGTH: 14
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 9
<223> OTHER INFORMATION: Xaa = Any Amino Acid

<400> SEQUENCE: 9

Pro Leu Ile Ala Ala Asp Gly Xaa Xaa Asn Val Tyr Ile Met
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 10

Pro Leu Ile Ala Ala Asp Xaa Xaa Asn Val Tyr Ile Met
 1               5                  10

<210> SEQ ID NO 11
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 9, 10
<223> OTHER INFORMATION: Xaa = Any Amino Acid

<400> SEQUENCE: 11

Pro Leu Ile Ala Ala Asp Gly Gly Xaa Xaa Asn Val Tyr Ile Met
 1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 12

Pro Leu Ile Ala Ala Asp Gly Xaa Pro Asn Val Tyr Ile Met Gly
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
```

```
<222> LOCATION: 9
<223> OTHER INFORMATION: Xaa = Any Amino Acid

<400> SEQUENCE: 13

Pro Leu Ile Ala Ala Asp Gly Ile Xaa Asn Val Tyr Ile Met Gly
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 14

Pro Leu Ile Ala Ala Asp Pro Xaa Ser His Asn Val Tyr Ile Met
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7
<223> OTHER INFORMATION: Xaa = Any Amino Acid

<400> SEQUENCE: 15

Pro Leu Ile Ala Ala Asp Xaa Pro Ser His Asn Val Tyr Ile Met
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 16

Pro Leu Ile Ala Ala Asp Xaa Xaa Ser His Asn Val Tyr Ile Met
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 17

Pro Leu Ile Ala Ala Asp Xaa Xaa Ser His Asn Val Phe Ile Met
1               5                   10                  15

<210> SEQ ID NO 18
<211> LENGTH: 15
```

```
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 18

Pro Leu Ile Ala Ala Asp Pro Xaa Ser His Asn Val Phe Ile Met
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 19

Pro Leu Ile Ala Ala Asp Pro Xaa Ser Tyr Asn Val Phe Ile Met
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 20

Pro Leu Ile Ala Ala Asp Xaa Xaa Ser Tyr Asn Val Phe Ile Met
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 21

Pro Leu Ile Ala Ala Asp Pro Xaa Ser Tyr Asn Val Phe Ile Met
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 22
```

Pro Leu Ile Ala Ala Asp Xaa Xaa Ser Tyr Asn Val Phe Ile Met
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 10
<223> OTHER INFORMATION: Xaa = Any Amino Acid

<400> SEQUENCE: 23

Pro Leu Ile Ala Ala Asp Pro Xaa Ser Xaa Asn Val Tyr Ile Met
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 11
<223> OTHER INFORMATION: Xaa = Any Amino Acid

<400> SEQUENCE: 24

Pro Leu Ile Ala Ala Asp Pro Xaa Ser His Xaa Val Tyr Ile Met
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 12
<223> OTHER INFORMATION: Xaa = Any Amino Acid

<400> SEQUENCE: 25

Pro Leu Ile Ala Ala Asp Pro Xaa Ser His Asn Xaa Tyr Ile Met
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 13
<223> OTHER INFORMATION: Xaa = Any Amino Acid

<400> SEQUENCE: 26

Pro Leu Ile Ala Ala Asp Pro Xaa Ser His Asn Val Xaa Ile Met
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: synthetic oligopeptide
<220> FEATURE:

```
<221> NAME/KEY: VARIANT
<222> LOCATION: 8, 9
<223> OTHER INFORMATION: Xaa = Any Amino Acid

<400> SEQUENCE: 27

Lys Leu Glu Tyr Asn Phe Asn Xaa Xaa Tyr Ala Phe Lys Tyr Glu Asn
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 28

Lys Leu Glu Tyr Asn Phe Asn Xaa Tyr Ala Phe Lys Tyr Glu Asn
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: synthetic oligopeptide

<400> SEQUENCE: 29

Lys Leu Glu Tyr Asn Phe Asn Tyr Ala Phe Lys Tyr Glu Asn
1               5                   10

<210> SEQ ID NO 30
<211> LENGTH: 14
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7
<223> OTHER INFORMATION: Xaa = Any Amino Acid

<400> SEQUENCE: 30

Lys Leu Glu Tyr Asn Phe Xaa Tyr Ala Phe Lys Tyr Glu Asn
1               5                   10

<210> SEQ ID NO 31
<211> LENGTH: 14
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 6, 7
<223> OTHER INFORMATION: Xaa = Any Amino Acid

<400> SEQUENCE: 31

Lys Leu Glu Tyr Asn Xaa Xaa Tyr Ala Phe Lys Tyr Glu Asn
1               5                   10

<210> SEQ ID NO 32
<211> LENGTH: 14
<212> TYPE: PRT
<213> ORGANISM: Artificial Sequence
<220> FEATURE:
```

<223> OTHER INFORMATION: synthetic oligopeptide
<220> FEATURE:
<221> NAME/KEY: VARIANT
<222> LOCATION: 7
<223> OTHER INFORMATION: Xaa = Any Amino Acid

<400> SEQUENCE: 32

Lys Leu Glu Tyr Asn Trp Xaa Tyr Ala Phe Lys Tyr Glu Asn
1               5                   10

<210> SEQ ID NO 33
<211> LENGTH: 14
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 6
<223> OTHER INFORMATION: Xaa = Any Amino Acid

<400> SEQUENCE: 33

Lys Leu Glu Tyr Asn Xaa Lys Tyr Ala Phe Lys Tyr Glu Asn
1               5                   10

<210> SEQ ID NO 34
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 9
<223> OTHER INFORMATION: Xaa = Any Amino Acid

<400> SEQUENCE: 34

Lys Leu Glu Tyr Asn Phe Asn Pro Xaa Tyr Ala Phe Lys Tyr Glu Asn
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 35

Lys Leu Glu Tyr Asn Phe Asn Xaa Pro Tyr Ala Phe Lys Tyr Glu Asn
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 36

Ala Phe Lys Tyr Glu Asn Xaa Xaa Ser His Asn Val Tyr Ile Met
1               5                   10                  15

```
<210> SEQ ID NO 37
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 9
<223> OTHER INFORMATION: Xaa = Any Amino Acid

<400> SEQUENCE: 37

Lys Leu Glu Tyr Asn Phe Asn Xaa Xaa Lys Tyr Asp Ile Lys Asp Val
 1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 38

Lys Ser Tyr Glu Glu Leu Xaa Xaa Ser His Asn Val Tyr Ile Met
 1               5                  10                  15

<210> SEQ ID NO 39
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 39

Lys Ser Tyr Glu Glu Leu Pro Xaa Ser His Asn Val Tyr Ile Met
 1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7
<223> OTHER INFORMATION: Xaa = Any Amino Acid

<400> SEQUENCE: 40

Lys Ser Tyr Glu Glu Leu Xaa Pro Ser His Asn Val Tyr Ile Met
 1               5                  10                  15

<210> SEQ ID NO 41
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 9
<223> OTHER INFORMATION: Xaa = Any Amino Acid
```

<400> SEQUENCE: 41

Lys Leu Glu Tyr Asn Phe Asn Xaa Xaa Ala Lys Asp Pro Arg Ile Ala
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 9
<223> OTHER INFORMATION: Xaa = Any Amino Acid

<400> SEQUENCE: 42

Lys Leu Glu Tyr Asn Phe Asn Pro Xaa Ala Lys Asp Pro Arg Ile Ala
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 43

Lys Leu Glu Tyr Asn Phe Asn Xaa Pro Ala Lys Asp Pro Arg Ile Ala
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 44

Glu Leu Ala Lys Asp Pro Arg Xaa Ser His Asn Val Tyr Ile Met
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 9
<223> OTHER INFORMATION: Xaa = Any Amino Acid

<400> SEQUENCE: 45

Glu Leu Ala Lys Asp Pro Arg Xaa Xaa Ser His Asn Val Tyr Ile Met
1               5                   10                  15

<210> SEQ ID NO 46
<211> LENGTH: 17
<212> TYPE: PRT
<213> ORGANISM: Artificial Sequence

```
<220> FEATURE:
<223> OTHER INFORMATION: synthetic oligopeptide
<220> FEATURE:
<221> NAME/KEY: VARIANT
<222> LOCATION: 8, 9, 10
<223> OTHER INFORMATION: Xaa = Any Amino Acid

<400> SEQUENCE: 46

Glu Leu Ala Lys Asp Pro Arg Xaa Xaa Xaa Ser His Asn Val Tyr Ile
 1               5                  10                  15

Met

<210> SEQ ID NO 47
<211> LENGTH: 15
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 47

Lys Leu Glu Tyr Asn Phe Asn Xaa Ala Ala Thr Met Glu Asn Ala
 1               5                  10                  15

<210> SEQ ID NO 48
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 9
<223> OTHER INFORMATION: Xaa = Any Amino Acid

<400> SEQUENCE: 48

Lys Leu Glu Tyr Asn Phe Asn Xaa Xaa Ala Ala Thr Met Glu Asn Ala
 1               5                  10                  15

<210> SEQ ID NO 49
<211> LENGTH: 17
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 9, 10
<223> OTHER INFORMATION: Xaa = Any Amino Acid

<400> SEQUENCE: 49

Lys Leu Glu Tyr Asn Phe Asn Xaa Xaa Xaa Ala Ala Thr Met Glu Asn
 1               5                  10                  15

Ala

<210> SEQ ID NO 50
<211> LENGTH: 671
<212> TYPE: PRT
<213> ORGANISM: Artificial Sequence
<220> FEATURE:
<223> OTHER INFORMATION: recombinant peptide biosensor

<400> SEQUENCE: 50

Met Arg Gly Ser His His His His His His Gly Met Ala Ser Met Thr
 1               5                  10                  15
```

```
Gly Gly Gln Gln Met Gly Arg Asp Leu Tyr Asp Asp Asp Lys Asp
            20                  25                  30

Arg Trp Gly Ser Lys Ile Glu Glu Gly Lys Val Val Ile Trp His Ala
        35                  40                  45

Met Gln Pro Asn Glu Leu Glu Val Phe Gln Ser Leu Ala Glu Tyr
50                  55                  60

Met Ala Leu Cys Pro Glu Val Glu Ile Val Phe Glu Gln Lys Pro Asn
65                  70                  75                  80

Leu Glu Asp Ala Leu Lys Ala Ala Ile Pro Thr Gly Gln Gly Pro Asp
                85                  90                  95

Leu Phe Ile Trp Ala His Asp Trp Ile Gly Lys Phe Ala Glu Ala Gly
                100                 105                 110

Leu Leu Glu Pro Ile Asp Glu Tyr Val Thr Glu Asp Leu Leu Asn Glu
            115                 120                 125

Phe Ala Pro Met Ala Gln Asp Ala Met Gln Tyr Lys Gly His Tyr Tyr
            130                 135                 140

Ala Leu Pro Phe Ala Ala Glu Thr Val Ala Ile Ile Tyr Ser Lys Glu
145                 150                 155                 160

Met Val Ser Glu Pro Pro Lys Thr Phe Asp Glu Met Lys Ala Ile Met
                165                 170                 175

Glu Lys Tyr Tyr Asp Pro Ala Asn Glu Lys Tyr Gly Ile Ala Trp Pro
            180                 185                 190

Ile Asn Ala Tyr Phe Ile Ser Ala Ile Ala Gln Ala Phe Gly Gly Ser
            195                 200                 205

His Asn Val Tyr Ile Met Ala Asp Lys Gln Lys Asn Gly Ile Lys Ala
            210                 215                 220

Asn Phe Lys Ile Arg His Asn Ile Glu Asp Gly Gly Val Gln Leu Ala
225                 230                 235                 240

Tyr His Tyr Gln Gln Asn Thr Pro Ile Gly Asp Gly Pro Val Leu Leu
            245                 250                 255

Pro Asp Asn His Tyr Leu Ser Thr Gln Ser Lys Leu Ser Lys Asp Pro
            260                 265                 270

Asn Glu Lys Arg Asp His Met Val Leu Leu Glu Phe Val Thr Ala Ala
            275                 280                 285

Gly Ile Thr Leu Gly Met Asp Glu Leu Tyr Lys Gly Gly Thr Gly Gly
290                 295                 300

Ser Met Val Ser Lys Gly Glu Glu Leu Phe Thr Gly Val Val Pro Ile
305                 310                 315                 320

Leu Val Glu Leu Asp Gly Asp Val Asn Gly His Lys Phe Ser Val Ser
                325                 330                 335

Gly Glu Gly Glu Gly Asp Ala Thr Tyr Gly Lys Leu Thr Leu Lys Phe
            340                 345                 350

Ile Cys Thr Thr Gly Lys Leu Pro Val Pro Trp Pro Thr Leu Val Thr
            355                 360                 365

Thr Leu Thr Tyr Gly Val Gln Cys Phe Ser Arg Tyr Pro Asp His Met
            370                 375                 380

Lys Gln His Asp Phe Phe Lys Ser Ala Met Pro Glu Gly Tyr Ile Gln
385                 390                 395                 400

Glu Arg Thr Ile Phe Phe Lys Asp Asp Gly Asn Tyr Lys Thr Arg Ala
                405                 410                 415

Glu Val Lys Phe Glu Gly Asp Thr Leu Val Asn Arg Ile Glu Leu Lys
                420                 425                 430
```

-continued

Gly Ile Asp Phe Lys Glu Asp Gly Asn Ile Leu Gly His Lys Leu Glu
            435                 440                 445

Tyr Asn Phe Asn Gly Gly Tyr Tyr Phe Asp Asp Lys Thr Glu Gln Pro
        450                 455                 460

Gly Leu Asp Lys Pro Glu Thr Ile Glu Gly Phe Lys Phe Phe Phe Thr
465                 470                 475                 480

Glu Ile Trp Pro Tyr Met Ala Pro Thr Gly Asp Tyr Asn Thr Gln Gln
                485                 490                 495

Ser Ile Phe Leu Glu Gly Arg Ala Pro Met Met Val Asn Gly Pro Trp
            500                 505                 510

Ser Ile Asn Asp Val Lys Lys Ala Gly Ile Asn Phe Gly Val Val Pro
            515                 520                 525

Leu Pro Pro Ile Ile Lys Asp Gly Lys Glu Tyr Trp Pro Arg Pro Tyr
        530                 535                 540

Gly Gly Val Lys Leu Ile Tyr Phe Ala Ala Gly Ile Lys Asn Lys Asp
545                 550                 555                 560

Ala Ala Trp Lys Phe Ala Lys Trp Leu Thr Thr Ser Glu Glu Ser Ile
                565                 570                 575

Lys Thr Leu Ala Leu Glu Leu Gly Tyr Ile Pro Val Leu Thr Lys Val
            580                 585                 590

Leu Asp Asp Pro Glu Ile Lys Asn Asp Pro Val Ile Tyr Gly Phe Gly
        595                 600                 605

Gln Ala Val Gln His Ala Tyr Leu Met Pro Lys Ser Pro Lys Met Ser
610                 615                 620

Ala Val Trp Gly Gly Val Asp Gly Ala Ile Asn Glu Ile Leu Gln Asp
625                 630                 635                 640

Pro Gln Asn Ala Asp Ile Glu Gly Ile Leu Lys Lys Tyr Gln Gln Glu
                645                 650                 655

Ile Leu Asn Asn Met Gln Gly Ser His His His His His Gly
            660                 665                 670

<210> SEQ ID NO 51
<211> LENGTH: 671
<212> TYPE: PRT
<213> ORGANISM: Artificial Sequence
<220> FEATURE:
<223> OTHER INFORMATION: recombinant peptide biosensor

<400> SEQUENCE: 51

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Ile Glu Glu Gly Lys Val Val Ile Trp His Ala
        35                  40                  45

Met Gln Pro Asn Glu Leu Glu Val Phe Gln Ser Leu Ala Glu Glu Tyr
    50                  55                  60

Met Ala Leu Cys Pro Glu Val Glu Ile Val Phe Glu Gln Lys Pro Asn
65                  70                  75                  80

Leu Glu Asp Ala Leu Lys Ala Ala Ile Pro Thr Gly Gln Gly Pro Asp
                85                  90                  95

Leu Phe Ile Trp Ala His Asp Trp Ile Gly Lys Phe Ala Glu Ala Gly
            100                 105                 110

Leu Leu Glu Pro Ile Asp Glu Tyr Val Thr Glu Asp Leu Leu Asn Glu
        115                 120                 125

Phe Ala Pro Met Ala Gln Asp Ala Met Gln Tyr Lys Gly His Tyr Tyr
130                 135                 140

Ala Leu Pro Phe Ala Ala Glu Thr Val Ala Ile Ile Tyr Ser Lys Glu
145                 150                 155                 160

Met Val Ser Glu Pro Pro Lys Thr Phe Asp Glu Met Lys Ala Ile Met
                165                 170                 175

Glu Lys Tyr Tyr Asp Pro Ala Asn Glu Lys Tyr Gly Ile Ala Trp Pro
            180                 185                 190

Ile Asn Ala Tyr Phe Ile Ser Ala Ile Ala Gln Ala Phe Gly Gly Ser
        195                 200                 205

His Asn Val Tyr Ile Met Ala Asp Lys Gln Lys Asn Gly Ile Lys Ala
    210                 215                 220

Asn Phe Lys Ile Arg His Asn Ile Glu Asp Gly Gly Val Gln Leu Ala
225                 230                 235                 240

Tyr His Tyr Gln Gln Asn Thr Pro Ile Gly Asp Gly Pro Val Leu Leu
                245                 250                 255

Pro Asp Asn His Tyr Leu Ser Thr Gln Ser Lys Leu Ser Lys Asp Pro
            260                 265                 270

Asn Glu Lys Arg Asp His Met Val Leu Leu Glu Phe Val Thr Ala Ala
        275                 280                 285

Gly Ile Thr Leu Gly Met Asp Glu Leu Tyr Lys Gly Gly Thr Gly Gly
    290                 295                 300

Ser Met Val Ser Lys Gly Glu Glu Leu Phe Thr Gly Val Val Pro Ile
305                 310                 315                 320

Leu Val Glu Leu Asp Gly Asp Val Asn Gly His Lys Phe Ser Val Ser
                325                 330                 335

Gly Glu Gly Glu Gly Asp Ala Thr Tyr Gly Lys Leu Thr Leu Lys Phe
            340                 345                 350

Ile Cys Thr Thr Gly Lys Leu Pro Val Pro Trp Pro Thr Leu Val Thr
        355                 360                 365

Thr Leu Thr Tyr Gly Val Gln Cys Phe Ser Arg Tyr Pro Asp His Met
    370                 375                 380

Lys Gln His Asp Phe Phe Lys Ser Ala Met Pro Glu Gly Tyr Ile Gln
385                 390                 395                 400

Glu Arg Thr Ile Phe Phe Lys Asp Asp Gly Asn Tyr Lys Thr Arg Ala
                405                 410                 415

Glu Val Lys Phe Glu Gly Asp Thr Leu Val Asn Arg Ile Glu Leu Lys
            420                 425                 430

Gly Ile Asp Phe Lys Glu Asp Gly Asn Ile Leu Gly His Lys Leu Glu
        435                 440                 445

Tyr Asn Phe Asn Phe Glu Tyr Tyr Phe Asp Asp Lys Thr Glu Gln Pro
    450                 455                 460

Gly Leu Asp Lys Pro Glu Thr Ile Glu Gly Phe Lys Phe Phe Phe Thr
465                 470                 475                 480

Glu Ile Trp Pro Tyr Met Ala Pro Thr Gly Asp Tyr Asn Thr Gln Gln
                485                 490                 495

Ser Ile Phe Leu Glu Gly Arg Ala Pro Met Met Val Asn Gly Pro Trp
            500                 505                 510

Ser Ile Asn Asp Val Lys Lys Ala Gly Ile Asn Phe Gly Val Val Pro
        515                 520                 525

Leu Pro Pro Ile Ile Lys Asp Gly Lys Glu Tyr Trp Pro Arg Pro Tyr
530                 535                 540

Gly Gly Val Lys Leu Ile Tyr Phe Ala Ala Gly Ile Lys Asn Lys Asp

-continued

```
            545                 550                 555                 560
Ala Ala Trp Lys Phe Ala Lys Trp Leu Thr Thr Ser Glu Ser Ile
                    565                 570                 575
Lys Thr Leu Ala Leu Glu Leu Gly Tyr Ile Pro Val Leu Thr Lys Val
                580                 585                 590
Leu Asp Asp Pro Glu Ile Lys Asn Asp Pro Val Ile Tyr Gly Phe Gly
                595                 600                 605
Gln Ala Val Gln His Ala Tyr Leu Met Pro Lys Ser Pro Lys Met Ser
                610                 615                 620
Ala Val Trp Gly Gly Val Asp Gly Ala Ile Asn Glu Ile Leu Gln Asp
625                 630                 635                 640
Pro Gln Asn Ala Asp Ile Glu Gly Ile Leu Lys Lys Tyr Gln Gln Glu
                    645                 650                 655
Ile Leu Asn Asn Met Gln Gly Ser His His His His His Gly
                660                 665                 670

<210> SEQ ID NO 52
<211> LENGTH: 662
<212> TYPE: PRT
<213> ORGANISM: Artificial Sequence
<220> FEATURE:
<223> OTHER INFORMATION: recombinant peptide biosensor

<400> SEQUENCE: 52

Met Arg Gly Ser His His His His His Gly Met Ala Ser Met Thr
1                   5                   10                  15
Gly Gly Gln Gln Met Gly Arg Asp Leu Tyr Asp Asp Asp Lys Asp
                20                  25                  30
Arg Trp Gly Ser Lys Ile Glu Glu Gly Lys Val Val Ile Trp His Ala
                35                  40                  45
Met Gln Pro Asn Glu Leu Glu Val Phe Gln Ser Leu Ala Glu Glu Tyr
            50                  55                  60
Met Ala Leu Cys Pro Glu Val Glu Ile Val Phe Glu Gln Lys Pro Asn
65                  70                  75                  80
Leu Glu Asp Ala Leu Lys Ala Ala Ile Pro Thr Gly Gln Gly Pro Asp
                85                  90                  95
Leu Phe Ile Trp Ala His Asp Trp Ile Gly Lys Phe Ala Glu Ala Gly
                100                 105                 110
Leu Leu Glu Pro Ile Asp Glu Tyr Val Thr Glu Asp Leu Leu Asn Glu
                115                 120                 125
Phe Ala Pro Met Ala Gln Asp Ala Met Gln Tyr Lys Gly His Tyr Tyr
            130                 135                 140
Ala Leu Pro Phe Ala Ala Glu Thr Val Ala Ile Ile Tyr Ser Lys Glu
145                 150                 155                 160
Met Val Ser Glu Pro Pro Lys Thr Phe Asp Glu Met Lys Ala Ile Met
                    165                 170                 175
Glu Lys Tyr Tyr Asp Pro Ala Asn Glu Lys Tyr Gly Ile Ala Trp Pro
                180                 185                 190
Ile Asn Ala Tyr Phe Ile Ser Ala Ile Ala Gln Ala Phe Gly Gly Tyr
                195                 200                 205
Tyr Phe Asp Asp Lys Thr Glu Gln Pro Gly Leu Asp Lys Pro Glu Thr
                210                 215                 220
Ile Glu Gly Phe Lys Phe Phe Thr Glu Ile Trp Pro Tyr Met Ala
225                 230                 235                 240
Pro Thr Gly Asp Tyr Asn Thr Gln Gln Ser Ile Phe Leu Glu Gly Arg
```

```
                    245                 250                 255
        Ala Pro Met Met Val Asn Gly Pro Trp Ser Ile Asn Asp Val Lys Lys
                    260                 265                 270

Ala Gly Ile Asn Phe Gly Val Val Pro Leu Pro Pro Ile Ile Lys Asp
                    275                 280                 285

Gly Lys Glu Tyr Trp Pro Arg Pro Tyr Gly Gly Val Lys Leu Ile Tyr
                    290                 295                 300

Phe Ala Ala Gly Ile Lys Asn Lys Asp Ala Ala Trp Lys Phe Ala Lys
        305                 310                 315                 320

Trp Leu Thr Thr Ser Glu Glu Ser Ile Lys Thr Leu Ala Leu Glu Leu
                            325                 330                 335

Gly Tyr Ile Pro Val Leu Thr Lys Val Leu Asp Asp Pro Glu Ile Ser
                            340                 345                 350

His Asn Val Tyr Ile Met Ala Asp Lys Gln Lys Asn Gly Ile Lys Ala
                            355                 360                 365

Asn Phe Lys Ile Arg His Asn Ile Glu Asp Gly Gly Val Gln Leu Ala
                370                 375                 380

Tyr His Tyr Gln Gln Asn Thr Pro Ile Gly Asp Gly Pro Val Leu Leu
        385                 390                 395                 400

Pro Asp Asn His Tyr Leu Ser Thr Gln Ser Lys Leu Ser Lys Asp Pro
                            405                 410                 415

Asn Glu Lys Arg Asp His Met Val Leu Leu Glu Phe Val Thr Ala Ala
                    420                 425                 430

Gly Ile Thr Leu Gly Met Asp Glu Leu Tyr Lys Gly Gly Thr Gly Gly
                            435                 440                 445

Ser Met Val Ser Lys Gly Glu Glu Leu Phe Thr Gly Val Val Pro Ile
                    450                 455                 460

Leu Val Glu Leu Asp Gly Asp Val Asn Gly His Lys Phe Ser Val Ser
        465                 470                 475                 480

Gly Glu Gly Glu Gly Asp Ala Thr Tyr Gly Lys Leu Thr Leu Lys Phe
                            485                 490                 495

Ile Cys Thr Thr Gly Lys Leu Pro Val Pro Trp Pro Thr Leu Val Thr
                            500                 505                 510

Thr Leu Thr Tyr Gly Val Gln Cys Phe Ser Arg Tyr Pro Asp His Met
                    515                 520                 525

Lys Gln His Asp Phe Phe Lys Ser Ala Met Pro Glu Gly Tyr Ile Gln
                    530                 535                 540

Glu Arg Thr Ile Phe Phe Lys Asp Asp Gly Asn Tyr Lys Thr Arg Ala
        545                 550                 555                 560

Glu Val Lys Phe Glu Gly Asp Thr Leu Val Asn Arg Ile Glu Leu Lys
                            565                 570                 575

Gly Ile Asp Phe Lys Glu Asp Gly Asn Ile Leu Gly His Lys Leu Glu
                            580                 585                 590

Tyr Asn Phe Asn Lys Asn Asp Pro Val Ile Tyr Gly Phe Gly Gln Ala
                    595                 600                 605

Val Gln His Ala Tyr Leu Met Pro Lys Ser Pro Lys Met Ser Ala Val
                    610                 615                 620

Trp Gly Gly Val Asp Gly Ala Ile Asn Glu Ile Leu Gln Asp Pro Gln
        625                 630                 635                 640

Asn Ala Asp Ile Glu Gly Ile Leu Lys Lys Tyr Gln Gln Glu Ile Leu
                            645                 650                 655

Asn Asn Met Gln Gly Ser
                    660
```

<210> SEQ ID NO 53
<211> LENGTH: 664
<212> TYPE: PRT
<213> ORGANISM: Artificial Sequence
<220> FEATURE:
<223> OTHER INFORMATION: recombinant peptide biosensor

<400> SEQUENCE: 53

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Ile Glu Glu Gly Lys Val Val Ile Trp His Ala
            35                  40                  45

Met Gln Pro Asn Glu Leu Glu Val Phe Gln Ser Leu Ala Glu Glu Tyr
    50                  55                  60

Met Ala Leu Cys Pro Glu Val Glu Ile Val Phe Glu Gln Lys Pro Asn
65                  70                  75                  80

Leu Glu Asp Ala Leu Lys Ala Ala Ile Pro Thr Gly Gln Gly Pro Asp
                85                  90                  95

Leu Phe Ile Trp Ala His Asp Trp Ile Gly Lys Phe Ala Glu Ala Gly
            100                 105                 110

Leu Leu Glu Pro Ile Asp Glu Tyr Val Thr Glu Asp Leu Leu Asn Glu
        115                 120                 125

Phe Ala Pro Met Ala Gln Asp Ala Met Gln Tyr Lys Gly His Tyr Tyr
    130                 135                 140

Ala Leu Pro Phe Ala Ala Glu Thr Val Ala Ile Ile Tyr Ser Lys Glu
145                 150                 155                 160

Met Val Ser Glu Pro Pro Lys Thr Phe Asp Glu Met Lys Ala Ile Met
                165                 170                 175

Glu Lys Tyr Tyr Asp Pro Ala Asn Glu Lys Tyr Gly Ile Ala Trp Pro
            180                 185                 190

Ile Asn Ala Tyr Phe Ile Ser Ala Ile Ala Gln Ala Phe Gly Gly Tyr
        195                 200                 205

Tyr Phe Asp Asp Lys Thr Glu Gln Pro Gly Leu Asp Lys Pro Glu Thr
    210                 215                 220

Ile Glu Gly Phe Lys Phe Phe Thr Glu Ile Trp Pro Tyr Met Ala
225                 230                 235                 240

Pro Thr Gly Asp Tyr Asn Thr Gln Gln Ser Ile Phe Leu Glu Gly Arg
                245                 250                 255

Ala Pro Met Met Val Asn Gly Pro Trp Ser Ile Asn Asp Val Lys Lys
            260                 265                 270

Ala Gly Ile Asn Phe Gly Val Val Pro Leu Pro Ile Ile Lys Asp
        275                 280                 285

Gly Lys Glu Tyr Trp Pro Arg Pro Tyr Gly Gly Val Lys Leu Ile Tyr
    290                 295                 300

Phe Ala Ala Gly Ile Lys Asn Lys Asp Ala Ala Trp Lys Phe Ala Lys
305                 310                 315                 320

Trp Leu Thr Thr Ser Glu Glu Ser Ile Lys Thr Leu Ala Leu Glu Leu
                325                 330                 335

Gly Tyr Ile Pro Val Leu Thr Lys Val Leu Asp Asp Pro Glu Ile Pro
            340                 345                 350

Pro Ser His Asn Val Tyr Ile Met Ala Asp Lys Gln Lys Asn Gly Ile
        355                 360                 365
```

```
Lys Ala Asn Phe Lys Ile Arg His Asn Ile Glu Asp Gly Gly Val Gln
        370                 375                 380

Leu Ala Tyr His Tyr Gln Gln Asn Thr Pro Ile Gly Asp Gly Pro Val
385                 390                 395                 400

Leu Leu Pro Asp Asn His Tyr Leu Ser Thr Gln Ser Lys Leu Ser Lys
                405                 410                 415

Asp Pro Asn Glu Lys Arg Asp His Met Val Leu Leu Glu Phe Val Thr
            420                 425                 430

Ala Ala Gly Ile Thr Leu Gly Met Asp Glu Leu Tyr Lys Gly Gly Thr
                435                 440                 445

Gly Gly Ser Met Val Ser Lys Gly Glu Glu Leu Phe Thr Gly Val Val
        450                 455                 460

Pro Ile Leu Val Glu Leu Asp Gly Asp Val Asn Gly His Lys Phe Ser
465                 470                 475                 480

Val Ser Gly Glu Gly Glu Gly Asp Ala Thr Tyr Gly Lys Leu Thr Leu
                485                 490                 495

Lys Phe Ile Cys Thr Thr Gly Lys Leu Pro Val Pro Trp Pro Thr Leu
                500                 505                 510

Val Thr Thr Leu Thr Tyr Gly Val Gln Cys Phe Ser Arg Tyr Pro Asp
            515                 520                 525

His Met Lys Gln His Asp Phe Phe Lys Ser Ala Met Pro Glu Gly Tyr
        530                 535                 540

Ile Gln Glu Arg Thr Ile Phe Phe Lys Asp Asp Gly Asn Tyr Lys Thr
545                 550                 555                 560

Arg Ala Glu Val Lys Phe Glu Gly Asp Thr Leu Val Asn Arg Ile Glu
                565                 570                 575

Leu Lys Gly Ile Asp Phe Lys Glu Asp Gly Asn Ile Leu Gly His Lys
            580                 585                 590

Leu Glu Tyr Asn Phe Asn Lys Asn Asp Pro Val Ile Tyr Gly Phe Gly
        595                 600                 605

Gln Ala Val Gln His Ala Tyr Leu Met Pro Lys Ser Pro Lys Met Ser
610                 615                 620

Ala Val Trp Gly Gly Val Asp Gly Ala Ile Asn Glu Ile Leu Gln Asp
625                 630                 635                 640

Pro Gln Asn Ala Asp Ile Glu Gly Ile Leu Lys Lys Tyr Gln Gln Glu
            645                 650                 655

Ile Leu Asn Asn Met Gln Gly Ser
            660

<210> SEQ ID NO 54
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 54

Ala Ile Ala Gln Ala Phe Xaa Xaa Ser His Asn Val Tyr Ile Met Ala
 1               5                  10                  15

<210> SEQ ID NO 55
<211> LENGTH: 16
<212> TYPE: PRT
```

```
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 55

Ala Ile Ala Gln Ala Phe Pro Xaa Ser His Asn Val Tyr Ile Met Ala
 1               5                  10                  15

<210> SEQ ID NO 56
<211> LENGTH: 17
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 9
<223> OTHER INFORMATION: Xaa = Any Amino Acid

<400> SEQUENCE: 56

Lys Leu Glu Tyr Asn Phe Asn Xaa Xaa Tyr Tyr Phe Asp Asp Lys Thr
 1               5                  10                  15

Glu

<210> SEQ ID NO 57
<211> LENGTH: 14
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 57

Val Leu Asp Asp Pro Glu Xaa Xaa His Asn Val Tyr Ile Met
 1               5                  10

<210> SEQ ID NO 58
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 9
<223> OTHER INFORMATION: Xaa = Any Amino Acid

<400> SEQUENCE: 58

Val Leu Asp Asp Pro Glu Ile Xaa Xaa Ser His Asn Val Tyr Ile Met
 1               5                  10                  15

<210> SEQ ID NO 59
<211> LENGTH: 14
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 59
```

```
Lys Leu Glu Tyr Asn Phe Xaa Xaa Asn Asp Pro Val Ile Tyr
 1               5                  10
```

<210> SEQ ID NO 60
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 60

```
Lys Leu Glu Tyr Asn Phe Asn Xaa Pro Lys Asn Asp Pro Val Ile Tyr
 1               5                  10                  15
```

<210> SEQ ID NO 61
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 9
<223> OTHER INFORMATION: Xaa = Any Amino Acid

<400> SEQUENCE: 61

```
Lys Leu Glu Tyr Asn Phe Asn Pro Xaa Lys Asn Asp Pro Val Ile Tyr
 1               5                  10                  15
```

<210> SEQ ID NO 62
<211> LENGTH: 556
<212> TYPE: PRT
<213> ORGANISM: Artificial Sequence
<220> FEATURE:
<223> OTHER INFORMATION: recombinant peptide biosensor

<400> SEQUENCE: 62

```
Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
                20                  25                  30

Arg Trp Gly Ser Ala Ala Gly Ser Thr Leu Asp Lys Ile Ala Lys Asn
            35                  40                  45

Gly Val Ile Val Val Gly His Arg Glu Ser Ser Val Pro Phe Ser Tyr
        50                  55                  60

Tyr Asp Asn Gln Gln Lys Val Val Gly Tyr Ser Gln Asp Tyr Ser Asn
65                  70                  75                  80

Ala Ile Val Glu Ala Val Lys Lys Lys Leu Asn Lys Pro Asp Leu Gln
                85                  90                  95

Val Lys Leu Ile Pro Ile Thr Ser Gln Asn Arg Ile Pro Leu Leu Gln
            100                 105                 110

Asn Gly Thr Phe Asp Phe Glu Cys Gly Ser Thr Thr Asn Asn Val Glu
        115                 120                 125

Arg Gln Lys Gln Ala Ala Phe Ser Asp Thr Ile Phe Val Val Gly Thr
    130                 135                 140

Arg Leu Leu Thr Lys Lys Gly Gly Asp Ile Lys Asp Phe Ala Asn Leu
145                 150                 155                 160

Lys Asp Lys Ala Val Val Val Thr Ser Gly Thr Thr Ser Glu Val Leu
```

```
                      165                 170                 175
Leu Asn Lys Leu Asn Glu Glu Gln Lys Met Asn Met Arg Ile Ile Ser
            180                 185                 190

Ala Lys Asp His Gly Asp Ser Phe Arg Thr Leu Glu Ser Gly Arg Ala
            195                 200                 205

Val Ala Phe Met Met Asp Asp Val Leu Leu Ala Gly Glu Arg Ala Lys
            210                 215                 220

Ala Lys Lys Pro Asp Asn Trp Glu Ile Val Gly Lys Pro Gln Ser Gln
225                 230                 235                 240

Glu Ala Tyr Gly Cys Met Leu Arg Lys Asp Asp Pro Gln Phe Lys Lys
                245                 250                 255

Leu Met Asp Asp Thr Ile Ala Gln Val Gln Thr Ser Gly Glu Ala Glu
            260                 265                 270

Lys Trp Phe Asp Lys Trp Phe Lys Asn Pro Ile Leu Val Ser His Asn
            275                 280                 285

Val Tyr Ile Met Ala Asp Lys Gln Lys Asn Gly Ile Lys Ala Asn Phe
            290                 295                 300

Lys Ile Arg His Asn Ile Glu Asp Gly Gly Val Gln Leu Ala Tyr His
305                 310                 315                 320

Tyr Gln Gln Asn Thr Pro Ile Gly Asp Gly Pro Val Leu Leu Pro Asp
                325                 330                 335

Asn His Tyr Leu Ser Thr Gln Ser Lys Leu Ser Lys Asp Pro Asn Glu
            340                 345                 350

Lys Arg Asp His Met Val Leu Leu Glu Phe Val Thr Ala Ala Gly Ile
            355                 360                 365

Thr Leu Gly Met Asp Glu Leu Tyr Lys Gly Gly Thr Gly Gly Ser Met
            370                 375                 380

Val Ser Lys Gly Glu Glu Leu Phe Thr Gly Val Val Pro Ile Leu Val
385                 390                 395                 400

Glu Leu Asp Gly Asp Val Asn Gly His Lys Phe Ser Val Ser Gly Glu
                405                 410                 415

Gly Glu Gly Asp Ala Thr Tyr Gly Lys Leu Thr Leu Lys Phe Ile Cys
            420                 425                 430

Thr Thr Gly Lys Leu Pro Val Pro Trp Pro Thr Leu Val Thr Thr Leu
            435                 440                 445

Thr Tyr Gly Val Gln Cys Phe Ser Arg Tyr Pro Asp His Met Lys Gln
            450                 455                 460

His Asp Phe Phe Lys Ser Ala Met Pro Glu Gly Tyr Ile Gln Glu Arg
465                 470                 475                 480

Thr Ile Phe Phe Lys Asp Asp Gly Asn Tyr Lys Thr Arg Ala Glu Val
                485                 490                 495

Lys Phe Glu Gly Asp Thr Leu Val Asn Arg Ile Glu Leu Lys Gly Ile
            500                 505                 510

Asp Phe Lys Glu Asp Gly Asn Ile Leu Gly His Lys Leu Glu Tyr Asn
            515                 520                 525

Phe Asn Asn Pro Leu Asn Met Asn Phe Glu Leu Ser Asp Glu Met Lys
            530                 535                 540

Ala Leu Phe Lys Glu Pro Asn Asp Lys Ala Leu Lys
545                 550                 555

<210> SEQ ID NO 63
<211> LENGTH: 556
<212> TYPE: PRT
<213> ORGANISM: Artificial Sequence
```

<220> FEATURE:
<223> OTHER INFORMATION: recombinant peptide biosensor

<400> SEQUENCE: 63

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Ala Ala Gly Ser Thr Leu Asp Lys Ile Ala Lys Asn
                35                  40                  45

Gly Val Ile Val Val Gly His Arg Glu Ser Ser Val Pro Phe Ser Tyr
            50                  55                  60

Tyr Asp Asn Gln Gln Lys Val Val Gly Tyr Ser Gln Asp Tyr Ser Asn
65                  70                  75                  80

Ala Ile Val Glu Ala Val Lys Lys Leu Asn Lys Pro Asp Leu Gln
                85                  90                  95

Val Lys Leu Ile Pro Ile Thr Ser Gln Asn Arg Ile Pro Leu Leu Gln
                100                 105                 110

Asn Gly Thr Phe Asp Phe Glu Cys Gly Ser Thr Thr Asn Asn Val Glu
            115                 120                 125

Arg Gln Lys Gln Ala Ala Phe Ser Asp Thr Ile Phe Val Val Gly Thr
            130                 135                 140

Arg Leu Leu Thr Lys Lys Gly Gly Asp Ile Lys Asp Phe Ala Asn Leu
145                 150                 155                 160

Lys Asp Lys Ala Val Val Val Thr Ser Gly Thr Thr Ser Glu Val Leu
                165                 170                 175

Leu Asn Lys Leu Asn Glu Glu Gln Lys Met Asn Met Arg Ile Ile Ser
            180                 185                 190

Ala Lys Asp His Gly Asp Ser Phe Arg Thr Leu Glu Ser Gly Arg Ala
            195                 200                 205

Val Ala Phe Met Met Asp Asp Val Leu Leu Ala Gly Glu Arg Ala Lys
            210                 215                 220

Ala Lys Lys Pro Asp Asn Trp Glu Ile Val Gly Lys Pro Gln Ser Gln
225                 230                 235                 240

Glu Ala Tyr Gly Cys Met Leu Arg Lys Asp Asp Pro Gln Phe Lys Lys
                245                 250                 255

Leu Met Asp Asp Thr Ile Ala Gln Val Gln Thr Ser Gly Glu Ala Glu
            260                 265                 270

Lys Trp Phe Asp Lys Trp Phe Lys Asn Pro Ile Leu Val Ser His Asn
            275                 280                 285

Val Tyr Ile Met Ala Asp Lys Gln Lys Asn Gly Ile Lys Ala Asn Phe
            290                 295                 300

Lys Ile Arg His Asn Ile Glu Asp Gly Gly Val Gln Leu Ala Tyr His
305                 310                 315                 320

Tyr Gln Gln Asn Thr Pro Ile Gly Asp Gly Pro Val Leu Leu Pro Asp
                325                 330                 335

Asn His Tyr Leu Ser Thr Gln Ser Lys Leu Ser Lys Asp Pro Asn Glu
            340                 345                 350

Lys Arg Asp His Met Val Leu Leu Glu Phe Val Thr Ala Ala Gly Ile
            355                 360                 365

Thr Leu Gly Met Asp Glu Leu Tyr Lys Gly Gly Thr Gly Gly Ser Met
            370                 375                 380

Val Ser Lys Gly Glu Glu Leu Phe Thr Gly Val Val Pro Ile Leu Val
385                 390                 395                 400
```

```
Glu Leu Asp Gly Asp Val Asn Gly His Lys Phe Ser Val Ser Gly Glu
            405                 410                 415

Gly Glu Gly Asp Ala Thr Tyr Gly Lys Leu Thr Leu Lys Phe Ile Cys
            420                 425                 430

Thr Thr Gly Lys Leu Pro Val Pro Trp Pro Thr Leu Val Thr Thr Leu
            435                 440                 445

Thr Tyr Gly Val Gln Cys Phe Ser Arg Tyr Pro Asp His Met Lys Gln
        450                 455                 460

His Asp Phe Phe Lys Ser Ala Met Pro Glu Gly Tyr Ile Gln Glu Arg
465                 470                 475                 480

Thr Ile Phe Phe Lys Asp Asp Gly Asn Tyr Lys Thr Arg Ala Glu Val
            485                 490                 495

Lys Phe Glu Gly Asp Thr Leu Val Asn Arg Ile Glu Leu Lys Gly Ile
            500                 505                 510

Asp Phe Lys Glu Asp Gly Asn Ile Leu Gly His Lys Leu Glu Tyr Asn
        515                 520                 525

Phe Asn Asn Pro Leu Asn Met Asn Phe Glu Leu Ser Asp Glu Met Lys
    530                 535                 540

Ala Leu Phe Lys Glu Pro Asn Asp Lys Ala Leu Lys
545                 550                 555
```

<210> SEQ ID NO 64
<211> LENGTH: 16
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 8
<223> OTHER INFORMATION: Xaa = Any Amino Acid

<400> SEQUENCE: 64

```
Phe Lys Asn Pro Ile Pro Pro Xaa Ser His Asn Val Tyr Ile Met Ala
1               5                   10                  15
```

<210> SEQ ID NO 65
<211> LENGTH: 17
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 8, 9
<223> OTHER INFORMATION: Xaa = Any Amino Acid

<400> SEQUENCE: 65

```
Phe Lys Asn Pro Ile Pro Pro Xaa Xaa Ser His Asn Val Tyr Ile Met
1               5                   10                  15

Ala
```

<210> SEQ ID NO 66
<211> LENGTH: 17
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 9
<223> OTHER INFORMATION: Xaa = Any Amino Acid

```
<400> SEQUENCE: 66

Phe Lys Asn Pro Ile Pro Pro Xaa Ser His Asn Val Tyr Ile Met
1               5                   10                  15

Ala

<210> SEQ ID NO 67
<211> LENGTH: 17
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 8
<223> OTHER INFORMATION: Xaa = Any Amino Acid

<400> SEQUENCE: 67

Phe Lys Asn Pro Ile Pro Pro Xaa Pro Ser His Asn Val Tyr Ile Met
1               5                   10                  15

Ala

<210> SEQ ID NO 68
<211> LENGTH: 17
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 8, 9
<223> OTHER INFORMATION: Xaa = Any Amino Acid

<400> SEQUENCE: 68

Lys Trp Phe Lys Asn Pro Ile Xaa Xaa Ser His Asn Val Tyr Ile Met
1               5                   10                  15

Ala

<210> SEQ ID NO 69
<211> LENGTH: 16
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 8, 9
<223> OTHER INFORMATION: Xaa = Any Amino Acid

<400> SEQUENCE: 69

Phe Lys Asn Pro Ile Pro Pro Xaa Xaa Asn Val Tyr Ile Met Ala Asp
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 8, 9
<223> OTHER INFORMATION: Xaa = Any Amino Acid

<400> SEQUENCE: 70

Lys Trp Phe Lys Asn Pro Ile Xaa Xaa Asn Val Tyr Ile Met Ala Asp
1               5                   10                  15
```

```
<210> SEQ ID NO 71
<211> LENGTH: 15
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 8
<223> OTHER INFORMATION: Xaa = Any Amino Acid

<400> SEQUENCE: 71

Lys Leu Glu Tyr Asn Phe Asn Xaa Lys Asn Leu Asn Met Asn Phe
 1               5                  10                  15

<210> SEQ ID NO 72
<211> LENGTH: 16
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 8, 9
<223> OTHER INFORMATION: Xaa = Any Amino Acid

<400> SEQUENCE: 72

Lys Leu Glu Tyr Asn Phe Asn Xaa Xaa Lys Asn Leu Asn Met Asn Phe
 1               5                  10                  15

<210> SEQ ID NO 73
<211> LENGTH: 16
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 8
<223> OTHER INFORMATION: Xaa = Any Amino Acid

<400> SEQUENCE: 73

Lys Leu Glu Tyr Asn Phe Asn Xaa Pro Lys Asn Leu Asn Met Asn Phe
 1               5                  10                  15

<210> SEQ ID NO 74
<211> LENGTH: 16
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 9
<223> OTHER INFORMATION: Xaa = Any Amino Acid

<400> SEQUENCE: 74

Lys Leu Glu Tyr Asn Phe Asn Pro Xaa Lys Asn Leu Asn Met Asn Phe
 1               5                  10                  15

<210> SEQ ID NO 75
<211> LENGTH: 14
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 8, 9
<223> OTHER INFORMATION: Xaa = Any Amino Acid
```

<400> SEQUENCE: 75

Gly His Lys Leu Glu Tyr Asn Xaa Xaa Leu Asn Met Asn Phe
1               5                   10

<210> SEQ ID NO 76
<211> LENGTH: 14
<212> TYPE: PRT
<213> ORGANISM: Artificial Sequence
<220> FEATURE:
<223> OTHER INFORMATION: recombinant peptide biosensor
<220> FEATURE:
<221> NAME/KEY: VARIANT
<222> LOCATION: 8, 9
<223> OTHER INFORMATION: Xaa = Any Amino Acid

<400> SEQUENCE: 76

Lys Leu Glu Tyr Asn Phe Asn Xaa Xaa Leu Asn Met Asn Phe
1               5                   10

<210> SEQ ID NO 77
<211> LENGTH: 567
<212> TYPE: PRT
<213> ORGANISM: Artificial Sequence
<220> FEATURE:
<223> OTHER INFORMATION: recombinant peptide biosensor

<400> SEQUENCE: 77

Met His His His His His Gly Ser Glu Glu Gln Glu Lys Ala Leu
1               5                   10                  15

Asn Phe Gly Ile Ile Ser Thr Glu Ser Gln Gln Asn Leu Lys Pro Gln
                20                  25                  30

Trp Thr Pro Phe Leu Gln Asp Met Glu Lys Lys Leu Gly Val Lys Val
            35                  40                  45

Asn Ala Phe Phe Ala Pro Asp Tyr Ala Gly Ile Ile Gln Gly Met Arg
        50                  55                  60

Phe Asn Lys Val Asp Ile Ala Trp Tyr Gly Asn Leu Ser Ala Met Glu
65                  70                  75                  80

Ala Val Asp Arg Ala Asn Gly Gln Val Phe Ala Gln Thr Val Ala Ala
                85                  90                  95

Asp Gly Ser Ser His Asn Val Tyr Ile Met Ala Asp Lys Gln Arg Asn
            100                 105                 110

Gly Ile Lys Ala Asn Phe Lys Ile Arg His Asn Ile Glu Asp Gly Gly
        115                 120                 125

Val Gln Leu Ala Tyr His Tyr Gln Gln Asn Thr Pro Ile Gly Asp Gly
    130                 135                 140

Pro Val Leu Leu Pro Asp Asn His Tyr Leu Ser Thr Gln Ser Lys Leu
145                 150                 155                 160

Ser Lys Asp Pro Asn Glu Lys Arg Asp His Met Val Leu Leu Glu Phe
                165                 170                 175

Val Thr Ala Ala Gly Ile Thr Leu Gly Met Asp Glu Leu Tyr Lys Gly
            180                 185                 190

Gly Thr Gly Gly Ser Met Val Ser Lys Gly Glu Glu Leu Phe Thr Gly
        195                 200                 205

Val Val Pro Ile Leu Val Glu Leu Asp Gly Asp Val Asn Gly His Lys
    210                 215                 220

Phe Ser Val Ser Gly Glu Gly Glu Gly Asp Ala Thr Tyr Gly Lys Leu
225                 230                 235                 240

Thr Leu Lys Phe Ile Cys Thr Thr Gly Lys Leu Pro Val Pro Trp Pro 245                 250                 255
Thr Leu Val Thr Thr Leu Thr Tyr Gly Val Gln Cys Phe Ser Arg Tyr
                260                 265                 270

Pro Asp His Met Lys Gln His Asp Phe Phe Lys Ser Ala Met Pro Glu
            275                 280                 285

Gly Tyr Ile Gln Glu Arg Thr Ile Phe Phe Lys Asp Asp Gly Asn Tyr
        290                 295                 300

Lys Thr Arg Ala Glu Val Lys Phe Glu Gly Asp Thr Leu Val Asn Arg
305                 310                 315                 320

Ile Glu Leu Lys Gly Ile Asp Phe Lys Glu Asp Gly Asn Ile Leu Gly
                325                 330                 335

His Lys Leu Glu Tyr Asn Phe Asn Pro Gly Tyr Trp Ser Val Leu Ile
            340                 345                 350

Val Asn Lys Asp Ser Pro Ile Asn Asn Leu Asn Asp Leu Leu Ala Lys
        355                 360                 365

Arg Lys Asp Leu Thr Phe Gly Asn Gly Asp Pro Asn Ser Thr Ser Gly
370                 375                 380

Phe Leu Val Pro Gly Tyr Tyr Val Phe Ala Lys Asn Ile Asn Ile Ser
385                 390                 395                 400

Ala Ser Asp Phe Lys Arg Thr Val Asn Ala Gly His Glu Thr Asn Ala
                405                 410                 415

Leu Ala Val Ala Asn Lys Gln Val Asp Val Ala Thr Asn Asn Thr Glu
            420                 425                 430

Asn Leu Asp Lys Leu Lys Thr Ser Ala Pro Glu Lys Leu Lys Glu Leu
        435                 440                 445

Lys Val Ile Trp Lys Ser Pro Leu Ile Pro Gly Asp Pro Ile Val Trp
    450                 455                 460

Arg Lys Asn Leu Ser Glu Thr Thr Lys Asp Lys Ile Tyr Asp Phe Phe
465                 470                 475                 480

Met Asn Tyr Gly Lys Thr Pro Glu Glu Lys Ala Val Leu Glu Arg Leu
                485                 490                 495

Gly Trp Ala Pro Phe Arg Ala Ser Ser Asp Leu Gln Leu Val Pro Ile
            500                 505                 510

Arg Gln Leu Ala Leu Phe Lys Glu Met Gln Ser Val Lys Asp Asn Lys
        515                 520                 525

Gly Leu Asn Glu Gln Asp Lys Leu Ala Lys Thr Thr Ala Ile Gln Ala
    530                 535                 540

Gln Leu Asp Asp Leu Asp Arg Leu Asn Asn Ala Leu Ser Ala Met Ser
545                 550                 555                 560

Ser Val Ser Lys Ala Val Gln
                565

<210> SEQ ID NO 78
<211> LENGTH: 566
<212> TYPE: PRT
<213> ORGANISM: Artificial Sequence
<220> FEATURE:
<223> OTHER INFORMATION: recombinant peptide biosensor

<400> SEQUENCE: 78

Met His His His His His Gly Ser Glu Glu Gln Glu Lys Ala Leu
  1               5                  10                  15

Asn Phe Gly Ile Ile Ser Thr Glu Ser Gln Gln Asn Leu Lys Pro Gln
                20                  25                  30

Trp Thr Pro Phe Leu Gln Asp Met Glu Lys Lys Leu Gly Val Lys Val

```
            35                  40                  45
Asn Ala Phe Phe Ala Pro Asp Tyr Ala Gly Ile Ile Gln Gly Met Arg
            50                  55                  60
Phe Asn Lys Val Asp Ile Ala Trp Tyr Gly Asn Leu Ser Ala Met Glu
 65                  70                  75                  80
Ala Val Asp Arg Ala Asn Gly Gln Val Phe Ala Gln Thr Val Ala Ala
                85                  90                  95
Asp Ala Asp Asn Val Tyr Ile Met Ala Asp Lys Gln Arg Asn Gly Ile
                    100                 105                 110
Lys Ala Asn Phe Lys Ile Arg His Asn Ile Glu Asp Gly Gly Val Gln
                115                 120                 125
Leu Ala Tyr His Tyr Gln Gln Asn Thr Pro Ile Gly Asp Gly Pro Val
                130                 135                 140
Leu Leu Pro Asp Asn His Tyr Leu Ser Thr Gln Ser Lys Leu Ser Lys
145                 150                 155                 160
Ser Lys Asp Pro Asn Glu Lys Arg Asp His Met Val Leu Leu Glu Phe
                    165                 170                 175
Val Thr Ala Ala Gly Ile Thr Leu Gly Met Asp Glu Leu Tyr Lys Gly
                180                 185                 190
Gly Thr Gly Gly Ser Met Val Ser Lys Gly Glu Glu Leu Phe Thr Gly
                195                 200                 205
Val Val Pro Ile Leu Val Glu Leu Asp Gly Asp Val Asn Gly His Lys
                210                 215                 220
Phe Ser Val Ser Gly Glu Gly Glu Gly Asp Ala Thr Tyr Gly Lys Leu
225                 230                 235                 240
Thr Leu Lys Phe Ile Cys Thr Thr Gly Lys Leu Pro Val Pro Trp Pro
                    245                 250                 255
Thr Leu Val Thr Thr Leu Thr Tyr Gly Val Gln Cys Phe Ser Arg Tyr
                260                 265                 270
Pro Asp His Met Lys Gln His Asp Phe Phe Lys Ser Ala Met Pro Glu
                275                 280                 285
Gly Tyr Ile Gln Glu Arg Thr Ile Phe Phe Lys Asp Asp Gly Asn Tyr
                290                 295                 300
Lys Thr Arg Ala Glu Val Lys Phe Glu Gly Asp Thr Leu Val Asn Arg
305                 310                 315                 320
Ile Glu Leu Lys Gly Ile Asp Phe Lys Glu Asp Gly Asn Ile Leu Gly
                    325                 330                 335
His Lys Leu Glu Tyr Asn Phe Asn Pro Gly Tyr Trp Ser Val Leu Ile
                340                 345                 350
Val Asn Lys Asp Ser Pro Ile Asn Asn Leu Asn Asp Leu Leu Ala Lys
                355                 360                 365
Arg Lys Asp Leu Thr Phe Gly Asn Gly Asp Pro Asn Ser Thr Ser Gly
                370                 375                 380
Phe Leu Val Pro Gly Tyr Tyr Val Phe Ala Lys Asn Asn Ile Ser Ala
385                 390                 395                 400
Gly Lys Thr Pro Glu Glu Lys Ala Val Leu Glu Arg Leu Gly Trp Ala
                    405                 410                 415
Pro Phe Arg Ala Ser Ser Asp Leu Gln Leu Val Pro Ile Arg Gln Leu
                420                 425                 430
Ala Leu Phe Lys Glu Met Gln Ser Val Lys Asp Asn Lys Gly Leu Asn
                435                 440                 445
Glu Gln Asp Lys Leu Ala Lys Thr Thr Ala Ile Gln Ala Gln Leu Asp
                450                 455                 460
```

```
Asp Leu Asp Arg Arg Asn Asn Ala Arg Ser Ala Met Ser Ser Val Ser
465                 470                 475                 480

Asn Tyr Gly Lys Thr Pro Glu Glu Lys Ala Val Leu Glu Arg Leu Gly
            485                 490                 495

Trp Ala Pro Phe Arg Ala Ser Ser Asp Leu Gln Leu Val Pro Ile Arg
        500                 505                 510

Gln Leu Ala Leu Phe Lys Glu Met Gln Ser Val Lys Asp Asn Lys Gly
            515                 520                 525

Leu Asn Glu Gln Asp Lys Leu Ala Lys Thr Thr Ala Ile Gln Ala Gln
        530                 535                 540

Leu Asp Asp Leu Asp Arg Leu Asn Asn Ala Leu Ser Ala Met Ser Ser
545                 550                 555                 560

Val Ser Lys Ala Val Gln
                565

<210> SEQ ID NO 79
<211> LENGTH: 16
<212> TYPE: PRT
<213> ORGANISM: Artificial Sequence
<220> FEATURE:
<223> OTHER INFORMATION: synthetic oligopeptide

<400> SEQUENCE: 79

Gln Thr Val Ala Ala Asp Gly Ser Ser His Asn Val Tyr Ile Met Ala
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 80

Gln Thr Val Ala Ala Asp Xaa Xaa Ser His Asn Val Tyr Ile Met Ala
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7
<223> OTHER INFORMATION: Xaa = Any Amino Acid

<400> SEQUENCE: 81

Gln Thr Val Ala Ala Asp Xaa Pro Ser His Asn Val Tyr Ile Met Ala
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
```

```
<223> OTHER INFORMATION: Xaa = Any Amino Acid

<400> SEQUENCE: 82

Gln Thr Val Ala Ala Asp Pro Xaa Ser His Asn Val Tyr Ile Met Ala
 1               5                  10                  15

<210> SEQ ID NO 83
<211> LENGTH: 14
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 83

Gln Thr Val Ala Ala Asp Xaa Xaa Asn Val Tyr Ile Met Ala
 1               5                  10

<210> SEQ ID NO 84
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 84

Gln Thr Val Ala Ala Asp Xaa Xaa Ser His Asn Val Tyr Ile Met Ala
 1               5                  10                  15

<210> SEQ ID NO 85
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 85

Val Phe Gln Thr Val Ala Xaa Xaa Ser His Asn Val Tyr Ile Met Ala
 1               5                  10                  15

<210> SEQ ID NO 86
<211> LENGTH: 16
<212> TYPE: PRT
<213> ORGANISM: Artificial Sequence
<220> FEATURE:
<223> OTHER INFORMATION: synthetic oligopeptide

<400> SEQUENCE: 86

His Lys Leu Glu Tyr Asn Phe Asn Pro Gly Tyr Trp Ser Val Leu Ile
 1               5                  10                  15

<210> SEQ ID NO 87
<211> LENGTH: 18
<212> TYPE: PRT
<213> ORGANISM: Artificial Sequence
<220> FEATURE:
<223> OTHER INFORMATION: synthetic oligopeptide
<220> FEATURE:
```

-continued

```
<221> NAME/KEY: VARIANT
<222> LOCATION: 9, 10
<223> OTHER INFORMATION: Xaa = Any Amino Acid

<400> SEQUENCE: 87

His Lys Leu Glu Tyr Asn Phe Asn Xaa Xaa Pro Gly Tyr Trp Ser Val
 1               5                  10                  15

Leu Ile

<210> SEQ ID NO 88
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 88

His Lys Leu Glu Tyr Asn Xaa Xaa Pro Gly Tyr Trp Ser Val Leu Ile
 1               5                  10                  15

<210> SEQ ID NO 89
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 9, 10
<223> OTHER INFORMATION: Xaa = Any Amino Acid

<400> SEQUENCE: 89

His Lys Leu Glu Tyr Asn Phe Asn Xaa Xaa Tyr Trp Ser Val Leu Ile
 1               5                  10                  15

<210> SEQ ID NO 90
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 10
<223> OTHER INFORMATION: Xaa = Any Amino Acid

<400> SEQUENCE: 90

His Lys Leu Glu Tyr Asn Phe Asn Pro Xaa Tyr Trp Ser Val Leu Ile
 1               5                  10                  15

<210> SEQ ID NO 91
<211> LENGTH: 678
<212> TYPE: PRT
<213> ORGANISM: Artificial Sequence
<220> FEATURE:
<223> OTHER INFORMATION: recombinant peptide biosensor

<400> SEQUENCE: 91

Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
            20                  25                  30

Arg Trp Gly Ser Lys Leu Glu Ile Phe Ser Trp Trp Ala Gly Asp Glu
```

```
            35                  40                  45
Gly Pro Ala Leu Glu Ala Leu Ile Arg Leu Tyr Lys Gln Lys Tyr Pro
 50                  55                  60

Gly Val Glu Val Ile Asn Ala Thr Val Thr Gly Gly Ala Gly Val Asn
 65                  70                  75                  80

Ala Arg Ala Val Leu Lys Thr Arg Met Leu Gly Gly Asp Pro Pro Asp
                     85                  90                  95

Thr Phe Gln Val His Ala Gly Met Glu Leu Ile Gly Thr Trp Val Val
                    100                 105                 110

Ala Asn Arg Met Glu Asp Leu Ser Ala Leu Phe Arg Gln Glu Gly Trp
                115                 120                 125

Leu Gln Ala Phe Pro Lys Gly Leu Ile Asp Leu Ile Ser Tyr Lys Gly
            130                 135                 140

Gly Ile Trp Ser Val Pro Val Asn Ile His Arg Ser Asn Val Met Trp
145                 150                 155                 160

Tyr Leu Pro Ala Lys Leu Lys Glu Trp Gly Val Asn Pro Pro Arg Thr
                    165                 170                 175

Trp Asp Glu Phe Leu Ala Thr Cys Gln Thr Leu Lys Gln Lys Gly Leu
                180                 185                 190

Glu Ala Pro Leu Ala Leu Gly Glu Asn Trp Thr Gln Gln His Leu Trp
            195                 200                 205

Glu Ser Val Ala Leu Ala Val Leu Gly Pro Asp Asp Trp Asn Asn Leu
210                 215                 220

Trp Asn Gly Lys Leu Lys Phe Thr Asp Pro Lys Ala Val Arg Ala Trp
225                 230                 235                 240

Glu Val Phe Gly Arg Val Leu Asp Cys Ala Asn Lys Asp Ala Ala Gly
                    245                 250                 255

Leu Ser Trp Gln Gln Ala Val Asp Arg Val Val Gln Gly Lys Ala Ala
                260                 265                 270

Phe Asn Val Met Gly Asp Trp Ala Ala Gly Tyr Met Thr Thr Thr Leu
            275                 280                 285

Lys Leu Lys Pro Gly Thr Asp Phe Ala Trp Ala Pro Ser Pro Gly Thr
            290                 295                 300

Gln Gly Val Phe Met Met Leu Ser Asp Ser Phe Gly Leu Pro Lys Gly
305                 310                 315                 320

Ala Lys Asn Arg Gln Asn Ala Ile Asn Trp Leu Arg Leu Val Gly Ser
                    325                 330                 335

Lys Glu Gly Gln Asp Thr Phe Asn Pro Leu Lys Gly Ser Ile Ala Ala
                340                 345                 350

Arg Leu Asp Ser Asp Pro Ser Lys Tyr Gly Gly Ser His Asn Val Tyr
            355                 360                 365

Ile Met Ala Asp Lys Gln Arg Asn Gly Ile Lys Ala Asn Phe Lys Ile
            370                 375                 380

Arg His Asn Ile Glu Asp Gly Val Gln Leu Ala Tyr His Tyr Gln
385                 390                 395                 400

Gln Asn Thr Pro Ile Gly Asp Gly Pro Val Leu Leu Pro Asp Asn His
                    405                 410                 415

Tyr Leu Ser Thr Gln Ser Lys Leu Ser Lys Asp Pro Asn Glu Lys Arg
                420                 425                 430

Asp His Met Val Leu Leu Glu Phe Val Thr Ala Ala Gly Ile Thr Leu
            435                 440                 445

Gly Met Asp Glu Leu Tyr Lys Gly Gly Thr Gly Gly Ser Met Val Ser
450                 455                 460
```

```
Lys Gly Glu Glu Leu Phe Thr Gly Val Val Pro Ile Leu Val Glu Leu
465                 470                 475                 480

Asp Gly Asp Val Asn Gly His Lys Phe Ser Val Ser Gly Glu Gly Glu
            485                 490                 495

Gly Asp Ala Thr Tyr Gly Lys Leu Thr Leu Lys Phe Ile Cys Thr Thr
        500                 505                 510

Gly Lys Leu Pro Val Pro Trp Pro Thr Leu Val Thr Thr Leu Thr Tyr
    515                 520                 525

Gly Val Gln Cys Phe Ser Arg Tyr Pro Asp His Met Lys Gln His Asp
530                 535                 540

Phe Phe Lys Ser Ala Met Pro Glu Gly Tyr Ile Gln Glu Arg Thr Ile
545                 550                 555                 560

Phe Phe Lys Asp Asp Gly Asn Tyr Lys Thr Arg Ala Glu Val Lys Phe
                565                 570                 575

Glu Gly Asp Thr Leu Val Asn Arg Ile Glu Leu Lys Gly Ile Asp Phe
            580                 585                 590

Lys Glu Asp Gly Asn Ile Leu Gly His Lys Leu Glu Tyr Asn Phe Asn
        595                 600                 605

Asn Pro Asn Ala Tyr Gly Gln Ser Ala Met Arg Asp Trp Arg Ser Asn
    610                 615                 620

Arg Ile Val Gly Ser Leu Val His Gly Val Ala Pro Glu Ser Phe
625                 630                 635                 640

Met Ser Gln Phe Gly Thr Val Met Glu Ile Phe Leu Gln Thr Arg Asn
                645                 650                 655

Pro Gln Ala Ala Asn Ala Ala Gln Ala Ile Ala Asp Gln Val Gly
            660                 665                 670

Leu Gly Arg Leu Gly Gln
            675

<210> SEQ ID NO 92
<211> LENGTH: 678
<212> TYPE: PRT
<213> ORGANISM: Artificial Sequence
<220> FEATURE:
<223> OTHER INFORMATION: recombinant peptide biosensor

<400> SEQUENCE: 92

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Leu Glu Ile Phe Ser Trp Trp Ala Gly Asp Glu
        35                  40                  45

Gly Pro Ala Leu Glu Ala Leu Ile Arg Leu Tyr Lys Gln Lys Tyr Pro
    50                  55                  60

Gly Val Glu Val Ile Asn Ala Thr Val Thr Gly Gly Ala Gly Val Asn
65                  70                  75                  80

Ala Arg Ala Val Leu Lys Thr Arg Met Leu Gly Gly Asp Pro Pro Asp
                85                  90                  95

Thr Phe Gln Val His Ala Gly Met Glu Leu Ile Gly Thr Trp Val Val
            100                 105                 110

Ala Asn Arg Met Glu Asp Leu Ser Ala Leu Phe Arg Gln Glu Gly Trp
        115                 120                 125

Leu Gln Ala Phe Pro Lys Gly Leu Ile Asp Leu Ile Ser Tyr Lys Gly
    130                 135                 140
```

-continued

```
Gly Ile Trp Ser Val Pro Val Asn Ile His Arg Ser Asn Val Met Trp
145                 150                 155                 160

Tyr Leu Pro Ala Lys Leu Lys Glu Trp Gly Val Asn Pro Pro Arg Thr
            165                 170                 175

Trp Asp Glu Phe Leu Ala Thr Cys Gln Thr Leu Lys Gln Lys Gly Leu
        180                 185                 190

Glu Ala Pro Leu Ala Leu Gly Glu Asn Trp Thr Gln Gln His Leu Trp
    195                 200                 205

Glu Ser Val Ala Leu Ala Val Leu Gly Pro Asp Asp Trp Asn Asn Leu
210                 215                 220

Trp Asn Gly Lys Leu Lys Phe Thr Asp Pro Lys Ala Val Arg Ala Trp
225                 230                 235                 240

Glu Val Phe Gly Arg Val Leu Asp Cys Ala Asn Lys Asp Ala Ala Gly
                245                 250                 255

Leu Ser Trp Gln Gln Ala Val Asp Arg Val Val Gln Gly Lys Ala Ala
            260                 265                 270

Phe Asn Val Met Gly Asp Trp Ala Ala Gly Tyr Met Thr Thr Thr Leu
        275                 280                 285

Lys Leu Lys Pro Gly Thr Asp Phe Ala Trp Ala Pro Ser Pro Gly Thr
    290                 295                 300

Gln Gly Val Phe Met Met Leu Ser Asp Ser Phe Gly Leu Pro Lys Gly
305                 310                 315                 320

Ala Lys Asn Arg Gln Asn Ala Ile Asn Trp Leu Arg Leu Val Gly Ser
                325                 330                 335

Lys Glu Gly Gln Asp Thr Phe Asn Pro Leu Lys Gly Ser Ile Ala Ala
            340                 345                 350

Arg Leu Asp Ser Asp Pro Ser Lys Tyr Pro Ala Ser His Asn Val Tyr
        355                 360                 365

Ile Met Ala Asp Lys Gln Arg Asn Gly Ile Lys Ala Asn Phe Lys Ile
    370                 375                 380

Arg His Asn Ile Glu Asp Gly Gly Val Gln Leu Ala Tyr His Tyr Gln
385                 390                 395                 400

Gln Asn Thr Pro Ile Gly Asp Gly Pro Val Leu Leu Pro Asp Asn His
                405                 410                 415

Tyr Leu Ser Thr Gln Ser Lys Leu Ser Lys Asp Pro Asn Glu Lys Arg
            420                 425                 430

Asp His Met Val Leu Leu Glu Phe Val Thr Ala Ala Gly Ile Thr Leu
        435                 440                 445

Gly Met Asp Glu Leu Tyr Lys Gly Gly Thr Gly Gly Ser Met Val Ser
    450                 455                 460

Lys Gly Glu Glu Leu Phe Thr Gly Val Val Pro Ile Leu Val Glu Leu
465                 470                 475                 480

Asp Gly Asp Val Asn Gly His Lys Phe Ser Val Ser Gly Glu Gly Glu
                485                 490                 495

Gly Asp Ala Thr Tyr Gly Lys Leu Thr Leu Lys Phe Ile Cys Thr Thr
            500                 505                 510

Gly Lys Leu Pro Val Pro Trp Pro Thr Leu Val Thr Thr Leu Thr Tyr
        515                 520                 525

Gly Val Gln Cys Phe Ser Arg Tyr Pro Asp His Met Lys Gln His Asp
    530                 535                 540

Phe Phe Lys Ser Ala Met Pro Glu Gly Tyr Ile Gln Glu Arg Thr Ile
545                 550                 555                 560
```

-continued

```
Phe Phe Lys Asp Asp Gly Asn Tyr Lys Thr Arg Ala Glu Val Lys Phe
                565                 570                 575

Glu Gly Asp Thr Leu Val Asn Arg Ile Glu Leu Lys Gly Ile Asp Phe
            580                 585                 590

Lys Glu Asp Gly Asn Ile Leu Gly His Lys Leu Glu Tyr Asn Phe Asn
        595                 600                 605

Asn Pro Asn Ala Tyr Gly Gln Ser Ala Met Arg Asp Trp Arg Ser Asn
    610                 615                 620

Arg Ile Val Gly Ser Leu Val His Gly Ala Val Ala Pro Glu Ser Phe
625                 630                 635                 640

Met Ser Gln Phe Gly Thr Val Met Glu Ile Phe Leu Gln Thr Arg Asn
                645                 650                 655

Pro Gln Ala Ala Ala Asn Ala Ala Gln Ala Ile Ala Asp Gln Val Gly
            660                 665                 670

Leu Gly Arg Leu Gly Gln
            675

<210> SEQ ID NO 93
<211> LENGTH: 678
<212> TYPE: PRT
<213> ORGANISM: Artificial Sequence
<220> FEATURE:
<223> OTHER INFORMATION: recombinant peptide biosensor

<400> SEQUENCE: 93

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Leu Glu Ile Phe Ser Trp Trp Ala Gly Asp Glu
        35                  40                  45

Gly Pro Ala Leu Glu Ala Leu Ile Arg Leu Tyr Lys Gln Lys Tyr Pro
    50                  55                  60

Gly Val Glu Val Ile Asn Ala Thr Val Thr Gly Gly Ala Gly Val Asn
65                  70                  75                  80

Ala Arg Ala Val Leu Lys Thr Arg Met Leu Gly Asp Pro Pro Asp
                85                  90                  95

Thr Phe Gln Val His Ala Gly Met Glu Leu Ile Gly Thr Trp Val Val
            100                 105                 110

Ala Asn Arg Met Glu Asp Leu Ser Ala Leu Phe Arg Gln Glu Gly Trp
        115                 120                 125

Leu Gln Ala Phe Pro Lys Gly Leu Ile Asp Leu Ile Ser Tyr Lys Gly
    130                 135                 140

Gly Ile Trp Ser Val Pro Val Asn Ile His Arg Ser Asn Val Met Trp
145                 150                 155                 160

Tyr Leu Pro Ala Lys Leu Lys Glu Trp Gly Val Asn Pro Pro Arg Thr
                165                 170                 175

Trp Asp Glu Phe Leu Ala Thr Cys Gln Thr Leu Lys Gln Lys Gly Leu
            180                 185                 190

Glu Ala Pro Leu Ala Leu Gly Glu Asn Trp Thr Gln Gln His Leu Trp
        195                 200                 205

Glu Ser Val Ala Leu Ala Val Leu Gly Pro Asp Asp Trp Asn Asn Leu
    210                 215                 220

Trp Asn Gly Lys Leu Lys Phe Thr Asp Pro Lys Ala Val Arg Ala Trp
225                 230                 235                 240
```

```
Ala Arg Ala Val Leu Lys Thr Arg Met Leu Gly Gly Asp Pro Pro Asp
            245                 250                 255

Thr Phe Gln Val Ala Ala Gly Met Glu Leu Ile Gly Thr Trp Val Val
            260                 265                 270

Ala Asn Arg Met Glu Asp Leu Ser Ala Leu Phe Arg Gln Glu Gly Trp
            275                 280                 285

Leu Gln Ala Phe Pro Lys Gly Leu Ile Asp Leu Ile Ser Tyr Lys Gly
            290                 295                 300

Gly Ile Trp Ser Val Pro Val Asn Ile His Arg Ser Asn Val Met Trp
305                 310                 315                 320

Ala Lys Asn Arg Gln Asn Ala Ile Asn Trp Leu Arg Leu Val Gly Ser
                325                 330                 335

Lys Glu Gly Gln Asp Thr Phe Asn Pro Leu Lys Gly Ser Ile Ala Ala
            340                 345                 350

Arg Leu Asp Ser Asp Pro Ser Lys Tyr Gly Gly Ser His Asn Val Tyr
            355                 360                 365

Ile Met Ala Asp Lys Gln Arg Asn Gly Ile Lys Ala Asn Phe Lys Ile
        370                 375                 380

Arg His Asn Ile Glu Asp Gly Gly Val Gln Leu Ala Tyr His Tyr Gln
385                 390                 395                 400

Gln Asn Thr Pro Ile Gly Asp Gly Pro Val Leu Leu Pro Asp Asn His
            405                 410                 415

Tyr Leu Ser Thr Gln Ser Lys Leu Ser Lys Asp Pro Asn Glu Lys Arg
            420                 425                 430

Asp His Met Val Leu Leu Glu Phe Val Thr Ala Ala Gly Ile Thr Leu
        435                 440                 445

Gly Met Asp Glu Leu Tyr Lys Gly Gly Thr Gly Gly Ser Met Val Ser
450                 455                 460

Lys Gly Glu Glu Leu Phe Thr Gly Val Val Pro Ile Leu Val Glu Leu
465                 470                 475                 480

Asp Gly Asp Val Asn Gly His Lys Phe Ser Val Ser Gly Glu Gly Glu
            485                 490                 495

Gly Asp Ala Thr Tyr Gly Lys Leu Thr Leu Lys Phe Ile Cys Thr Thr
            500                 505                 510

Gly Lys Leu Pro Val Pro Trp Pro Thr Leu Val Thr Thr Leu Thr Tyr
        515                 520                 525

Gly Val Gln Cys Phe Ser Arg Tyr Pro Asp His Met Lys Gln His Asp
            530                 535                 540

Phe Phe Lys Ser Ala Met Pro Glu Gly Tyr Ile Gln Glu Arg Thr Ile
545                 550                 555                 560

Phe Phe Lys Asp Asp Gly Asn Tyr Lys Thr Arg Ala Glu Val Lys Phe
            565                 570                 575

Glu Gly Asp Thr Leu Val Asn Arg Ile Glu Leu Lys Gly Ile Asp Phe
            580                 585                 590

Lys Glu Asp Gly Asn Ile Leu Gly His Lys Leu Glu Tyr Asn Phe Asn
        595                 600                 605

Asn Pro Asn Ala Tyr Gly Gln Ser Ala Met Arg Asp Trp Arg Ser Asn
            610                 615                 620

Arg Ile Val Gly Ser Leu Val His Gly Ala Val Ala Pro Glu Ser Phe
625                 630                 635                 640

Met Ser Gln Phe Gly Thr Val Met Glu Ile Phe Leu Gln Thr Arg Asn
            645                 650                 655

Pro Gln Ala Ala Ala Asn Ala Ala Gln Ala Ile Ala Asp Gln Val Gly
```

```
                    660                 665                 670
Leu Gly Arg Leu Gly Gln
            675

<210> SEQ ID NO 94
<211> LENGTH: 678
<212> TYPE: PRT
<213> ORGANISM: Artificial Sequence
<220> FEATURE:
<223> OTHER INFORMATION: recombinant peptide biosensor

<400> SEQUENCE: 94

Met Arg Gly Ser His His His His His Gly Met Ala Ser Met Thr
 1               5                  10                  15

Gly Gly Gln Gln Met Gly Arg Asp Leu Tyr Asp Asp Asp Lys Asp
                20                  25                  30

Arg Trp Gly Ser Lys Leu Glu Ile Phe Ser Trp Trp Ala Gly Asp Glu
            35                  40                  45

Gly Pro Ala Leu Glu Ala Leu Ile Arg Leu Tyr Lys Gln Lys Tyr Pro
 50                  55                  60

Gly Val Glu Val Ile Asn Ala Thr Val Thr Gly Gly Ala Gly Val Asn
65                   70                  75                  80

Ala Arg Ala Val Leu Lys Thr Arg Met Leu Gly Gly Asp Pro Pro Asp
                85                  90                  95

Thr Phe Gln Val His Ala Gly Met Glu Leu Ile Gly Thr Trp Val Val
                100                 105                 110

Ala Asn Arg Met Glu Asp Leu Ser Ala Leu Phe Arg Gln Glu Gly Trp
            115                 120                 125

Leu Gln Ala Phe Pro Lys Gly Leu Ile Asp Leu Ile Ser Tyr Lys Gly
    130                 135                 140

Gly Ile Trp Ser Val Pro Val Asn Ile His Arg Ser Asn Val Met Trp
145                 150                 155                 160

Tyr Leu Pro Ala Lys Leu Lys Glu Trp Gly Val Asn Pro Pro Arg Thr
                165                 170                 175

Trp Asp Glu Phe Leu Ala Thr Cys Gln Thr Leu Lys Gln Lys Gly Leu
            180                 185                 190

Glu Ala Pro Leu Ala Leu Gly Glu Asn Trp Thr Gln Gln His Leu Trp
        195                 200                 205

Glu Ser Val Ala Leu Ala Val Leu Gly Pro Asp Asp Trp Asn Asn Leu
    210                 215                 220

Trp Asn Gly Lys Leu Lys Phe Thr Asp Pro Lys Ala Val Arg Ala Trp
225                 230                 235                 240

Glu Val Phe Gly Arg Val Leu Asp Cys Ala Asn Lys Asp Ala Ala Gly
                245                 250                 255

Leu Ser Trp Gln Gln Ala Val Asp Arg Val Val Gln Gly Lys Ala Ala
            260                 265                 270

Phe Asn Val Met Gly Asp Trp Ala Ala Gly Tyr Met Thr Thr Thr Leu
        275                 280                 285

Lys Leu Lys Pro Gly Thr Asp Phe Ala Trp Ala Pro Ser Pro Gly Thr
    290                 295                 300

Gln Gly Val Phe Met Met Leu Ser Asp Ser Phe Gly Leu Pro Lys Gly
305                 310                 315                 320

Ala Lys Asn Arg Gln Asn Ala Ile Asn Trp Leu Arg Leu Val Gly Ser
                325                 330                 335

Lys Glu Gly Gln Asp Thr Phe Asn Pro Leu Lys Gly Ser Ile Ala Ala
```

```
                    340                 345                 350
Arg Leu Asp Ser Asp Pro Ser Lys Tyr Gly Gly Ser His Asn Val Tyr
            355                 360                 365

Ile Met Ala Asp Lys Gln Arg Asn Gly Ile Lys Ala Asn Phe Lys Ile
        370                 375                 380

Arg His Asn Ile Glu Asp Gly Val Gln Leu Ala Tyr His Tyr Gln
385                 390                 395                 400

Gln Asn Thr Pro Ile Gly Asp Gly Pro Val Leu Leu Pro Asp Asn His
                405                 410                 415

Tyr Leu Ser Thr Gln Ser Lys Leu Ser Lys Asp Pro Asn Glu Lys Arg
            420                 425                 430

Asp His Met Val Leu Leu Glu Phe Val Thr Ala Ala Gly Ile Thr Leu
        435                 440                 445

Gly Met Asp Glu Leu Tyr Lys Gly Gly Thr Gly Gly Ser Met Val Ser
    450                 455                 460

Lys Gly Glu Glu Leu Phe Thr Gly Val Val Pro Ile Leu Val Glu Leu
465                 470                 475                 480

Asp Gly Asp Val Asn Gly His Lys Phe Ser Val Ser Gly Glu Gly Glu
                485                 490                 495

Gly Asp Ala Thr Tyr Gly Lys Leu Thr Leu Lys Phe Ile Cys Thr Thr
            500                 505                 510

Gly Lys Leu Pro Val Pro Trp Pro Thr Leu Val Thr Thr Leu Thr Tyr
        515                 520                 525

Gly Val Gln Cys Phe Ser Arg Tyr Pro Asp His Met Lys Gln His Asp
    530                 535                 540

Phe Phe Lys Ser Ala Met Pro Glu Gly Tyr Ile Gln Glu Arg Thr Ile
545                 550                 555                 560

Phe Phe Lys Asp Asp Gly Asn Tyr Lys Thr Arg Ala Glu Val Lys Phe
                565                 570                 575

Glu Gly Asp Thr Leu Val Asn Arg Ile Glu Leu Lys Gly Ile Asp Phe
            580                 585                 590

Lys Glu Asp Gly Asn Ile Leu Gly His Lys Leu Glu Tyr Asn Phe Asn
        595                 600                 605

Asn Pro Asn Ala Tyr Gly Gln Ser Ala Met Arg Asp Trp Arg Ser Asn
    610                 615                 620

Arg Ile Val Gly Ser Leu Val Ala Gly Ala Val Ala Pro Glu Ser Phe
625                 630                 635                 640

Met Ser Gln Phe Gly Thr Val Met Glu Ile Phe Leu Gln Thr Arg Asn
                645                 650                 655

Pro Gln Ala Ala Ala Asn Ala Ala Gln Ala Ile Ala Asp Gln Val Gly
            660                 665                 670

Leu Gly Arg Leu Gly Gln
        675

<210> SEQ ID NO 95
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 9
<223> OTHER INFORMATION: Xaa = Any Amino Acid

<400> SEQUENCE: 95
```

```
Asp Ser Asp Pro Ser Lys Tyr Xaa Xaa Ser His Asn Val Tyr Ile Met
1               5                   10                  15
```

<210> SEQ ID NO 96
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 9
<223> OTHER INFORMATION: Xaa = Any Amino Acid

<400> SEQUENCE: 96

```
Asp Ser Asp Pro Ser Lys Tyr Pro Xaa Ser His Asn Val Tyr Ile Met
1               5                   10                  15
```

<210> SEQ ID NO 97
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 97

```
Asp Ser Asp Pro Ser Lys Tyr Xaa Pro Ser His Asn Val Tyr Ile Met
1               5                   10                  15
```

<210> SEQ ID NO 98
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 9
<223> OTHER INFORMATION: Xaa = Any Amino Acid

<400> SEQUENCE: 98

```
Arg Leu Asp Ser Asp Pro Ser Xaa Xaa Ser His Asn Val Tyr Ile Met
1               5                   10                  15
```

<210> SEQ ID NO 99
<211> LENGTH: 14
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 9
<223> OTHER INFORMATION: Xaa = Any Amino Acid

<400> SEQUENCE: 99

```
Asp Ser Asp Pro Ser Lys Tyr Xaa Xaa Asn Val Tyr Ile Met
1               5                   10
```

<210> SEQ ID NO 100
<211> LENGTH: 16
<212> TYPE: PRT
<213> ORGANISM: Artificial Sequence
<220> FEATURE:
<223> OTHER INFORMATION: synthetic oligopeptide
<220> FEATURE:

```
<221> NAME/KEY: VARIANT
<222> LOCATION: 8, 9
<223> OTHER INFORMATION: Xaa = Any Amino Acid

<400> SEQUENCE: 100

Lys Leu Glu Tyr Asn Phe Asn Xaa Xaa Asn Ala Tyr Gly Gln Ser Ala
 1               5                  10                  15

<210> SEQ ID NO 101
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 7, 8
<223> OTHER INFORMATION: Xaa = Any Amino Acid

<400> SEQUENCE: 101

Lys Leu Glu Tyr Asn Phe Xaa Xaa Pro Asn Ala Tyr Gly Gln Ser Ala
 1               5                  10                  15

<210> SEQ ID NO 102
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8, 9
<223> OTHER INFORMATION: Xaa = Any Amino Acid

<400> SEQUENCE: 102

Gly His Lys Leu Glu Tyr Asn Xaa Xaa Asn Ala Tyr Gly Gln Ser Ala
 1               5                  10                  15

<210> SEQ ID NO 103
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 8
<223> OTHER INFORMATION: Xaa = Any Amino Acid

<400> SEQUENCE: 103

Lys Leu Glu Tyr Asn Phe Asn Xaa Pro Asn Ala Tyr Gly Gln Ser Ala
 1               5                  10                  15

<210> SEQ ID NO 104
<211> LENGTH: 16
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 9
<223> OTHER INFORMATION: Xaa = Any Amino Acid

<400> SEQUENCE: 104

Lys Leu Glu Tyr Asn Phe Asn Pro Xaa Asn Ala Tyr Gly Gln Ser Ala
 1               5                  10                  15

<210> SEQ ID NO 105
```

```
<211> LENGTH: 396
<212> TYPE: PRT
<213> ORGANISM: Escherichia coli

<400> SEQUENCE: 105
```

| | | | | | | | | | | | | | | |
|---|---|---|---|---|---|---|---|---|---|---|---|---|---|---|
| Met | Lys | Ile | Lys | Thr | Gly | Ala | Arg | Ile | Leu | Ala | Leu | Ser | Ala | Leu | Thr |
| 1 | | | | 5 | | | | | 10 | | | | | 15 | |
| Thr | Met | Met | Phe | Ser | Ala | Ser | Ala | Leu | Ala | Lys | Ile | Glu | Glu | Gly | Lys |
| | | | 20 | | | | | 25 | | | | | 30 | | |
| Leu | Val | Ile | Trp | Ile | Asn | Gly | Asp | Lys | Gly | Tyr | Asn | Gly | Leu | Ala | Glu |
| | | | 35 | | | | | 40 | | | | | 45 | | |
| Val | Gly | Lys | Lys | Phe | Glu | Lys | Asp | Thr | Gly | Ile | Lys | Val | Thr | Val | Glu |
| | 50 | | | | | 55 | | | | | 60 | | | | |
| His | Pro | Asp | Lys | Leu | Glu | Glu | Lys | Phe | Pro | Gln | Val | Ala | Ala | Thr | Gly |
| 65 | | | | | 70 | | | | | 75 | | | | | 80 |
| Asp | Gly | Pro | Asp | Ile | Ile | Phe | Trp | Ala | His | Asp | Arg | Phe | Gly | Gly | Tyr |
| | | | | 85 | | | | | 90 | | | | | 95 | |
| Ala | Gln | Ser | Gly | Leu | Leu | Ala | Glu | Ile | Thr | Pro | Asp | Lys | Ala | Phe | Gln |
| | | | 100 | | | | | 105 | | | | | 110 | | |
| Asp | Lys | Leu | Tyr | Pro | Phe | Thr | Trp | Asp | Ala | Val | Arg | Tyr | Asn | Gly | Lys |
| | | | 115 | | | | | 120 | | | | | 125 | | |
| Leu | Ile | Ala | Tyr | Pro | Ile | Ala | Val | Glu | Ala | Leu | Ser | Leu | Ile | Tyr | Asn |
| | 130 | | | | | 135 | | | | | 140 | | | | |
| Lys | Asp | Leu | Leu | Pro | Asn | Pro | Pro | Lys | Thr | Trp | Glu | Glu | Ile | Pro | Ala |
| 145 | | | | | 150 | | | | | 155 | | | | | 160 |
| Leu | Asp | Lys | Glu | Leu | Lys | Ala | Lys | Gly | Lys | Ser | Ala | Leu | Met | Phe | Asn |
| | | | | 165 | | | | | 170 | | | | | 175 | |
| Leu | Gln | Glu | Pro | Tyr | Phe | Thr | Trp | Pro | Leu | Ile | Ala | Ala | Asp | Gly | Gly |
| | | | 180 | | | | | 185 | | | | | 190 | | |
| Tyr | Ala | Phe | Lys | Tyr | Glu | Asn | Gly | Lys | Tyr | Asp | Ile | Lys | Asp | Val | Gly |
| | | | 195 | | | | | 200 | | | | | 205 | | |
| Val | Asp | Asn | Ala | Gly | Ala | Lys | Ala | Gly | Leu | Thr | Phe | Leu | Val | Asp | Leu |
| | 210 | | | | | 215 | | | | | 220 | | | | |
| Ile | Lys | Asn | Lys | His | Met | Asn | Ala | Asp | Thr | Asp | Tyr | Ser | Ile | Ala | Glu |
| 225 | | | | | 230 | | | | | 235 | | | | | 240 |
| Ala | Ala | Phe | Asn | Lys | Gly | Glu | Thr | Ala | Met | Thr | Ile | Asn | Gly | Pro | Trp |
| | | | | 245 | | | | | 250 | | | | | 255 | |
| Ala | Trp | Ser | Asn | Ile | Asp | Thr | Ser | Lys | Val | Asn | Tyr | Gly | Val | Thr | Val |
| | | | 260 | | | | | 265 | | | | | 270 | | |
| Leu | Pro | Thr | Phe | Lys | Gly | Gln | Pro | Ser | Lys | Pro | Phe | Val | Gly | Val | Leu |
| | | | 275 | | | | | 280 | | | | | 285 | | |
| Ser | Ala | Gly | Ile | Asn | Ala | Ala | Ser | Pro | Asn | Lys | Glu | Leu | Ala | Lys | Glu |
| | 290 | | | | | 295 | | | | | 300 | | | | |
| Phe | Leu | Glu | Asn | Tyr | Leu | Leu | Thr | Asp | Glu | Gly | Leu | Glu | Ala | Val | Asn |
| 305 | | | | | 310 | | | | | 315 | | | | | 320 |
| Lys | Asp | Lys | Pro | Leu | Gly | Ala | Val | Ala | Leu | Lys | Ser | Tyr | Glu | Glu | Glu |
| | | | | 325 | | | | | 330 | | | | | 335 | |
| Leu | Ala | Lys | Asp | Pro | Arg | Ile | Ala | Ala | Thr | Met | Glu | Asn | Ala | Gln | Lys |
| | | | 340 | | | | | 345 | | | | | 350 | | |
| Gly | Glu | Ile | Met | Pro | Asn | Ile | Pro | Gln | Met | Ser | Ala | Phe | Trp | Tyr | Ala |
| | | | 355 | | | | | 360 | | | | | 365 | | |
| Val | Arg | Thr | Ala | Val | Ile | Asn | Ala | Ala | Ser | Gly | Arg | Gln | Thr | Val | Asp |
| | 370 | | | | | 375 | | | | | 380 | | | | |
| Glu | Ala | Leu | Lys | Asp | Ala | Gln | Thr | Arg | Ile | Thr | Lys | | | | |

<210> SEQ ID NO 106
<211> LENGTH: 433
<212> TYPE: PRT
<213> ORGANISM: Pyrococcus furiosus

<400> SEQUENCE: 106

Met Arg Arg Ala Thr Tyr Ala Phe Ala Leu Leu Ala Ile Leu Val Leu
1               5                   10                  15

Gly Val Val Ala Ser Gly Cys Ile Gly Gly Thr Thr Thr Pro Thr
            20                  25                  30

Gln Thr Ser Pro Ala Thr Gln Pro Thr Thr Gln Thr Pro Thr Gln
        35                  40                  45

Thr Glu Thr Gln Ala Val Glu Cys Gly Ser Gly Lys Val Val Ile Trp
    50                  55                  60

His Ala Met Gln Pro Asn Glu Leu Glu Val Phe Gln Ser Leu Ala Glu
65                  70                  75                  80

Glu Tyr Met Ala Leu Cys Pro Glu Val Glu Ile Val Phe Glu Gln Lys
                85                  90                  95

Pro Asn Leu Glu Asp Ala Leu Lys Ala Ala Ile Pro Thr Gly Gln Gly
            100                 105                 110

Pro Asp Leu Phe Ile Trp Ala His Asp Trp Ile Gly Lys Phe Ala Glu
        115                 120                 125

Ala Gly Leu Leu Glu Pro Ile Asp Glu Tyr Val Thr Glu Asp Leu Leu
130                 135                 140

Asn Glu Phe Ala Pro Met Ala Gln Asp Ala Met Gln Tyr Lys Gly His
145                 150                 155                 160

Tyr Tyr Ala Leu Pro Phe Ala Ala Glu Thr Val Ala Ile Ile Tyr Asn
                165                 170                 175

Lys Glu Met Val Ser Glu Pro Pro Lys Thr Phe Asp Glu Met Lys Ala
            180                 185                 190

Ile Met Glu Lys Tyr Tyr Asp Pro Ala Asn Glu Lys Tyr Gly Ile Ala
        195                 200                 205

Trp Pro Ile Asn Ala Tyr Phe Ile Ser Ala Ile Ala Gln Ala Phe Gly
210                 215                 220

Gly Tyr Tyr Phe Asp Asp Lys Thr Glu Gln Pro Gly Leu Asp Lys Pro
225                 230                 235                 240

Glu Thr Ile Gly Phe Lys Phe Phe Thr Glu Ile Trp Pro Tyr Met
                245                 250                 255

Ala Pro Thr Gly Asp Tyr Asn Thr Gln Gln Ser Ile Phe Leu Glu Gly
            260                 265                 270

Arg Ala Pro Met Met Val Asn Gly Pro Trp Ser Ile Asn Asp Val Lys
        275                 280                 285

Lys Ala Gly Ile Asn Phe Gly Val Val Pro Leu Pro Pro Ile Ile Lys
290                 295                 300

Asp Gly Lys Glu Tyr Trp Pro Arg Pro Tyr Gly Val Lys Leu Ile
305                 310                 315                 320

Tyr Phe Ala Ala Gly Ile Lys Asn Lys Asp Ala Ala Trp Lys Phe Ala
                325                 330                 335

Lys Trp Leu Thr Thr Ser Glu Glu Ser Ile Lys Thr Leu Ala Leu Glu
            340                 345                 350

Leu Gly Tyr Ile Pro Val Leu Thr Lys Val Leu Asp Asp Pro Glu Ile
        355                 360                 365

Lys Asn Asp Pro Val Ile Tyr Gly Phe Gly Gln Ala Val Gln His Ala
370                 375                 380

Tyr Leu Met Pro Lys Ser Pro Lys Met Ser Ala Val Trp Gly Gly Val
385                 390                 395                 400

Asp Gly Ala Ile Asn Glu Ile Leu Gln Asp Pro Gln Asn Ala Asp Ile
            405                 410                 415

Glu Gly Ile Leu Lys Lys Tyr Gln Gln Glu Ile Leu Asn Asn Met Gln
420                 425                 430

Gly

<210> SEQ ID NO 107
<211> LENGTH: 338
<212> TYPE: PRT
<213> ORGANISM: Escherichia coli

<400> SEQUENCE: 107

Met Asn Ala Lys Ile Ile Ala Ser Leu Ala Phe Thr Ser Met Phe Ser
1               5                   10                  15

Leu Ser Thr Leu Leu Asn Pro Ala Tyr Ala Glu Gln Glu Lys Ala
            20                  25                  30

Leu Asn Phe Gly Ile Ile Ser Thr Glu Ser Gln Gln Asn Leu Lys Pro
            35                  40                  45

Gln Trp Thr Pro Phe Leu Gln Asp Met Glu Lys Lys Leu Gly Val Lys
50                  55                  60

Val Asn Ala Phe Phe Ala Pro Asp Tyr Ala Gly Ile Ile Gln Gly Met
65                  70                  75                  80

Arg Phe Asn Lys Val Asp Ile Ala Trp Tyr Gly Asn Leu Ser Ala Met
                85                  90                  95

Glu Ala Val Asp Arg Ala Asn Gly Gln Val Phe Ala Gln Thr Val Ala
            100                 105                 110

Ala Asp Gly Ser Pro Gly Tyr Trp Ser Val Leu Ile Val Asn Lys Asp
            115                 120                 125

Ser Pro Ile Asn Asn Leu Asn Asp Leu Leu Ala Lys Arg Lys Asp Leu
130                 135                 140

Thr Phe Gly Asn Gly Asp Pro Asn Ser Thr Ser Gly Phe Leu Val Pro
145                 150                 155                 160

Gly Tyr Tyr Val Phe Ala Lys Asn Asn Ile Ser Ala Ser Asp Phe Lys
                165                 170                 175

Arg Thr Val Asn Ala Gly His Glu Thr Asn Ala Leu Ala Val Ala Asn
            180                 185                 190

Lys Gln Val Asp Val Ala Thr Asn Asn Thr Glu Asn Leu Asp Lys Leu
            195                 200                 205

Lys Thr Ser Ala Pro Gln Lys Leu Lys Glu Leu Lys Val Ile Trp Lys
210                 215                 220

Ser Pro Leu Ile Pro Gly Asp Pro Ile Val Trp Arg Lys Asn Leu Ser
225                 230                 235                 240

Glu Thr Thr Lys Asp Lys Ile Tyr Asp Phe Phe Met Asn Tyr Gly Lys
                245                 250                 255

Thr Pro Glu Glu Lys Ala Val Leu Glu Arg Leu Gly Trp Ala Pro Phe
            260                 265                 270

Arg Ala Ser Ser Asp Leu Gln Leu Val Pro Ile Arg Gln Leu Ala Leu
            275                 280                 285

Phe Lys Glu Met Gln Ser Val Lys Asp Asn Lys Gly Leu Asn Glu Gln
290                 295                 300

Asp Lys Leu Ala Lys Thr Thr Ala Ile Gln Ala Gln Leu Asp Asp Leu
305                 310                 315                 320

Asp Arg Leu Asn Asn Ala Leu Ser Ala Met Ser Ser Val Ser Lys Ala
            325                 330                 335

Val Gln

<210> SEQ ID NO 108
<211> LENGTH: 302
<212> TYPE: PRT
<213> ORGANISM: Escherichia coli

<400> SEQUENCE: 108

Met Gln Leu Arg Lys Pro Ala Thr Ala Ile Leu Ala Leu Ala Leu Ser
1               5                   10                  15

Ala Gly Leu Ala Gln Ala Asp Asp Ala Ala Pro Ala Ala Gly Ser Thr
            20                  25                  30

Leu Asp Lys Ile Ala Lys Asn Gly Val Ile Val Gly His Arg Glu
        35                  40                  45

Ser Ser Val Pro Phe Ser Tyr Tyr Asp Asn Gln Gln Lys Val Val Gly
    50                  55                  60

Tyr Ser Gln Asp Tyr Ser Asn Ala Ile Val Glu Ala Val Lys Lys Lys
65                  70                  75                  80

Leu Asn Lys Pro Asp Leu Gln Val Lys Leu Ile Pro Ile Thr Ser Gln
                85                  90                  95

Asn Arg Ile Pro Leu Leu Gln Asn Gly Thr Phe Asp Phe Glu Cys Gly
            100                 105                 110

Ser Thr Thr Asn Asn Val Glu Arg Gln Lys Gln Ala Ala Phe Ser Asp
        115                 120                 125

Thr Ile Phe Val Val Gly Thr Arg Leu Leu Thr Lys Lys Gly Gly Asp
    130                 135                 140

Ile Lys Asp Phe Ala Asn Leu Lys Asp Lys Ala Val Val Val Thr Ser
145                 150                 155                 160

Gly Thr Thr Ser Glu Val Leu Leu Asn Lys Leu Asn Glu Glu Gln Lys
                165                 170                 175

Met Asn Met Arg Ile Ile Ser Ala Lys Asp His Gly Asp Ser Phe Arg
            180                 185                 190

Thr Leu Glu Ser Gly Arg Ala Val Ala Phe Met Met Asp Asp Ala Leu
        195                 200                 205

Leu Ala Gly Glu Arg Ala Lys Ala Lys Pro Asp Asn Trp Glu Ile
    210                 215                 220

Val Gly Lys Pro Gln Ser Gln Glu Ala Tyr Gly Cys Met Leu Arg Lys
225                 230                 235                 240

Asp Asp Pro Gln Phe Lys Lys Leu Met Asp Asp Thr Ile Ala Gln Val
            245                 250                 255

Gln Thr Ser Gly Glu Ala Glu Lys Trp Phe Asp Lys Trp Phe Lys Asn
        260                 265                 270

Pro Ile Pro Pro Lys Asn Leu Asn Met Asn Phe Glu Leu Ser Asp Glu
    275                 280                 285

Met Lys Ala Leu Phe Lys Glu Pro Asn Asp Lys Ala Leu Asn
290                 295                 300

<210> SEQ ID NO 109
<211> LENGTH: 414
<212> TYPE: PRT
<213> ORGANISM: Thermus thermophilus

<400> SEQUENCE: 109

Met Arg Lys Trp Leu Leu Ala Ile Gly Met Val Leu Gly Leu Ser Ala
1               5                   10                  15

Leu Ala Gln Gly Gly Lys Leu Glu Ile Phe Ser Trp Trp Ala Gly Asp
            20                  25                  30

Glu Gly Pro Ala Leu Glu Ala Leu Ile Arg Leu Tyr Lys Gln Lys Tyr
        35                  40                  45

Pro Gly Val Glu Val Ile Asn Ala Thr Val Thr Gly Gly Ala Gly Val
    50                  55                  60

Asn Ala Arg Ala Val Leu Lys Thr Arg Met Leu Gly Gly Asp Pro Pro
65                  70                  75                  80

Asp Thr Phe Gln Val His Ala Gly Met Glu Leu Ile Gly Thr Trp Val
                85                  90                  95

Val Ala Asn Arg Met Glu Asp Leu Ser Ala Leu Phe Arg Gln Glu Gly
            100                 105                 110

Trp Leu Gln Ala Phe Pro Lys Gly Leu Ile Asp Leu Ile Ser Tyr Lys
        115                 120                 125

Gly Gly Ile Trp Ser Val Pro Val Asn Ile His Arg Ser Asn Val Met
130                 135                 140

Trp Tyr Leu Pro Ala Lys Leu Lys Glu Trp Gly Val Asn Pro Pro Arg
145                 150                 155                 160

Thr Trp Asp Glu Phe Leu Ala Thr Cys Gln Thr Leu Lys Gln Lys Gly
                165                 170                 175

Leu Glu Ala Pro Leu Ala Leu Gly Glu Asn Trp Thr Gln Gln His Leu
            180                 185                 190

Trp Glu Ser Val Ala Leu Ala Val Leu Gly Pro Asp Asp Trp Asn Asn
        195                 200                 205

Leu Trp Asn Gly Lys Leu Lys Phe Thr Asp Pro Lys Ala Val Arg Ala
    210                 215                 220

Trp Glu Val Phe Gly Arg Val Leu Asp Cys Ala Asn Lys Asp Ala Ala
225                 230                 235                 240

Gly Leu Ser Trp Gln Gln Ala Val Asp Arg Val Val Gln Gly Lys Ala
                245                 250                 255

Ala Phe Asn Val Met Gly Asp Trp Ala Ala Gly Tyr Met Thr Thr Thr
            260                 265                 270

Leu Lys Leu Lys Pro Gly Thr Asp Phe Ala Trp Ala Pro Ser Pro Gly
        275                 280                 285

Thr Gln Gly Val Phe Met Met Leu Ser Asp Ser Phe Gly Leu Pro Lys
    290                 295                 300

Gly Ala Lys Asn Arg Gln Asn Ala Ile Asn Trp Leu Arg Leu Val Gly
305                 310                 315                 320

Ser Lys Glu Gly Gln Asp Thr Phe Asn Pro Leu Lys Gly Ser Ile Ala
                325                 330                 335

Ala Arg Leu Asp Ser Asp Pro Ser Lys Tyr Asn Ala Tyr Gly Gln Ser
            340                 345                 350

Ala Met Arg Asp Trp Arg Ser Asn Arg Ile Val Gly Ser Leu Val His
        355                 360                 365

Gly Ala Val Ala Pro Glu Ser Phe Met Ser Gln Phe Gly Thr Val Met
    370                 375                 380

Glu Ile Phe Leu Gln Thr Arg Asn Pro Gln Ala Ala Asn Ala Ala
385                 390                 395                 400

Gln Ala Ile Ala Asp Gln Val Gly Leu Gly Arg Leu Gly Gln
                405                 410

<210> SEQ ID NO 110
<211> LENGTH: 318
<212> TYPE: PRT
<213> ORGANISM: Rhizobium meliloti

<400> SEQUENCE: 110

Met Ile Arg Thr Leu Ser Leu Lys Phe Met Leu Ala Gly Ala Val Cys
1               5                   10                  15

Met Ala Thr Leu Thr Ala Gly Ser Ala Phe Ala Ala Glu Pro Glu Ser
            20                  25                  30

Cys Gly Thr Val Arg Phe Ser Asp Val Gly Trp Thr Asp Ile Thr Ala
        35                  40                  45

Thr Thr Ala Thr Ala Thr Thr Ile Leu Glu Ala Leu Gly Tyr Glu Thr
    50                  55                  60

Asp Val Lys Val Leu Ser Val Pro Val Thr Tyr Thr Ser Leu Lys Asn
65                  70                  75                  80

Lys Asp Ile Asp Val Phe Leu Gly Asn Trp Met Pro Thr Met Glu Ala
                85                  90                  95

Asp Ile Ala Pro Tyr Arg Glu Asp Lys Ser Val Glu Thr Val Arg Glu
            100                 105                 110

Asn Leu Ala Gly Ala Lys Tyr Thr Leu Ala Thr Asn Ala Lys Gly Ala
        115                 120                 125

Glu Leu Gly Ile Lys Asp Phe Lys Asp Ile Ala Ala His Lys Asp Glu
    130                 135                 140

Leu Asp Gly Lys Ile Tyr Gly Ile Glu Pro Gly Asn Asp Gly Asn Arg
145                 150                 155                 160

Leu Ile Ile Asp Met Val Glu Lys Gly Thr Phe Asp Leu Lys Gly Phe
                165                 170                 175

Glu Val Val Glu Ser Ser Glu Gln Gly Met Leu Ala Gln Val Ala Arg
            180                 185                 190

Ala Glu Lys Ser Gly Asp Pro Ile Val Phe Leu Gly Trp Glu Pro His
        195                 200                 205

Pro Met Asn Ala Asn Phe Lys Leu Thr Tyr Leu Ser Gly Gly Asp Asp
    210                 215                 220

Val Phe Gly Pro Asn Tyr Gly Ala Thr Val His Thr Asn Val Arg
225                 230                 235                 240

Ala Gly Tyr Thr Thr Glu Cys Pro Asn Val Gly Lys Leu Leu Gln Asn
                245                 250                 255

Leu Ser Phe Ser Leu Gln Met Glu Asn Glu Ile Met Gly Lys Ile Leu
            260                 265                 270

Asn Asp Gly Glu Asp Pro Glu Lys Ala Ala Ala Trp Leu Lys Asp
        275                 280                 285

Asn Pro Gln Ser Ile Glu Pro Trp Leu Ser Val Ala Thr Lys Asp
    290                 295                 300

Gly Gly Asp Gly Leu Ala Ala Val Lys Ala Ala Leu Gly Leu
305                 310                 315

<210> SEQ ID NO 111
<211> LENGTH: 249
<212> TYPE: PRT
<213> ORGANISM: Geobacillus stearothermophilus

<400> SEQUENCE: 111

Met Gly Gly Gly Arg Ser Thr Glu Thr Ser Ser Ser Gly Gly Asp
1               5                   10                  15

```
Gly Gly Ala Thr Lys Lys Val Val Gly Thr Asp Ala Ala Phe
            20              25              30

Ala Pro Phe Glu Tyr Met Gln Lys Gly Lys Ile Val Gly Phe Asp Val
        35                  40                  45

Asp Leu Leu Asp Ala Val Met Lys Ala Gly Leu Asp Tyr Glu Leu
50                  55                  60

Lys Asn Ile Gly Trp Asp Pro Leu Phe Ala Ser Leu Gln Ser Lys Glu
65              70                  75                  80

Val Asp Met Gly Ile Ser Gly Ile Thr Ile Thr Asp Glu Arg Lys Gln
                    85                  90                  95

Ser Tyr Asp Phe Ser Asp Pro Tyr Phe Glu Ala Thr Gln Val Ile Leu
                100                 105                 110

Val Lys Gln Gly Ser Pro Val Lys Asn Ala Leu Asp Leu Lys Gly Thr
            115                 120                 125

Ile Gly Val Gln Asn Ala Thr Thr Gly Gln Glu Ala Ala Glu Lys Leu
        130                 135                 140

Phe Gly Lys Gly Pro His Ile Lys Lys Phe Glu Thr Val Val Ala
145                 150                 155                 160

Ile Met Glu Leu Leu Asn Gly Gly Val Asp Ala Val Ile Thr Asp Asn
                165                 170                 175

Ala Val Ala Asn Glu Tyr Val Lys Asn Pro Asn Lys Lys Leu Gln
            180                 185                 190

Val Ile Glu Asp Pro Lys Asn Phe Ala Ser Glu Tyr Tyr Gly Met Ile
        195                 200                 205

Phe Pro Lys Asn Ser Glu Leu Lys Ala Lys Val Asp Glu Ala Leu Lys
        210                 215                 220

Asn Val Ile Asn Ser Gly Lys Tyr Thr Glu Ile Tyr Lys Lys Trp Phe
225                 230                 235                 240

Gly Lys Glu Pro Lys Leu Asp Arg Leu
                    245

<210> SEQ ID NO 112
<211> LENGTH: 370
<212> TYPE: PRT
<213> ORGANISM: Agrobacterium tumefaciens

<400> SEQUENCE: 112

Met Lys Lys Ser Leu Leu Ser Ala Val Ala Leu Thr Ala Met Val Ala
 1                5                  10                  15

Phe Gly Gly Ser Ala Trp Ala Asp Val Val Ile Ala Val Gly Ala Pro
            20                  25                  30

Leu Thr Gly Pro Asn Ala Ala Phe Gly Ala Gln Ile Gln Lys Gly Ala
        35                  40                  45

Glu Gln Ala Ala Lys Asp Ile Asn Ala Ala Gly Gly Ile Asn Gly Glu
    50                  55                  60

Gln Ile Lys Ile Val Leu Gly Asp Asp Val Ser Asp Pro Lys Gln Gly
65                  70                  75                  80

Ile Ser Val Ala Asn Lys Phe Val Ala Asp Gly Val Lys Phe Val Val
                    85                  90                  95

Gly His Phe Asn Ser Gly Val Ser Ile Pro Ala Ser Glu Val Tyr Ala
                100                 105                 110

Glu Asn Gly Ile Leu Glu Ile Thr Pro Ala Ala Thr Asn Pro Val Phe
            115                 120                 125

Thr Glu Arg Gly Leu Trp Asn Thr Phe Arg Thr Cys Gly Arg Asp Asp
```

```
                130                 135                 140
Gln Gln Gly Gly Ile Ala Gly Lys Tyr Leu Ala Asp His Phe Lys Asp
145                 150                 155                 160

Ala Lys Val Ala Ile Ile His Asp Lys Thr Pro Tyr Gly Gln Gly Leu
                165                 170                 175

Ala Asp Glu Thr Lys Lys Ala Ala Asn Ala Ala Gly Val Thr Glu Val
                180                 185                 190

Met Tyr Glu Gly Val Asn Val Gly Asp Lys Asp Phe Ser Ala Leu Ile
                195                 200                 205

Ser Lys Met Lys Glu Ala Gly Val Ser Ile Ile Tyr Trp Gly Gly Leu
                210                 215                 220

His Thr Glu Ala Gly Leu Ile Ile Arg Gln Ala Ala Asp Gln Gly Leu
225                 230                 235                 240

Lys Ala Lys Leu Val Ser Gly Asp Gly Ile Val Ser Asn Glu Leu Ala
                245                 250                 255

Ser Ile Ala Gly Asp Ala Val Glu Gly Thr Leu Asn Thr Phe Gly Pro
                260                 265                 270

Asp Pro Thr Leu Arg Pro Glu Asn Lys Glu Leu Val Glu Lys Phe Lys
                275                 280                 285

Ala Ala Gly Phe Asn Pro Glu Ala Tyr Thr Leu Tyr Ser Tyr Ala Ala
                290                 295                 300

Met Gln Ala Ile Ala Gly Ala Lys Ala Ala Gly Ser Val Glu Pro
305                 310                 315                 320

Glu Lys Val Ala Glu Ala Leu Lys Lys Gly Ser Phe Pro Thr Ala Leu
                325                 330                 335

Gly Glu Ile Ser Phe Asp Glu Lys Gly Asp Pro Lys Leu Pro Gly Tyr
                340                 345                 350

Val Met Tyr Glu Trp Lys Lys Gly Pro Asp Gly Lys Phe Thr Tyr Ile
                355                 360                 365

Gln Gln
    370

<210> SEQ ID NO 113
<211> LENGTH: 368
<212> TYPE: PRT
<213> ORGANISM: Escherichia coli

<400> SEQUENCE: 113

Met Asn Ile Lys Gly Lys Ala Leu Leu Ala Gly Cys Ile Ala Leu Ala
1               5                   10                  15

Phe Ser Asn Met Ala Leu Ala Glu Asp Ile Lys Val Ala Val Val Gly
                20                  25                  30

Ala Met Ser Gly Pro Val Ala Gln Tyr Gly Asp Gln Glu Phe Thr Gly
            35                  40                  45

Ala Glu Gln Ala Val Ala Asp Ile Asn Ala Lys Gly Gly Ile Lys Gly
        50                  55                  60

Asn Lys Leu Gln Ile Val Lys Tyr Asp Asp Ala Cys Asp Pro Lys Gln
65                  70                  75                  80

Ala Val Ala Val Ala Asn Lys Val Val Asn Asp Gly Ile Lys Tyr Val
                85                  90                  95

Ile Gly His Leu Cys Ser Ser Ser Thr Gln Pro Ala Ser Asp Ile Tyr
            100                 105                 110

Glu Asp Glu Gly Ile Leu Met Ile Thr Pro Ala Ala Thr Ala Pro Glu
        115                 120                 125
```

-continued

```
Leu Thr Ala Arg Gly Tyr Gln Leu Ile Leu Arg Thr Thr Gly Leu Asp
        130                 135                 140

Ser Asp Gln Gly Pro Thr Ala Ala Lys Tyr Ile Leu Glu Lys Val Lys
145                 150                 155                 160

Pro Gln Arg Ile Ala Ile Val His Asp Lys Gln Gln Tyr Gly Glu Gly
                165                 170                 175

Leu Ala Arg Ala Val Gln Asp Gly Leu Ile Lys Lys Gly Asn Ala Asn
            180                 185                 190

Val Val Phe Phe Asp Gly Ile Thr Ala Gly Glu Lys Asp Phe Ser Thr
        195                 200                 205

Leu Val Ala Arg Leu Lys Lys Glu Asn Ile Asp Phe Val Tyr Tyr Gly
    210                 215                 220

Gly Tyr His Pro Glu Met Gly Gln Ile Leu Arg Gln Ala Arg Ala Ala
225                 230                 235                 240

Gly Leu Lys Thr Gln Phe Met Gly Pro Glu Gly Val Ala Asn Val Ser
                245                 250                 255

Leu Ser Asn Ile Ala Gly Glu Ser Ala Glu Gly Leu Leu Val Thr Lys
            260                 265                 270

Pro Lys Asn Tyr Asp Gln Val Pro Ala Asn Lys Pro Ile Val Asp Ala
        275                 280                 285

Ile Lys Ala Lys Lys Gln Asp Pro Ser Gly Ala Phe Val Trp Thr Thr
    290                 295                 300

Tyr Ala Ala Leu Gln Ser Leu Gln Ala Gly Leu Asn Gln Ser Asp Asp
305                 310                 315                 320

Pro Ala Glu Ile Ala Lys Tyr Leu Lys Ala Asn Ser Val Asp Thr Val
                325                 330                 335

Met Gly Pro Leu Thr Trp Asp Glu Lys Gly Asp Leu Lys Gly Phe Glu
            340                 345                 350

Phe Gly Val Phe Asp Trp His Ala Asn Gly Thr Ala Thr Asp Ala Lys
        355                 360                 365

<210> SEQ ID NO 114
<211> LENGTH: 677
<212> TYPE: PRT
<213> ORGANISM: Artificial Sequence
<220> FEATURE:
<223> OTHER INFORMATION: recombinant peptide biosensor

<400> SEQUENCE: 114

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Leu Glu Ile Phe Ser Trp Trp Ala Gly Asp Glu
        35                  40                  45

Gly Pro Ala Leu Glu Ala Leu Ile Arg Leu Tyr Lys Gln Lys Tyr Pro
    50                  55                  60

Gly Val Glu Val Ile Asn Ala Thr Val Thr Gly Ala Gly Val Asn
65                  70                  75                  80

Ala Arg Ala Val Leu Lys Thr Arg Met Leu Gly Gly Asp Pro Pro Asp
                85                  90                  95

Thr Phe Gln Val Ala Ala Gly Met Glu Leu Ile Gly Thr Trp Val Val
            100                 105                 110

Ala Asn Arg Met Glu Asp Leu Ser Ala Leu Phe Arg Gln Glu Gly Trp
        115                 120                 125
```

```
Leu Gln Ala Phe Pro Lys Gly Leu Ile Asp Leu Ile Ser Tyr Lys Gly
130                 135                 140

Gly Ile Trp Ser Val Pro Val Asn Ile His Arg Ser Asn Val Met Trp
145                 150                 155                 160

Tyr Leu Pro Ala Lys Leu Lys Glu Trp Gly Val Asn Pro Pro Arg Thr
                165                 170                 175

Trp Glu Phe Leu Ala Thr Cys Gln Thr Leu Lys Gln Lys Gly Leu Glu
                180                 185                 190

Ala Pro Leu Ala Leu Gly Glu Asn Trp Thr Gln Gln His Leu Trp Glu
                195                 200                 205

Ser Val Ala Leu Ala Val Leu Gly Pro Asp Asp Trp Asn Asn Leu Trp
210                 215                 220

Asn Gly Lys Leu Lys Phe Thr Asp Pro Lys Ala Val Arg Ala Trp Glu
225                 230                 235                 240

Val Phe Gly Arg Val Leu Asp Cys Ala Asn Lys Asp Ala Ala Gly Leu
                245                 250                 255

Ser Trp Gln Gln Ala Val Asp Arg Val Val Gln Gly Lys Ala Ala Phe
                260                 265                 270

Asn Val Met Gly Asp Trp Ala Ala Gly Tyr Met Thr Thr Thr Leu Lys
                275                 280                 285

Leu Lys Pro Gly Thr Asp Phe Ala Trp Ala Pro Ser Pro Gly Thr Gln
                290                 295                 300

Gly Val Phe Met Met Val Ser Asp Ser Phe Gly Leu Pro Lys Gly Ala
305                 310                 315                 320

Lys Asn Arg Gln Asn Ala Ile Asn Trp Leu Arg Leu Val Gly Ser Lys
                325                 330                 335

Glu Gly Gln Asp Thr Phe Asn Pro Leu Lys Gly Ser Ile Ala Ala Arg
                340                 345                 350

Leu Asp Ser Asp Pro Ser Lys Tyr Pro Ala Ser His Asn Val Tyr Ile
                355                 360                 365

Met Ala Asp Lys Gln Arg Asn Gly Ile Lys Ala Asn Phe Lys Ile Arg
                370                 375                 380

His Asn Ile Glu Asp Gly Gly Val Gln Leu Ala Tyr His Tyr Gln Gln
385                 390                 395                 400

Asn Thr Pro Ile Gly Asp Gly Pro Val Leu Leu Pro Asp Asn His Tyr
                405                 410                 415

Leu Ser Thr Gln Ser Lys Leu Ser Lys Asp Pro Asn Glu Lys Arg Asp
                420                 425                 430

His Met Val Leu Leu Glu Phe Val Thr Ala Ala Gly Ile Thr Leu Gly
                435                 440                 445

Met Asp Glu Leu Tyr Lys Gly Gly Thr Gly Gly Ser Met Val Ser Lys
450                 455                 460

Gly Glu Glu Leu Phe Thr Gly Val Val Pro Ile Leu Val Glu Leu Asp
465                 470                 475                 480

Gly Asp Val Asn Gly His Lys Phe Ser Val Ser Gly Glu Gly Glu Gly
                485                 490                 495

Asp Ala Thr Tyr Gly Lys Leu Thr Leu Lys Phe Ile Cys Thr Thr Gly
                500                 505                 510

Lys Leu Pro Val Pro Trp Pro Thr Leu Val Thr Thr Leu Thr Tyr Gly
                515                 520                 525

Val Gln Cys Phe Ser Arg Tyr Pro Asp His Met Lys Gln His Asp Phe
530                 535                 540

Phe Lys Ser Ala Met Pro Glu Gly Tyr Ile Gln Glu Arg Thr Ile Phe
```

```
                545                 550                 555                 560
            Phe Lys Asp Asp Gly Asn Tyr Lys Thr Arg Ala Glu Val Lys Phe Glu
                            565                 570                 575

Gly Asp Thr Leu Val Asn Arg Ile Glu Leu Lys Gly Ile Asp Phe Lys
                        580                 585                 590

Glu Asp Gly Asn Ile Leu Gly His Lys Leu Glu Tyr Asn Phe Asn Asn
                    595                 600                 605

Pro Asn Ala Tyr Gly Gln Ser Ala Met Arg Asp Trp Arg Ser Asn Arg
                610                 615                 620

Ile Val Gly Ser Leu Val Ala Gly Ala Val Ala Pro Glu Ser Phe Met
            625                 630                 635                 640

Ser Gln Phe Gly Thr Val Met Glu Ile Phe Leu Gln Thr Arg Asn Pro
                            645                 650                 655

Gln Ala Ala Ala Asn Ala Ala Gln Ala Ile Ala Asp Gln Val Gly Leu
                        660                 665                 670

Gly Arg Leu Gly Gln
                    675

<210> SEQ ID NO 115
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 1
<223> OTHER INFORMATION: Xaa = Any Amino Acid

<400> SEQUENCE: 115

Xaa Pro Ser His Asn Val Tyr
 1               5

<210> SEQ ID NO 116
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 1, 2
<223> OTHER INFORMATION: Xaa = Any Amino Acid

<400> SEQUENCE: 116

Xaa Xaa Ser His Asn Val Tyr
 1               5

<210> SEQ ID NO 117
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 1, 2
<223> OTHER INFORMATION: Xaa = Any Amino Acid

<400> SEQUENCE: 117

Xaa Xaa Ser His Asn Val Phe
 1               5

<210> SEQ ID NO 118
```

```
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2
<223> OTHER INFORMATION: Xaa = Any Amino Acid

<400> SEQUENCE: 118

Pro Xaa Ser His Asn Val Phe
 1               5

<210> SEQ ID NO 119
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2
<223> OTHER INFORMATION: Xaa = Any Amino Acid

<400> SEQUENCE: 119

Pro Xaa Ser Tyr Asn Val Phe
 1               5

<210> SEQ ID NO 120
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 1, 2
<223> OTHER INFORMATION: Xaa = Any Amino Acid

<400> SEQUENCE: 120

Xaa Xaa Ser Tyr Asn Val Phe
 1               5

<210> SEQ ID NO 121
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2
<223> OTHER INFORMATION: Xaa = Any Amino Acid

<400> SEQUENCE: 121

Pro Xaa Ser Tyr Asn Val Phe
 1               5

<210> SEQ ID NO 122
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 1, 2
<223> OTHER INFORMATION: Xaa = Any Amino Acid

<400> SEQUENCE: 122
```

```
Xaa Xaa Ser Tyr Asn Val Phe
1               5

<210> SEQ ID NO 123
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2, 4
<223> OTHER INFORMATION: Xaa = Any Amino Acid

<400> SEQUENCE: 123

Pro Xaa Ser Xaa Asn Val Tyr
1               5

<210> SEQ ID NO 124
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2, 5
<223> OTHER INFORMATION: Xaa = Any Amino Acid

<400> SEQUENCE: 124

Pro Xaa Ser His Xaa Val Tyr
1               5

<210> SEQ ID NO 125
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2, 6
<223> OTHER INFORMATION: Xaa = Any Amino Acid

<400> SEQUENCE: 125

Pro Xaa Ser His Asn Xaa Tyr
1               5

<210> SEQ ID NO 126
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2, 7
<223> OTHER INFORMATION: Xaa = Any Amino Acid

<400> SEQUENCE: 126

Pro Xaa Ser His Asn Val Xaa
1               5

<210> SEQ ID NO 127
<211> LENGTH: 5
<212> TYPE: PRT
<213> ORGANISM: Artificial Sequence
<220> FEATURE:
<223> OTHER INFORMATION: synthetic oligopeptide
```

```
<220> FEATURE:
<221> NAME/KEY: VARIANT
<222> LOCATION: 3, 4
<223> OTHER INFORMATION: Xaa = Any Amino Acid

<400> SEQUENCE: 127

Phe Asn Xaa Xaa Tyr
 1               5

<210> SEQ ID NO 128
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3
<223> OTHER INFORMATION: Xaa = Any Amino Acid

<400> SEQUENCE: 128

Phe Asn Xaa Tyr
 1

<210> SEQ ID NO 129
<211> LENGTH: 3
<212> TYPE: PRT
<213> ORGANISM: Artificial Sequence
<220> FEATURE:
<223> OTHER INFORMATION: synthetic oligopeptide

<400> SEQUENCE: 129

Phe Asn Tyr
 1

<210> SEQ ID NO 130
<211> LENGTH: 3
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2
<223> OTHER INFORMATION: Xaa = Any Amino Acid

<400> SEQUENCE: 130

Phe Xaa Tyr
 1

<210> SEQ ID NO 131
<211> LENGTH: 3
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 1, 2
<223> OTHER INFORMATION: Xaa = Any Amino Acid

<400> SEQUENCE: 131

Xaa Xaa Tyr
 1

<210> SEQ ID NO 132
<211> LENGTH: 3
<212> TYPE: PRT
<213> ORGANISM: Artificial Sequence
```

```
<220> FEATURE:
<223> OTHER INFORMATION: synthetic oligopeptide
<220> FEATURE:
<221> NAME/KEY: VARIANT
<222> LOCATION: 2
<223> OTHER INFORMATION: Xaa = Any Amino Acid

<400> SEQUENCE: 132

Trp Xaa Tyr
 1

<210> SEQ ID NO 133
<211> LENGTH: 3
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 1
<223> OTHER INFORMATION: Xaa = Any Amino Acid

<400> SEQUENCE: 133

Xaa Lys Tyr
 1

<210> SEQ ID NO 134
<211> LENGTH: 5
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 4
<223> OTHER INFORMATION: Xaa = Any Amino Acid

<400> SEQUENCE: 134

Phe Asn Pro Xaa Tyr
 1               5

<210> SEQ ID NO 135
<211> LENGTH: 5
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3
<223> OTHER INFORMATION: Xaa = Any Amino Acid

<400> SEQUENCE: 135

Phe Asn Xaa Pro Tyr
 1               5

<210> SEQ ID NO 136
<211> LENGTH: 3
<212> TYPE: PRT
<213> ORGANISM: Artificial Sequence
<220> FEATURE:
<223> OTHER INFORMATION: synthetic oligopeptide

<400> SEQUENCE: 136

His Asn Ser
 1

<210> SEQ ID NO 137
<211> LENGTH: 3
```

```
<212> TYPE: PRT
<213> ORGANISM: Artificial Sequence
<220> FEATURE:
<223> OTHER INFORMATION: synthetic oligopeptide

<400> SEQUENCE: 137

Gly Gly Ser
  1

<210> SEQ ID NO 138
<211> LENGTH: 3
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 1, 2
<223> OTHER INFORMATION: Xaa = Any Amino Acid

<400> SEQUENCE: 138

Xaa Xaa Ser
  1

<210> SEQ ID NO 139
<211> LENGTH: 3
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 1, 2
<223> OTHER INFORMATION: Xaa = Any Amino Acid

<400> SEQUENCE: 139

Xaa Xaa Lys
  1

<210> SEQ ID NO 140
<211> LENGTH: 3
<212> TYPE: PRT
<213> ORGANISM: Artificial Sequence
<220> FEATURE:
<223> OTHER INFORMATION: synthetic oligopeptide

<400> SEQUENCE: 140

Gly Gly Lys
  1

<210> SEQ ID NO 141
<211> LENGTH: 3
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2
<223> OTHER INFORMATION: Xaa = Any Amino Acid

<400> SEQUENCE: 141

Pro Xaa Ser
  1

<210> SEQ ID NO 142
<211> LENGTH: 3
<212> TYPE: PRT
<213> ORGANISM: Artificial Sequence
```

```
<220> FEATURE:
<223> OTHER INFORMATION: synthetic oligopeptide
<220> FEATURE:
<221> NAME/KEY: VARIANT
<222> LOCATION: 1
<223> OTHER INFORMATION: Xaa = Any Amino Acid

<400> SEQUENCE: 142

Xaa Pro Ser
 1

<210> SEQ ID NO 143
<211> LENGTH: 2
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2
<223> OTHER INFORMATION: Xaa = Any Amino Acid

<400> SEQUENCE: 143

Pro Xaa
 1

<210> SEQ ID NO 144
<211> LENGTH: 2
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 1
<223> OTHER INFORMATION: Xaa = Any Amino Acid

<400> SEQUENCE: 144

Xaa Pro
 1

<210> SEQ ID NO 145
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2, 3
<223> OTHER INFORMATION: Xaa = Any Amino Acid

<400> SEQUENCE: 145

Ile Xaa Xaa Ser
 1

<210> SEQ ID NO 146
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2
<223> OTHER INFORMATION: Xaa = Any Amino Acid

<400> SEQUENCE: 146

Asn Xaa Pro Lys
 1
```

```
<210> SEQ ID NO 147
<211> LENGTH: 4
<212> TYPE: PRT
<213> ORGANISM: Artificial Sequence
<220> FEATURE:
<223> OTHER INFORMATION: synthetic oligopeptide

<400> SEQUENCE: 147

Asn Pro Cys Lys
  1

<210> SEQ ID NO 148
<211> LENGTH: 5
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3
<223> OTHER INFORMATION: Xaa = Any Amino Acid

<400> SEQUENCE: 148

Pro Pro Xaa Ser His
  1               5

<210> SEQ ID NO 149
<211> LENGTH: 6
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3, 4
<223> OTHER INFORMATION: Xaa = Any Amino Acid

<400> SEQUENCE: 149

Pro Pro Xaa Xaa Ser His
  1               5

<210> SEQ ID NO 150
<211> LENGTH: 6
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 4
<223> OTHER INFORMATION: Xaa = Any Amino Acid

<400> SEQUENCE: 150

Pro Pro Pro Xaa Ser His
  1               5

<210> SEQ ID NO 151
<211> LENGTH: 6
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3
<223> OTHER INFORMATION: Xaa = Any Amino Acid

<400> SEQUENCE: 151
```

```
Pro Pro Xaa Pro Ser His
1               5
```

<210> SEQ ID NO 152
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 1, 2
<223> OTHER INFORMATION: Xaa = Any Amino Acid

<400> SEQUENCE: 152

```
Xaa Xaa Ser His
1
```

<210> SEQ ID NO 153
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3, 4
<223> OTHER INFORMATION: Xaa = Any Amino Acid

<400> SEQUENCE: 153

```
Pro Pro Xaa Xaa
1
```

<210> SEQ ID NO 154
<211> LENGTH: 5
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3
<223> OTHER INFORMATION: Xaa = Any Amino Acid

<400> SEQUENCE: 154

```
Phe Asn Xaa Lys Asn
1               5
```

<210> SEQ ID NO 155
<211> LENGTH: 6
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3, 4
<223> OTHER INFORMATION: Xaa = Any Amino Acid

<400> SEQUENCE: 155

```
Phe Asn Xaa Xaa Lys Asn
1               5
```

<210> SEQ ID NO 156
<211> LENGTH: 6
<212> TYPE: PRT
<213> ORGANISM: Artificial Sequence
<220> FEATURE:
<223> OTHER INFORMATION: synthetic oligopeptide
<220> FEATURE:

```
<221> NAME/KEY: VARIANT
<222> LOCATION: 3
<223> OTHER INFORMATION: Xaa = Any Amino Acid

<400> SEQUENCE: 156

Phe Asn Xaa Pro Lys Asn
1               5

<210> SEQ ID NO 157
<211> LENGTH: 6
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 4
<223> OTHER INFORMATION: Xaa = Any Amino Acid

<400> SEQUENCE: 157

Phe Asn Pro Xaa Lys Asn
1               5

<210> SEQ ID NO 158
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3, 4
<223> OTHER INFORMATION: Xaa = Any Amino Acid

<400> SEQUENCE: 158

Phe Asn Xaa Xaa
1

<210> SEQ ID NO 159
<211> LENGTH: 7
<212> TYPE: PRT
<213> ORGANISM: Artificial Sequence
<220> FEATURE:
<223> OTHER INFORMATION: synthetic oligopeptide

<400> SEQUENCE: 159

Asn Ala Asp Gly Ser Ser His
1               5

<210> SEQ ID NO 160
<211> LENGTH: 6
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3, 4
<223> OTHER INFORMATION: Xaa = Any Amino Acid

<400> SEQUENCE: 160

Ala Asp Xaa Xaa Ser His
1               5

<210> SEQ ID NO 161
<211> LENGTH: 6
<212> TYPE: PRT
<213> ORGANISM: Artificial Sequence
<220> FEATURE:
```

<223> OTHER INFORMATION: synthetic oligopeptide
<220> FEATURE:
<221> NAME/KEY: VARIANT
<222> LOCATION: 3
<223> OTHER INFORMATION: Xaa = Any Amino Acid

<400> SEQUENCE: 161

Ala Asp Xaa Pro Ser His
1               5

<210> SEQ ID NO 162
<211> LENGTH: 6
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 4
<223> OTHER INFORMATION: Xaa = Any Amino Acid

<400> SEQUENCE: 162

Ala Asp Pro Xaa Ser His
1               5

<210> SEQ ID NO 163
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3, 4
<223> OTHER INFORMATION: Xaa = Any Amino Acid

<400> SEQUENCE: 163

Ala Asp Xaa Xaa
1

<210> SEQ ID NO 164
<211> LENGTH: 6
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3, 4
<223> OTHER INFORMATION: Xaa = Any Amino Acid

<400> SEQUENCE: 164

Ala Asp Xaa Xaa Ser His
1               5

<210> SEQ ID NO 165
<211> LENGTH: 4
<212> TYPE: PRT
<213> ORGANISM: Artificial Sequence
<220> FEATURE:
<223> OTHER INFORMATION: synthetic oligopeptide

<400> SEQUENCE: 165

Phe Asn Pro Gly
1

<210> SEQ ID NO 166
<211> LENGTH: 6
<212> TYPE: PRT

<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3, 4
<223> OTHER INFORMATION: Xaa = Any Amino Acid

<400> SEQUENCE: 166

Phe Asn Xaa Xaa Pro Gly
 1               5

<210> SEQ ID NO 167
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 1, 2
<223> OTHER INFORMATION: Xaa = Any Amino Acid

<400> SEQUENCE: 167

Xaa Xaa Pro Gly
 1

<210> SEQ ID NO 168
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3, 4
<223> OTHER INFORMATION: Xaa = Any Amino Acid

<400> SEQUENCE: 168

Phe Asn Xaa Xaa
 1

<210> SEQ ID NO 169
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 4
<223> OTHER INFORMATION: Xaa = Any Amino Acid

<400> SEQUENCE: 169

Phe Asn Pro Xaa
 1

<210> SEQ ID NO 170
<211> LENGTH: 6
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3, 4
<223> OTHER INFORMATION: Xaa = Any Amino Acid

<400> SEQUENCE: 170

Lys Tyr Xaa Xaa Ser His

```
                           1               5

<210> SEQ ID NO 171
<211> LENGTH: 6
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 4
<223> OTHER INFORMATION: Xaa = Any Amino Acid

<400> SEQUENCE: 171

Lys Tyr Pro Xaa Ser His
  1               5

<210> SEQ ID NO 172
<211> LENGTH: 6
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3
<223> OTHER INFORMATION: Xaa = Any Amino Acid

<400> SEQUENCE: 172

Lys Tyr Xaa Pro Ser His
  1               5

<210> SEQ ID NO 173
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2, 3
<223> OTHER INFORMATION: Xaa = Any Amino Acid

<400> SEQUENCE: 173

Phe Xaa Xaa Pro
  1

<210> SEQ ID NO 174
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 3
<223> OTHER INFORMATION: Xaa = Any Amino Acid

<400> SEQUENCE: 174

Phe Asn Xaa Pro
  1

<210> SEQ ID NO 175
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
```

```
<222> LOCATION: 4
<223> OTHER INFORMATION: Xaa = Any Amino Acid

<400> SEQUENCE: 175

Phe Asn Pro Xaa
 1

<210> SEQ ID NO 176
<211> LENGTH: 7
<212> TYPE: PRT
<213> ORGANISM: Artificial Sequence
<220> FEATURE:
<223> OTHER INFORMATION: synthetic oligopeptide
<220> FEATURE:
<221> NAME/KEY: VARIANT
<222> LOCATION: 2
<223> OTHER INFORMATION: Xaa = Any Amino Acid

<400> SEQUENCE: 176

Pro Xaa Ser His Asn Val Tyr
 1               5
```

What is claimed is:

1. A recombinant peptide biosensor comprising an analyte-binding framework portion and a signaling portion, wherein the signaling portion is present within the framework portion at a site or amino acid position that undergoes a conformational change upon interaction of the framework portion with a defined, specific, or selected analyte, wherein the recombinant peptide biosensor comprises an amino acid sequence having at least 85% identity to a sequence selected from the group consisting of SEQ ID NO: 62 and 63.

2. The recombinant peptide biosensor of claim 1, wherein the signaling portion is allosterically regulated by the framework portion such that signaling from the signaling portion is altered upon interaction of the framework portion with the analyte.

3. The recombinant peptide biosensor of claim 1, wherein signaling by the signaling portion detectably increases upon interaction of the framework portion with the analyte.

4. The recombinant peptide biosensor of claim 1, wherein signaling by the signaling portion detectably decreases upon interaction of the framework portion with the analyte.

5. The recombinant peptide biosensor of claim 1, wherein signaling by the signaling portion is proportional to the level of interaction between the framework portion and the analyte.

6. The recombinant peptide biosensor of claim 1, wherein the framework portion has a first structure in the absence of an analyte and a second structure, that is detectably distinct from the first structure, in the presence of the analyte.

7. The recombinant peptide biosensor of claim 6, wherein the conformational change between the first structure and the second structure allosterically regulates the signaling portion.

8. The recombinant peptide biosensor of claim 1, wherein the framework portion is a periplasmic binding protein (PBP) or a variant of a PBP.

9. The recombinant peptide biosensor of claim 1, wherein the signaling portion is a circularly permuted fluorescent protein (cpFP).

10. The recombinant peptide biosensor of claim 1, wherein the analyte-binding framework portion binds specifically to glutamate.

11. A recombinant peptide biosensor comprising an amino acid sequence with at least 95% identity to a recombinant peptide biosensor selected from the group consisting of SEQ ID NO: 62 and 63, wherein the recombinant peptide biosensor binds specifically to glutamate.

12. The recombinant peptide biosensor of claim 11, comprising a recombinant peptide biosensor selected from the group consisting of SEQ ID NO: 62 and 63.

13. A nucleic acid encoding the recombinant peptide biosensor of claim 1.

14. A nucleic acid encoding the recombinant peptide biosensor of claim 11.

15. A vector comprising the nucleic acid of claim 13.

16. A vector comprising the nucleic acid of claim 14.

17. A cell comprising the nucleic acid of claim 13.

18. A cell comprising the nucleic acid of claim 14.

19. A cell comprising the vector of claim 15.

20. A cell comprising the vector of claim 16.

21. A method for detecting glutamate, the method comprising detecting a level of fluorescence emitted by the recombinant peptide biosensor of claim 1, and correlating the level of fluorescence with the presence of glutamate.

22. The method of claim 21, wherein the recombinant peptide biosensor is expressed from a nucleic acid.

23. The method of claim 21, comprising contacting the recombinant peptide biosensor with a sample comprising glutamate.

24. The method of claim 21, comprising correlating the level of fluorescence with a concentration of glutamate.

25. The method of claim 24, comprising comparing the level of fluorescence with a level of fluorescence emitted by the recombinant peptide biosensor in the presence of a sample comprising a known concentration or range of concentrations of glutamate.

26. A method for detecting glutamate, the method comprising detecting a level of fluorescence emitted by a recombinant peptide biosensor expressed from the nucleic acid of claim 13 and correlating the level of fluorescence with the presence of glutamate.

27. The method of claim 26, comprising contacting the recombinant peptide biosensor with a sample comprising the glutamate.

28. The method of claim 27, comprising correlating the level of fluorescence with a concentration of the glutamate.

29. The method of claim 28, comprising comparing the level of fluorescence with a level of fluorescence emitted by the recombinant peptide biosensor in the presence of a sample comprising a known concentration or range of concentrations of the glutamate.

\* \* \* \* \*

UNITED STATES PATENT AND TRADEMARK OFFICE
CERTIFICATE OF CORRECTION

PATENT NO. : 10,060,920 B2  
APPLICATION NO. : 15/904574  
DATED : August 28, 2018  
INVENTOR(S) : Jonathan S. Marvin et al.

Page 1 of 1

It is certified that error appears in the above-identified patent and that said Letters Patent is hereby corrected as shown below:

On the Title Page

Item (62), Column 1 (Related U.S. Application Data), Line 4, delete "Aug. 8, 2012," and insert -- Oct. 8, 2012, --;

Item (56), Column 2 (Other Publications), Line 33, delete "di-saccharidc" and insert -- di-saccharide --.

Signed and Sealed this
Twenty-sixth Day of May, 2020

Andrei Iancu
*Director of the United States Patent and Trademark Office*